(12) United States Patent
Gabor Miklos

(10) Patent No.: US 10,302,661 B2
(45) Date of Patent: May 28, 2019

(54) METHOD FOR TREATING A CANCER PATIENT BASED ON ATOMIC THERAPEUTIC INDEXES AND NON-RADIATION THERAPY

(71) Applicant: Atomic Oncology Pty Ltd, Newport Beach (AU)

(72) Inventor: George L. Gabor Miklos, Newport Beach (AU)

(73) Assignee: Atomic Oncology Pty Ltd, Newport Beach, New South Wales (AU)

( * ) Notice: Subject to any disclaimer, the term of this patent is extended or adjusted under 35 U.S.C. 154(b) by 0 days.

(21) Appl. No.: 15/717,246

(22) Filed: Sep. 27, 2017

(65) Prior Publication Data

US 2018/0067136 A1   Mar. 8, 2018

Related U.S. Application Data

(62) Division of application No. 15/517,112, filed as application No. PCT/AU2016/050603 on Jul. 11, 2016, now Pat. No. 10,254,284.

(30) Foreign Application Priority Data

Jul. 9, 2015   (AU) ............... 2015902706

(51) Int. Cl.
| | |
|---|---|
| G01N 21/31 | (2006.01) |
| G01N 21/71 | (2006.01) |
| G01N 22/00 | (2006.01) |
| G01N 33/84 | (2006.01) |
| H01J 49/16 | (2006.01) |
| G01N 23/085 | (2018.01) |
| G01N 23/223 | (2006.01) |
| G01N 33/574 | (2006.01) |
| G01N 33/48 | (2006.01) |

(52) U.S. Cl.
CPC ........... *G01N 33/84* (2013.01); *G01N 23/085* (2018.02); *G01N 23/223* (2013.01); *G01N 33/574* (2013.01); *G01N 21/3103* (2013.01); *G01N 21/718* (2013.01); *G01N 22/00* (2013.01); *G01N 2223/402* (2013.01); *G01N 2223/6126* (2013.01); *G01N 2800/52* (2013.01); *H01J 49/161* (2013.01)

(58) Field of Classification Search
None
See application file for complete search history.

(56) References Cited

U.S. PATENT DOCUMENTS

| | | |
|---|---|---|
| 6,261,795 B1 | 7/2001 | Fruehauf et al. |
| 2012/0184841 A1 | 7/2012 | Nielsen et al. |
| 2018/0067136 A1 | 3/2018 | Gabor Miklos |
| 2018/0143197 A1 | 5/2018 | Gabor Miklos |

FOREIGN PATENT DOCUMENTS

| | | |
|---|---|---|
| WO | WO-2008/040116 A1 | 4/2008 |
| WO | WO-2015/042446 A2 | 3/2015 |

OTHER PUBLICATIONS

Ye et al. (Bioanalysis. Feb. 2011 ; 3(3): 313-332) (Year: 2011).*
Austin et al., "Factors Affecting Internal Standard Selection for Quantitative Elemental Bio-Imaging of Soft Tissues by LA-ICP-MS," The Royal Society of Chemisty, 26:1494-1501 (2011).
Bobba et al., "Classical and Anaplastic Seminoma: Difference in Survival," Radiology, 167:849-852 (1998).
Brozyna et al., "Melanin Content in Melanoma Metastases Affects the Outcome of Radiotherapy," Oncotarget, 7(14):17844-17853 (2016).
Doble et al., "Distributions of manganese in diverse human cancers provide insights into tumour radioresistance," Metallomics: 1-20 (2018).
Gupta et al., "MDP: A Deinococcus Mn2+-Decapeptide Complex Protexts Mice From Ionizing Radiation," PlosOne (2016).
Hare et al., "Protocol for Production of Matrix-Matched Brain Tissue Standards for Imaging by Laser Ablation-Inductively Coupled Plasma-Mass Spectrometry," Analytical Methods 5:1915-1921 (2013).
Hernroth et al., "Manganese Inhibits Viability of Prostate Cancer Cells," Anticancer Research, 38: 137-145 (2018).

(Continued)

*Primary Examiner* — Pablo S Whaley
(74) *Attorney, Agent, or Firm* — Foley Hoag LLP

(57) ABSTRACT

The present invention relates to the generation of an Atomic Therapeutic Indicator (ATI) for a test sample by the quantification of manganese; in voxels of a 3D region of the sample, wherein the 3D region is topographically defined by co-ordinates X'×Y'×Z. The ATI is used to assess the radio-responsiveness i.e. sensitivity or resistance to radiation treatment, of a cancer i.e. a tumor/neoplasm. In a preferred embodiment, the present invention relates to a method of generating the ATI, assessing the radio-responsiveness of a tumor/neoplasm based on the ATI and, based on the assessment, either treating or not treating the tumor with radiation.

The present invention also relates to a method of determining if a cancer is likely to reoccur post radiation treatment comprising quantifying the level of manganese in voxels of a 3D region of a test sample from the cancer and determining the frequency of high metallomic regions (HMRs) in the cancer, wherein a high frequency of HMRs is indicative that the cancer is likely to reoccur and a low frequency of HMRs is indicative that the cancer is unlikely to reoccur; and associated methods of treatment.

The invention further relates to a method of determining the radio-responsiveness of a melanoma, the method comprising determining the level of melanin in a test sample from the melanoma, wherein the lower the level of melanin the more sensitive the melanoma is to radiation and the higher the level of melanin the more resistant the melanoma is to radiation; and associated methods of treatment.

2 Claims, 83 Drawing Sheets

(56) References Cited

OTHER PUBLICATIONS

Serdar et al., "Adjuvant Radiotherapy in Stage 1 Seminoma: Evaluation of Prognostic Factors and Results of Survival," Journal of Cancer Research and Therapeutics 11(2):313-318 (2015).

Sharma et al., "Across the Tree of Life, Radiation Resistance is Governed by Antioxidant Mn2+, Gauged by Paramagnetic Resonance," PNAS E9253-E9260 (2017).

Shen et al., "The Association Between Deficient Manganese Levels and Breast Cancer: A Meta-Analysis," Int J Clin Exp Med, 8(3): 3671-3180 (2015).

Daly, et al., "Small-Molecule Antioxidant Proteome-Shields in *Deinococcus radiodurans*," PLoS ONE 5(9): e12570. doi:10.1371/journal.pone.0012570, (2010).

Lear, et al., "Improving acquisition times of elemental bio-imaging for quadrupole-based LA-ICP-MS," J. Anal. At. Spectrom., 27, 159-164 (2012).

Supplementary European Search Report for European Patent Application No. 16820580.5 dated Jan. 2, 2019.

Brozyna et al., "Inhibition of melanogenesis as a radiation sensitizer for melanoma therapy," Int. J. Cancer, 123(6): 1448-1456 (2008).

Gross, "Paradox resolved? The strange case of the radiation-resistant bacteria," PLoS biology.

Guo et al., "Manganese Superoxide Dismutase-Mediated Gene Expression in Radiation-Induced Adaptive Responses," Mol. Cell. Biol., 23(7): 2362-2378 (2003).

Hill et al., "Does melanin affect the low LET radiation response of Cloudman S91 mouse melanoma cell lines?" Pigm. Cell Melanoma R., 4(2): 80-86 (1991).

Hsu et al., "Is Melanin a Radioprotector or Radiosensitizer? It's Implication for Radiotherapy." Therapeutic Radiology and Oncology, 10(4): 237-246 (2003).

International Search Report and Written Opinion for International Application No. PCT/AU2016/050603, dated Jan. 1, 2017.

Kalen et al., "Mn-Superoxide Dismutase Overexpression Enhances G2 Accumulation and Radioresistance in Human Oral Squamous Carcinoma Cells," Antioxid. Redox Sign., 8(7,8): (2006).

Kinnaert et al., "The degree of pigmentation modulated the radiosensitivity of human melanoma cells," Radiat. Res., 154(5) 497-502 (2000).

Nature News: Secret of radiation-proof bugs proposed [retrieved from the internet on Jun. 23, 2017].

Schäfer et al., "In situ, real-time identification of biological tissues by ultraviolet and infrared laser desorption ionization mass spectrometry," Anal Chem, 83(5): 1632-1640 (2011).

Schäfer et al., "In vivo, in situ tissue analysis using rapid evaporative ionization mass spectrometry," Angew Chem Int Edit, 48(44): 8240-8242 (2009).

Ye et al., "From pixel to voxel: a deeper view of biological tissue by 3D mass spectral imaging," Bioanalysis, 3(3): 313-332 (2011).

* cited by examiner

Fig. 3B: 50 year old female H2 normal cortex

| | Ablation Track | v1 | v2 | v3 | v4 | v5 | v6 | v7 | v8 | v9 | v10 | v11 | v12 | v13 |
|---|---|---|---|---|---|---|---|---|---|---|---|---|---|---|
| Mn | n | 503 | 449 | 653 | 517 | 639 | 585 | 721 | 381 | 476 | 844 | 2898 | 3415 | 4000 |
| Mn | n+1 | 367 | 435 | 612 | 476 | 490 | 286 | 1660 | 585 | 395 | 1401 | 3388 | 3687 | 3878 |
| Mn | n+2 | 490 | 449 | 476 | 558 | 476 | 585 | 313 | 503 | 395 | 1605 | 3388 | 4204 | 3306 |
| | | v1 | v2 | v3 | v4 | v5 | v6 | v7 | v8 | v9 | v10 | v11 | v12 | v13 |
| Zn | n | 97 | 235 | 152 | 276 | 152 | 166 | 152 | 207 | 483 | 3810 | 5909 | 6807 | 5881 |
| Zn | n+1 | 55 | 124 | 138 | 110 | 69 | 262 | 138 | 331 | 1560 | 5122 | 6199 | 5412 | 6807 |
| Zn | n+2 | 55 | 41 | 1201 | 97 | 124 | 55 | 41 | 110 | 1436 | 4569 | 6489 | 5798 | 5647 |
| | | v1 | v2 | v3 | v4 | v5 | v6 | v7 | v8 | v9 | v10 | v11 | v12 | v13 |
| Fe | n | 16688 | 6618 | 5852 | 5448 | 3341 | 2468 | 2724 | 3979 | 2107 | 109492 | 301462 | 457158 | 515911 |
| Fe | n+1 | 2192 | 1298 | 1128 | 1170 | 574 | 702 | 7576 | 13260 | 6874 | 240188 | 418468 | 416013 | 551836 |
| Fe | n+2 | 1255 | 723 | 723 | 851 | 1170 | 915 | 255 | 362 | 4745 | 259579 | 434248 | 463842 | 426204 |

| | Ablation Track | v14 | v15 | v16 | v17 | v18 | v19 | v20 | v21 | v22 | v23 | v24 | v25 |
|---|---|---|---|---|---|---|---|---|---|---|---|---|---|
| Mn | n | 4041 | 3075 | 3769 | 3565 | 3402 | 4000 | 3402 | 3510 | 3891 | 3075 | 4218 | 4028 |
| Mn | n+1 | 3823 | 3905 | 3783 | 3524 | 4136 | 3238 | 3334 | 3674 | 4000 | 3578 | 4613 | 3483 |
| Mn | n+2 | 3891 | 3510 | 3524 | 3592 | 4082 | 3456 | 3932 | 4272 | 4245 | 3225 | 3551 | 3674 |
| | | v14 | v15 | v16 | v17 | v18 | v19 | v20 | v21 | v22 | v23 | v24 | v25 |
| Zn | n | 5798 | 5246 | 6309 | 5550 | 5785 | 7221 | 5729 | 6447 | 5716 | 6627 | 7221 | 6737 |
| Zn | n+1 | 6019 | 6309 | 5357 | 5729 | 6931 | 5647 | 5950 | 6737 | 6807 | 6130 | 5798 | 6544 |
| Zn | n+2 | 5467 | 6558 | 5495 | 7207 | 5094 | 6365 | 6779 | 6641 | 6365 | 5798 | 5950 | 6047 |
| | | v14 | v15 | v16 | v17 | v18 | v19 | v20 | v21 | v22 | v23 | v24 | v25 |
| Fe | n | 512746 | 369685 | 425987 | 426030 | 453827 | 528360 | 429204 | 392152 | 379679 | 392694 | 594707 | 497449 |
| Fe | n+1 | 466085 | 488900 | 422597 | 339147 | 464648 | 440011 | 427030 | 487636 | 554702 | 497165 | 474798 | 422901 |
| Fe | n+2 | 442012 | 487418 | 467457 | 434205 | 438945 | 441099 | 461577 | 560149 | 467239 | 422575 | 448778 | 524318 |

Fig. 3B (continued): 50 year old female H2 normal cortex

|  | Ablation Track | v26 | v27 | v28 | v29 | v30 | v31 | v32 | v33 | v34 | v35 | v36 | v37 |
|---|---|---|---|---|---|---|---|---|---|---|---|---|---|
| Mn | n | 4082 | 3810 | 3524 | 3891 | 4300 | 4259 | 4449 | 3919 | 4041 | 3470 | 3932 | 4041 |
| Mn | n+1 | 3334 | 4055 | 3878 | 3483 | 3769 | 3959 | 4028 | 3837 | 3647 | 4245 | 3891 | 3388 |
| Mn | n+2 | 3959 | 3606 | 4245 | 4354 | 4014 | 3524 | 4504 | 3810 | 3578 | 3783 | 4150 | 3837 |
|  |  | v26 | v27 | v28 | v29 | v30 | v31 | v32 | v33 | v34 | v35 | v36 | v37 |
| Zn | n | 7207 | 6889 | 6724 | 6378 | 6862 | 6793 | 7221 | 6378 | 6489 | 7097 | 6793 | 7317 |
| Zn | n+1 | 6655 | 6641 | 6613 | 6461 | 6254 | 6503 | 6682 | 7069 | 8768 | 6710 | 6365 | 6282 |
| Zn | n+2 | 4832 | 6710 | 6240 | 6033 | 6724 | 6737 | 6213 | 5923 | 6185 | 7317 | 6157 | 7400 |
|  |  | v26 | v27 | v28 | v29 | v30 | v31 | v32 | v33 | v34 | v35 | v36 | v37 |
| Fe | n | 402440 | 391349 | 377966 | 415209 | 479069 | 443644 | 457876 | 410257 | 405523 | 352244 | 344363 | 370812 |
| Fe | n+1 | 446124 | 437973 | 523445 | 505238 | 490514 | 474820 | 457354 | 395255 | 368753 | 419337 | 395385 | 366694 |
| Fe | n+2 | 549583 | 647797 | 661822 | 512571 | 472772 | 518204 | 429508 | 452717 | 410583 | 587124 | 529780 | 474276 |

|  | Ablation Track | v38 | v39 | v40 | v41 | v42 | v43 | v44 | v45 | v46 | v47 | v48 | v49 |
|---|---|---|---|---|---|---|---|---|---|---|---|---|---|
| Mn | n | 4028 | 4055 | 4681 | 3619 | 4218 | 3538 | 3823 | 4341 | 3919 | 4626 | 4381 | 3742 |
| Mn | n+1 | 3647 | 3279 | 4204 | 4218 | 3769 | 3987 | 4259 | 3742 | 3470 | 3932 | 4245 | 3987 |
| Mn | n+2 | 4218 | 4014 | 3878 | 3905 | 3647 | 4028 | 3728 | 4204 | 3687 | 3919 | 3510 | 2435 |
|  |  | v38 | v39 | v40 | v41 | v42 | v43 | v44 | v45 | v46 | v47 | v48 | v49 |
| Zn | n | 6807 | 7152 | 6889 | 6392 | 6420 | 6006 | 7124 | 7373 | 7248 | 6931 | 6572 | 7387 |
| Zn | n+1 | 6710 | 7442 | 9141 | 6862 | 6365 | 7704 | 6378 | 7939 | 6627 | 7538 | 6599 | 5964 |
| Zn | n+2 | 6268 | 7000 | 6365 | 6848 | 6144 | 6668 | 7608 | 5771 | 7953 | 8049 | 5564 | 4003 |
|  |  | v38 | v39 | v40 | v41 | v42 | v43 | v44 | v45 | v46 | v47 | v48 | v49 |
| Fe | n | 478830 | 471923 | 483690 | 454502 | 432900 | 446951 | 416143 | 368168 | 412494 | 530850 | 464321 | 397208 |
| Fe | n+1 | 435618 | 527923 | 557130 | 527049 | 440968 | 489816 | 483734 | 427987 | 397859 | 413623 | 441686 | 466281 |
| Fe | n+2 | 480290 | 498147 | 451281 | 435509 | 437401 | 464386 | 447603 | 400095 | 400942 | 372849 | 346701 | 214191 |

Fig. 3B (continued): 50 year old female H2 normal cortex

| | Ablation Track | v50 | v51 | v52 | v53 | v54 | v55 | v56 | v57 | v58 | v59 | v60 | v61 |
|---|---|---|---|---|---|---|---|---|---|---|---|---|---|
| Mn | n | 5103 | 4626 | 3674 | 4096 | 3796 | 4014 | 3102 | 2640 | 3973 | 4545 | 4150 | 3184 |
| Mn | n+1 | 3755 | 3551 | 4218 | 3442 | 4994 | 8273 | 4844 | 4204 | 4123 | 3089 | 4395 | 3007 |
| Mn | n+2 | 2014 | 4463 | 4082 | 4354 | 4000 | 4436 | 4014 | 4041 | 4477 | 4313 | 4327 | 3796 |
| | | v50 | v51 | v52 | v53 | v54 | v55 | v56 | v57 | v58 | v59 | v60 | v61 |
| Zn | n | 7000 | 6323 | 6972 | 7566 | 7759 | 6337 | 5508 | 5260 | 7773 | 6751 | 5881 | 3465 |
| Zn | n+1 | 6447 | 6876 | 7345 | 7704 | 9085 | 6986 | 8105 | 6903 | 7580 | 6779 | 5605 | 3465 |
| Zn | n+2 | 5605 | 7317 | 7773 | 8008 | 6710 | 7677 | 7511 | 8422 | 7635 | 7400 | 6655 | 4721 |
| | | v50 | v51 | v52 | v53 | v54 | v55 | v56 | v57 | v58 | v59 | v60 | v61 |
| Fe | n | 421249 | 443905 | 480508 | 433878 | 484649 | 493610 | 352916 | 340316 | 430334 | 455416 | 354020 | 266283 |
| Fe | n+1 | 450780 | 502488 | 511021 | 430617 | 424835 | 425596 | 482600 | 493022 | 564920 | 410669 | 384277 | 238013 |
| Fe | n+2 | 202774 | 321431 | 380416 | 452043 | 442817 | 407868 | 340078 | 427574 | 445471 | 404784 | 366087 | 265292 |

| | Ablation Track | v62 | v63 | v64 | v65 | v66 | v67 | v68 | v69 | v70 |
|---|---|---|---|---|---|---|---|---|---|---|
| Mn | n | 2163 | 1197 | 1020 | 571 | 667 | 503 | 653 | 544 | 571 |
| Mn | n+1 | 1646 | 1646 | 980 | 585 | 558 | 653 | 585 | 517 | 340 |
| Mn | n+2 | 1823 | 1061 | 844 | 735 | 585 | 558 | 544 | 367 | 639 |
| | | v62 | v63 | v64 | v65 | v66 | v67 | v68 | v69 | v70 |
| Zn | n | 1933 | 1104 | 690 | 331 | 317 | 345 | 248 | 193 | 152 |
| Zn | n+1 | 1725 | 1159 | 663 | 359 | 317 | 400 | 248 | 97 | 179 |
| Zn | n+2 | 2098 | 497 | 428 | 331 | 235 | 124 | 166 | 55 | 14 |
| | | v62 | v63 | v64 | v65 | v66 | v67 | v68 | v69 | v70 |
| Fe | n | 139059 | 75227 | 38164 | 18221 | 12983 | 6022 | 5575 | 4128 | 2617 |
| Fe | n+1 | 127707 | 74565 | 69355 | 18093 | 8853 | 6554 | 6384 | 3383 | 2958 |
| Fe | n+2 | 124838 | 65405 | 32686 | 21480 | 10769 | 8619 | 5894 | 3426 | 3341 |

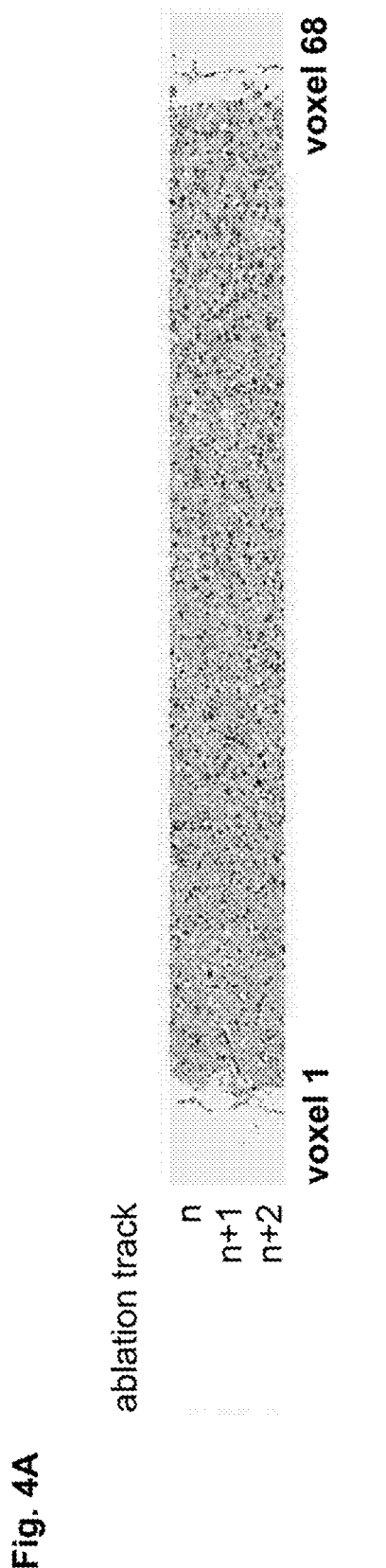

Fig. 4B: 19 year old female A7 glioblastoma

| | Ablation Track | v1 | v2 | v3 | v4 | v5 | v6 | v7 | v8 | v9 | v10 | v11 | v12 | v13 |
|---|---|---|---|---|---|---|---|---|---|---|---|---|---|---|
| Mn | n | 707 | 748 | 476 | 340 | 503 | 367 | 639 | 667 | 517 | 435 | 585 | 558 | 531 |
| Mn | n+1 | 776 | 776 | 599 | 599 | 449 | 435 | 544 | 381 | 517 | 639 | 789 | 503 | 680 |
| Mn | n+2 | 639 | 898 | 544 | 544 | 571 | 381 | 517 | 626 | 531 | 571 | 218 | 558 | 612 |
| | | v1 | v2 | v3 | v4 | v5 | v6 | v7 | v8 | v9 | v10 | v11 | v12 | v13 |
| Zn | n | 400 | 262 | 262 | 221 | 663 | 193 | 248 | 138 | 14 | 566 | 69 | 110 | 718 |
| Zn | n+1 | 193 | 442 | 290 | 207 | 179 | 83 | 138 | 97 | 110 | 124 | 124 | 152 | 455 |
| Zn | n+2 | 469 | 442 | 676 | 304 | 497 | 152 | 414 | 124 | 179 | 138 | 97 | 193 | 635 |
| | | v1 | v2 | v3 | v4 | v5 | v6 | v7 | v8 | v9 | v10 | v11 | v12 | v13 |
| Fe | n | 11429 | 6320 | 4894 | 3128 | 2234 | 1532 | 1192 | 2277 | 894 | 574 | 681 | 723 | 298 |
| Fe | n+1 | 12280 | 8044 | 5809 | 3149 | 2021 | 1787 | 1213 | 745 | 1213 | 553 | 638 | 723 | 660 |
| Fe | n+2 | 15261 | 13473 | 71533 | 5767 | 4894 | 3000 | 2745 | 2426 | 8342 | 766 | 745 | 979 | 1234 |

| | Ablation Track | v14 | v15 | v16 | v17 | v18 | v19 | v20 | v21 | v22 | v23 | v24 | v25 |
|---|---|---|---|---|---|---|---|---|---|---|---|---|---|
| Mn | n | 626 | 1565 | 3266 | 3184 | 3810 | 3034 | 3592 | 3715 | 4517 | 2898 | 3116 | 3184 |
| Mn | n+1 | 1279 | 2408 | 3470 | 3293 | 3551 | 3470 | 3347 | 4341 | 3619 | 3442 | 3660 | 4068 |
| Mn | n+2 | 1578 | 3306 | 3116 | 3524 | 3783 | 3510 | 3715 | 3320 | 3742 | 3851 | 3578 | 3823 |
| | | v14 | v15 | v16 | v17 | v18 | v19 | v20 | v21 | v22 | v23 | v24 | v25 |
| Zn | n | 1311 | 4390 | 5647 | 5053 | 5274 | 4942 | 5439 | 5785 | 4763 | 4887 | 5398 | 5301 |
| Zn | n+1 | 4141 | 4625 | 4721 | 5564 | 4859 | 4887 | 5577 | 5246 | 5149 | 5218 | 6088 | 6130 |
| Zn | n+2 | 3796 | 5950 | 5218 | 4915 | 3852 | 7911 | 4735 | 5039 | 4514 | 5550 | 5177 | 5798 |
| | | v14 | v15 | v16 | v17 | v18 | v19 | v20 | v21 | v22 | v23 | v24 | v25 |
| Fe | n | 7321 | 122740 | 211632 | 218557 | 187390 | 181592 | 207762 | 201936 | 214041 | 194522 | 171267 | 188700 |
| Fe | n+1 | 74352 | 130877 | 205074 | 244474 | 255052 | 212879 | 264666 | 221203 | 210170 | 265205 | 260656 | 256496 |
| Fe | n+2 | 134860 | 203978 | 211030 | 227831 | 180476 | 251432 | 240899 | 256324 | 274954 | 219719 | 215804 | 225464 |

Fig. 4B (continued): 19 year old female A7 glioblastoma

| | Ablation Track | v26 | v27 | v28 | v29 | v30 | v31 | v32 | v33 | v34 | v35 | v36 |
|---|---|---|---|---|---|---|---|---|---|---|---|---|
| Mn | n | 3048 | 3524 | 3959 | 3919 | 3905 | 4300 | 4259 | 3279 | 3810 | 3565 | 4150 |
| Mn | n+1 | 3973 | 3510 | 3442 | 4164 | 3987 | 5035 | 3415 | 3361 | 3837 | 3456 | 3538 |
| Mn | n+2 | 4000 | 4204 | 3823 | 4096 | 3891 | 3266 | 4232 | 3715 | 3796 | 2612 | 3143 |
| | | v26 | v27 | v28 | v29 | v30 | v31 | v32 | v33 | v34 | v35 | v36 |
| Zn | n | 5149 | 6323 | 5826 | 5481 | 6655 | 6088 | 5964 | 5232 | 5053 | 5453 | 6061 |
| Zn | n+1 | 5108 | 5564 | 6586 | 5163 | 5246 | 5426 | 5591 | 4804 | 5633 | 5122 | 5702 |
| Zn | n+2 | 4942 | 5688 | 5412 | 5716 | 5260 | 5826 | 5854 | 5840 | 5771 | 4183 | 4873 |
| | | v26 | v27 | v28 | v29 | v30 | v31 | v32 | v33 | v34 | v35 | v36 |
| Fe | n | 217267 | 223204 | 245486 | 218428 | 231275 | 213073 | 247059 | 210428 | 187648 | 188271 | 255828 |
| Fe | n+1 | 223355 | 212772 | 206429 | 222150 | 207826 | 201506 | 174980 | 166718 | 206687 | 191815 | 226561 |
| Fe | n+2 | 210557 | 211933 | 202538 | 177728 | 190397 | 238465 | 252962 | 217826 | 188507 | 153184 | 157108 |

| | Ablation Track | v37 | v38 | v39 | v40 | v41 | v42 | v43 | v44 | v45 | v46 | v47 |
|---|---|---|---|---|---|---|---|---|---|---|---|---|
| Mn | n | 4585 | 3347 | 3633 | 3470 | 3565 | 3783 | 3619 | 3783 | 4381 | 3687 | 3932 |
| Mn | n+1 | 3796 | 3919 | 3633 | 3415 | 4504 | 3388 | 3606 | 4177 | 4109 | 3293 | 4218 |
| Mn | n+2 | 4082 | 4096 | 3946 | 3919 | 3701 | 4177 | 3429 | 3279 | 2953 | 4381 | 4204 |
| | | v37 | v38 | v39 | v40 | v41 | v42 | v43 | v44 | v45 | v46 | v47 |
| Zn | n | 5771 | 5605 | 5149 | 5467 | 5122 | 4763 | 5481 | 5577 | 4639 | 4155 | 4970 |
| Zn | n+1 | 6475 | 5937 | 5729 | 6102 | 4708 | 5357 | 4708 | 5260 | 3727 | 5716 | 5909 |
| Zn | n+2 | 4224 | 5246 | 5536 | 5467 | 5274 | 6517 | 5481 | 3907 | 4998 | 5923 | 4887 |
| | | v37 | v38 | v39 | v40 | v41 | v42 | v43 | v44 | v45 | v46 | v47 |
| Fe | n | 253501 | 224990 | 221892 | 233729 | 235860 | 228111 | 233556 | 217761 | 221354 | 161655 | 201549 |
| Fe | n+1 | 213675 | 219181 | 205289 | 286217 | 268310 | 224495 | 228692 | 245766 | 158931 | 203118 | 232050 |
| Fe | n+2 | 217848 | 191149 | 235343 | 247382 | 277715 | 268483 | 223441 | 192567 | 201227 | 247705 | 302498 |

Fig. 4B (continued): 19 year old female A7 glioblastoma

| | Ablation Track | v48 | v49 | v50 | v51 | v52 | v53 | v54 | v55 | v56 | v57 | v58 |
|---|---|---|---|---|---|---|---|---|---|---|---|---|
| Mn | n | 3429 | 3538 | 4490 | 3388 | 3864 | 4272 | 4694 | 3755 | 3742 | 3347 | 3402 |
| Mn | n+1 | 3429 | 3864 | 3402 | 3279 | 5606 | 3402 | 3293 | 3415 | 3442 | 4735 | 3932 |
| Mn | n+2 | 4477 | 4136 | 3864 | 4109 | 3551 | 4898 | 4259 | 3755 | 3647 | 3266 | 4123 |
| | | v48 | v49 | v50 | v51 | v52 | v53 | v54 | v55 | v56 | v57 | v58 |
| Zn | n | 5039 | 5743 | 5218 | 5053 | 5246 | 5136 | 5053 | 4735 | 4666 | 3617 | 4100 |
| Zn | n+1 | 4942 | 5039 | 4639 | 3810 | 4569 | 4611 | 4128 | 4528 | 5854 | 4818 | 3810 |
| Zn | n+2 | 5467 | 5964 | 4956 | 4970 | 5205 | 5149 | 5287 | 6710 | 4445 | 4293 | 4224 |
| | | v48 | v49 | v50 | v51 | v52 | v53 | v54 | v55 | v56 | v57 | v58 |
| Fe | n | 209095 | 267254 | 230973 | 228261 | 242169 | 274587 | 258695 | 216342 | 213524 | 180776 | 202839 |
| Fe | n+1 | 207934 | 230371 | 202129 | 191643 | 189560 | 194221 | 226884 | 223850 | 276507 | 231770 | 207912 |
| Fe | n+2 | 373543 | 253134 | 253501 | 236484 | 263588 | 234956 | 222301 | 215137 | 231038 | 228391 | 241394 |

| | Ablation Track | v59 | v60 | v61 | v62 | v63 | v64 | v65 | v66 | v67 | v68 |
|---|---|---|---|---|---|---|---|---|---|---|---|
| Mn | n | 2585 | 3578 | 3415 | 2953 | 1837 | 939 | 707 | 1333 | 476 | 599 |
| Mn | n+1 | 2830 | 3143 | 2816 | 2136 | 1537 | 776 | 667 | 531 | 381 | 422 |
| Mn | n+2 | 4014 | 3810 | 3143 | 2504 | 1116 | 653 | 993 | 857 | 585 | 721 |
| | | v59 | v60 | v61 | v62 | v63 | v64 | v65 | v66 | v67 | v68 |
| Zn | n | 3741 | 4556 | 4224 | 2374 | 745 | 455 | 511 | 414 | 345 | 166 |
| Zn | n+1 | 3644 | 3299 | 3230 | 1532 | 732 | 745 | 262 | 414 | 235 | 262 |
| Zn | n+2 | 4141 | 3907 | 3534 | 1518 | 3203 | 621 | 483 | 386 | 331 | 290 |
| | | v59 | v60 | v61 | v62 | v63 | v64 | v65 | v66 | v67 | v68 |
| Fe | n | 181077 | 220752 | 196241 | 128992 | 53604 | 22843 | 14771 | 11471 | 6384 | 4234 |
| Fe | n+1 | 165302 | 158566 | 216449 | 114135 | 50874 | 23077 | 18179 | 9321 | 6490 | 3681 |
| Fe | n+2 | 192030 | 200324 | 177599 | 96617 | 40190 | 19691 | 11769 | 12515 | 11791 | 7746 |

Fig. 5B: 19 year old female A8 glioblastoma

| | Ablation Track | v1 | v2 | v3 | v4 | v5 | v6 | v7 | v8 | v9 | v10 | v11 | v12 | v13 |
|---|---|---|---|---|---|---|---|---|---|---|---|---|---|---|
| Mn | n | 544 | 367 | 463 | 626 | 680 | 476 | 340 | 408 | 503 | 694 | 626 | 476 | 449 |
| Mn | n+1 | 735 | 816 | 830 | 490 | 517 | 476 | 612 | 503 | 449 | 694 | 490 | 354 | 490 |
| Mn | n+2 | 1265 | 748 | 667 | 449 | 476 | 707 | 585 | 381 | 667 | 503 | 490 | 490 | 395 |
| | | v1 | v2 | v3 | v4 | v5 | v6 | v7 | v8 | v9 | v10 | v11 | v12 | v13 |
| Zn | n | 317 | 221 | 138 | 138 | 276 | 221 | 235 | 828 | 110 | 414 | 69 | 69 | 124 |
| Zn | n+1 | 345 | 345 | 248 | 248 | 83 | 166 | 152 | 304 | 55 | 69 | 124 | 110 | 83 |
| Zn | n+2 | 1035 | 455 | 304 | 1325 | 304 | 248 | 207 | 235 | 124 | 138 | 1104 | 124 | 124 |
| | | v1 | v2 | v3 | v4 | v5 | v6 | v7 | v8 | v9 | v10 | v11 | v12 | v13 |
| Fe | n | 22396 | 9577 | 6469 | 5256 | 3107 | 2766 | 1851 | 1277 | 12089 | 10066 | 1000 | 851 | 511 |
| Fe | n+1 | 18285 | 12131 | 7661 | 35010 | 4639 | 1787 | 2702 | 1277 | 1489 | 1000 | 787 | 511 | 1319 |
| Fe | n+2 | 37781 | 25974 | 13196 | 7725 | 8853 | 3830 | 4788 | 20841 | 2319 | 1128 | 553 | 1128 | 596 |

| | Ablation Track | v14 | v15 | v16 | v17 | v18 | v19 | v20 | v21 | v22 | v23 | v24 | v25 |
|---|---|---|---|---|---|---|---|---|---|---|---|---|---|
| Mn | n | 612 | 476 | 395 | 2231 | 3320 | 3919 | 3864 | 3470 | 3415 | 3184 | 3143 | 3810 |
| Mn | n+1 | 463 | 435 | 544 | 1565 | 3606 | 4000 | 3334 | 2816 | 4109 | 4517 | 3715 | 3061 |
| Mn | n+2 | 571 | 531 | 531 | 762 | 3293 | 3320 | 2939 | 3415 | 3143 | 3252 | 3619 | 3687 |
| | | v14 | v15 | v16 | v17 | v18 | v19 | v20 | v21 | v22 | v23 | v24 | v25 |
| Zn | n | 207 | 442 | 1670 | 4086 | 4859 | 4390 | 4956 | 3852 | 4224 | 4666 | 4680 | 4431 |
| Zn | n+1 | 207 | 124 | 1146 | 3382 | 4431 | 4280 | 4031 | 4804 | 4542 | 4708 | 4210 | 4266 |
| Zn | n+2 | 152 | 179 | 235 | 2706 | 4418 | 4293 | 3865 | 4280 | 3990 | 4307 | 4818 | 5246 |
| | | v14 | v15 | v16 | v17 | v18 | v19 | v20 | v21 | v22 | v23 | v24 | v25 |
| Fe | n | 787 | 468 | 12110 | 129227 | 146217 | 215955 | 178114 | 198218 | 197853 | 231404 | 233643 | 230241 |
| Fe | n+1 | 511 | 1213 | 8278 | 141288 | 227917 | 188786 | 187412 | 185951 | 247403 | 259967 | 177234 | 208772 |
| Fe | n+2 | 681 | 574 | 660 | 62588 | 245012 | 234224 | 208385 | 192352 | 178801 | 216363 | 189452 | 203699 |

Fig. 5B (continued): 19 year old female A8 glioblastoma

|    | Ablation Track | v26 | v27 | v28 | v29 | v30 | v31 | v32 | v33 | v34 | v35 | v36 |
|----|----------------|-----|-----|-----|-----|-----|-----|-----|-----|-----|-----|-----|
| Mn | n              | 3143 | 3878 | 18102 | 4368 | 3783 | 3687 | 3388 | 3402 | 4286 | 3184 | 3279 |
| Mn | n+1            | 3374 | 3565 | 3973 | 3987 | 3402 | 4082 | 4000 | 3211 | 3633 | 3306 | 4109 |
| Mn | n+2            | 3660 | 3266 | 3143 | 3919 | 3878 | 3919 | 3442 | 4898 | 2980 | 3538 | 3551 |
|    |                | v26 | v27 | v28 | v29 | v30 | v31 | v32 | v33 | v34 | v35 | v36 |
| Zn | n              | 4418 | 4583 | 4183 | 4238 | 4666 | 3741 | 4666 | 5039 | 4445 | 4390 | 4984 |
| Zn | n+1            | 4252 | 3603 | 5149 | 4583 | 4901 | 4942 | 4418 | 4473 | 4349 | 4141 | 3644 |
| Zn | n+2            | 4418 | 4059 | 4708 | 4873 | 4445 | 4763 | 4942 | 4266 | 4487 | 5508 | 4749 |
|    |                | v26 | v27 | v28 | v29 | v30 | v31 | v32 | v33 | v34 | v35 | v36 |
| Fe | n              | 194436 | 224237 | 190548 | 184856 | 204902 | 210772 | 171825 | 191772 | 295004 | 189238 | 200732 |
| Fe | n+1            | 256065 | 267556 | 225808 | 190526 | 175924 | 223613 | 171117 | 184405 | 192095 | 232006 | 222968 |
| Fe | n+2            | 219289 | 208794 | 201958 | 201936 | 195446 | 215998 | 228326 | 196499 | 163135 | 188958 | 206085 |

|    | Ablation Track | v37 | v38 | v39 | v40 | v41 | v42 | v43 | v44 | v45 | v46 | v47 |
|----|----------------|-----|-----|-----|-----|-----|-----|-----|-----|-----|-----|-----|
| Mn | n              | 3483 | 3755 | 4735 | 4068 | 3279 | 3891 | 3388 | 3442 | 3197 | 3715 | 3415 |
| Mn | n+1            | 3034 | 3211 | 3987 | 4300 | 4000 | 3388 | 3075 | 3660 | 2789 | 3034 | 3510 |
| Mn | n+2            | 3592 | 3715 | 3483 | 4000 | 3524 | 3905 | 3851 | 4722 | 4123 | 3402 | 3470 |
|    |                | v37 | v38 | v39 | v40 | v41 | v42 | v43 | v44 | v45 | v46 | v47 |
| Zn | n              | 12622 | 5205 | 4956 | 3617 | 4998 | 4500 | 4956 | 3534 | 3410 | 4680 | 5067 |
| Zn | n+1            | 4266 | 4956 | 5163 | 5011 | 4086 | 3879 | 4790 | 3175 | 3879 | 3782 | 4625 |
| Zn | n+2            | 4942 | 3603 | 4846 | 4266 | 5522 | 4445 | 4169 | 4708 | 4003 | 3865 | 4293 |
|    |                | v37 | v38 | v39 | v40 | v41 | v42 | v43 | v44 | v45 | v46 | v47 |
| Fe | n              | 163200 | 211954 | 191471 | 163607 | 170258 | 201807 | 180647 | 177320 | 148146 | 175323 | 172941 |
| Fe | n+1            | 196048 | 156379 | 174744 | 186338 | 165645 | 188142 | 218837 | 162470 | 174980 | 176268 | 183654 |
| Fe | n+2            | 198734 | 164787 | 166739 | 154449 | 174615 | 137303 | 139102 | 186939 | 164830 | 206816 | 213761 |

Fig. 5B (continued): 19 year old female A8 glioblastoma

| | Ablation Track | v48 | v49 | v50 | v51 | v52 | v53 | v54 | v55 | v56 | v57 | v58 |
|---|---|---|---|---|---|---|---|---|---|---|---|---|
| Mn | n | 3279 | 3456 | 3361 | 3102 | 3415 | 3061 | 2871 | 4354 | 3157 | 2748 | 3293 |
| Mn | n+1 | 4123 | 3347 | 3266 | 3647 | 4259 | 3674 | 3987 | 3143 | 3048 | 3048 | 3565 |
| Mn | n+2 | 3470 | 3415 | 3429 | 2966 | 3048 | 3796 | 15896 | 3783 | 3987 | 4272 | 3238 |
| | | v48 | v49 | v50 | v51 | v52 | v53 | v54 | v55 | v56 | v57 | v58 |
| Zn | n | 3879 | 3879 | 3272 | 3644 | 3631 | 3907 | 4210 | 3907 | 3382 | 4514 | 4349 |
| Zn | n+1 | 4473 | 3727 | 3672 | 4183 | 4970 | 3976 | 3631 | 3575 | 3741 | 3755 | 4252 |
| Zn | n+2 | 3879 | 3037 | 2816 | 4652 | 4045 | 4252 | 3658 | 4100 | 3852 | 3147 | 4390 |
| | | v48 | v49 | v50 | v51 | v52 | v53 | v54 | v55 | v56 | v57 | v58 |
| Fe | n | 167662 | 191386 | 192846 | 165516 | 182408 | 170173 | 168392 | 192846 | 168542 | 181313 | 201141 |
| Fe | n+1 | 226497 | 167447 | 203204 | 218170 | 243871 | 210342 | 171031 | 179123 | 199400 | 189302 | 187390 |
| Fe | n+2 | 204709 | 186982 | 167447 | 207676 | 212320 | 207525 | 230457 | 187047 | 212879 | 178887 | 203785 |

| | Ablation Track | v59 | v60 | v61 | v62 | v63 | v64 | v65 | v66 | v67 | v68 | v69 |
|---|---|---|---|---|---|---|---|---|---|---|---|---|
| Mn | n | 3524 | 3769 | 3823 | 3388 | 3551 | 3157 | 1918 | 1129 | 1143 | 803 | 653 |
| Mn | n+1 | 3483 | 4341 | 3905 | 2953 | 3225 | 3837 | 2789 | 1918 | 1102 | 1238 | 844 |
| Mn | n+2 | 4055 | 4096 | 6286 | 3959 | 3796 | 3932 | 3878 | 3129 | 1592 | 1238 | 1048 |
| | | v59 | v60 | v61 | v62 | v63 | v64 | v65 | v66 | v67 | v68 | v69 |
| Zn | n | 4390 | 3962 | 4321 | 3727 | 3203 | 2581 | 1159 | 1049 | 566 | 345 | 124 |
| Zn | n+1 | 4252 | 5025 | 4459 | 3713 | 4086 | 3534 | 1739 | 1021 | 1242 | 635 | 262 |
| Zn | n+2 | 4680 | 3713 | 4873 | 4652 | 4155 | 5660 | 4556 | 2526 | 1422 | 911 | 373 |
| | | v59 | v60 | v61 | v62 | v63 | v64 | v65 | v66 | v67 | v68 | v69 |
| Fe | n | 209611 | 190526 | 194393 | 173027 | 171289 | 131969 | 73198 | 50511 | 26337 | 17646 | 9662 |
| Fe | n+1 | 194114 | 196198 | 188679 | 160690 | 192159 | 168434 | 91530 | 35478 | 37503 | 24100 | 14409 |
| Fe | n+2 | 231770 | 192288 | 195811 | 197681 | 187369 | 197638 | 158738 | 115612 | 63079 | 33006 | 18732 |

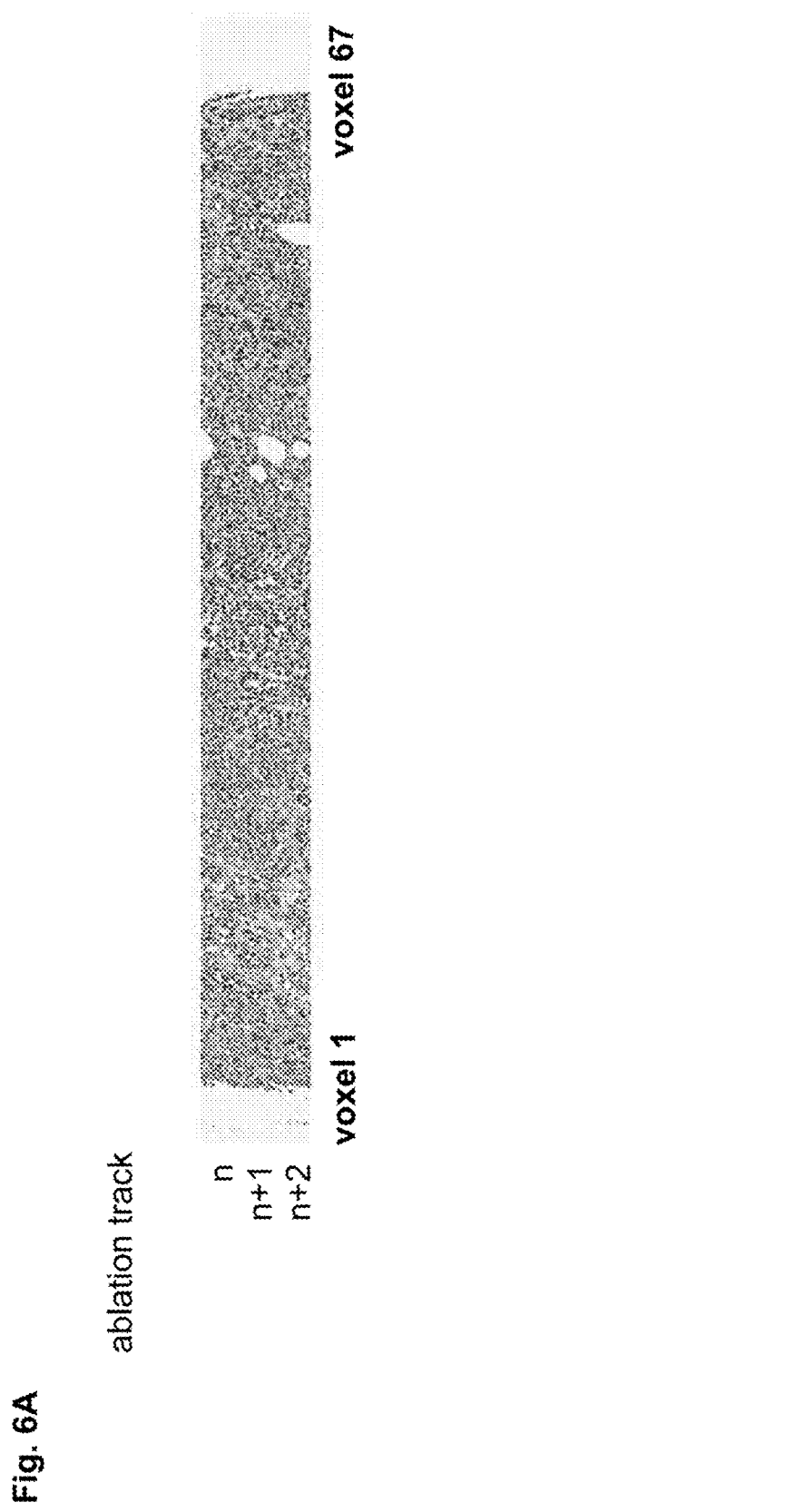

Fig. 6B: B3 mesothelioma male 60 years old

| | Ablation Track | v1 | v2 | v3 | v4 | v5 | v6 | v7 | v8 | v9 | v10 | v11 | v12 |
|---|---|---|---|---|---|---|---|---|---|---|---|---|---|
| Mn | n | 902 | 825 | 803 | 1221 | 495 | 594 | 462 | 451 | 341 | 319 | 2905 | 6404 |
| Mn | n+1 | 946 | 704 | 671 | 517 | 418 | 528 | 418 | 440 | 1430 | 2464 | 5666 | 6338 |
| Mn | n+2 | 693 | 517 | 363 | 308 | 374 | 297 | 1122 | 407 | 374 | 495 | 3070 | 6437 |
| | | v1 | v2 | v3 | v4 | v5 | v6 | v7 | v8 | v9 | v10 | v11 | v12 |
| Zn | n | 636 | 331 | 331 | 93 | 26 | 278 | 66 | 79 | 53 | 1007 | 7989 | 8387 |
| Zn | n+1 | 397 | 358 | 437 | 119 | 66 | 159 | 172 | 2411 | 66 | 4438 | 9010 | 9580 |
| Zn | n+2 | 185 | 265 | 159 | 238 | 79 | 371 | 53 | 212 | 172 | 1563 | 6479 | 9355 |
| | | v1 | v2 | v3 | v4 | v5 | v6 | v7 | v8 | v9 | v10 | v11 | v12 |
| Fe | n | 871 | 980 | 780 | 690 | 544 | 3503 | 236 | 436 | 290 | 490 | 58777 | 100552 |
| Fe | n+1 | 1071 | 889 | 762 | 653 | 399 | 744 | 653 | 5863 | 1398 | 17305 | 115236 | 111783 |
| Fe | n+2 | 1216 | 2269 | 744 | 835 | 544 | 1198 | 363 | 617 | 690 | 1343 | 71056 | 86938 |
| | | v1 | v2 | v3 | v4 | v5 | v6 | v7 | v8 | v9 | v10 | v11 | v12 |
| Cu | n | 28 | 97 | 14 | 0 | 28 | 14 | 0 | 0 | 28 | 28 | 662 | 1241 |
| Cu | n+1 | 0 | 97 | 83 | 28 | 0 | 14 | 28 | 303 | 41 | 538 | 938 | 1021 |
| Cu | n+2 | 14 | 14 | 138 | 83 | 14 | 0 | 14 | 28 | 0 | 124 | 883 | 1103 |

Fig. 6B (continued): B3 mesothelioma male 60 years old

|    | Ablation Track | v13 | v14 | v15 | v16 | v17 | v18 | v19 | v20 | v21 | v22 | v23 | v24 |
|----|----------------|-----|-----|-----|-----|-----|-----|-----|-----|-----|-----|-----|-----|
| Mn | n              | 6668 | 5457 | 6239 | 6316 | 5644 | 4786 | 4720 | 5677 | 4445 | 5325 | 4676 | 5843 |
| Mn | n+1            | 7427 | 5887 | 6800 | 5820 | 5798 | 5446 | 5391 | 5226 | 5732 | 5160 | 4885 | 5182 |
| Mn | n+2            | 6448 | 6349 | 5633 | 6547 | 5688 | 5017 | 4962 | 5039 | 4588 | 4676 | 5666 | 5479 |
|    |                | v13 | v14 | v15 | v16 | v17 | v18 | v19 | v20 | v21 | v22 | v23 | v24 |
| Zn | n              | 8626 | 10813 | 13849 | 14857 | 9925 | 7910 | 8387 | 7207 | 8745 | 7685 | 8480 | 8944 |
| Zn | n+1            | 8281 | 11157 | 11316 | 10269 | 7751 | 8824 | 8241 | 8003 | 8917 | 7897 | 8838 | 7923 |
| Zn | n+2            | 9249 | 9659 | 9328 | 8771 | 7923 | 7658 | 7923 | 7274 | 6664 | 7486 | 8347 | 8904 |
|    |                | v13 | v14 | v15 | v16 | v17 | v18 | v19 | v20 | v21 | v22 | v23 | v24 |
| Fe | n              | 102742 | 88525 | 162096 | 175239 | 130757 | 98470 | 98270 | 108093 | 81375 | 101026 | 102140 | 115748 |
| Fe | n+1            | 104276 | 96882 | 137598 | 115949 | 109646 | 118197 | 102980 | 101665 | 137049 | 113519 | 128251 | 101117 |
| Fe | n+2            | 102195 | 107417 | 103948 | 115181 | 86098 | 97539 | 93232 | 99164 | 87193 | 108075 | 113007 | 128343 |
|    |                | v13 | v14 | v15 | v16 | v17 | v18 | v19 | v20 | v21 | v22 | v23 | v24 |
| Cu | n              | 1531 | 938 | 1145 | 1090 | 1048 | 993 | 1228 | 993 | 869 | 1186 | 1090 | 828 |
| Cu | n+1            | 1021 | 1159 | 1241 | 897 | 979 | 1159 | 814 | 1103 | 1035 | 786 | 1090 | 1021 |
| Cu | n+2            | 1062 | 1462 | 1200 | 745 | 1048 | 1090 | 910 | 1159 | 1103 | 772 | 1283 | 1159 |

Fig. 6B (continued): B3 mesothelioma male 60 years old

|    | Ablation Track | v25 | v26 | v27 | v28 | v29 | v30 | v31 | v32 | v33 | v34 | v35 |
|----|----|------|------|------|------|------|------|------|------|------|------|------|
| Mn | n | 5105 | 4665 | 4324 | 5512 | 4786 | 4995 | 4698 | 5006 | 4225 | 4621 | 4918 |
| Mn | n+1 | 4434 | 5259 | 4643 | 4885 | 7042 | 7141 | 4742 | 4907 | 4676 | 4373 | 5281 |
| Mn | n+2 | 5501 | 5457 | 5512 | 4522 | 4522 | 5666 | 4830 | 4951 | 4588 | 5017 | 4808 |
|    |   | v25 | v26 | v27 | v28 | v29 | v30 | v31 | v32 | v33 | v34 | v35 |
| Zn | n | 8520 | 8573 | 9368 | 9089 | 9527 | 9673 | 8639 | 8466 | 8520 | 10309 | 9275 |
| Zn | n+1 | 8824 | 9010 | 8559 | 8745 | 9368 | 9368 | 8321 | 9355 | 8665 | 9408 | 10269 |
| Zn | n+2 | 8546 | 9010 | 10070 | 7592 | 8930 | 8347 | 7327 | 8162 | 9275 | 9408 | 9872 |
|    |   | v25 | v26 | v27 | v28 | v29 | v30 | v31 | v32 | v33 | v34 | v35 |
| Fe | n | 104057 | 107764 | 114377 | 129824 | 124978 | 133390 | 127721 | 121359 | 95805 | 119129 | 121596 |
| Fe | n+1 | 93597 | 109408 | 103765 | 104295 | 110724 | 119896 | 113354 | 103911 | 113318 | 109171 | 123698 |
| Fe | n+2 | 127282 | 125691 | 119293 | 102925 | 116479 | 115602 | 106303 | 127959 | 121998 | 136189 | 135147 |
|    |   | v25 | v26 | v27 | v28 | v29 | v30 | v31 | v32 | v33 | v34 | v35 |
| Cu | n | 662 | 1269 | 1103 | 1021 | 924 | 979 | 1186 | 1035 | 855 | 869 | 1103 |
| Cu | n+1 | 1186 | 938 | 1021 | 938 | 1103 | 1035 | 1145 | 1021 | 1062 | 814 | 814 |
| Cu | n+2 | 1145 | 1269 | 1297 | 869 | 1159 | 1035 | 897 | 1117 | 1310 | 1145 | 993 |

Fig. 6B (continued): B3 mesothelioma male 60 years old

|    | Ablation Track | v36 | v37 | v38 | v39 | v40 | v41 | v42 | v43 | v44 | v45 | v46 |
|----|---|---|---|---|---|---|---|---|---|---|---|---|
| Mn | n | 4280 | 4544 | 4687 | 4830 | 5457 | 4093 | 3521 | 5149 | 4742 | 6118 | 4082 |
| Mn | n+1 | 4841 | 4500 | 4434 | 5094 | 4764 | 4324 | 5039 | 4709 | 4060 | 4940 | 4830 |
| Mn | n+2 | 5843 | 4709 | 5479 | 4819 | 3785 | 3081 | 3114 | 3917 | 5336 | 4577 | 4346 |
|    |   | v36 | v37 | v38 | v39 | v40 | v41 | v42 | v43 | v44 | v45 | v46 |
| Zn | n | 9381 | 9288 | 8970 | 9381 | 8559 | 8334 | 9050 | 8917 | 9116 | 10402 | 8228 |
| Zn | n+1 | 8360 | 8573 | 8652 | 8838 | 9010 | 8321 | 8215 | 7976 | 8732 | 9288 | 8294 |
| Zn | n+2 | 10428 | 9262 | 9010 | 9275 | 5697 | 4623 | 5776 | 8374 | 8069 | 8201 | 8188 |
|    |   | v36 | v37 | v38 | v39 | v40 | v41 | v42 | v43 | v44 | v45 | v46 |
| Fe | n | 113208 | 104550 | 108513 | 133884 | 133098 | 106102 | 108751 | 130482 | 115035 | 106559 | 159513 |
| Fe | n+1 | 143655 | 104842 | 105062 | 118580 | 106139 | 100278 | 106961 | 98835 | 115401 | 110924 | 126350 |
| Fe | n+2 | 140691 | 129513 | 144186 | 128635 | 107217 | 68013 | 66883 | 109153 | 129092 | 101738 | 96298 |
|    |   | v36 | v37 | v38 | v39 | v40 | v41 | v42 | v43 | v44 | v45 | v46 |
| Cu | n | 1076 | 966 | 979 | 1131 | 1048 | 745 | 1117 | 1186 | 1241 | 1214 | 938 |
| Cu | n+1 | 1131 | 1062 | 1103 | 1076 | 717 | 1186 | 1131 | 924 | 966 | 938 | 1131 |
| Cu | n+2 | 1145 | 1255 | 1117 | 1076 | 538 | 455 | 469 | 1407 | 1297 | 814 | 1338 |

Fig. 6B (continued): B3 mesothelioma male 60 years old

|    | Ablation Track | v47 | v48 | v49 | v50 | v51 | v52 | v53 | v54 | v55 | v56 | v57 |
|----|---|---|---|---|---|---|---|---|---|---|---|---|
| Mn | n    | 5215 | 5050 | 4995 | 4588 | 4731 | 4346 | 3983 | 6415 | 4786 | 4797 | 4973 |
| Mn | n+1  | 4401 | 5468 | 4984 | 4632 | 4214 | 4676 | 5721 | 4687 | 5193 | 4522 | 4313 |
| Mn | n+2  | 5193 | 4324 | 4082 | 4258 | 4786 | 4533 | 4907 | 4434 | 4599 | 4324 | 4962 |
|    |      | v47 | v48 | v49 | v50 | v51 | v52 | v53 | v54 | v55 | v56 | v57 |
| Zn | n    | 9036 | 8705 | 9712 | 9355 | 7088 | 7287 | 8360 | 8851 | 9540 | 9182 | 8944 |
| Zn | n+1  | 9341 | 9805 | 8374 | 8148 | 9355 | 9567 | 9500 | 9620 | 8016 | 8599 | 8281 |
| Zn | n+2  | 9249 | 10137 | 8241 | 9222 | 9381 | 8983 | 9646 | 9461 | 8665 | 9275 | 8533 |
|    |      | v47 | v48 | v49 | v50 | v51 | v52 | v53 | v54 | v55 | v56 | v57 |
| Fe | n    | 100570 | 110322 | 115328 | 131470 | 119092 | 87649 | 97120 | 106997 | 102980 | 116387 | 107454 |
| Fe | n+1  | 118416 | 132586 | 113062 | 117612 | 123315 | 114980 | 152278 | 149550 | 114213 | 125015 | 121285 |
| Fe | n+2  | 120646 | 120445 | 100460 | 93141 | 130080 | 104897 | 135970 | 116552 | 118708 | 126112 | 119056 |
|    |      | v47 | v48 | v49 | v50 | v51 | v52 | v53 | v54 | v55 | v56 | v57 |
| Cu | n    | 1035 | 1407 | 938 | 1062 | 1145 | 1035 | 1366 | 1048 | 1338 | 1117 | 1241 |
| Cu | n+1  | 1241 | 1200 | 1062 | 1021 | 993 | 1172 | 1366 | 1269 | 1007 | 1269 | 1393 |
| Cu | n+2  | 1310 | 979 | 910 | 1517 | 1476 | 1200 | 1103 | 1283 | 1103 | 1021 | 1448 |

Fig. 6B (continued): B3 mesothelioma male 60 years old

|    | Ablation Track | v58 | v59 | v60 | v61 | v62 | v63 | v64 | v65 | v66 | v67 |
|----|---|---|---|---|---|---|---|---|---|---|---|
| Mn | n | 4797 | 5843 | 3268 | 2068 | 1419 | 814 | 583 | 407 | 517 | 451 |
| Mn | n+1 | 4060 | 4049 | 3334 | 1650 | 693 | 704 | 418 | 374 | 693 | 869 |
| Mn | n+2 | 4390 | 4896 | 5171 | 1804 | 1221 | 473 | 781 | 671 | 341 | 396 |
|    |   | v58 | v59 | v60 | v61 | v62 | v63 | v64 | v65 | v66 | v67 |
| Zn | n | 9434 | 7565 | 2861 | 1431 | 834 | 728 | 331 | 159 | 146 | 93 |
| Zn | n+1 | 7287 | 6783 | 3033 | 834 | 530 | 371 | 212 | 238 | 172 | 26 |
| Zn | n+2 | 8838 | 8546 | 4425 | 1682 | 1099 | 503 | 212 | 79 | 172 | 66 |
|    |   | v58 | v59 | v60 | v61 | v62 | v63 | v64 | v65 | v66 | v67 |
| Fe | n | 118215 | 101117 | 54680 | 27281 | 12291 | 9494 | 5972 | 5754 | 1978 | 1652 |
| Fe | n+1 | 96864 | 88214 | 54134 | 21538 | 12800 | 5863 | 2831 | 2160 | 2105 | 2305 |
| Fe | n+2 | 111491 | 124777 | 84056 | 34918 | 15506 | 7352 | 3322 | 3412 | 3775 | 4393 |
|    |   | v58 | v59 | v60 | v61 | v62 | v63 | v64 | v65 | v66 | v67 |
| Cu | n | 1476 | 1172 | 648 | 469 | 221 | 938 | 41 | 28 | 55 | 0 |
| Cu | n+1 | 1338 | 690 | 607 | 166 | 55 | 69 | 0 | 0 | 0 | 28 |
| Cu | n+2 | 1228 | 1255 | 566 | 152 | 110 | 28 | 124 | 55 | 14 | 28 |

Fig. 7B: A1 melanoma male 50 years old

| Ablation Track | | v1 | v2 | v3 | v4 | v5 | v6 | v7 | v8 | v9 | v10 | v11 | v12 |
|---|---|---|---|---|---|---|---|---|---|---|---|---|---|
| Mn | n | 589 | 367 | 456 | 756 | 456 | 678 | 489 | 2200 | 14072 | 14784 | 9569 | 7679 |
| Mn | n+1 | 500 | 578 | 567 | 378 | 622 | 511 | 622 | 9336 | 16674 | 12904 | 9058 | 11248 |
| Mn | n+2 | 444 | 389 | 500 | 667 | 467 | 422 | 622 | 1311 | 14016 | 11971 | 10192 | 8746 |
| | | v1 | v2 | v3 | v4 | v5 | v6 | v7 | v8 | v9 | v10 | v11 | v12 |
| Zn | n | 160 | 140 | 140 | 260 | 220 | 180 | 840 | 6621 | 8022 | 6861 | 4701 | 5121 |
| Zn | n+1 | 240 | 2020 | 4220 | 160 | 100 | 120 | 4441 | 14546 | 9022 | 4441 | 5901 | 8302 |
| Zn | n+2 | 240 | 180 | 60 | 120 | 180 | 80 | 500 | 6361 | 8882 | 6181 | 4381 | 6001 |
| | | v1 | v2 | v3 | v4 | v5 | v6 | v7 | v8 | v9 | v10 | v11 | v12 |
| Fe | n | 380 | 180 | 280 | 320 | 300 | 160 | 460 | 45796 | 122058 | 117790 | 75954 | 55462 |
| Fe | n+1 | 280 | 40 | 220 | 160 | 200 | 120 | 4961 | 102440 | 155525 | 95705 | 80955 | 88770 |
| Fe | n+2 | 360 | 260 | 180 | 320 | 120 | 200 | 240 | 37337 | 152198 | 108434 | 76215 | 85314 |

| Ablation Track | | v13 | v14 | v15 | v16 | v17 | v18 | v19 | v20 | v21 | v22 | v23 | v24 |
|---|---|---|---|---|---|---|---|---|---|---|---|---|---|
| Mn | n | 14339 | 16741 | 14394 | 14350 | 18720 | 15640 | 18987 | 10636 | 16874 | 19811 | 23159 | 21601 |
| Mn | n+1 | 16919 | 13972 | 13850 | 12304 | 16474 | 11859 | 8569 | 7446 | 9691 | 21479 | 27231 | 18910 |
| Mn | n+2 | 10003 | 12404 | 17163 | 15684 | 8847 | 9636 | 11659 | 11070 | 6679 | 9836 | 22736 | 22480 |
| | | v13 | v14 | v15 | v16 | v17 | v18 | v19 | v20 | v21 | v22 | v23 | v24 |
| Zn | n | 11884 | 8582 | 10243 | 12044 | 10883 | 10343 | 7602 | 6901 | 12784 | 13105 | 14446 | 12284 |
| Zn | n+1 | 9623 | 8382 | 6901 | 10643 | 9162 | 6141 | 5561 | 5801 | 10663 | 16688 | 14205 | 11363 |
| Zn | n+2 | 6841 | 8442 | 10803 | 5921 | 5621 | 7401 | 7421 | 5341 | 5941 | 12704 | 16027 | 11123 |
| | | v13 | v14 | v15 | v16 | v17 | v18 | v19 | v20 | v21 | v22 | v23 | v24 |
| Fe | n | 145243 | 149597 | 138149 | 164844 | 175642 | 140144 | 135228 | 89896 | 154557 | 156231 | 172231 | 136275 |
| Fe | n+1 | 149980 | 127715 | 148226 | 179075 | 204655 | 111190 | 99263 | 82341 | 142401 | 213574 | 191598 | 150706 |
| Fe | n+2 | 93855 | 93694 | 191659 | 138733 | 131904 | 144799 | 149919 | 115899 | 91202 | 158066 | 178873 | 139922 |

Fig. 7B (continued): A1 melanoma male 50 years old

| | Ablation Track | v25 | v26 | v27 | v28 | v29 | v30 | v31 | v32 | v33 | v34 | v35 | v36 |
|---|---|---|---|---|---|---|---|---|---|---|---|---|---|
| Mn | n | 18287 | 21312 | 11537 | 11504 | 10470 | 8357 | 4245 | 3145 | 8269 | 16652 | 8702 | 8969 |
| Mn | n+1 | 15907 | 7279 | 6157 | 12526 | 7746 | 15529 | 6045 | 9102 | 12526 | 9202 | 11770 | 20322 |
| Mn | n+2 | 13182 | 7802 | 11259 | 21490 | 11715 | 15273 | 7991 | 11381 | 10992 | 5001 | 2400 | 3278 |
| | | v25 | v26 | v27 | v28 | v29 | v30 | v31 | v32 | v33 | v34 | v35 | v36 |
| Zn | n | 12804 | 9883 | 6601 | 6701 | 7201 | 3740 | 1720 | 4301 | 9402 | 6701 | 8302 | 3880 |
| Zn | n+1 | 7722 | 4881 | 9162 | 6361 | 8162 | 5201 | 3420 | 7962 | 5841 | 7041 | 5941 | 5041 |
| Zn | n+2 | 6201 | 7401 | 12985 | 9663 | 10803 | 6901 | 5401 | 7361 | 3420 | 1160 | 3900 | 1660 |
| | | v25 | v26 | v27 | v28 | v29 | v30 | v31 | v32 | v33 | v34 | v35 | v36 |
| Fe | n | 155848 | 229623 | 130494 | 159478 | 120850 | 122702 | 41566 | 60739 | 128501 | 179579 | 116039 | 117609 |
| Fe | n+1 | 121373 | 81698 | 99323 | 133616 | 130051 | 133072 | 50007 | 91061 | 119078 | 97755 | 132347 | 75773 |
| Fe | n+2 | 104391 | 87484 | 138713 | 164219 | 116563 | 105960 | 62705 | 107710 | 80895 | 45576 | 14806 | 37057 |

| | Ablation Track | v37 | v38 | v39 | v40 | v41 | v42 | v43 | v44 | v45 | v46 | v47 | v48 |
|---|---|---|---|---|---|---|---|---|---|---|---|---|---|
| Mn | n | 5745 | 2422 | 8502 | 11203 | 10303 | 9225 | 7190 | 5290 | 6101 | 11081 | 11092 | 11793 |
| Mn | n+1 | 3589 | 5690 | 9958 | 6635 | 14628 | 17264 | 17163 | 13560 | 11025 | 10314 | 8835 | 8446 |
| Mn | n+2 | 3100 | 5367 | 9614 | 13549 | 10081 | 15006 | 11303 | 13538 | 10959 | 8746 | 6912 | 6068 |
| | | v37 | v38 | v39 | v40 | v41 | v42 | v43 | v44 | v45 | v46 | v47 | v48 |
| Zn | n | 1220 | 5241 | 6581 | 8902 | 7862 | 5481 | 6641 | 4020 | 7121 | 7942 | 5941 | 5481 |
| Zn | n+1 | 2240 | 7361 | 4160 | 9623 | 12044 | 14105 | 10603 | 8962 | 7141 | 6541 | 6061 | 7041 |
| Zn | n+2 | 2240 | 5101 | 8282 | 5641 | 10383 | 8262 | 8942 | 8802 | 6361 | 3860 | 4841 | 5061 |
| | | v37 | v38 | v39 | v40 | v41 | v42 | v43 | v44 | v45 | v46 | v47 | v48 |
| Fe | n | 54740 | 41887 | 132367 | 150302 | 156755 | 126124 | 94700 | 86480 | 82341 | 123366 | 167569 | 123648 |
| Fe | n+1 | 27721 | 122098 | 122581 | 148589 | 200228 | 190204 | 200875 | 158066 | 119702 | 104934 | 93373 | 87143 |
| Fe | n+2 | 17929 | 68686 | 116502 | 124574 | 134100 | 174471 | 163815 | 153811 | 107026 | 74629 | 79388 | 71818 |

Fig. 7B (continued): A1 melanoma male 50 years old

| | Ablation Track | v49 | v50 | v51 | v52 | v53 | v54 | v55 | v56 | v57 | v58 | v59 |
|---|---|---|---|---|---|---|---|---|---|---|---|---|
| Mn | n | 12482 | 14450 | 9013 | 8157 | 7457 | 4417 | 4234 | 2211 | 978 | 678 | 689 |
| Mn | n+1 | 11993 | 12404 | 11882 | 10047 | 8535 | 5401 | 5234 | 2534 | 1089 | 733 | 433 |
| Mn | n+2 | 8913 | 10781 | 9091 | 8791 | 7146 | 8802 | 6990 | 3534 | 1356 | 900 | 667 |
| | | v49 | v50 | v51 | v52 | v53 | v54 | v55 | v56 | v57 | v58 | v59 |
| Zn | n | 10303 | 6801 | 7081 | 6141 | 7822 | 4040 | 1840 | 1080 | 560 | 340 | 180 |
| Zn | n+1 | 11404 | 7381 | 9402 | 7401 | 3920 | 5581 | 2760 | 840 | 400 | 520 | 300 |
| Zn | n+2 | 8982 | 6501 | 5021 | 5081 | 6081 | 6641 | 3940 | 1260 | 400 | 480 | 140 |
| | | v49 | v50 | v51 | v52 | v53 | v54 | v55 | v56 | v57 | v58 | v59 |
| Fe | n | 159539 | 129910 | 102963 | 73183 | 53015 | 34151 | 29724 | 13825 | 5501 | 2640 | 2580 |
| Fe | n+1 | 139318 | 98962 | 109440 | 65194 | 58251 | 43370 | 26379 | 12504 | 3840 | 1580 | 1060 |
| Fe | n+2 | 117448 | 94740 | 74368 | 64431 | 77701 | 72119 | 44633 | 21332 | 5621 | 4461 | 1120 |

| | Ablation Track | v60 | v61 | v62 | v63 | v64 | v65 | v66 | v67 | v68 |
|---|---|---|---|---|---|---|---|---|---|---|
| Mn | n | 911 | 556 | 711 | 444 | 378 | 522 | 567 | 433 | 478 |
| Mn | n+1 | 678 | 478 | 400 | 789 | 467 | 500 | 489 | 956 | 433 |
| Mn | n+2 | 656 | 656 | 600 | 578 | 633 | 656 | 567 | 522 | 378 |
| | | v60 | v61 | v62 | v63 | v64 | v65 | v66 | v67 | v68 |
| Zn | n | 200 | 360 | 220 | 200 | 80 | 80 | 220 | 180 | 140 |
| Zn | n+1 | 240 | 100 | 160 | 220 | 160 | 80 | 220 | 100 | 240 |
| Zn | n+2 | 240 | 140 | 200 | 220 | 60 | 280 | 100 | 120 | 80 |
| | | v60 | v61 | v62 | v63 | v64 | v65 | v66 | v67 | v68 |
| Fe | n | 1440 | 1040 | 700 | 740 | 17528 | 360 | 380 | 280 | 260 |
| Fe | n+1 | 700 | 520 | 380 | 300 | 420 | 360 | 400 | 260 | 320 |
| Fe | n+2 | 1040 | 920 | 880 | 400 | 340 | 200 | 320 | 220 | 140 |

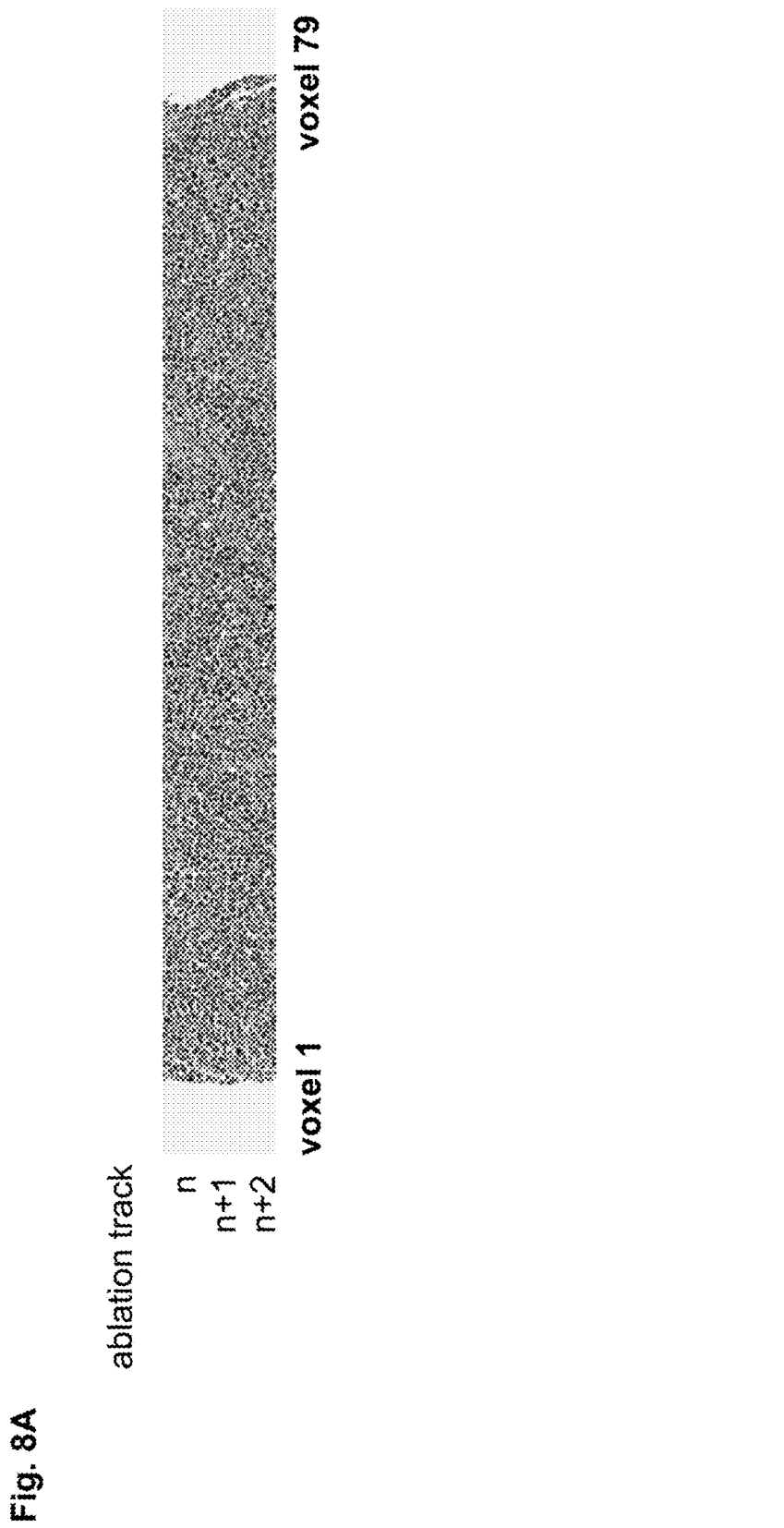

Fig. 8B: H5 lymphoma male 57 year old

|    | Ablation Track | v1   | v2    | v3   | v4   | v5   | v6    | v7   | v8   | v9   | v10  | v11  | v12  |
|----|----------------|------|-------|------|------|------|-------|------|------|------|------|------|------|
| Mn | n              | 763  | 776   | 789  | 1249 | 473  | 960   | 881  | 618  | 723  | 828  | 684  | 802  |
| Mn | n+1            | 1039 | 1052  | 815  | 776  | 736  | 802   | 802  | 513  | 934  | 934  | 960  | 828  |
| Mn | n+2            | 907  | 1446  | 776  | 881  | 736  | 934   | 736  | 815  | 999  | 750  | 842  | 579  |
|    |                | v1   | v2    | v3   | v4   | v5   | v6    | v7   | v8   | v9   | v10  | v11  | v12  |
| Zn | n              | 18   | 1028  | 128  | 73   | 147  | 165   | 92   | 18   | 257  | 679  | 37   | 55   |
| Zn | n+1            | 165  | 37    | 73   | 73   | 92   | 73    | 128  | 202  | 110  | 128  | 165  | 881  |
| Zn | n+2            | 165  | 92    | 55   | 92   | 55   | 202   | 1064 | 294  | 2000 | 73   | 165  | 110  |
|    |                | v1   | v2    | v3   | v4   | v5   | v6    | v7   | v8   | v9   | v10  | v11  | v12  |
| Fe | n              | 547  | 11551 | 151  | 189  | 208  | 151   | 245  | 321  | 8172 | 245  | 132  | 302  |
| Fe | n+1            | 906  | 358   | 1491 | 2736 | 1076 | 61049 | 189  | 321  | 830  | 264  | 170  | 151  |
| Fe | n+2            | 1151 | 1076  | 434  | 189  | 7285 | 75    | 132  | 547  | 189  | 321  | 189  | 151  |

|    | Ablation Track | v13 | v14  | v15   | v16    | v17    | v18    | v19    | v20    | v21    | v22    | v23    | v24    |
|----|----------------|-----|------|-------|--------|--------|--------|--------|--------|--------|--------|--------|--------|
| Mn | n              | 631 | 421  | 815   | 2406   | 1473   | 1499   | 1867   | 2354   | 1604   | 2117   | 1933   | 1604   |
| Mn | n+1            | 894 | 697  | 999   | 1381   | 1302   | 1802   | 2117   | 1999   | 1644   | 1512   | 1815   | 1841   |
| Mn | n+2            | 605 | 986  | 736   | 1815   | 1854   | 1907   | 1959   | 2051   | 1920   | 1644   | 1723   | 1565   |
|    |                | v13 | v14  | v15   | v16    | v17    | v18    | v19    | v20    | v21    | v22    | v23    | v24    |
| Zn | n              | 37  | 697  | 15714 | 14226  | 10701  | 21059  | 22382  | 20306  | 26222  | 22345  | 20838  | 19755  |
| Zn | n+1            | 330 | 1395 | 10701 | 5450   | 15273  | 20838  | 22859  | 20802  | 17587  | 18561  | 27196  | 29677  |
| Zn | n+2            | 110 | 954  | 9342  | 17679  | 22290  | 22290  | 24384  | 24090  | 19993  | 19846  | 22271  | 20912  |
|    |                | v13 | v14  | v15   | v16    | v17    | v18    | v19    | v20    | v21    | v22    | v23    | v24    |
| Fe | n              | 151 | 283  | 78325 | 175569 | 80523  | 136945 | 341005 | 369880 | 311849 | 271606 | 261684 | 283029 |
| Fe | n+1            | 264 | 132  | 87822 | 800087 | 115244 | 326969 | 386650 | 338350 | 300907 | 313059 | 238815 | 230995 |
| Fe | n+2            | 132 | 151  | 76619 | 214276 | 364833 | 348989 | 330294 | 306319 | 246276 | 238165 | 295073 | 279387 |

Fig. 8B (continued): H5 lymphoma male 57 year old

|    | Ablation Track | v25 | v26 | v27 | v28 | v29 | v30 | v31 | v32 | v33 | v34 | v35 | v36 |
|----|---|---|---|---|---|---|---|---|---|---|---|---|---|
| Mn | n   | 1946 | 1578 | 1749 | 1762 | 1381 | 2143 | 1828 | 1946 | 1578 | 1657 | 1591 | 1709 |
| Mn | n+1 | 1723 | 1433 | 1486 | 1696 | 1762 | 1999 | 1486 | 1565 | 1368 | 1565 | 1604 | 1539 |
| Mn | n+2 | 1631 | 1815 | 1341 | 1775 | 1631 | 1328 | 2459 | 1788 | 1762 | 1591 | 1723 | 920 |
|    |     | v25 | v26 | v27 | v28 | v29 | v30 | v31 | v32 | v33 | v34 | v35 | v36 |
| Zn | n   | 20673 | 20802 | 17697 | 17789 | 18377 | 17459 | 19497 | 19442 | 20838 | 17734 | 24807 | 31846 |
| Zn | n+1 | 18965 | 20691 | 19148 | 18579 | 17238 | 18487 | 16559 | 17459 | 18561 | 15199 | 19718 | 22124 |
| Zn | n+2 | 20195 | 17220 | 15181 | 17459 | 17220 | 17716 | 15548 | 16724 | 17293 | 18634 | 16485 | 16026 |
|    |     | v25 | v26 | v27 | v28 | v29 | v30 | v31 | v32 | v33 | v34 | v35 | v36 |
| Fe | n   | 245874 | 258850 | 235182 | 286615 | 280729 | 269863 | 236425 | 239619 | 252724 | 246907 | 253145 | 251691 |
| Fe | n+1 | 215881 | 250294 | 274921 | 236516 | 209636 | 275515 | 253069 | 242641 | 265457 | 287056 | 259750 | 271434 |
| Fe | n+2 | 299563 | 264001 | 202058 | 203585 | 211316 | 227344 | 229542 | 196600 | 194235 | 206333 | 234876 | 231664 |

|    | Ablation Track | v37 | v38 | v39 | v40 | v41 | v42 | v43 | v44 | v45 | v46 | v47 | v48 |
|----|---|---|---|---|---|---|---|---|---|---|---|---|---|
| Mn | n   | 1591 | 1631 | 1473 | 1802 | 1578 | 1552 | 1368 | 1302 | 1302 | 1604 | 1460 | 1552 |
| Mn | n+1 | 1578 | 2025 | 1486 | 1157 | 1525 | 1525 | 1539 | 1407 | 1525 | 1473 | 1420 | 1815 |
| Mn | n+2 | 1946 | 1617 | 1617 | 1762 | 1552 | 1394 | 1920 | 1617 | 1381 | 1709 | 1354 | 1736 |
|    |     | v37 | v38 | v39 | v40 | v41 | v42 | v43 | v44 | v45 | v46 | v47 | v48 |
| Zn | n   | 32269 | 21978 | 19773 | 16981 | 18524 | 22216 | 24237 | 21978 | 18763 | 16191 | 15126 | 17018 |
| Zn | n+1 | 22033 | 17477 | 25561 | 29806 | 23264 | 17844 | 17054 | 17954 | 17807 | 18322 | 16724 | 19001 |
| Zn | n+2 | 17679 | 20710 | 30247 | 26957 | 21922 | 19442 | 18469 | 17312 | 17844 | 19626 | 19957 | 18928 |
|    |     | v37 | v38 | v39 | v40 | v41 | v42 | v43 | v44 | v45 | v46 | v47 | v48 |
| Fe | n   | 315805 | 327564 | 265610 | 241589 | 284179 | 246696 | 305686 | 249280 | 234494 | 285752 | 269020 | 261990 |
| Fe | n+1 | 237247 | 248093 | 256725 | 259042 | 292560 | 241493 | 207574 | 263542 | 238509 | 214716 | 217542 | 213245 |
| Fe | n+2 | 189924 | 213111 | 262450 | 245223 | 258180 | 243521 | 247309 | 288839 | 322529 | 279425 | 293117 | 334197 |

Fig. 8B (continued): H5 lymphoma male 57 year old

|    | Ablation Track | v49 | v50 | v51 | v52 | v53 | v54 | v55 | v56 | v57 | v58 | v59 |
|----|---|---|---|---|---|---|---|---|---|---|---|---|
| Mn | n | 1591 | 1460 | 1473 | 1802 | 1565 | 1473 | 1604 | 1460 | 1407 | 1552 | 1394 |
| Mn | n+1 | 1552 | 1315 | 1302 | 1394 | 1486 | 1552 | 1578 | 1407 | 1197 | 2012 | 1525 |
| Mn | n+2 | 2012 | 1302 | 1276 | 1381 | 1565 | 1394 | 1341 | 1762 | 1565 | 1354 | 1433 |
|    |   | v49 | v50 | v51 | v52 | v53 | v54 | v55 | v56 | v57 | v58 | v59 |
| Zn | n | 17495 | 20508 | 20085 | 19093 | 23172 | 24807 | 20085 | 22621 | 24825 | 18138 | 13841 |
| Zn | n+1 | 21041 | 26681 | 20067 | 23576 | 26222 | 20820 | 17569 | 18230 | 16724 | 15457 | 14300 |
| Zn | n+2 | 20195 | 18928 | 18983 | 18487 | 17036 | 20049 | 18359 | 17807 | 16577 | 14759 | 16375 |
|    |   | v49 | v50 | v51 | v52 | v53 | v54 | v55 | v56 | v57 | v58 | v59 |
| Fe | n | 226771 | 210992 | 272449 | 281476 | 222204 | 218135 | 215881 | 219969 | 215919 | 228644 | 196009 |
| Fe | n+1 | 242851 | 281783 | 251155 | 273714 | 261607 | 241780 | 254619 | 244133 | 221363 | 205856 | 172787 |
| Fe | n+2 | 310678 | 316286 | 295208 | 342601 | 256687 | 289127 | 240632 | 230517 | 203470 | 185671 | 190191 |

|    | Ablation Track | v60 | v61 | v62 | v63 | v64 | v65 | v66 | v67 | v68 | v69 | v70 |
|----|---|---|---|---|---|---|---|---|---|---|---|---|
| Mn | n | 1539 | 1539 | 894 | 960 | 763 | 1144 | 907 | 894 | 750 | 789 | 1105 |
| Mn | n+1 | 1617 | 1433 | 986 | 947 | 697 | 763 | 644 | 657 | 1026 | 710 | 736 |
| Mn | n+2 | 1433 | 1525 | 1210 | 986 | 947 | 881 | 920 | 1157 | 736 | 750 | 763 |
|    |   | v60 | v61 | v62 | v63 | v64 | v65 | v66 | v67 | v68 | v69 | v70 |
| Zn | n | 12518 | 6570 | 3009 | 1009 | 422 | 991 | 275 | 110 | 183 | 37 | 183 |
| Zn | n+1 | 14098 | 8149 | 3156 | 1762 | 2441 | 532 | 312 | 110 | 202 | 128 | 239 |
| Zn | n+2 | 16320 | 12665 | 7286 | 3101 | 1560 | 752 | 330 | 220 | 459 | 239 | 128 |
|    |   | v60 | v61 | v62 | v63 | v64 | v65 | v66 | v67 | v68 | v69 | v70 |
| Fe | n | 169091 | 106092 | 53099 | 21069 | 11136 | 6152 | 3246 | 1510 | 1038 | 774 | 472 |
| Fe | n+1 | 177989 | 145523 | 76278 | 36339 | 16026 | 8663 | 2736 | 1774 | 1793 | 849 | 755 |
| Fe | n+2 | 204463 | 190897 | 128657 | 55843 | 27247 | 11853 | 5265 | 2812 | 1283 | 1170 | 377 |

Fig. 8B (continued): H5 lymphoma male 57 year old

|    | Ablation Track | v71 | v72 | v73 | v74 | v75 | v76 | v77 | v78 | v79 |
|----|----------------|-----|------|------|------|------|-----|-----|-----|------|
| Mn | n              | 960 | 1341 | 776  | 999  | 460  | 881 | 868 | 539 | 881  |
| Mn | n+1            | 618 | 447  | 934  | 894  | 618  | 855 | 671 | 828 | 1039 |
| Mn | n+2            | 907 | 657  | 1105 | 723  | 815  | 592 | 855 | 763 | 763  |
|    |                | v71 | v72  | v73  | v74  | v75  | v76 | v77 | v78 | v79  |
| Zn | n              | 183 | 202  | 606  | 73   | 92   | 495 | 367 | 55  | 37   |
| Zn | n+1            | 183 | 110  | 110  | 73   | 73   | 18  | 220 | 92  | 37   |
| Zn | n+2            | 92  | 110  | 128  | 147  | 55   | 440 | 37  | 92  | 147  |
|    |                | v71 | v72  | v73  | v74  | v75  | v76 | v77 | v78 | v79  |
| Fe | n              | 377 | 245  | 283  | 415  | 189  | 358 | 208 | 113 | 170  |
| Fe | n+1            | 321 | 321  | 415  | 189  | 132  | 283 | 75  | 396 | 151  |
| Fe | n+2            | 245 | 151  | 264  | 7039 | 8172 | 94  | 170 | 283 | 38   |

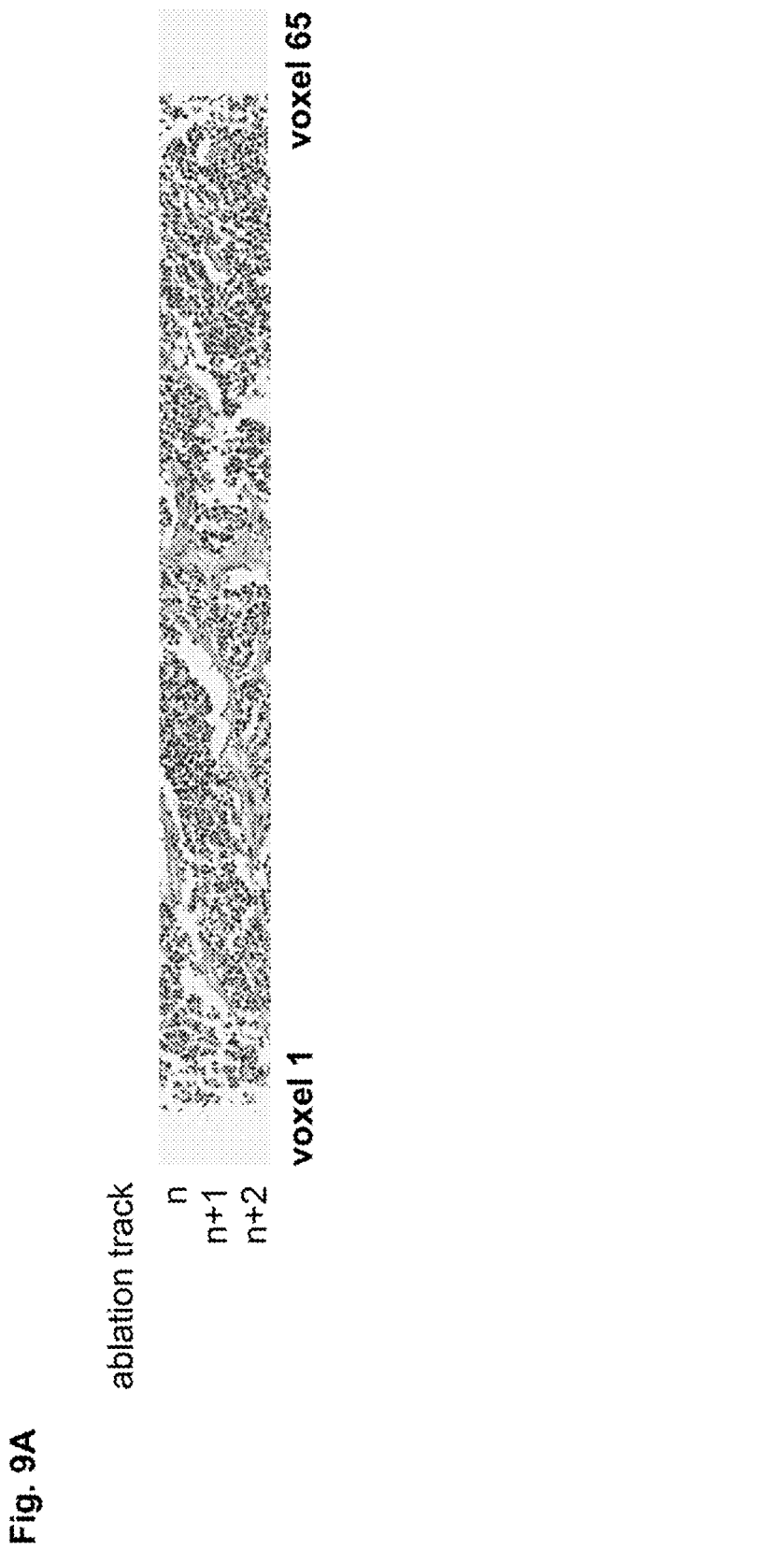

Fig. 9B: A9 small cell lung male 38 year old

| | Ablation Track | v1 | v2 | v3 | v4 | v5 | v6 | v7 | v8 | v9 | v10 | v11 | v12 |
|---|---|---|---|---|---|---|---|---|---|---|---|---|---|
| Mn | n | 1235 | 767 | 1704 | 507 | 572 | 806 | 559 | 507 | 897 | 611 | 481 | 728 |
| Mn | n+1 | 715 | 624 | 637 | 676 | 585 | 676 | 559 | 910 | 585 | 650 | 884 | 533 |
| Mn | n+2 | 910 | 819 | 533 | 533 | 767 | 611 | 598 | 494 | 442 | 663 | 637 | 572 |
| | | v1 | v2 | v3 | v4 | v5 | v6 | v7 | v8 | v9 | v10 | v11 | v12 |
| Zn | n | 1028 | 679 | 330 | 128 | 165 | 128 | 110 | 55 | 128 | 37 | 37 | 330 |
| Zn | n+1 | 495 | 385 | 532 | 73 | 147 | 18 | 37 | 92 | 55 | 0 | 1670 | 459 |
| Zn | n+2 | 642 | 4900 | 165 | 220 | 128 | 92 | 0 | 165 | 147 | 73 | 92 | 459 |
| | | v1 | v2 | v3 | v4 | v5 | v6 | v7 | v8 | v9 | v10 | v11 | v12 |
| Fe | n | 6964 | 4076 | 1585 | 1264 | 1132 | 1566 | 2227 | 1283 | 1057 | 1000 | 1057 | 717 |
| Fe | n+1 | 4472 | 2472 | 5907 | 755 | 604 | 1226 | 698 | 1981 | 1811 | 6435 | 4453 | 2472 |
| Fe | n+2 | 5812 | 3132 | 13326 | 887 | 943 | 698 | 660 | 943 | 623 | 604 | 434 | 698 |

| | Ablation Track | v13 | v14 | v15 | v16 | v17 | v18 | v19 | v20 | v21 | v22 | v23 | v24 |
|---|---|---|---|---|---|---|---|---|---|---|---|---|---|
| Mn | n | 1014 | 2263 | 3017 | 3160 | 2809 | 3433 | 3082 | 2705 | 2198 | 2380 | 1704 | 2302 |
| Mn | n+1 | 1079 | 2601 | 7661 | 3173 | 3056 | 2549 | 2107 | 2913 | 2484 | 2289 | 2172 | 2536 |
| Mn | n+2 | 819 | 2302 | 2523 | 2588 | 2874 | 2835 | 2952 | 1743 | 1443 | 1756 | 1613 | 1860 |
| | | v13 | v14 | v15 | v16 | v17 | v18 | v19 | v20 | v21 | v22 | v23 | v24 |
| Zn | n | 3468 | 5249 | 5561 | 5928 | 12500 | 5102 | 5359 | 3927 | 5193 | 4037 | 4000 | 6607 |
| Zn | n+1 | 5964 | 4753 | 5744 | 5249 | 5762 | 5193 | 5891 | 5909 | 5836 | 5212 | 5450 | 3542 |
| Zn | n+2 | 3725 | 4735 | 4184 | 5212 | 4992 | 5395 | 4551 | 2697 | 2349 | 3009 | 4459 | 4202 |
| | | v13 | v14 | v15 | v16 | v17 | v18 | v19 | v20 | v21 | v22 | v23 | v24 |
| Fe | n | 44301 | 116174 | 227765 | 182240 | 186625 | 327257 | 208013 | 124704 | 105561 | 97571 | 67506 | 115111 |
| Fe | n+1 | 77908 | 119479 | 124115 | 128144 | 126205 | 106035 | 113819 | 123678 | 120543 | 110174 | 98235 | 83784 |
| Fe | n+2 | 42485 | 107895 | 99412 | 90325 | 130843 | 151288 | 158959 | 67260 | 34695 | 64003 | 59194 | 89206 |

Fig. 9B (continued): A9 small cell lung male 38 year old

|    | Ablation Track | v25 | v26 | v27 | v28 | v29 | v30 | v31 | v32 | v33 | v34 | v35 |
|----|---|---|---|---|---|---|---|---|---|---|---|---|
| Mn | n | 2809 | 2692 | 1522 | 2484 | 2224 | 1860 | 2354 | 2484 | 2939 | 2627 | 2250 |
| Mn | n+1 | 1587 | 1847 | 1613 | 1079 | 2302 | 2471 | 2783 | 2705 | 2380 | 2978 | 2263 |
| Mn | n+2 | 2328 | 2562 | 2341 | 3160 | 2393 | 2718 | 2601 | 2614 | 2107 | 2133 | 1938 |
|    |   | v25 | v26 | v27 | v28 | v29 | v30 | v31 | v32 | v33 | v34 | v35 |
| Zn | n | 5157 | 3487 | 5377 | 5450 | 4845 | 5028 | 4845 | 5597 | 6552 | 5175 | 4643 |
| Zn | n+1 | 3028 | 3523 | 3083 | 3211 | 4808 | 4936 | 5524 | 5028 | 4680 | 4459 | 4441 |
| Zn | n+2 | 4239 | 4826 | 3193 | 5065 | 5193 | 5028 | 4863 | 5359 | 4166 | 3780 | 4936 |
|    |   | v25 | v26 | v27 | v28 | v29 | v30 | v31 | v32 | v33 | v34 | v35 |
| Fe | n | 130957 | 78685 | 108047 | 138714 | 110819 | 85566 | 92905 | 103321 | 115699 | 105447 | 73227 |
| Fe | n+1 | 62318 | 49125 | 66976 | 42977 | 92449 | 102600 | 108883 | 104820 | 88258 | 86931 | 74232 |
| Fe | n+2 | 68889 | 95750 | 70348 | 113478 | 94536 | 94821 | 106605 | 97514 | 81698 | 63435 | 75368 |

|    | Ablation Track | v36 | v37 | v38 | v39 | v40 | v41 | v42 | v43 | v44 | v45 | v46 | v47 | v48 |
|----|---|---|---|---|---|---|---|---|---|---|---|---|---|---|
| Mn | n | 2432 | 2393 | 1496 | 1977 | 2601 | 2068 | 1743 | 2081 | 2822 | 2575 | 2276 | 2588 | 3017 |
| Mn | n+1 | 1938 | 1899 | 1600 | 2146 | 2497 | 2913 | 2276 | 2328 | 2315 | 3147 | 2328 | 2783 | 1808 |
| Mn | n+2 | 1860 | 2055 | 2718 | 1704 | 1899 | 2172 | 2380 | 2679 | 2211 | 2380 | 2133 | 2471 | 2263 |
|    |   | v36 | v37 | v38 | v39 | v40 | v41 | v42 | v43 | v44 | v45 | v46 | v47 | v48 |
| Zn | n | 5395 | 3725 | 3927 | 5083 | 4441 | 3303 | 4423 | 5065 | 5304 | 6111 | 5175 | 5909 | 6240 |
| Zn | n+1 | 3909 | 3523 | 3266 | 5102 | 5579 | 5726 | 4845 | 4900 | 6350 | 5267 | 5138 | 4643 | 4826 |
| Zn | n+2 | 3799 | 4936 | 3854 | 4735 | 5120 | 5726 | 6093 | 4569 | 5193 | 4881 | 4973 | 5505 | 4312 |
|    |   | v36 | v37 | v38 | v39 | v40 | v41 | v42 | v43 | v44 | v45 | v46 | v47 | v48 |
| Fe | n | 96547 | 71939 | 53950 | 69022 | 81414 | 56297 | 65139 | 91653 | 86286 | 93113 | 80068 | 82343 | 89965 |
| Fe | n+1 | 63113 | 66313 | 55900 | 96414 | 107421 | 103112 | 92525 | 78723 | 90686 | 88144 | 73493 | 72735 | 70405 |
| Fe | n+2 | 75198 | 72451 | 74743 | 102714 | 167948 | 112186 | 103207 | 81281 | 75065 | 71693 | 84807 | 84352 | 66427 |

Fig. 9B (continued): A9 small cell lung male 38 year old

| Ablation Track | v49 | v50 | v51 | v52 | v53 | v54 | v55 | v56 | v57 |
|---|---|---|---|---|---|---|---|---|---|
| Mn n | 3121 | 2913 | 2328 | 1873 | 2250 | 3316 | 3004 | 3082 | 2419 |
| Mn n+1 | 2679 | 2354 | 2432 | 2120 | 2276 | 2211 | 1743 | 2029 | 2198 |
| Mn n+2 | 1886 | 2276 | 2133 | 1925 | 2341 | 2341 | 2211 | 1157 | 1509 |
| | v49 | v50 | v51 | v52 | v53 | v54 | v55 | v56 | v57 |
| Zn n | 6625 | 4698 | 4386 | 3285 | 6497 | 5873 | 6570 | 5267 | 3909 |
| Zn n+1 | 4459 | 5505 | 4771 | 3817 | 7396 | 4459 | 4698 | 4092 | 3156 |
| Zn n+2 | 3321 | 3303 | 2881 | 5304 | 6331 | 3945 | 2165 | 1725 | 1303 |
| | v49 | v50 | v51 | v52 | v53 | v54 | v55 | v56 | v57 |
| Fe n | 77889 | 88050 | 70101 | 49239 | 73966 | 100626 | 96888 | 111408 | 91767 |
| Fe n+1 | 64912 | 81793 | 63492 | 62867 | 72299 | 87481 | 66067 | 104744 | 91463 |
| Fe n+2 | 55143 | 45455 | 48614 | 66408 | 104631 | 100209 | 57717 | 31972 | 25868 |

| Ablation Track | v58 | v59 | v60 | v61 | v62 | v63 | v64 | v65 |
|---|---|---|---|---|---|---|---|---|
| Mn n | 2016 | 897 | 767 | 780 | 663 | 910 | 559 | 624 |
| Mn n+1 | 1105 | 728 | 689 | 663 | 637 | 572 | 546 | 715 |
| Mn n+2 | 767 | 884 | 962 | 559 | 702 | 793 | 585 | 637 |
| | v58 | v59 | v60 | v61 | v62 | v63 | v64 | v65 |
| Zn n | 3688 | 514 | 312 | 183 | 110 | 165 | 110 | 477 |
| Zn n+1 | 2239 | 606 | 257 | 183 | 165 | 110 | 92 | 73 |
| Zn n+2 | 569 | 3358 | 367 | 110 | 165 | 239 | 110 | 183 |
| | v58 | v59 | v60 | v61 | v62 | v63 | v64 | v65 |
| Fe n | 38608 | 15837 | 6548 | 3604 | 1830 | 1076 | 774 | 1000 |
| Fe n+1 | 38911 | 18349 | 11796 | 3717 | 9512 | 1359 | 962 | 1208 |
| Fe n+2 | 13798 | 8285 | 7417 | 3000 | 2623 | 2283 | 1245 | 1585 |

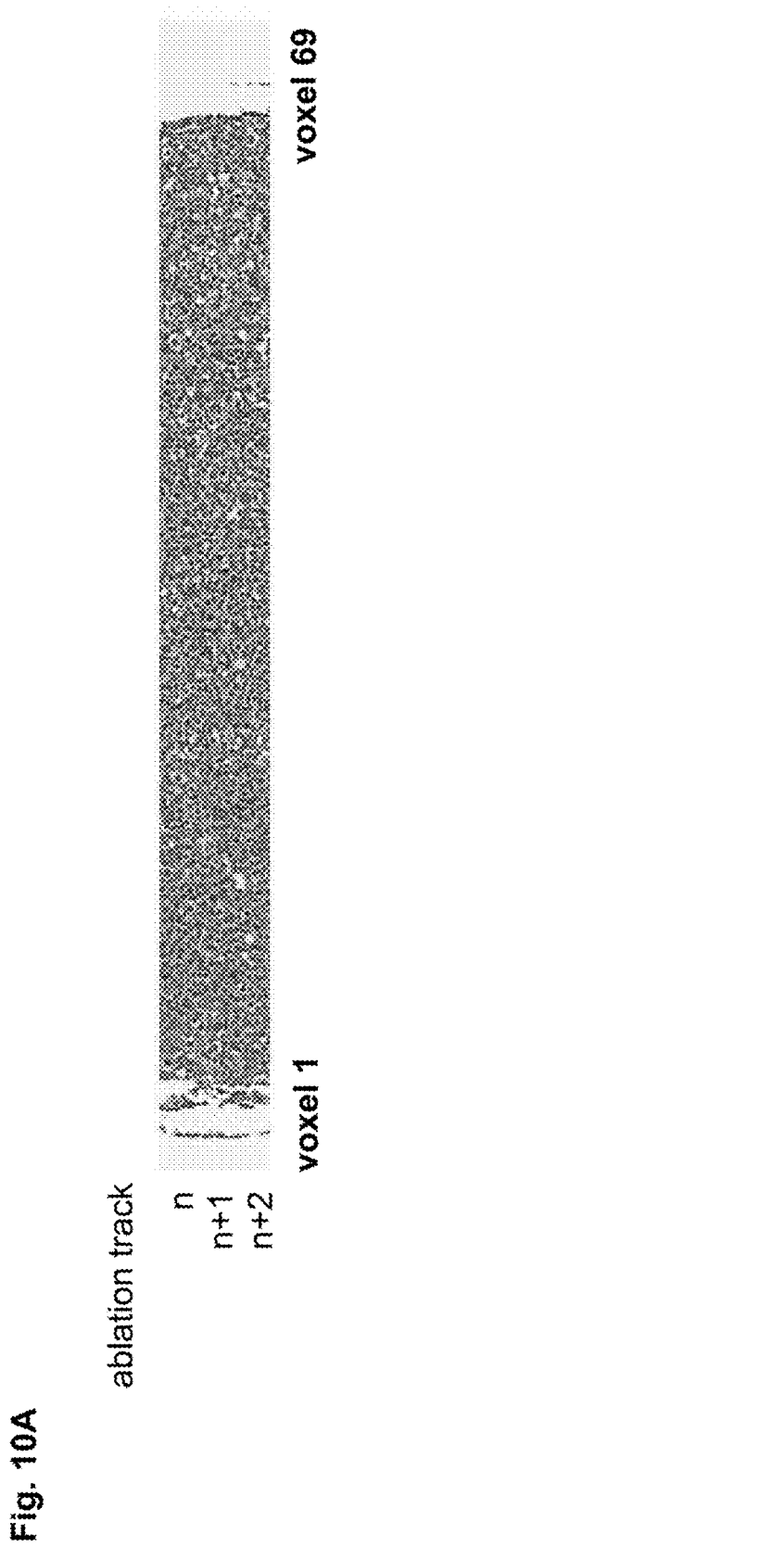

Fig. 10B: G5 seminoma male 52 years old

| | Ablation Track | v1 | v2 | v3 | v4 | v5 | v6 | v7 | v8 | v9 | v10 | v11 | v12 | v13 | v14 |
|---|---|---|---|---|---|---|---|---|---|---|---|---|---|---|---|
| Mn | n | 4011 | 723 | 920 | 920 | 710 | 710 | 999 | 934 | 868 | 894 | 1013 | 947 | 907 | 1118 |
| Mn | n+1 | 631 | 1197 | 605 | 736 | 500 | 1013 | 828 | 513 | 750 | 947 | 1631 | 842 | 1328 | 1460 |
| Mn | n+2 | 1026 | 828 | 776 | 579 | 907 | 855 | 710 | 855 | 789 | 579 | 789 | 736 | 1144 | 1802 |
| | | v1 | v2 | v3 | v4 | v5 | v6 | v7 | v8 | v9 | v10 | v11 | v12 | v13 | v14 |
| Zn | n | 0 | 18 | 606 | 73 | 73 | 55 | 624 | 2459 | 18 | 110 | 73 | 679 | 2055 | 2679 |
| Zn | n+1 | 92 | 128 | 73 | 92 | 73 | 55 | 110 | 73 | 37 | 110 | 55 | 1340 | 4569 | 3230 |
| Zn | n+2 | 55 | 92 | 936 | 37 | 128 | 92 | 18 | 55 | 92 | 92 | 110 | 1468 | 4386 | 2973 |
| | | v1 | v2 | v3 | v4 | v5 | v6 | v7 | v8 | v9 | v10 | v11 | v12 | v13 | v14 |
| Fe | n | 217008 | 415 | 44471 | 6020 | 151 | 151 | 132 | 245 | 453 | 170 | 208 | 57 | 2755 | 9474 |
| Fe | n+1 | 302 | 623 | 302 | 642 | 2340 | 1019 | 113 | 2227 | 245 | 415 | 283 | 321 | 15082 | 10192 |
| Fe | n+2 | 170 | 283 | 208 | 151 | 283 | 8058 | 132 | 94 | 208 | 208 | 226 | 283 | 41407 | 52039 |

| | Ablation Track | v15 | v16 | v17 | v18 | v19 | v20 | v21 | v22 | v23 | v24 | v25 | v26 | v27 |
|---|---|---|---|---|---|---|---|---|---|---|---|---|---|---|
| Mn | n | 1683 | 3064 | 2183 | 2143 | 2433 | 2341 | 2512 | 2683 | 1959 | 2591 | 2459 | 2932 | 2656 |
| Mn | n+1 | 1854 | 3025 | 2775 | 2498 | 2446 | 1972 | 2446 | 2065 | 2262 | 2525 | 2512 | 2314 | 2564 |
| Mn | n+2 | 1289 | 2209 | 2946 | 2591 | 2446 | 1880 | 1736 | 3274 | 2564 | 2117 | 2669 | 2735 | 2472 |
| | | v15 | v16 | v17 | v18 | v19 | v20 | v21 | v22 | v23 | v24 | v25 | v26 | v27 |
| Zn | n | 12445 | 13143 | 11710 | 15071 | 14630 | 17073 | 17918 | 15530 | 13951 | 15163 | 16118 | 15310 | 13932 |
| Zn | n+1 | 14153 | 15714 | 13694 | 12390 | 12720 | 8589 | 11435 | 12390 | 14520 | 15328 | 14483 | 13014 | 13381 |
| Zn | n+2 | 7561 | 27968 | 18065 | 13602 | 13345 | 10370 | 17165 | 14979 | 12922 | 15181 | 15255 | 14281 | 13528 |
| | | v15 | v16 | v17 | v18 | v19 | v20 | v21 | v22 | v23 | v24 | v25 | v26 | v27 |
| Fe | n | 89662 | 118738 | 65897 | 45360 | 42769 | 49693 | 60784 | 52266 | 50279 | 49749 | 52834 | 47971 | 53307 |
| Fe | n+1 | 65063 | 104991 | 58645 | 53364 | 39686 | 33901 | 67563 | 54461 | 57395 | 53326 | 54007 | 46779 | 54726 |
| Fe | n+2 | 7738 | 50525 | 55730 | 46211 | 43809 | 30611 | 88998 | 127098 | 68757 | 49730 | 51131 | 58682 | 56846 |

Fig. 10B (continued): G5 seminoma male 52 years old

|    | Ablation Track | v28   | v29   | v30   | v31   | v32   | v33   | v34   | v35   | v36   | v37   | v38   | v39   | v40   |
|----|----------------|-------|-------|-------|-------|-------|-------|-------|-------|-------|-------|-------|-------|-------|
| Mn | n              | 2354  | 2446  | 2946  | 2880  | 2959  | 2314  | 2406  | 2354  | 2498  | 2932  | 3117  | 2551  | 2275  |
| Mn | n+1            | 2446  | 1867  | 2932  | 3011  | 2038  | 2157  | 2748  | 2472  | 2380  | 2143  | 2406  | 2604  | 1946  |
| Mn | n+2            | 2354  | 2604  | 2433  | 1696  | 2301  | 2459  | 2209  | 2275  | 2183  | 2314  | 2591  | 2643  | 3025  |
|    |                | v28   | v29   | v30   | v31   | v32   | v33   | v34   | v35   | v36   | v37   | v38   | v39   | v40   |
| Zn | n              | 14355 | 15346 | 15053 | 15108 | 13841 | 12702 | 14410 | 14281 | 16356 | 17201 | 17661 | 14593 | 11968 |
| Zn | n+1            | 13620 | 15108 | 18763 | 19699 | 16963 | 15401 | 11894 | 14263 | 9654  | 13308 | 17954 | 13877 | 12004 |
| Zn | n+2            | 15548 | 15089 | 17165 | 12573 | 16026 | 18101 | 15163 | 13822 | 14281 | 15181 | 14740 | 18910 | 17954 |
|    |                | v28   | v29   | v30   | v31   | v32   | v33   | v34   | v35   | v36   | v37   | v38   | v39   | v40   |
| Fe | n              | 62128 | 59951 | 69666 | 92222 | 63984 | 52323 | 53174 | 42164 | 50695 | 74648 | 82665 | 63170 | 52266 |
| Fe | n+1            | 57622 | 70083 | 83632 | 87822 | 62980 | 48444 | 45152 | 43677 | 50185 | 42542 | 56884 | 58417 | 43090 |
| Fe | n+2            | 63946 | 56543 | 48728 | 38722 | 52985 | 53553 | 51225 | 44452 | 47176 | 45285 | 44225 | 73701 | 79822 |

|    | Ablation Track | v41   | v42   | v43   | v44   | v45   | v46   | v47   | v48   | v49   | v50   | v51   | v52   | v53   |
|----|----------------|-------|-------|-------|-------|-------|-------|-------|-------|-------|-------|-------|-------|-------|
| Mn | n              | 2972  | 2577  | 2367  | 2275  | 2235  | 2301  | 2643  | 1946  | 2762  | 2341  | 2367  | 1880  | 1499  |
| Mn | n+1            | 2617  | 2393  | 2498  | 2288  | 2222  | 2314  | 2249  | 2235  | 2025  | 2262  | 2262  | 2301  | 1999  |
| Mn | n+2            | 2814  | 2196  | 2328  | 2012  | 2091  | 2183  | 2630  | 2130  | 2801  | 2249  | 2748  | 2065  | 2538  |
|    |                | v41   | v42   | v43   | v44   | v45   | v46   | v47   | v48   | v49   | v50   | v51   | v52   | v53   |
| Zn | n              | 13033 | 12518 | 14906 | 11729 | 13271 | 14593 | 11876 | 12941 | 14208 | 13381 | 10462 | 12629 | 14979 |
| Zn | n+1            | 14575 | 12794 | 14171 | 15989 | 13657 | 12831 | 14447 | 13712 | 13400 | 12096 | 11949 | 13510 | 12959 |
| Zn | n+2            | 14685 | 14300 | 15199 | 14704 | 12941 | 12941 | 10976 | 13859 | 11912 | 14649 | 11013 | 12537 | 14795 |
|    |                | v41   | v42   | v43   | v44   | v45   | v46   | v47   | v48   | v49   | v50   | v51   | v52   | v53   |
| Fe | n              | 53780 | 53572 | 49655 | 46817 | 48747 | 55370 | 54613 | 60330 | 47857 | 47630 | 44112 | 48860 | 50979 |
| Fe | n+1            | 44906 | 55597 | 52796 | 50412 | 63889 | 46249 | 48690 | 39554 | 43015 | 49295 | 43715 | 47876 | 49674 |
| Fe | n+2            | 53610 | 56827 | 46987 | 47328 | 61958 | 91217 | 57073 | 51547 | 40480 | 42655 | 46968 | 41218 | 51093 |

Fig. 10B (continued): G5 seminoma male 52 years old

| | Ablation Track | v54 | v55 | v56 | v57 | v58 | v59 | v60 | v61 | v62 | v63 | v64 | v65 |
|---|---|---|---|---|---|---|---|---|---|---|---|---|---|
| Mn | n | 2406 | 2314 | 2065 | 2919 | 3051 | 1894 | 2551 | 2367 | 2354 | 2262 | 4918 | 2354 |
| Mn | n+1 | 2262 | 2472 | 1802 | 2065 | 2525 | 1749 | 1788 | 1959 | 2104 | 2249 | 2183 | 2485 |
| Mn | n+2 | 2393 | 2235 | 2919 | 3051 | 2459 | 2406 | 2091 | 2341 | 3222 | 2012 | 2669 | 2130 |
| | | v54 | v55 | v56 | v57 | v58 | v59 | v60 | v61 | v62 | v63 | v64 | v65 |
| Zn | n | 13914 | 13363 | 13363 | 13437 | 10847 | 9801 | 11912 | 13767 | 13859 | 13400 | 12922 | 9764 |
| Zn | n+1 | 12114 | 11564 | 12298 | 13437 | 12427 | 9581 | 12500 | 12243 | 13069 | 11876 | 12555 | 12573 |
| Zn | n+2 | 12004 | 12316 | 15401 | 18303 | 15255 | 13253 | 16834 | 13841 | 12371 | 14024 | 10976 | 16522 |
| | | v54 | v55 | v56 | v57 | v58 | v59 | v60 | v61 | v62 | v63 | v64 | v65 |
| Fe | n | 53383 | 69988 | 56600 | 64495 | 49995 | 46495 | 40632 | 54196 | 61106 | 56903 | 60689 | 60292 |
| Fe | n+1 | 49182 | 45984 | 53023 | 51433 | 44131 | 47498 | 34203 | 41086 | 49087 | 60178 | 54802 | 74686 |
| Fe | n+2 | 46174 | 53080 | 63340 | 53212 | 50487 | 50336 | 52342 | 48898 | 51036 | 58474 | 62507 | 83480 |

| | Ablation Track | v66 | v67 | v68 | v69 | v70 | v71 | v72 | v73 | v74 | v75 | v76 | v77 | v78 | v79 |
|---|---|---|---|---|---|---|---|---|---|---|---|---|---|---|---|
| Mn | n | 1828 | 2117 | 1420 | 1039 | 960 | 855 | 565 | 684 | 750 | 868 | 723 | 789 | 644 | 973 |
| Mn | n+1 | 2762 | 2696 | 1604 | 1420 | 855 | 815 | 723 | 960 | 736 | 1105 | 539 | 684 | 579 | 723 |
| Mn | n+2 | 2420 | 2525 | 2551 | 1407 | 1052 | 828 | 802 | 934 | 920 | 1091 | 697 | 934 | 802 | 881 |
| | | v66 | v67 | v68 | v69 | v70 | v71 | v72 | v73 | v74 | v75 | v76 | v77 | v78 | v79 |
| Zn | n | 10554 | 8993 | 3652 | 2110 | 807 | 183 | 734 | 330 | 220 | 147 | 92 | 367 | 73 | 128 |
| Zn | n+1 | 10847 | 9122 | 3872 | 1211 | 807 | 679 | 349 | 110 | 183 | 165 | 165 | 128 | 37 | 37 |
| Zn | n+2 | 16063 | 12757 | 5762 | 3009 | 1211 | 1101 | 220 | 220 | 110 | 37 | 404 | 128 | 92 | 165 |
| | | v66 | v67 | v68 | v69 | v70 | v71 | v72 | v73 | v74 | v75 | v76 | v77 | v78 | v79 |
| Fe | n | 48311 | 48709 | 27493 | 19275 | 4491 | 1906 | 18727 | 925 | 698 | 736 | 868 | 736 | 283 | 340 |
| Fe | n+1 | 61901 | 53648 | 30026 | 11173 | 5114 | 2736 | 1377 | 6699 | 302 | 377 | 245 | 377 | 226 | 226 |
| Fe | n+2 | 81433 | 86779 | 53193 | 23676 | 10494 | 4567 | 1925 | 1151 | 736 | 340 | 245 | 396 | 226 | 321 |

Fig. 12
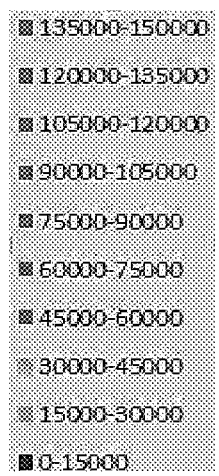

H&E

Mn

Zn

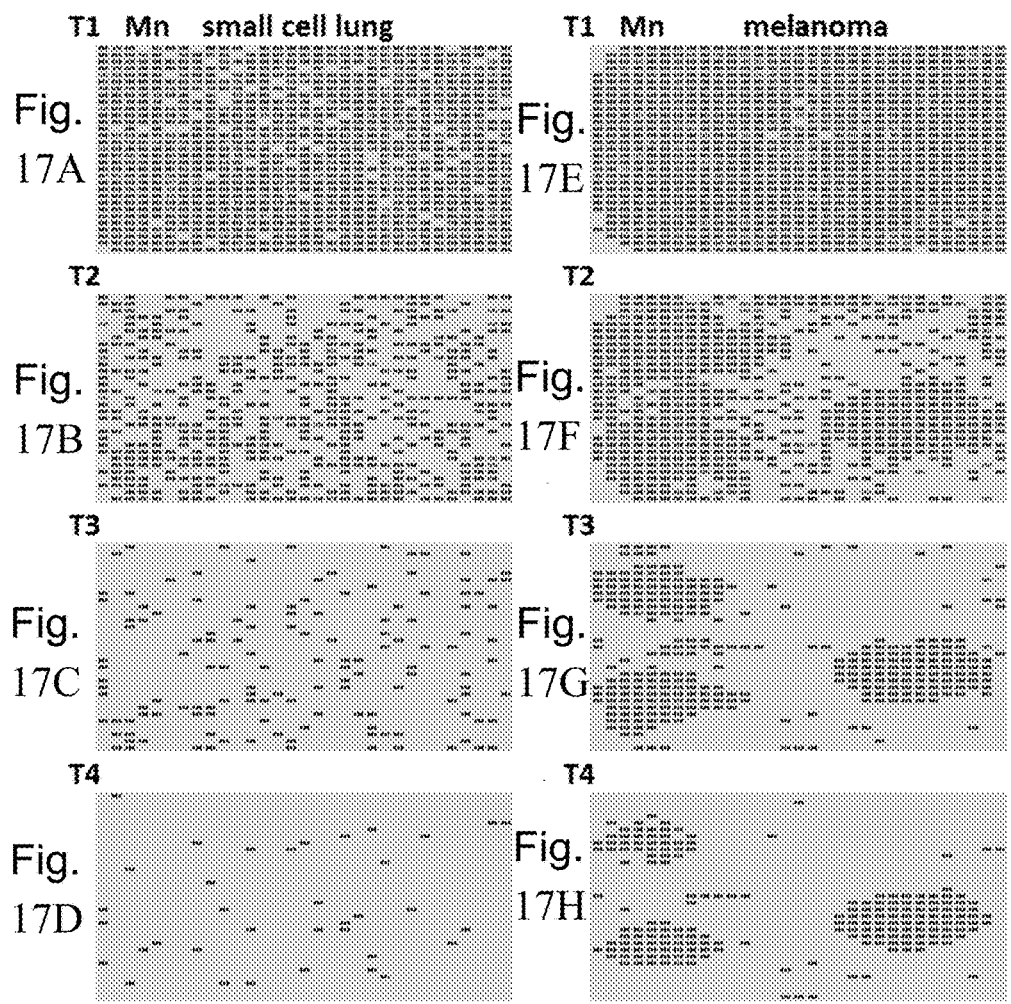

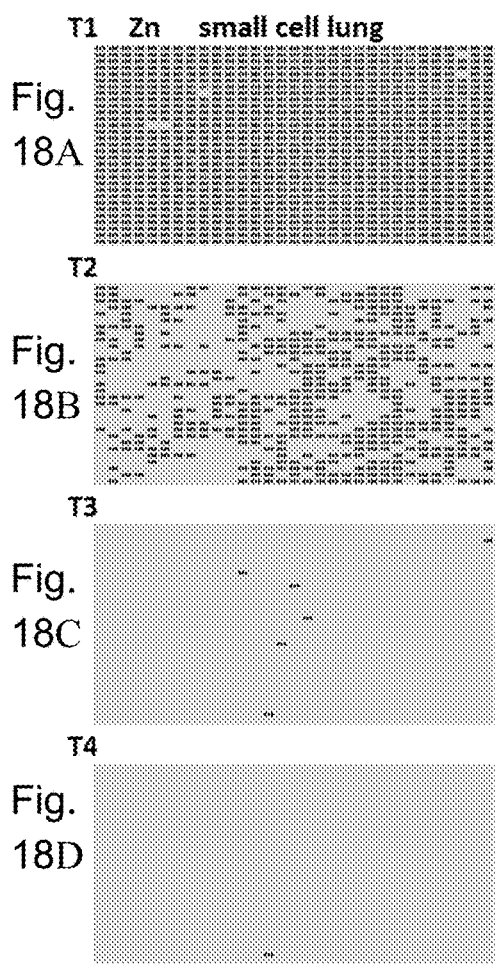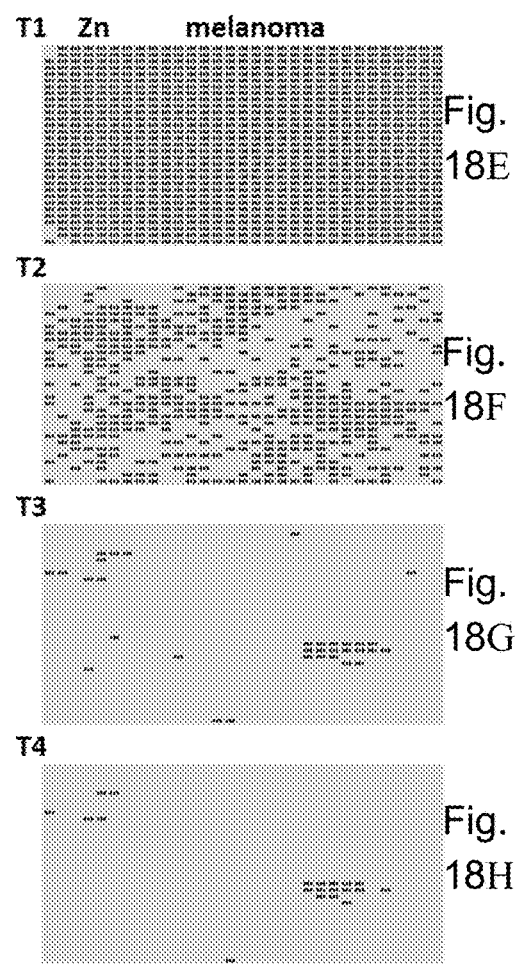

Fig. 20A
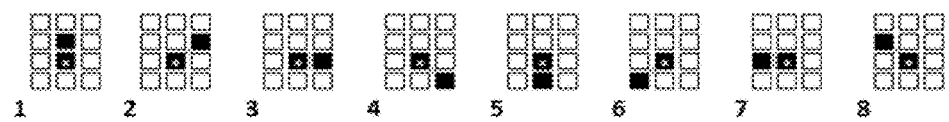
Fig. 20B  Fig. 20C  Fig. 20D
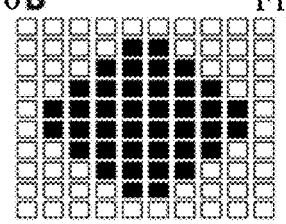 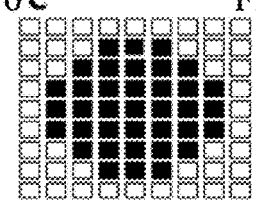 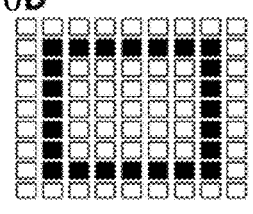
Fig. 20E  Fig. 20F  Fig. 20G
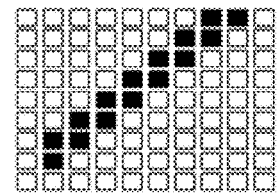 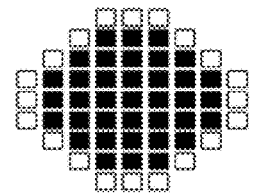 
Fig. 20H
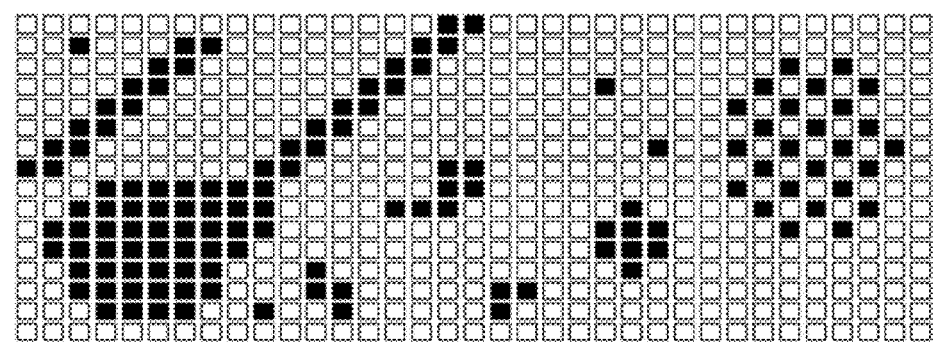

Fig. 23A MESOTHELIOMA — tumours without HMRs

Fig. 23B — tumour with an HMR cc/s

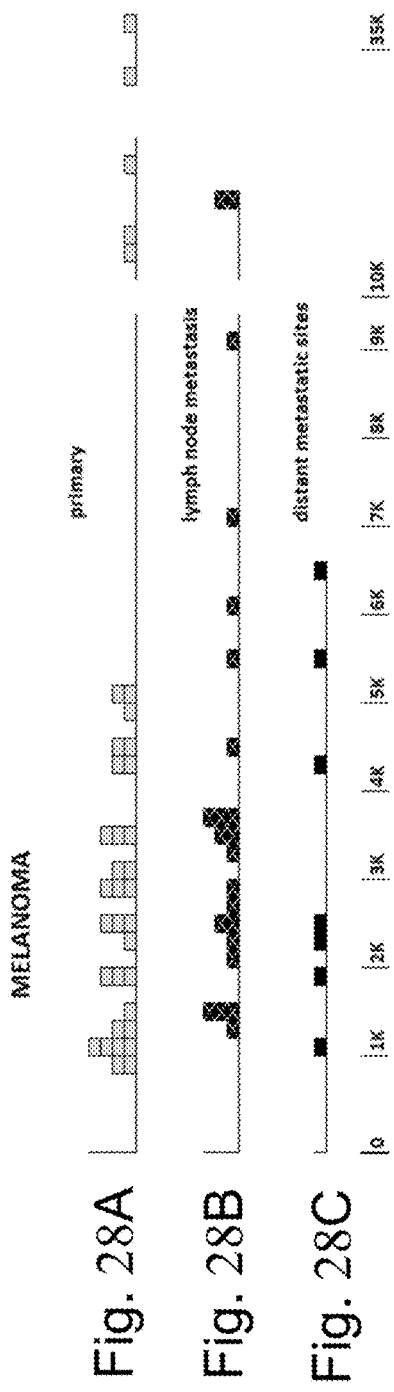

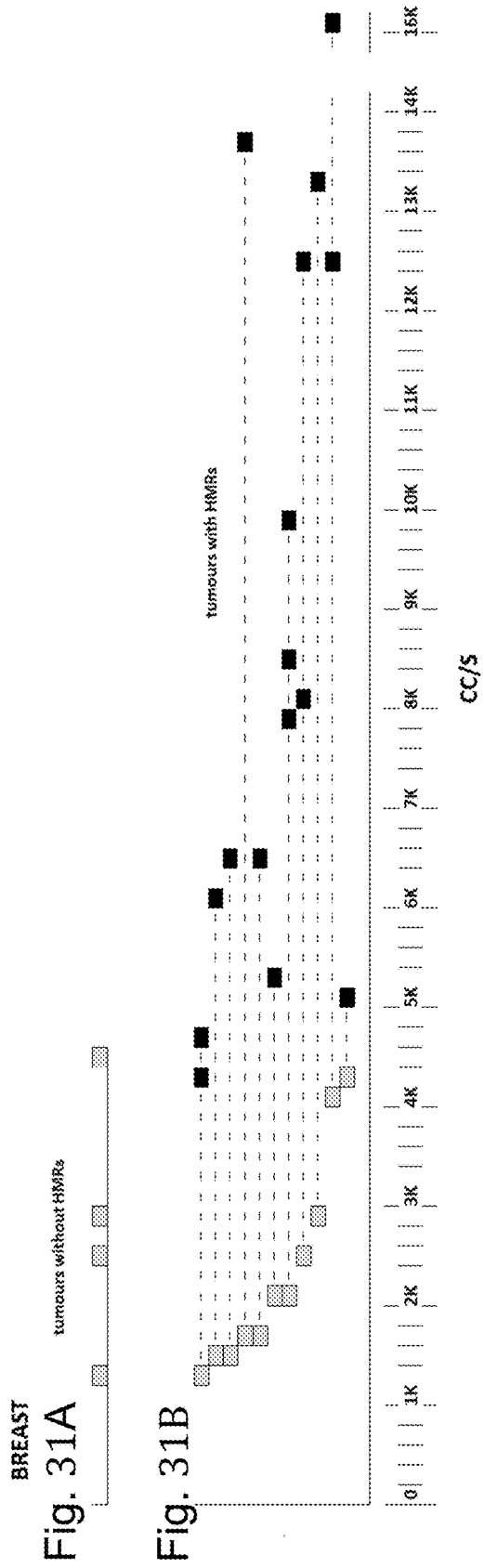

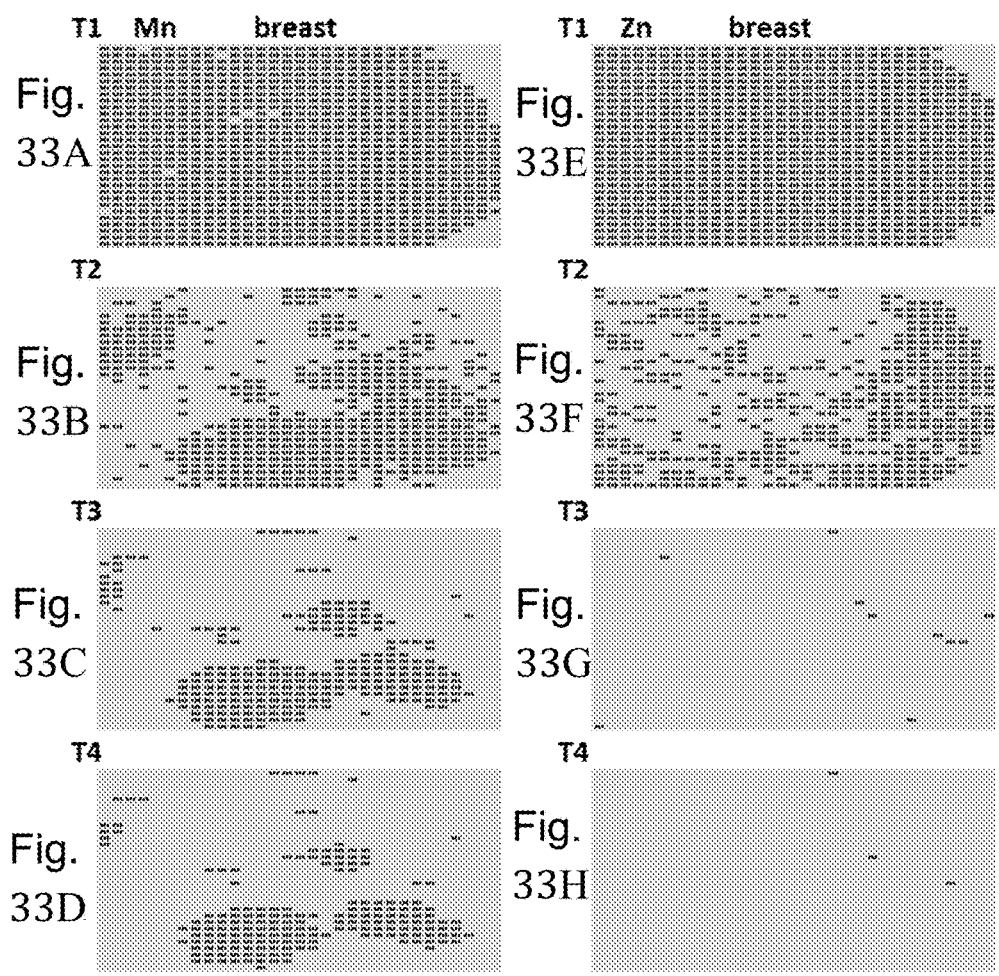

Fig. 36A H&E Fig. 36B
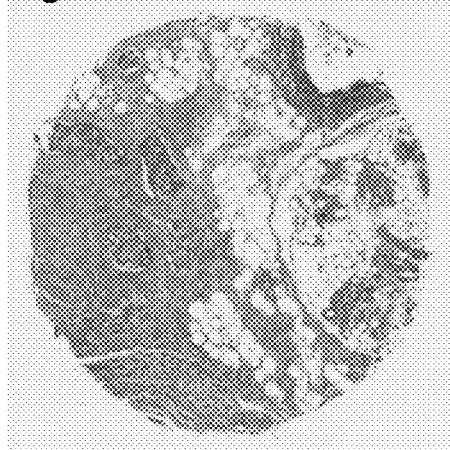
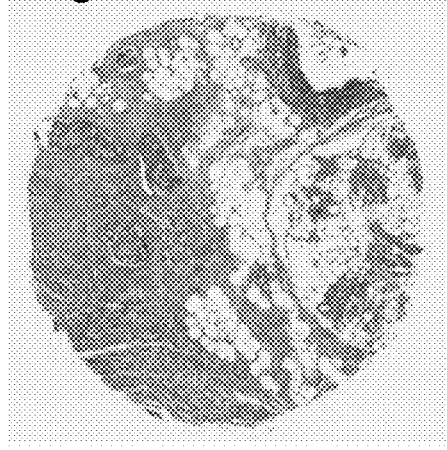
Mn Fig. 36C   Zn Fig. 36D
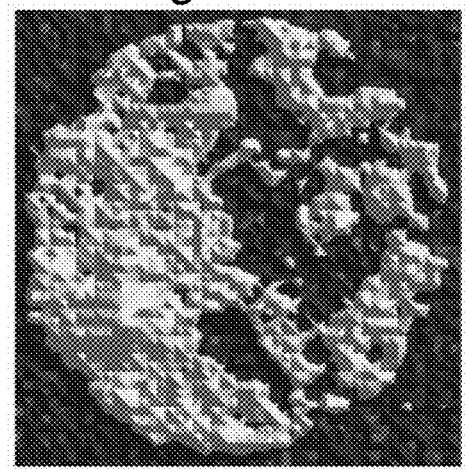
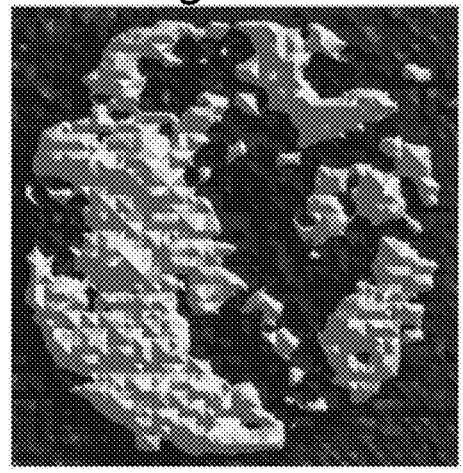
Cu Fig. 36E   Fe Fig. 36F
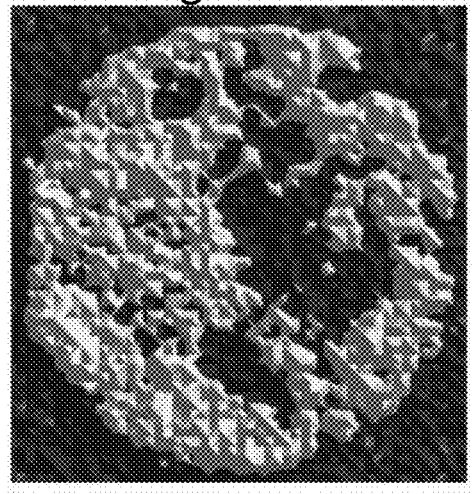
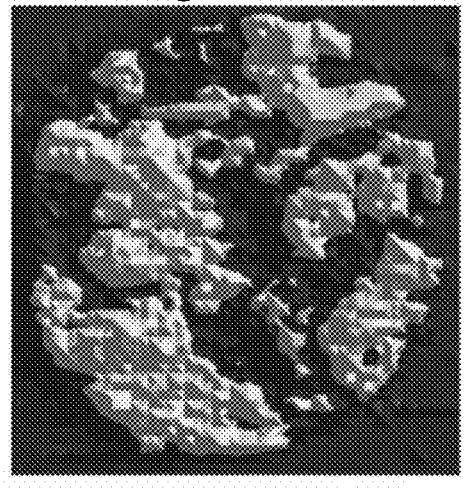

Fig. 37A

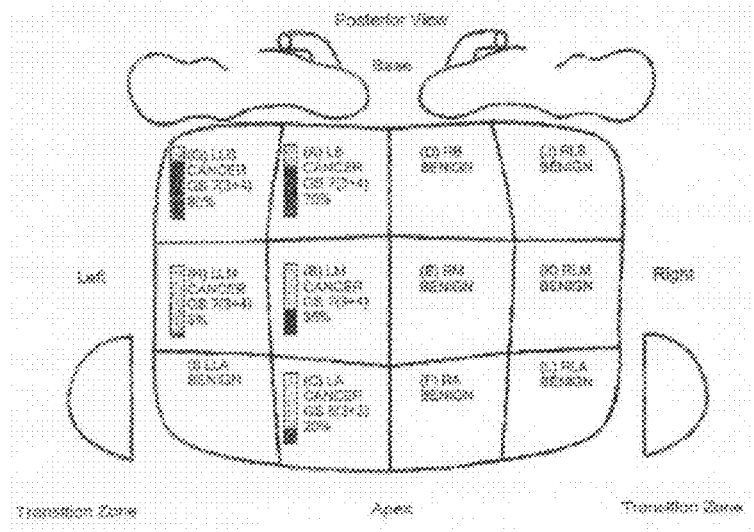

Fig. 37B

Diagnosis Summary
PART A: Left Base:
    Prostatic adenocarcinoma, Gleason's score 7(3+4) involving 70% of the needle core tissue. (ICD-9:185.00)
Part B: Left Mid:
    Prostatic adenocarcinoma, Gleason's score 7(3+4) involving 35% of the needle core tissue. (ICD-9:185.00)
Part C: Left Apex:
    Prostatic adenocarcinoma, Gleason's score 6(3+3) involving 20% of the needle core tissue. (ICD-9:185.00)
Part D: Right Base:
    Benign prostatic tissue.
Part E: Right Mid:
    Benign prostatic tissue.
    Acute nonspecific inflammation/prostatitis (ICD-9:601.00)
Part F: Right Apex:
    Benign prostatic tissue.
Part G: L Lat Base:
    Prostatic adenocarcinoma, Gleason's score 7(3+4) involving 80% of the needle core tissue. (ICD-9:185.00)
Part H: L Lat Mid:
    Prostatic adenocarcinomas, Gleason's score N/A involving 0% of the needle core tissue. (ICD-9:185.00)
Part I: L Lat Apex:
    Benign prostatic tissue.
Part J: R Lat Base:
    Benign prostatic tissue.
Part K: R Lat Mid:
    Benign prostatic tissue.
Part L: R Lat Apex :
    Benign prostatic tissue.

brain lesions primary melanoma

Fig. 40

| | | v101 | v102 | v103 | v104 | v105 | v106 | v107 | v108 | v109 | v110 | v111 | v112 | v113 | v114 | v115 |
|---|---|---|---|---|---|---|---|---|---|---|---|---|---|---|---|---|
| ↑ | 111 | 4485 | 4094 | 5083 | 4324 | 3680 | 3749 | 3519 | 2944 | 3979 | 4094 | 4830 | 4669 | 4531 | 4209 | 3933 |
| ↑ | 112 | 3956 | 4324 | 4301 | 4945 | 3818 | 4347 | 4002 | 4347 | 3703 | 4531 | 5152 | 3519 | 5106 | 3657 | 4186 |
| ↑ | 113 | 3910 | 3703 | 4416 | 4738 | 3841 | 3841 | 3381 | 3082 | 4255 | 4784 | 4370 | 5704 | 3887 | 4140 | 3795 |
| ↑ | 114 | 4393 | 4255 | 2714 | 3887 | 3450 | 2921 | 4416 | 4347 | 3197 | 4715 | 3979 | 5106 | 4094 | 5727 | 3979 |
| ↑ | 115 | 4508 | 4071 | 2944 | 4163 | 4554 | 3864 | 4094 | 4232 | 4554 | 3887 | 3726 | 3519 | 4577 | 4738 | 3864 |
| ↑ | 116 | 2829 | 3795 | 3703 | 3634 | 4232 | 3910 | 4830 | 3772 | 4209 | 3772 | 3864 | 4232 | 4140 | 4025 | 4807 |

| | | v116 | v117 | v118 | v119 |
|---|---|---|---|---|---|
| ↑ | 111 | 3680 | 4554 | 4186 | 3864 |
| ↑ | 112 | 3404 | 4623 | 4692 | 4577 |
| ↑ | 113 | 4025 | 4163 | 4232 | 4646 |
| ↑ | 114 | 4278 | 5451 | 4899 | 4370 |
| ↑ | 115 | 3657 | 4439 | 4991 | 5221 |
| ↑ | 116 | 5336 | 4163 | 4807 | 4163 |

VOXELS

Fig. 40 (continued)

VOXELS

| | v99 | v100 | v101 | v102 | v103 | v104 | v105 | v106 | v107 | v108 | v109 | v110 | v111 | v112 | v113 |
|---|---|---|---|---|---|---|---|---|---|---|---|---|---|---|---|
| 121 → | 3795 | 4048 | 4186 | 3588 | 4462 | 4370 | 5244 | 3933 | 4738 | 4163 | 3979 | 4347 | 4876 | 4738 | 3887 |
| 122 → | 3128 | 4393 | 3795 | 5267 | 5428 | 4899 | 4278 | 4623 | 3588 | 3795 | 4048 | 3266 | 3864 | 4439 | 4922 |
| 123 → | 4324 | 4508 | 3197 | 4784 | 3956 | 4324 | 4761 | 4439 | 4071 | 3979 | 3404 | 3956 | 4531 | 4761 | 3496 |
| 124 → | 5083 | 3933 | 3496 | 4692 | 4117 | 4830 | 4002 | 4324 | 4738 | 4117 | 4646 | 4209 | 4853 | 4623 | 3910 |
| 125 → | 4186 | 5106 | 5474 | 4485 | 4324 | 4140 | 4025 | 4462 | 4623 | 5221 | 3841 | 4163 | 4853 | 4048 | 5382 |
| 126 → | 4323 | 3749 | 4439 | 5290 | 4370 | 4485 | 4807 | 4071 | 4669 | 4163 | 4876 | 4761 | 5934 | 4807 | 4922 |

| | v114 | v115 | v116 | v117 |
|---|---|---|---|---|
| 121 → | 4025 | 4508 | 5106 | 5750 |
| 122 → | 3289 | 4830 | 5106 | 4807 |
| 123 → | 4255 | 4554 | 4715 | 5520 |
| 124 → | 4830 | 5198 | 4554 | 5704 |
| 125 → | 4255 | 4186 | 4807 | 4531 |
| 126 → | 5359 | 4922 | 4531 | 6072 |

Fig. 40 (continued)

VOXELS

| | v101 | v102 | v103 | v104 | v105 | v106 | v107 | v108 | v109 | v110 | v111 | v112 | v113 |
|---|---|---|---|---|---|---|---|---|---|---|---|---|---|
| → 131 | 3795 | 5750 | 5037 | 4324 | 3749 | 4554 | 4830 | 4830 | 5474 | 5152 | 4945 | 5152 | 4669 |
| → 132 | 4324 | 3703 | 4416 | 4623 | 4784 | 3933 | 4830 | 4876 | 5267 | 5290 | 5474 | 4370 | 5244 |
| → 133 | 3864 | 4416 | 5474 | 4784 | 4439 | 4278 | 4715 | 5474 | 4991 | 5037 | 4899 | 5474 | 4899 |
| → 134 | 4876 | 4600 | 4761 | 4623 | 4945 | 4830 | 4232 | 4715 | 4991 | 5566 | 566 | 5382 | 3864 |
| → 135 | 5267 | 4876 | 5428 | 5589 | 6624 | 7728 | 6210 | 5359 | 4807 | 5750 | 5474 | 4669 | 4278 |
| → 136 | 4646 | 5106 | 6187 | 5175 | 4278 | 4715 | 5129 | 4324 | 5704 | 5888 | 5290 | 4968 | 4830 |

Fig. 40 (continued)

VOXELS

| | v85 | v86 | v87 | v88 | v89 | v90 | v91 | v92 | v93 | v94 | v95 | v96 | v97 | v98 | v99 |
|---|---|---|---|---|---|---|---|---|---|---|---|---|---|---|---|
| → 141 | 5359 | 5221 | 5290 | 4715 | 5244 | 3795 | 3979 | 5566 | 4255 | 4692 | 5681 | 6003 | 4830 | 5681 | 5428 |
| → 142 | 5796 | 5060 | 4784 | 5175 | 4209 | 4209 | 3174 | 3611 | 4600 | 4876 | 5888 | 5520 | 5428 | 5382 | 4577 |
| → 143 | 4347 | 4255 | 5198 | 3772 | 4462 | 4646 | 4393 | 4485 | 3496 | 5612 | 4991 | 5106 | 6095 | 4761 | 5106 |
| → 144 | 4945 | 4876 | 5267 | 5658 | 4646 | 4186 | 5106 | 5244 | 4669 | 4853 | 4899 | 6049 | 5842 | 4945 | 5359 |
| → 145 | 4209 | 3910 | 5727 | 5980 | 4646 | 4853 | 5566 | 3956 | 4485 | 5750 | 5083 | 6302 | 7084 | 5359 | 5543 |
| → 146 | 3841 | 4094 | 5911 | 5704 | 52667 | 3519 | 5175 | 4899 | 4922 | 4738 | 5290 | 6624 | 5658 | 4577 | 4899 |

| | v100 | v101 | v102 | v103 |
|---|---|---|---|---|
| → 141 | 5497 | 5497 | 5014 | 5198 |
| → 142 | 4830 | 5888 | 6923 | 5842 |
| → 143 | 5175 | 4462 | 4738 | 4025 |
| → 144 | 4784 | 4669 | 4715 | 4163 |
| → 145 | 4853 | 4094 | 3864 | 3887 |
| → 146 | 4784 | 4278 | 5175 | 5152 |

Fig. 40 (continued)

VOXELS

| | v85 | v86 | v87 | v88 | v89 | v90 | v91 | v92 | v93 | v94 | v95 | v96 | v97 | v98 | v99 |
|---|---|---|---|---|---|---|---|---|---|---|---|---|---|---|---|
| ↑ 151 | 4324 | 4232 | 4002 | 3611 | 4876 | 4646 | 5267 | 4255 | 5198 | 4232 | 4439 | 4761 | 4922 | 4002 | 5313 |
| ↑ 152 | 4830 | 4324 | 4922 | 5175 | 5727 | 4761 | 5106 | 4462 | 4600 | 4646 | 4761 | 4669 | 5543 | 5359 | 4738 |
| ↑ 153 | 3979 | 4876 | 4945 | 4209 | 4600 | 4922 | 4738 | 5037 | 4071 | 5819 | 5244 | 5750 | 4922 | 5037 | 6900 |
| ↑ 154 | 3910 | 4577 | 4646 | 4715 | 5037 | 4117 | 4209 | 4554 | 5796 | 4577 | 4600 | 4899 | 4684 | 4393 | 3542 |
| ↑ 155 | 5520 | 4600 | 4462 | 5060 | 4669 | 4462 | 4922 | 4393 | 4853 | 4163 | 4922 | 4991 | 3404 | 4623 | 4163 |
| ↑ 156 | 5727 | 4968 | 4922 | 5336 | 4462 | 3910 | 4071 | 4784 | 5083 | 5428 | 5290 | 4485 | 3910 | 4324 | 4899 |

| | v100 | v101 | v102 | v103 |
|---|---|---|---|---|
| ↑ 151 | 4163 | 4393 | 4048 | 5566 |
| ↑ 152 | 6624 | 5336 | 4232 | 4485 |
| ↑ 153 | 6394 | 7613 | 4991 | 4684 |
| ↑ 154 | 4393 | 4646 | 5175 | 4439 |
| ↑ 155 | 4761 | 4094 | 3634 | 3542 |
| ↑ 156 | 4623 | 4439 | 4600 | 3335 |

METHOD FOR TREATING A CANCER PATIENT BASED ON ATOMIC THERAPEUTIC INDEXES AND NON-RADIATION THERAPY

This application is a divisional application of application Ser. No. 15/517,112, filed Apr. 5, 2017, which is a national stage application of the International Patent Application Serial no. PCT/AU2016/050603, filed Jul. 11, 2016, and which claims priority to Australian Patent Application No.: 2015902706 filed on Jul. 9, 2015, each of which is hereby incorporated by reference in its entirety.

FIELD OF THE INVENTION

The present invention relates to the generation of an Atomic Therapeutic Indicator (ATI) for a test sample by the quantification of manganese; in voxels of a 3D region of the sample, wherein the 3D region is topographically defined by co-ordinates X'×Y'×Z. The ATI is used to assess the radio-responsiveness i.e. sensitivity or resistance to radiation treatment, of a cancer i.e. a tumour/neoplasm. In a preferred embodiment, the present invention relates to a method of generating the ATI, assessing the radio-responsiveness of a tumour/neoplasm based on the ATI and, based on the assessment, either treating or not treating the tumour with radiation.

The present invention also relates to a method of determining if a cancer is likely to reoccur post radiation treatment comprising quantifying the level of manganese in voxels of a 3D region of a test sample from the cancer and determining the frequency of high metallomic regions (HMRs) in the cancer, wherein a high frequency of HMRs is indicative that the cancer is likely to reoccur and a low frequency of HMRs is indicative that the cancer is unlikely to reoccur; and associated methods of treatment.

The invention further relates to a method of determining the radio-responsiveness of a melanoma, the method comprising determining the level of melanin in a test sample from the melanoma, wherein the lower the level of melanin the more sensitive the melanoma is to radiation and the higher the level of melanin the more resistant the melanoma is to radiation; and associated methods of treatment.

BACKGROUND OF THE INVENTION

Any discussion of the prior art throughout the specification should in no way be considered as an admission that such prior art is widely known or forms part of common general knowledge in the field.

Over 60% of patients in the USA will receive radiation treatment during an illness, and these 600,000 or so individuals will make over 20 million radiation therapy visits, with each patient receiving, on average, 30 treatments of external beam radiation therapy with curative intent. Breast, lung and prostate cancer patients make up over 50% of all patients receiving radiation therapy (American Society for Radiation Oncology, ASTRO, 2012).

The clinical decision to treat "cancer patients" with radiation, or to avoid the use of this therapeutic modality, is currently based on a mixture of subjective, empirical and historical practice, commonly encapsulated within medical "art". The treatment and management decisions initially involve the suitability of the patients for definitive surgery, their age, extent of cardiopulmonary reserve, defined co-morbidities, the pathological grade of the tumour, and the stage of the disease as determined by various imaging modalities such as MRI, fMRI, CT, ultrasound, X-ray, PET, and combinations thereof. There is minimal quantitative input in terms of the properties of the tumour itself, with pathologists interpreting how tumourous cells "look" in terms of their morphological deviation from normal cells, the differences that are apparent in tumor architecture from that of normal tissues, and the extent of cell division within microscopic fields.

More specifically, the assessment of whether an individual is suspected of having a tumour or a cancer that requires treatment currently depends upon pathological examination of a sample of tissue, organ or blood sample. The results of the pathology uniquely determine the flow-on clinical events that are part of the current conveyor belt of medical art. In the United States of America (USA), more than 60% of cancer patients receive some form of radiation treatment, usually in combination with surgery and systemic therapies involving selected drugs, and more recently in combination with immunotherapies. The critical decision on whether a patient should, or should not, receive radiation, depends first and foremost on the report made by a pathologist (Davidson and Rimm; *JAMA;* 313; 1109-1110; 2015. Elmore et al., *JAMA;* 313; 1122-1132. 2015). This report is the current basis upon which a determination of patient management is made, which is usually carried out in a multidisciplinary setting involving radiation oncologists, medical oncologists and surgeons. However, such a critically important decision currently relies on a pathological diagnosis primarily based on the subjective analysis also described above, concerning cellular morphology and tissue architecture of formalin-fixed paraffin-embedded and Hematoxylin and Eosin (H&E) stained tissue sections (see FIG. 1, for example).

The concordance among pathologists of diagnostic interpretation is variable, and depends on the type of tumour under investigation. In the case of atypical hyperplasia of the breast, the concordance is only 48% (Elmore et al., *JAMA,* 313; 1122-1132. 2015). In terms of tumours of the thyroid, for example, it is very difficult to discriminate between normal tissue and "cancerous" tissue, except with very late stage tumours. This subjectivity of interpretation of the pathology results in overtreatment of those patients who achieve little benefit from radiotherapy, but suffer its well known harms, and results in under treatment of those patients who could benefit from radiation, but do not receive it. To avoid legal issues, physicians err on the side of caution, and radiation is given to many patients in the absence of any quantitative evidence of benefit, in the belief that following surgery, for example, radiation will minimize the effects of any residual cancer cells that have been left behind in the margins surrounding the resected tumour. For those patients whose tumours and associated stromal niches have some degree of radio-resistance, the radiation therapy is futile, since even if some radiation sensitive cells are killed, the surviving tumour and stromal cell populations have been selected for even more radio-resistance.

Medical practitioners generally rely upon evidence-based clinical decision support resources such as at the World Wide Web at uptodate.com. This resource provides a current clinical summary of radiation therapy techniques in cancer control at multiple levels, including types of radiation such as external beam radiotherapy, brachytherapy, intraoperative radiotherapy and targeted radionuclide therapy.

The Coverage and Analysis Group at the Centers for Medicare and Medicaid Services (the federal agency within the US Department of Health and Human Services) requested an assessment report on prostate cancer that was provided by Ip et al., 2010, at the Tufts Evidence-based Practice Center under contract to the Agency for Healthcare Research and Quality (RHQ), Rockville, Md., USA. (contract #290 2007 10055 I). This report addressed the evidence for the clinical and biochemical outcomes of different radiotherapies, such as stereotactic body radiation therapy, fractionated external beam radiation therapy and brachytherapy, on patients with localized prostate cancer (T1 and T2 disease). The external beam radiation therapies (EBRT) include intensity-modulated radiotherapy, conformal radiation, stereotactic body radiation, CyberKnife and proton beam radiation, while brachytherapy includes permanent implantation of radioactive isotopic "seeds" as well as temporary high dose radioactivity seeds.

The type of radiation delivered to a patient was also evaluated, whether it was photon or proton based, and whether the radiation was delivered via a linear accelerator, gamma rays (from a Cobalt-60 source), or via radioactive seeds comprising $^{125}$Iodine, $^{131}$Cesium or $^{103}$Palladium, for Low Dose Rate Brachytherapy (LDRBT); or $^{192}$Iridium (for High Dose Rate Brachytherapy (HDRBT). The evaluation also included the parameters that impinged on patient outcomes including radioactive dosages, adverse events, treatment planning algorithms, and the number of fractions delivered.

The rating system used by Ip et al. to evaluate the various clinical trials in terms of the strength of evidence emerging from any trial, was a subjective 3-tier one: high, moderate and insufficient.

In terms of the benefits versus harms of different radiotherapies, the results were as noted below.

In terms of the comparison of the benefits versus harms of radiotherapies, versus no radiation treatment, the strength of the evidence was found to be of category 3, insufficient.

The strength of the evidence was found to be insufficient for patient survival, when low dose rate brachytherapy was compared to external beam radiation therapy.

The strength of the evidence was found to be insufficient for biochemical control, when brachytherapy was compared to external beam radiation therapy and when high dose rate brachytherapy was compared to low dose rate brachytherapy.

The strength of the evidence was found to be insufficient for genitourinary and gastrointestinal toxicities, when low dose rate brachytherapy was compared to external beam radiation therapy.

The strength of the evidence was found to be insufficient for various combination therapies, LDRBT plus EBRT.

The strength of the evidence was found to be insufficient for different studies within the Stereotactic Body Radio-Therapy (SBRT) and EBRT umbrellas, namely bladder and rectal toxicities, freedom from biochemical failure and genitourinary or gastrointestinal toxicities.

The strength of the evidence was found to be insufficient for low dose rate brachytherapy in terms of radioactive seed comparisons, $^{125}$Iodine and $^{103}$Palladium.

The strength of the evidence was found to be insufficient for the contribution of age, race, ethnicity, co-morbidities, treatment-related adverse effects and disease progression to the baseline risk of a patient as a contributor to the outcome from radiotherapy.

The detailed report of Ip et al., 2010, concluded that in one of the two most extensively studied tumour types (localized prostate and localized breast), the evidence for the benefits of radiotherapy compared to no treatment for men with T1 or T2 prostate "cancer" revealed no quantitative indicators for radiation treatment of patients. Furthermore, there was substantial heterogeneity within and between studies, with many of the findings in this large evaluation being inconsistent.

The Ip et al. report indicates that the underlying risk of progression of the disease to the metastatic state varies widely between patients. The inability to objectively determine risk of progression means that patients deemed to be at "low" risk are advised to undergo brachytherapy, whereas those deemed to be at "intermediate" risk tend to be given external beam radiotherapy.

There is therefore an urgent need to identify those patients who have a biological parameter that favours one treatment modality compared with another, e.g., tumour characteristics that are favourable for radiation treatment, namely those whose tumours are sensitive to radiation versus those patients whose tumours are more radiation resistant, and therefore should be spared radiation treatment which is likely to be futile and harmful.

There is a further need for identifying biological parameters that might be useful in distinguishing characteristics of the abnormal tumour cells themselves, and the characteristics of the stroma, and the three dimensional (3D) distribution in which such abnormal cells are embedded. For example, a tumour that has abnormal cells evenly spread within a stromal component, is very different to a tumour where the abnormal cells are largely separate from stromal cells. In the case of prostate cancer, both of these situations occur within different foci of abnormal cells within the gland itself and also within metastases to bone. No current external imaging methods (MRI, CT or $^{18}$FDG imaging methods) can reliably identify these different areas, or their different characteristics.

To date, there are no available data pertaining to the use of radiotherapy for a given tumour of a particular patient: current data have no solid quantitative basis.

There remains a need for assays that provide quantitative indicators that enable the identification of a biological parameter in a sample, e.g., radio-sensitivity or radio-insensitivity/radio-resistance when making a suitable decision in respect of treating patients such as whether or not to treat "cancer patients" with radiation, or to avoid the use of radiation.

It is an objective of the present invention to overcome or ameliorate at least one of the disadvantages of the prior art treatments or/and to provide a useful alternative.

SUMMARY OF THE INVENTION

The inventor of the present invention has surprisingly found that the level of manganese in a cancer can be used as an indicatior of radio-responsiveness of the cancer. In particular, the higher the level of manganese in a cancer the more resistant the cancer to radiation; and the lower the level of manganese in the cancer, the more sensitive the cancer to radiation. Radio-responsiveness of a cancer can best be determined using a combination of 3D and 2D analysis. Accordingly, in one aspect, the present invention provides a method of generating an Atomic Therapeutic Indicator (ATI) of a biological test sample comprising quantifying the level of manganese in voxels in a 3D region of the test sample, wherein the method comprises:

(a) selecting a 2D region of said test sample, wherein the 2D region is topographically defined by an X':Y' coordinate system wherein X' is the length of the 2D region and Y' is the breadth of the 2D region, wherein the 3D region corresponds to said 2D region and has a selected height represented by Z, wherein the 3D region is divided into voxels of a pre-defined volume, the volume of each voxel being defined by X×Y×Z wherein X is the length of the voxel, Y is the breadth of the voxel and Z is the height of the voxel;
(b) quantifying the level of manganese in each voxel; and
(c) calculating the central tendency level of manganese in selected voxels;

wherein the central tendency level of manganese in the selected voxels defines the ATI.

In another aspect the present invention provides a method of determining the radio-responsiveness of a cancer, the method comprising generating an ATI of a test sample according to the invention, wherein the lower the ATI the more sensitive the cancer is to radiation and the higher the ATI the more resistant the cancer is to radiation.

In one embodiment, the ATI is compared to a pre-determined ATI threshold wherein the radio-responsiveness of the cancer is determined by assessing whether the ATI is above or below the ATI threshold, and wherein if the ATI is below the ATI threshold the cancer is determined to be sensitive to radiation; and wherein if the ATI is above the ATI threshold the cancer is determined to be resistant to radiation.

In another embodiment, the ATI is compared to two pre-determined ATI thresholds wherein the radio-responsiveness of the cancer is determined by assessing whether the ATI is above or below the two thresholds, and wherein if the ATI is below the lower ATI threshold the cancer is determined to be sensitive to radiation;

wherein if the ATI is above the second ATI threshold the cancer is determined to be resistant to radiation; and wherein if the ATI is between the two ATI thresholds the cancer is determined to be partially sensitive to radiation.

Preferably, quantification of the level of manganese in the voxels of the test sample is calibrated using a reference standard, wherein the reference standard comprises one or more reference voxels, and wherein each reference voxel comprises a known quantity of manganese.

In addition to the known quantity of manganese, the reference standard may comprise any additional material that allows the quantity of manganese in the reference standard to be compared with the quantity or level of manganese in the the test sample. Preferably the reference standard is a biological sample comprising a known quantity of endogenous or exogenous manganese. The biological sample may comprise human or animal tissue.

Preferably, the reference standard comprises tissue from an animal (including, for example, mammalian or avian species) to which a known amount of manganese is added. The skilled addressee will understand that matrix-matched reference standards with precisely defined amounts of manganese are useful for calculation of a calibrated counts per second correction factor to mitigate day-to-day signal variability. In one embodiment, the reference standard tissue is derived from chicken breast In one embodiment, the level of manganese quantified in a 3D region of one or more control sample(s) is quantified concurrently, or sequentially in any order, when the test sample is being quantified, or side-by-side with the test sample.

In one embodiment, the control sample is added to the test sample for analysis.

Preferably, the central tendency level is the median, arithmetic mean or mode.

It will be understood by the skilled addressee that the test sample may be stained or unstained. Preferably, the selected voxels are voxels in which cancer cells are detected. More preferably, the cancer cells are detected by visual inspection of the 2D region of the test sample stained with a stain that distinguishes cancer cells from other cells. When the cancer cells are detected by visual inspection of the 2D region of the test sample stained with a stain that distinguishes the cancer cells from other cells, preferably the stain is hematoxylin and eosin (H&E). In one embodiment, the cancer cells are detected by binding of an antibody, preferably a metal-labelled antibody, to the cancer cells.

In the context of the present invention, the length of the voxel, X, is in any range measurable and preferably in the range of about 1 micron to about 200 microns. In some embodiments, X is selected from about 10 to about 50 microns and any value in between, and preferably X is about 35 microns.

In the context of the present invention, the breadth of the voxel, Y, is in any range measurable and preferably in the range of about 1 micron to about 200 microns. In some embodiments, Y is selected from about 10 to about 50 microns and any value in between, and preferably Y is about 35 microns.

In the context of the present invention, Z is in any range measurable and preferably in the range of about 1 micron to about 20 microns. Preferably Z is selected from about 1 to about 20 microns and any value in between, preferably Z is about 1, or about 2, or about 3, or about 4, or about 5 microns.

In a preferred embodiment, X, Y and Z are selected respectively in ranges from about 1 to 200 microns, 1 to 200 microns, and 1 to 20 microns and any value in between in each range. Preferably X, Y and Z are 35 microns, 35 microns and 5 microns respectively.

In one embodiment of the invention, the pre-defined volume of each voxel is in the range of about 1 cubic micron to about $8 \times 10^5$ cubic microns, or about 1 cubic micron to about 10,000 cubic microns, or about 2000 cubic microns to about 8,000 cubic microns. In a preferred embodiment, the pre-defined volume is about 6,125 cubic microns.

The level of manganese in the voxels can be determined using any elemental analysis technique. Preferably, the elemental analysis technique is laser ablation-Inductively coupled plasma-mass spectrometry (LA-ICP-MS), laser ablation-time-of-flight-mass spectrometry (LA-TOF-MS), inductively coupled plasma-optical emission spectroscopy (ICP-OES), microwave plasma-atomic emission spectroscopy (MP-AES), laser induced break down spectroscopy (LIBS), secondary ion mass spectrometry (SIMS), or X-ray absorption near edge structure (XANES), atomic absorption spectroscopy (AA), or X-ray fluorescence (XRF).

The data obtained may be analyzed using computer assisted screening technology. For example, a five micron section may be laser ablated by rastering the laser across the slide laterally, one ablation track at a time from top to bottom. Alternatively, a five micron section may be laser ablated by rastering the laser across the slide from top to bottom, one ablation track at a time laterally. For example, an ATI according to the invention may be generated by laser ablation of at least one track across the test sample and/or control(s), wherein the ablation track comprises at least one voxel. In another example, the method of the invention comprises more than one ablation track and several voxels.

Preferably, the test sample is selected from a cell, a population of cells, one or more single celled organism(s), a tissue sample, or part thereof, an organ sample or part thereof, one or more cells obtained/derived from a prokaryotic or eukaryotic organism, a population of cells and its associated non-cellular stromal components, a neoplastic cell or population of neoplastic cells, a tissue sample from any organ or tissue from a subject, a tumour, a solid mass or a "liquid" population of cells, cells of any cancer of the hematopoietic system including leukemic cells, the circulating cellular derivatives of solid tumours, and a cell or population of cells that has metastasized.

In another aspect, the present invention provides a method of treating cancer in a subject comprising performing the method of the invention on a test sample from the subject, and including radiotherapy in treating said cancer in the subject if the cancer is determined to be sensitive to radiation.

In another aspect, the present invention provides a method of treating cancer in a subject comprising performing the method of the invention on a test sample from the subject, and not including radiotherapy in treating said cancer in the subject if cancer is determined to be resistant to radiation.

Preferably, the subject comprises a normal human or mammalian subject, a normal human or mammalian subject in need of a treatment or prophylaxis, a subject diagnosed with a cancer, a neoplasm/tumour suspected of having a cancer/neoplasm, a subject undergoing treatment and/or prophylaxis for any disorder including any cancer, an asymptomatic subject that has undergone a test or scan indicative of an underlying condition, a symptomatic subject that has undergone a test or scan indicative of an underlying condition, a subject undergoing clinical treatment including cancer therapy, or clinical intervention in the form of drugs, chemotherapy, immunotherapy, surgery, radiation or therapeutic devices, or a subject not yet undergoing any clinical treatment.

Preferably, the control sample comprises or is derived from a cell, a population of cells, one or more single celled organism(s), a tissue sample, or part thereof, an organ sample or part thereof, one or more cells obtained/derived from a prokaryotic or eukaryotic organism, a population of cells and its associated non-cellular stromal components, a neoplastic cell or population of neoplastic cells, a tissue sample from any organ or tissue from a subject, a tumour wherein the tumour for example, is a solid mass or a "liquid" population of cells, any cancer of the hematopoietic system including leukemic cells, the circulating cellular derivatives of solid tumours, or a cell or population of cells that has metastasized.

In one embodiment, the test and/or the control sample comprises or is derived from a cell, a population of cells or a tissue sample of a tumour/neoplasm of breast cancer, prostate cancer, cancer of the testes including seminoma, lymphoma including B-cell lymphoma, small cell lung cancer, cancer of the brain including glioblastoma multiforme, mesothelioma, or melanoma.

In another aspect, the present invention provides a method of determining the likelihood of reoccurrence of a cancer post radiation treatment comprising:
(a) quantifying the level of manganese in a 3D region of a test sample from the cancer by selecting a 2D region of said test sample, wherein the 2D region is topographically defined by an X':Y' coordinate system wherein X' is the length of the 2D region and Y' is the breadth of the 2D region, wherein the 3D region corresponds to said 2D region and has a selected height represented by Z, wherein the 3D region is divided into three or more voxels of a pre-defined volume, the volume of each voxel being defined by X×Y×Z, wherein X is the length of the voxel, Y is the breadth of the voxel and Z is the height of the voxel, and quantifying the level of manganese in each voxel;
(b) identifying in the 2D region corresponding to the X and Y coordinates of the voxel, high metallomic regions (HMRs), being regions in which the level of manganese is higher than in the surrounding areas as enabled by statistical thresholds that are multiples of a central tendency or any approximation between integers;
wherein the higher the frequency of HMRs the higher the likelihood of the cancer reoccurring and the lower the frequency of HMRs the lower the likelihood of the cancer reoccurring.

Preferably, the HMRs are also identified in the 2D region of the test sample stained with a stain that distinguishes cancer cells from stromal components, and preferably the stain is hematoxylin and eosin (H&E) stain.

In the context of the present invention, radio-responsiveness is a measure of sensitivity/resistance to radiation treatment.

In one example, the test sample is determined to be sensitive to radiation treatment if the ATI of the test sample is below a pre-determined threshold value obtained with the control sample that is known to be radiation sensitive. In another example, the test sample is determined to be resistant to radiation treatment if the ATI of the test sample is above a pre-determined threshold value obtained with the control sample that is known to be radiation resistant.

In one embodiment of the invention, test samples with an ATI at or below a lower threshold limit are determined to be sensitive to radiation treatment, and test samples at or above a higher threshold limit are determined to be resistant to radiation.

The volume of the voxels comprising the reference standard or the control sample can be the same or different to the volume of the voxels of the test sample.

The present invention further provides a method according to the invention herein, wherein an ATI is generated by quantifying the level of manganese in more than one 3D region of the test sample, and calculating the central tendency level of manganese across all of the 3D regions to thereby generate a further ATI.

The present invention further provides a method according to the invention herein, wherein an ATI is generated by quantifying the level of manganese in more than one test sample, calculating the central tendency level of manganese across the test samples to thereby generate a further ATI.

The present invention further provides a method according to the invention herein, wherein the level of manganese quantified in a 3D region of the control sample is quantified concurrently, or sequentially in any order, when the test sample is being quantified, or side-by-side with the test sample.

It is also contemplated that the control sample may be added to the test sample for analysis.

The Atomic Therapeutic Indicator (ATI) may be expressed in any units. For example, it may be expressed in calibrated counts/second (CC/S), or an equivalent proportional concentration unit, such as micrograms/gram, milligrams/kilogram, parts per million, micrograms/voxel, milligrams/voxel, moles or moles/voxel.

Until the present invention, it was not realized that the ATI from a radiation sensitive sample, e.g., cell/tissue, neoplastic cell/tumour, can be distinguished from the ATI of a sample that is radiation resistant, e.g., cell/tissue, neoplastic cell/tumour. This quantitative distinction enables the determination of radio-responsiveness (i.e. a determination of radiation sensitivity and/or radiation resistance) for a given selected cell, tissue sample or part thereof, neoplastic cell, or tumour sample or part thereof. It will be apparent to a person skilled in the art that the term "cell" includes neoplastic cell and the term "tissue sample or part thereof", includes a tumour sample or part thereof. The term "neoplastic" as used herein, includes any change in a cell that contributes to the potential to give rise to an abnormal growth of cells, whether pre-cancerous or cancerous.

The term "tumour" as used herein includes, but is not limited to, a collection of one or more neoplastic cells and/or its associated stromal component in that niche. For example, in the case of metastatic prostate cancer to the bone, one radiation treatment used prior to the present invention, is the use of $^{223}$Radium which has as its preferred target, hydroxyapatite ($Ca_5$ $(PO4)_3OH$), a major bone component. $^{223}$Radium efficiently "homes" to bone. When prostate, breast or any other cancer cells metastasize to bone, the cancer cells become intermixed with hydroxyapatite. The emission of the short range alpha particle destroys osteoblasts, but does not directly affect the cancer cells per se. Hence in this case, suppression of factors produced by the stroma (osteoblasts), which normally allow prostate cancer cells to grow in this niche, is disrupted, and the cancer cells do not grow as well, and survival of the patient is increased. Accordingly, a person skilled in the art will understand that different stromal niches support cancer cells to a different extent, and those niches themselves may also vary in their metallomic content, all the way from very high to very low and may also be radio-sensitive or radio-resistant. Thus when radiation is applied to a "tumour", there are four boundary condition-type possibilities. If both stromal and cancer cells are radio-resistant, then radiation to the "tumour" is ineffective and the tumour can undergo further growth. If both stromal and cancer cells are radio-sensitive, then the growth of a tumour is halted. If the stromal cells are radio-sensitive, and the cancer cells are radio-resistant, the stromal cells are effectively killed by radiation, and the growth of the tumour cells is also halted, because they now have no metabolic/factor support from their stroma, and so the tumour does not grow. If stromal cells are radio-resistant, and the cancer cells are radio-sensitive, tumour growth is halted. Accordingly, a person skilled in the art will understand that the term "tumour or part thereof" includes tumour cells and/or associated stromal cells in their complete diversity (blood vessels, infiltrating and resident immune cells, fibroblasts, pericytes and infiltrating exosomes).

Determining the level of manganese in a selected 3D region according to any aspect, embodiment or example described herein includes, but is not limited to, performing a direct measurement on the test sample, reference standard and/or control sample, e.g., the cell, tissue sample or part thereof, neoplastic cell, tumour sample or part thereof. In one example, the test sample and/or control sample may be directly processed in its natural environment, e.g., by direct scanning and quantifying the levels of manganese in a selected 3D region of the test sample and/or control sample according to known methods. In another example, the test sample and/or control sample comprising or derived from e.g., a cell, tissue sample or part thereof, neoplastic cell, tumour sample or part thereof is prepared for microscopic examination or for automated analysis by machine scanning according to known methods. The cell, tissue sample or part thereof, neoplastic cell, tumour sample or part thereof may be flash frozen, or formalin-fixed and paraffin-embedded, or one or more cells are deposited as a monolayer or near monolayer on a microscopic slide, e.g., via a SurePath-like system. The tissue/tumour sample or part thereof, may also be treated whereby a cell or cell population is obtained therefrom and deposited as a monolayer or near monolayer on a microscopic slide, e.g., via a SurePath-like system. Sections of the cell, tissue sample or part thereof, neoplastic cell, tumour sample or part thereof are then treated according to known methods to prepare the section for microscopic examination or for automated analysis by machine scanning. Optionally, one or more section(s) are stained with H&E stain and/or specific antibodies to visualize morphological aspects of interest. In one example, one or more sequential sections are fixed unstained and directly used for the determination of the level of manganese according to the invention. In another example, one or more section(s) are sequentially prepared e.g., matched, and at least one is stained with H&E stain and/or specific antibodies to visualize morphological aspects of interest and the stained sections are prepared alongside unstained sections, e.g., sequential sections are prepared, wherein at least one may be stained as described herein, and at least one is unstained. The stained section may be first visualized then directly used for the determination of the level of manganese according to the invention, or a stained section is prepared according to standard methods in the art, and visualized by a pathologist to determine morphological aspects, and a matched unstained section, e.g., sequential section, is chosen and used for the determination of the level of manganese according to the invention.

The level of manganese according to the invention is determined by any method known in the art that enables the selected 3D region to be topographically defined by an X':Y':Z coordinate system and divided into voxels of pre-determined volume. For example, the level of manganese is measured in a voxel of a pre-defined volume and the same or different pre-defined volume may be used for the reference standard or the control sample.

A person skilled in the art will understand that the ATI may be obtained for several ablation tracks comprising more than one voxel. For example, the number of ablation tracks may be any number that is conceivable to be processed and includes, but is not limited to, about 1 to 100 ablation tracks. In one example, the number of ablation tracks is at least 3. The length of the ablation track may also vary and comprises any number of voxels according to the invention.

A person skilled in the art will appreciate that the number of voxels will vary based on the voxel size. For example, the track length may be any length the instrumentation used permits. In one example, the track length may be between 0.5 to 1.0 cm. In another example, the track length is about 5.0 cm, or about 5.35 cm in length. For example, a single track wherein each voxel is about 35(length)×35(breadth)×5(height) with a volume of 6,125 cubic microns, and will yield approximately 1,500 voxels of analysis based on a track length of 5.35 cm. It is also contemplated that according to the invention, one or more areas of a sample is ablated to generate an ATI according to any aspect, embodiment or example herein. For example, a person skilled in the art will appreciate that a 1 mm×1 mm area is typically used by pathologists for measuring mitotic rate on a slide and such an area may also be ablated according to the invention. In this example, such an area corresponds to an approximately 30 voxel by 30 voxel area wherein each voxel is about 35(length)×35(breadth)×5(height) with a volume of 6,125 cubic microns. It is further contemplated that defining a minimal area for analysis will depend upon the sensitivity of the detection method. For example, the size of the area may vary from 2, 3, 4, 5, 6, 7, 8, 9, 10, 11, 12, 13, 14, 15, 16, 17, 18, 19, 20, 21, 22, 23, 24, 25, 26, 27, 28, 29, 30 etc contiguous voxels, to an integer which is the sample size chosen for analysis of that particular tumour. A person skilled in the art will appreciate that size area according to the invention is in any range measurable using existing technology.

It will also be understood that determining the level of manganese according to the invention may be corrected for background. For example, in the case of laser ablation mass spectrometry, a region without the test sample and/or control sample may be used for background correction. For example, a test sample and/or control sample on a slide may be laser ablated directly, and the background in an area of the slide without the test sample and/or control is used for background correction.

In one or more embodiments that background correction is set to a level that allows for regions of particularly high metallomic content to be revealed. These regions are referred to as high metallomic regions (HMRs).

A person skilled in the art will appreciate that the voxel of the test sample, reference standard and/or control sample according to the invention is in any range measurable using relevant technology. For example, X is in any range measurable and, as indicated above, is preferably in the range of about 1 micron to about 200 microns and any value in between. In one example, X is selected from about 10 to about 50 microns and any value in between. Preferably, X is about 35 microns. For example, Y is in any range measurable and preferably in the range of about 1 micron to about 200 microns and any value in between. In one example, Y is selected from about 10 to about 50 microns and any value in between. Preferably, Y is about 35 microns. For example, Z is in any range measurable and preferably in the range of about 1 micron to about 200 microns and any value in between. In one example, Z is selected from about 1 to about 20 microns and any value in between. Preferably, Z is about 1, or about 2, or about 3, or about 4, or about 5, or about 6, or about 7, or about 8, or about 9, or about 10 microns. A person skilled in the art will appreciate that the X' and Y' coordinates define the selected 2D area of the test sample and Z represents the thickness of the test sample. Accordingly, as indicated above, the voxel according to the invention e.g., X×Y×Z, includes, but is not limited to, a range selected from about 1 to 200:1 to 200:1 to 20 cubic microns and any value in between. For example, the X value is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 microns or any approximation between integers. For example, the Y value is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 microns or any approximation between integers. For example, the Z value is about 1, 2, 3, 4, 5, 6, 7, 8, 9, 10, 11, 12, 13, 14, 15, 16, 17, 18, 19, or 20 microns or any approximation between integers. Accordingly, any one of each X value listed may be combined with any one of each Y value listed, which may then be combined within any one of each Z value listed. It will also be understood that X, Y, and Z may not be equal in length. Alternatively, X, Y and Z may be equal in length. In another example, X and Y are equal in length and Z is not equal to X and Y. In another example, X and Z are equal in length and Y is not equal to X and Z. Preferably, X and Y are equal in length. For example, the voxel is about 1×1×1, or about 5×5×1, or about 10×10×1, or about 15×15×1, or about 20×20×1, or about 25×25×1, or about 30×30×1 or about 35×35×1 or about 40×40×1 or about 45×45×1 or about 50×50×1 or about 55×55×1 or about 60×60×1 or about 65×65×1 or about 70×70×1, or about 1×1×2, or about 5×5×2, or about 10×10×2, or about 15×15×2, or about 20×20×2, or about 25×25×2, or about 30×30×2 or about 35×35×2 or about 40×40×2 or about 45×45×2 or about 50×50×2 or about 55×55×2 or about 60×60×2 or about 65×65×2 or about 70×70×2, or about 1×1×3, or about 5×5×3, or about 10×10×3, or about 15×15×3, or about 20×20×3, or about 25×25×3, or about 30×30×3 or about 35×35×3 or about 40×40×3 or about 45×45×3 or about 50×50×3 or about 55×55×3 or about 60×60×3 or about 65×65×3 or about 70×70×3, or about 1×1×4, or about 5×5×4, or about 10×10×4, or about 15×15×4, or about 20×20×4, or about 25×25×4, or about 30×30×4 or about 35×35×4 or about 40×40×4 or about 45×45×4 or about 50×50×4 or about 55×55×4 or about 60×60×4 or about 65×65×4 or about 70×70×4, or about 1×1×5, or about 5×5×5, or about 10×10×5, or about 15×15×5, or about 20×20×5, or about 25×25×5, or about 30×30×5 or about 35×35×5 or about 40×40×5 or about 45×45×5 or about 50×50×5 or about 55×55×5 or about 60×60×5 or about 65×65×5 or about 70×70×5, or about 1×1×6, or about 5×5×6, or about 10×10×6, or about 15×15×6, or about 20×20×6, or about 25×25×6, or about 30×30×6 or about 35×35×6 or about 40×40×6 or about 45×45×6 or about 50×50×6 or about 55×55×6 or about 60×60×6 or about 65×65×6 or about 70×70×6, or about 1×1×7, or about 5×5×7, or about 10×10×7, or about 15×15×7, or about 20×20×7, or about 25×25×7, or about 30×30×7 or about 35×35×7 or about 40×40×7 or about 45×45×7 or about 50×50×7 or about 55×55×7 or about 60×60×7 or about 65×65×7 or about 70×70×7, or about 1×1×8, or about 5×5×8, or about 10×10×8, or about 15×15×8, or about 20×20×8, or about 25×25×8, or about 30×30×8 or about 35×35×8 or about 40×40×8 or about 45×45×8 or about 50×50×8 or about 55×55×8 or about 60×60×8 or about 65×65×8 or about 70×70×8 or about 1×1×9, or about 5×5×9, or about 10×10×9, or about 15×15×9, or about 20×20×9, or about 25×25×9, or about 30×30×9 or about 35×35×9 or about 40×40×9 or about 45×45×9 or about 50×50×9 or about 55×55×9 or about 60×60×9 or about 65×65×9 or about 70×70×9, or about 1×1×10, or about 5×5×10, or about 10×10×10, or about 15×15×10, or about 20×20×10, or about 25×25×10, or about 30×30×10 or about 35×35×10 or about 40×40×10 or about 45×45×10 or about 50×50×10 or about 55×55×10 or about 60×60×10 or about 65×65×10 or about 70×70×10 cubic microns. Preferably, the voxel is 35×35×5 cubic microns.

A person skilled in the art will also appreciate that the voxel(s) of the reference standard and control sample(s) may be any dimensions. As indicated above, the reference standard(s) and control sample(s) may be the same volume as the test sample or they may be a different volume and the skilled addressee will understand that calculations comparing the test, reference standard(s) and control sample(s) must allow for any variations in volume between the test, reference standards and control samples. Accordingly, as described herein, the pre-defined voxel includes, but is not limited to, a range of about 1 cubic micron to about $8 \times 10^5$ cubic microns. For example, the pre-defined voxel is in the range of about 1 cubic micron to 10,000 cubic microns, or about 10,000 to 100,000 cubic microns, or about 100,000 to 800,000 cubic microns, In one example, the pre-defined voxel is about 1 cubic micron to 10,000 cubic microns, or about 2,000 cubic microns to about 8,000 cubic microns. In another example, the voxel is about 6,125 cubic microns.

The two-dimensional (2D) mapping between the pathological topography and the atomic topography, reveals the relative abundance of manganese.

The method according to any aspect, embodiment or example of the invention optionally includes a step of obtaining or deriving the test sample from a subject. For example, the sample is obtained from a "subject", "participant", or "patient" referred to herein as "subject". The sample may be from a tissue or organ of the subject. The subject as described according to any aspect, embodiment and/or example of the invention includes, but is not limited to, any normal human or mammalian subject or any human or mammalian subject in need of any treatment or prophylaxis as described according to the invention. The subject includes a subject diagnosed with a cancer, or any form of cancer or neoplasm described in accordance with the invention, or suspected of having a cancer, or any form of cancer or neoplasm described in accordance with the invention. It will also be understood by a person skilled in the art that the subject may be undergoing treatment and/or prophylaxis for any disorder including any cancer. The subject may be asymptomatic but has undergone a test or scan indicative of an underlying condition, or may also be symptomatic. The subject includes those undergoing clinical treatment including cancer therapy, or clinical intervention in the form of drugs, chemotherapy, immunotherapy, surgery, radiation or therapeutic devices, or those not yet undergoing any clinical treatment. Mammalian subjects include, but are not limited to, apes, gorillas, chimpanzees, endangered species, stock animals, e.g., cattle, pigs, horses, and companion animals, e.g., dogs and cats.

The control sample according to the invention may be any suitable sample and is preferably a biological sample. For example, the control sample may comprise or be derived from a cell, a population of cells, one or more single celled organism(s), a tissue sample or part thereof, an organ sample or part thereof, one or more cells obtained/derived from a prokaryotic or eukaryotic organism, a population of cells and its associated non-cellular stromal components, a neoplastic cell or population of neoplastic cells, a tissue sample from any organ or tissue from a subject, a tumour wherein the tumour for example, is a solid mass or a "liquid" population of cells, for example, any cancer of the hematopoietic systems including leukemic cells, or the circulating cellular derivatives of solid tumours, or derivatives of cells such as exosomes, including, but not limited to, a cell or population of cells that has metastasized. Preferably, the control sample comprises or is derived from a cell, a population of cells, a "normal" tissue sample, a tissue sample of a tumour/neoplasm of cancers of the testes (e.g., seminoma), lymphoma (e.g., B-cell lymphomas), small cell lung cancers, cancers of the brain (e.g., glioblastoma multiforme/astrocytoma), mesotheliomas, melanomas, and cancers of the breast and prostate.

In another aspect the present invention provides a method of identifying a cancer that is likely to reoccur post radiation treatment comprising:
  (a) quantifying level of manganese in a 3D region of a test sample from the tumour by selecting a 2D region of said test sample, wherein the 2D region is topographically defined by an X':Y' coordinate system, wherein the 3D region corresponds to said 2D region and has a selected height represented by Z, wherein the 3D region is divided into three or more voxels of a pre-defined volume, the volume of each voxel being defined by X×Y×Z;
  (b) measuring the central tendency level of manganese in each voxel;
  (c) identifying in the 2D region corresponding to the X and Y coordinates of the voxel, high metallomic regions (HMRs), being regions in which the level of manganese is higher than in the surrounding areas as enabled by statistical thresholds that are multiples of a central tendency or any approximation between integers;
wherein when the frequency of HMRs is high it is indicative of the likelihood of reoccurrence of the cancer post-radiation treatment, and wherein when the frequency of HMRs is low, it is indicative of the likelihood of non-reoccurrence of the cancer post-radiation.

In another aspect the present invention provides a method according to the invention, wherein the HMRs are also identified in the corresponding 2D region of the test sample stained with a stain that distinguishes cancer cells from others, preferably hematoxylin and eosin (H&E) stain.

In a further aspect, the present invention provides a method of determining the radio-responsiveness of a tumour, the method comprising determining the level of melanin in a test sample from the tumour, wherein the lower the level of melanin the more sensitive the tumour is to radiation and the higher the level of melanin the more resistant the tumour is to radiation.

The method or use according to any aspect, embodiment or example of the invention optionally includes a step of obtaining or deriving the control sample from a subject. For example, the control sample is obtained from a tissue or organ of a "subject", "participant", or "patient" referred to herein as "subject". The subject as described according to any aspect, embodiment and/or example of the invention includes, but is not limited to, any normal human or mammalian subject or any human or mammalian subject in need of any treatment or prophylaxis as described according to the invention. The subject includes a subject diagnosed with a cancer, or any form of cancer or neoplasm/tumour described in accordance with the invention, or suspected of having a cancer, or any form of cancer or neoplasm/tumour described in accordance with the invention. It will also be understood by a person skilled in the art that the subject may be undergoing treatment and/or prophylaxis for any disorder including any cancer. The subject may be asymptomatic but has undergone a test or scan indicative of an underlying condition, or may also be symptomatic. The subject includes those undergoing clinical treatment including cancer therapy, or clinical intervention in the form of drugs, chemotherapy, immunotherapy, surgery, radiation or therapeutic devices, or those not yet undergoing any clinical treatment. Mammalian subjects include, but are not limited to, apes, gorillas, chimpanzees, endangered species, stock animals, e.g., cattle, pigs, horses, and companion animals, e.g., dogs and cats. The control sample may also be obtained from other species including, but not limited to, avian species such as a chicken, duck or goose.

It will be understood by the person skilled in the art that all types of radiation are contemplated in any aspect, embodiment or example described herein for example, photon, or proton based, gamma rays, alpha rays, beta rays. Any type of radiation that ionizes water irrespective of any other primary effects. For example, $^{131}$iodine for internally irradiating rare tumours of the thyroid, or brachytherapy via inserted seeds for prostate cancer using radioactive $^{103}$palladium or $^{125}$iodine, all lead to radiolysis of water via low energy X-rays, or $^{223}$Radium dichloride for metastases to lesions of bone which irradiate via alpha particles. Similarly high dose brachytherapy which involves the temporary insertion of needles containing $^{192}$iridium, operates via exactly the same mechanism. Without being bound to any particular theory, whilst focus in the art has been on DNA repair, it is thought that protein damage may be the issue and DNA problems may be secondary. Various damaging ions cause major cellular problems via damage to proteins.

Common measures of central tendency are the median, arithmetic mean and mode. Any other measures of central tendency known in the art may also be used, including but not limited to geometric mean, medimean, winsorized k-times mean, K-times trimmed mean and weighted mean, and the data may also be transformed prior to calculating a central tendency.

Until the present invention, the clinical importance of manganese had not been recognised and manganese had not been quantified in order to determine the radio-sensitivity/ radio-resistance of a test sample in order to make clinical decisions regarding radiation treatment.

It will be understood that "radiation sensitivity" or "sensitive to radiation" as used herein means that cells are either killed or are disabled such that they do not divide further when exposed to radiation. "Radiation resistant" or "resistant to radiation" as used herein means that one or more cells remains viable after radiation treatment and is/are still able to divide allowing surviving tumour and stromal cells to repopulate the irradiated site—this would be indicative that, if treated with radiation, the primary tumour, or its metastatic derivatives in the subject, is likely to remain capable of growth and/or further metastasis.

It will be understood that the level of manganese in the test sample may be compared to the level of manganese in one or more reference standards(s) to calculate the ATI according to the invention.

The threshold ATI for use according to the invention will be apparent to the person skilled in the art selecting the test sample, reference standard(s) and/or controls for analysis. It will be understood that the ATI threshold or thresholds may be based on known or derived CC/S levels for radio-responsiveness derived from a control sample or samples wherein the control sample or samples comprise cells of the same cancer type as that of the test sample. For example, as shown by example herein, a radio-sensitivity threshold may be set at 2K calibrated counts per second (CC/S) for $^{55}$Mn, which applies to a 35×35×5 cubic micron voxel. The same numerical threshold may be set at 8K CC/S based on a 70×70×5 cubic micron voxel. The threshold may also be set, for example, at 1 standard deviation above the central tendency value (preferably the mean or median) obtained with the radiation sensitive control samples, or 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 or 4.0 standard deviations, or any approximation between integers. A threshold may also be set by empirical determination from different tumour types. As shown by example herein, using melanomas as an example, the threshold may be set at a factor of 1.0×, 1.1×, 1.2×, 1.3×, 1.4×, 1.5×, 1.6×, 1.7×, 1.8×, 1.9×, 2.0×, 2.1×, 2.2×, 2.3×, 2.4× or 2.5× above the central tendency value (preferably the median or mean), or any approximation between integers. A person skilled in the art will appreciate that the threshold will, in most cases, include allowing for the "background" values in a given sample. For example, any test sample ATI that falls below the pre-determined ATI threshold set by reference to the ATI of the radiation sensitive control, is considered to be an indication that the source of the test sample is sensitive to radiation; and any test sample ATI that falls above the pre-determined ATI threshold set by reference to the ATI of the radiation resistant control, is considered to be an indication that the source of the test sample is resistant to radiation.

As a further example, one pre-determined ATI threshold that can be used to measure radio-responsiveness is 2K CC/S, since 87% of the values in FIG. 11A to FIG. 11F for the three radio-sensitive tumour types (seminoma, lymphoma and small cell lung) fall below 2K. For the two tumour types that are clinically agreed to be radio-resistant, namely mesothelioma and brain, 86% of the values in FIG. 11A to FIG. 11F fall above 2K CC/S. However, the skilled addressee will understand that a 2K threshold, while appropriate in some circumstances, may not be in others as there will be variation between patients depending on other factors, such as their genetic background. Thus a radio-sensitive threshold could be set, in some circumstances, at 3K. The accepted clinical reality in oncology is that there are usually two thresholds for any given outcome. Below the first threshold there is one confident outcome, above the second threshold there is a different confident outcome, and between the two thresholds there is an "intermediate zone" that is clinically heterogeneous and where the outcome is varied. In the case of the data in FIG. 11A to FIG. 11F, one could set the two thresholds at 3K and 4K, with the intermediate zone being 3K-4K. These thresholds will become clearer as more metallomic and radiotherapeutic data become available.

It will be clear to the skilled addressee that the invention can also be used to identify voxels within the 3D regions of the invention that have particularly high levels of metals, including manganese. For example, it is also contemplated that by setting the threshold for a voxel to appear as positive for manganese at a relatively high level, regions of high metallomic content can be identified. As used herein, when referring to a specific metal in a High Metallomic Region (HMR), the HMR is designated as e.g., HMR($^{55}$Mn), HMR ($^{66}$Zn), HMR($^{56}$Fe) and HMR($^{63}$Cu) respectively, with HMR($^4$M) referring to the generic case of Any Metal. It will be understood by the skilled addressee that the HMR for any metal (HMR($^4$M)) will minimally contain two adjacent voxels to fulfill the criterion of voxel contiguity. The size of HMR($^4$M) can vary from 2, 3, 4, 5, 6, 7, 8, 9, 10, 11, 12, 13, 14, 15, 16, 17, 18, 19, 20, 21, 22, 23, 24, 25, 26, 27, 28, 29, 30 etc contiguous voxels, to an integer which is the sample size chosen for analysis of that particular tumour.

A person skilled in the art will appreciate that the size of HMR($^4$M) according to the invention is in any range measurable using existing technology. It will be appreciated that the maximum number that can be analysed if a conventional slide is loaded to the edges with tumour material will depend on the voxel size chosen. For example, HMR($^4$M) size can range from 2 voxels to about 800,000 voxels and any value in between based upon a 35×35 (length by breadth) square micron size. By way of illustration only, an empirically chosen 8×8 voxels (35×35 square microns in 2D) efficiently revealed regions of high metallomic content, as shown in the examples. A minimal 8×8 voxel HMR-containing landscape is bounded in both the X' and Y' directions. Thus HMRs above X8×Y8 voxels can individually increase by integers in the X' and Y' 2D directions, yielding HMRs of X[8+1]× Y[8]: X[8]×Y[8+1]: X[8+1]×Y[8+1]: X[8+2]×Y[8]: X[8+2]×Y[8+1]: X[8+2]×Y[8+2]: X[8+1]×Y[8+2]: X[8]×Y[8+2] through X[8+n]×Y[8+n] where n is an integer that can vary from 1 to thousands, but preferably from 1 to 22, when a sample of 30×30 voxels (in 2D representing 1 mm$^2$) is sampled. It will be appreciated that the threshold may be set lower than a minimum of 8 voxels. The value of 8 has been used here because it is an empirically-derived efficient search tool for HMRs.

A person skilled in the art will also appreciate that an HMR can apply to cancer cells in a tumour, or to a region of cellular and non-cellular material, generally referred to as associated stroma, which itself can exist in an "activated" state owing to its interaction with neighbouring cancer cells.

The amount of radiation and/or anti-cancer therapy actually administered according to the invention will typically be determined by a physician in the light of the relevant circumstances, including the condition to be treated, in view of other options such as chemotherapy and immunotherapies, the age, weight, and response of the individual patient, the severity of the patient's symptoms/condition, and the like. The radiation therapy includes, but is not limited to, stereotactic body radiation therapy, fractionated external beam radiation therapy and brachytherapy, the external beam radiation therapies (EBRT) include intensity-modulated radiotherapy, conformal radiation, stereotactic body radiation, proton beam radiation, GammaKnife and CyberKnife, and brachytherapy includes permanent implantation of radioactive isotopic "seeds" as well as temporary high dose radioactivity seeds. The type of radiation delivered to a patient may be photon or proton based, and may be delivered via a linear accelerator, gamma rays (from any source), or via radioactive seeds comprising $^{125}$Iodine, $^{131}$Cesium and $^{133}$Cesium or $^{103}$Palladium, for LDRBT, or $^{192}$Iridium (for High Dose Rate Brachytherapy (HDRBT), or $^{90}$Yttrium resin microspheres or $^{32}$P conjugated to silicon microparticles. The radiation can also be delivered via other entities set out below (Chellan and Sadler, 2015, *Phil. Trans. R. Soc, A.* 373: 20140182)—for example, $^9$Be bound to protein as a neoantigen stimulant of the immune response for immunotherapies combined with radiation; $^{89}$Strontium for osteoblastic bone metastases; $^{223}$Radium for treatment of bone metastases and castration-resistant prostate cancer; $^{47}$Scandium and $^{44}$Scandium as therapeutic radionuclides; $^{59}$Nickel bound to the surface of the MHC and peptides for triggering the immune response of T cells; % Yttrium targeted to somatostatin receptors for cancer treatment; $^{96}$Molybdenum as Molybdate as a preventative antioxidant of lipids and the treatment of breast and oesophageal cancer; $^{101}$Ruthenium delivery to cancer cells via serum transferrin; $^{105}$Rhodium for bone metastases; $^{103}$Palladium as brachytherapy for prostate cancer and choroidal melanoma; $^{178}$Hafnium as nanospheres for efficient uptake by tumour cells and its enhancement of radiation effects for soft tissue sarcomas and head and neck cancer; $^{184}$Tungsten as polyoxotungstates as anticancer agents; $^{188}$Rhenium and $^{186}$Rhenium for small cell lung cancer and prostate cancer; $^{190}$Osmium as a superoxide mimic and organo-osmium arene complexes as anticancer drugs; $^{195}$Platinum in cancer chemotherapy; $^{153}$Samarium for osteosarcoma and metastatic breast cancer to bones; $^{166}$Holmium for internal radiation therapy; $^{175}$Ytterbium labelled polyaminophosphonates for bone metastases; $^{177}$Lutetium labelled peptides and antibodies for small cell lung cancer; $^{225}$Actinium for myeloid cancers and its decay product $^{213}$Bismuth; % Silicon containing phthalocyanine as a photosensitizer for killing cancer cells; $^{212}$Lead generating $^{212}$Bi for radioimmunotherapy in combination with trastuzumab for binding to HER2 and delivering radiation upon internalization of different cancer cell types; $^{32}$P as phosphocol to treat different cancers; $^{75}$Arsenic as As$_2$O$_3$ for promyelocytic leukemia, unresectable hepatocellular carcinoma and non-small-cell lung cancer; $^{213}$Bismuth labelled lintuzumab for targeted radiotherapy of Acute Myeloid leukemia; $^{79}$Selenium for chemoprotection of prostate cancer; $^{127}$Iodine and $^{131}$Iodine for thyroid cancer; and $^{211}$Astatine for elimination of tumor cells in the brain and in recurrent ovarian cancer. In another example, the substance includes a radiosensitizer, such as, but not limited to boron ($^{10}$B), Rose Bengal, 2-deoxy-D-glucose, or immunotherapeutic additions that are combined with radiation (Sharabi et al., *Oncology* [Williston Park] 2015, 29(5), pii:211304; Formenti, *J Natl Cancer Inst* 105, 256-265, 2013).

In the context of the present invention, the letters X', Y' and Z in the term "X'×Y'×Z" refer to the dimensions of a "3D region" of the sample and "X'×Y'×Z" relates to length× breadth×height of the 3D region which provides a volume of the 3D region.

In the context of the present invention, the letters X, Y and Z in the term "X×Y×Z" refer to the dimensions of a voxel within a "3D region" of the sample and "X×Y×Z" relates to length×breadth×height of the voxel which provides a volume of the voxel.

Accordingly, in the context of the present invention, where terms such as "35×35×5" appear, they relate to a length×breadth×height and provide a measure of volume; whereas when terms "35×35" appear they relate to length× breadth and provide an area (2D).

In another aspect, the present invention provides a method of determining radio-responsiveness of a melanoma, the method comprising determining the level of melanin in a test sample from the melanoma, wherein the lower the level of melanin in the test sample the more sensitive the melanoma is to radiation and the higher the level of melanin in the test sample the more resistant the melanoma is to radiation.

In another aspect, the present invention provides a method of determining radio-responsiveness of a melanoma, the method comprising comparing the level of melanin in a test sample from the melanoma to a pre-determined melanin threshold wherein the radio-responsiveness of the melanoma is determined by assessing whether the level of melanin in the test sample is above or below the melanin threshold, wherein if the level of melanin in the test sample is below the melanin threshold the melanoma is determined to be sensitive to radiation; and wherein if the level of melanin in the test sample is above the melanin threshold the melanoma is determined to be resistant to radiation.

In one or more embodiments, the level of melanin in the test sample is compared to two pre-determined melanin thresholds wherein the radio-responsiveness of the melanoma is determined by assessing whether the level of melanin in the test sample is above or below the two thresholds, and wherein if the melanin in the test sample is below the lower melanin threshold the melanoma is determined to be sensitive to radiation;

wherein if the melanin in the test sample is above the higher melanin threshold the melanoma is determined to be resistant to radiation; and wherein if the melanin in the test sample is between the two melanin thresholds, the melanoma is determined to be partially sensitive to radiation.

It is well within the competence of the skilled addressee to set the pre-determined melanin threshold. Voxels containing melanin concentrations in a section can first be determined using metal-labelled melanin antibodies to the section that is ablated via any form of elemental analysis (such as LA-ICP-MS), while simultaneously measuring $^{55}$Mn levels in the same voxels. Voxels that contain a level of melanin that exceeds a threshold level of the same metal labelled antibody applied to an amelanotic melanoma sample, are informative. The percentage of melanotic voxels within a test sample, together with a weighted median of those voxels provides a radio-protective index. The skilled addressee will note that thresholds for melanin can be set in the same general manner as for the ATI in terms of a central tendency, preferably the median or mean, in appropriate units. It should also be noted that $^{55}$Mn may be measured simultaneously in the same voxels as those analyzed for melanin.

For example, the threshold could be set at the mean or median of melanin levels in melanomas from a cohort that has responded differently to radiation treatment (i.e. some were sensitive and some resistant). Alternatively, two thresholds could be set in which case, as an example, they could be set at one or at two standard deviations from the mean of melanin levels in a set of melanomas that have responded differently to radiation treatment eg a cohort in which there is an equal number of radiation resistant and radiation sensitive melanomas.

In another aspect, the present invention provides a method of treating melanoma in a subject comprising performing the method of the invention on a test sample from the subject, and including radiotherapy in treating said melanoma in the subject if the melanoma is determined to be sensitive to radiation.

In another aspect, the present invention provides a method of treating melanoma in a subject comprising, performing the method of the invention on a test sample from the subject, and not including radiotherapy in treating said melanoma in the subject if the melanoma is determined to be resistant to radiation.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each aspect, embodiment and/or example of the invention described herein is to be applied *mutatis mutandis* to each and every aspect, embodiment and/or example unless specifically stated otherwise.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purpose of exemplification only. Functionally-equivalent products, compositions and methods are clearly within the scope of the invention, as described herein.

It will be acknowledged by the skilled addressee that the methods of the present invention are not in any way routine or conventional in a clinical therapeutic content. The precision that the present invention provides currently does not exist. Distinguishing tumour types (in particular the eight tumour types exemplified) on the basis of, for example, LA-ICP-MS is entirely new; the results are unexpected and could not have been predicted from the prior art.

BRIEF DESCRIPTION OF THE DRAWINGS

FIG. 3B. The calibrated signal of each of three metals $^{55}$Mn, $^{66}$Zn, and $^{56}$Fe are shown for each voxel of three contiguous ablation tracks from a tissue section that ablated 70 voxels per track.

FIG. 4A. Photographic image of an H&E stained 5 micron tissue section from a block of a 19 year old human female with a brain neoplasm classified as glioblastoma multiforme.

The H&E stained area shown in the Figure corresponds to the equivalent unstained area analysed by LA-ICP-MS on a different slide. FIG. 4B. The calibrated signal of each of three metals $^{55}$Mn, $^{66}$Zn, and $^{56}$Fe are shown for each voxel of three contiguous ablation tracks from a tissue section that ablated 68 voxels per track.

FIG. 5B. The calibrated signal of each of three metals $^{55}$Mn, $^{66}$Zn and $^{56}$Fe are shown for each voxel of three contiguous ablation tracks from a tissue section that ablated 69 voxels per track.

FIG. 6A. Photographic image of an H&E stained 5 micron tissue section from a 60 year old human male with malignant mesothelioma. FIG. 6B. The calibrated signal of each of four metals $^{55}$Mn, $^{66}$Zn, $^{56}$Fe and $^{63}$Cu are shown for each voxel of three contiguous ablation tracks from a tissue section that ablated 67 voxels per track.

FIG. 7B. The calibrated signal of each of three metals $^{55}$Mn, $^{66}$Zn and $^{56}$Fe are shown for each voxel of three contiguous ablation tracks from a tissue section that ablated 68 voxels per track.

FIG. 8A. Photographic image of an H&E stained 5 micron tissue section from a 57 year old male with diffuse B-cell lymphoma. FIG. 8B. The calibrated signal of each of three metals $^{55}$Mn, $^{66}$Zn and $^{56}$Fe are shown for each voxel of three contiguous ablation tracks from a tissue section that ablated 79 voxels per track.

FIG. 9A. Photographic image of a representative H&E stained 5 micron tissue section from a 38 year old male with a small cell undifferentiated malignant carcinoma of the lung. FIG. 9B. The calibrated signal of each of three metals $^{55}$Mn, $^{66}$Zn and $^{56}$Fe are shown for each voxel of three contiguous ablation tracks from a tissue section that ablated 65 voxels per track.

FIG. 10A. Photographic image of a representative H&E stained 5 micron tissue section from a 52 year old male with seminoma. FIG. 10B. The calibrated signal of each of three metals $^{55}$Mn, $^{66}$Zn and $^{56}$Fe are shown for each voxel of three contiguous ablation tracks from a tissue section that ablated 79 voxels per track.

FIG. 12: Two-dimensional representation of laser ablation tracks across the top part of the tissue section shown in FIG. 1 of one of the melanoma patients whose tumour had two major lineages within it. Scale; right hand side, (dark grey), 0-15,000; middle, (whitish), 15,000-45,000; left hand side, (pale grey), 45,000-150,000 calibrated counts per second.

15C. Two-dimensional representation of $^{55}$Mn levels in individual voxels of the section of A and B were further analyzed by applying a threshold of 2× the median value per voxel of the whole area, (plus the machine background value). Black squares show those voxels that are above this particular (2× median) threshold.

FIG. 17A to FIG. 17H. Two-dimensional representation of the distribution and emergence of HMRs ($^{55}$Mn) in voxel matrices generated via LA-ICP-MS using different threshold criteria. The four left hand side panels (FIG. 17A:T1, FIG. 17B:T2, FIG. 17C:T3 and FIG. 17D:T4) show data from laser ablation of a 31×31 voxel area from a standard unstained 5 micron tissue section of a small cell undifferentiated carcinoma of the lung from a 51 year old female patient. The four right hand side panels (FIG. 17E:T1, FIG. 17F:T2, FIG. 17G:T3 and FIG. 17H:T4) show data from laser ablation of a 31×31 voxel area of the 54 year old melanoma patient described in FIG. 14A-FIG. 14B, FIG. 15A-FIG. 15D, and FIG. 16A-FIG. 16C. The $^{55}$Mn threshold values applied to the voxel matrix data are; T1, 0.5× median; T2, 1× median; T3, 1.5× median and T4, 2× median. Dark voxels in each panel are those in which $^{55}$Mn values exceed the threshold for that panel. Single non-contiguous voxels above threshold are designated as singletons, while two contiguous voxels are designated as doublets.

FIG. 18A to FIG. 18H. Two-dimensional representation of the distribution and no emergence of HMRs($^{66}$Zn) in voxel matrices generated via LA-ICP-MS for the same samples from the two patients of FIG. 17A-FIG. 17H. The four left hand side panels (FIG. 18A:T1, FIG. 18B:T2, FIG. 18C:T3 and FIG. 18D:T4) show data from laser ablation of the same 31×31 voxel area as in FIG. 17A-FIG. 17H which was simultaneously analyzed for $^{66}$Zn, $^{56}$Fe and $^{63}$Cu. The data for $^{66}$Zn are shown. The four right hand side panels (FIG. 18E:T1, FIG. 18F:T2, FIG. 18G:T3 and FIG. 18H:T4) show data from laser ablation of the same 31×31 voxel area as in FIG. 17A-FIG. 17H. The $^{66}$Zn threshold values applied to the voxel matrix data are as used previously; T1, 0.5× median; T2, 1× median; T3, 1.5× median and T4, 2× median. Dark voxels in each panel are those in which $^{66}$Zn values exceed the threshold for that panel.

FIG. 19A: The top histogram illustrates 14 patients with tumours without HMRs($^{55}$Mn). FIG. 19B: The lower histogram shows tumours with HMRs ($^{55}$Mn) from six patients denoted t1 through t6 which were determined at the standard T4 threshold of 2× median. Black squares are the median values of the HMRs($^{55}$Mn) found in the tumour from each of patients t1 to t6 determined using the standard T4 threshold of 2× median. The HMR($^{55}$Mn) values are joined via a dotted line to the bulk median $^{55}$Mn value of that tumour for each of patients t1 to t6. The bins in the histogram are 200 CC/S units.

FIG. 20A-FIG. 20H: Schematic representation of the size, shape and content of a selected sample of contiguous voxel configurations in a simulated 2D tumour landscape. Voxels containing cancerous cells above a designated threshold are shown in black. FIG. 20A illustrates the position of all eight possible voxel configurations when only voxel doublets are examined. FIG. 20B and FIG. 20E illustrate one of the many possible contiguous voxel configurations that satisfy the criterion of an 8×8 above threshold HMR($^A$M), where $^A$M represents Any Metal. FIG. 20C illustrates a voxel configuration that is only 7×7 voxels which would fall below an 8×8 minimal threshold. FIG. 20D and FIG. 20F illustrate voxel configurations that would be characteristic of lymphatic vessels or ducts. FIG. 20G illustrates a voxel configuration that is characteristic of "single file" movements of cancerous cells, or of significant machine "stutter". FIG. 20H is characteristic of the multiple voxel configurations seen in some melanomas where the voxels above threshold can be due either to cells with high levels of any metal, or melanin granules that bind any metal.

FIG. 22A. The top histogram illustrates the 51 seminomas without HMRs($^{55}$Mn). FIG. 22B. The lower histogram shows tumours with HMRs($^{55}$Mn) from four patients denoted S4 through S7 which were determined at the standard T4 threshold of 2× median. Black squares are the median values of the HMRs($^{55}$Mn) found in the tumour from each of patients S4 to S7. The HMR($^{55}$Mn) values are joined via a dotted line to the bulk median $^{55}$Mn value from the tumour of each of patients S4 to S7. The bins in the histogram are 200 CC/S units. Patients denoted S1, S2 and S3 are outliers with high median values, even though their tumours do not contain HMRs($^{55}$Mn) under the standard threshold.

FIG. 23A. The top histogram illustrates 9 tumours without HMRs($^{55}$Mn). FIG. 23B. The lower histogram shows a tumour with a single HMRs($^{55}$Mn) determined at the standard T4 threshold of 2× median. The black square is the median value of the HMR ($^{55}$Mn) found in the tumour of one mesothelioma patient. The HMR($^{55}$Mn) value is joined via a dotted line to the bulk median $^{55}$Mn value of that tumour. The bins in the histogram are 200 CC/S units.

FIG. 24A. The top histogram illustrates 24 tumours without HMRs($^{55}$Mn). FIG. 24B. The lower histogram shows a tumour with a single HMRs($^{55}$Mn) determined at the standard T4 threshold of 2× median. The black square is the median value of the HMR ($^{55}$Mn) found in that tumour. The HMR($^{55}$Mn) value is joined via a dotted line to the bulk median $^{55}$Mn value of that tumour. The bins in the histogram are 200 CC/S units.

FIG. 25A. The top histogram illustrates the tumours without HMRs($^{55}$Mn). FIG. 25B. The lower histogram shows the tumours with HMRs($^{55}$Mn) determined at the standard T4 threshold of 2× median. Black squares are the median values of the HMRs($^{55}$Mn) found in the tumours. The HMR$^{55}$Mn) values are joined via a dotted line to the bulk median $^{55}$Mn value of that tumour. Some tumours have multiple HMRs($^{55}$Mn) and these are shown on the same dotted line for that tumour. The bins in the histogram are 200 CC/S units. Note that the scale has been compressed since many CC/S values exceed values of 10,000.

FIG. 28A-FIG. 28C: Histograms showing median $^{55}$Mn contents expressed as Calibrated Counts per Second (CC/S) of $^{55}$Mn in laser ablated samples from a total area of approximately 1,800 voxels of the tumours of 64 patients with melanoma. As described previously, two of the 64 patients each had two major lineages within their tumours, and each such lineage is represented separately in the histogram with a square. The melanoma samples have been grouped into those that derive from the primary site (FIG. 28A: top histogram), those that derive from lymph nodes, (FIG. 28B: middle histogram), and those that derive from a distant site (FIG. 28C: lower histogram).

FIG. 31A-FIG. 31B: Histograms of median $^{55}$Mn contents expressed as Calibrated Counts per Second (CC/S) of $^{55}$Mn in laser ablated samples from tumours of 15 patients with breast cancer. Each grey square represents the median value calculated from a total area of approximately 1,800 voxels of the tumour of a single patient. FIG. 31A. The top histogram illustrates 4 tumours without HMRs($^{55}$Mn). FIG. 31B. The lower histogram shows 11 tumours with HMRs ($^{55}$Mn) determined at the standard T4 threshold of 2× median. Black squares are the median values of the HMRs ($^{55}$Mn) found in the tumour of each of the 11 patients. The HMR$^{55}$Mn) values are joined via a dotted line to the bulk median $^{55}$Mn value of that tumour. Some tumours have multiple HMRs($^{55}$Mn) and these are shown on the same dotted line for that tumour. The bins in the histogram are 200 CC/S units.

FIG. 33A-FIG. 33H: Two-dimensional representation of distribution and emergence of HMRs($^{55}$Mn), but no emergence of HMRs($^{66}$Zn) in voxel matrices generated via LA-ICP-MS using different threshold criteria from the 39 year old female in FIG. 32A-FIG. 32B. The four left hand side panels (FIG. 33A:T1, FIG. 33B:T2, FIG. 33C:T3 and FIG. 33D:T4) are $^{55}$Mn data from laser ablation of a 31×31 voxel area from carcinoma of the breast at the different standard thresholds, (T1, 0.5× median; T2, 1× median; T3, 1.5× median and T4, 2× median). The four right hand side panels (FIG. 33E:T1, FIG. 33F:T2, FIG. 33G:13 and FIG. 33H:T4) are $^{66}$Zn data from laser ablation of the identical 31×31 voxel area and the same threshold criteria. Dark voxels in each panel are those in which $^{55}$Mn or $^{66}$Zn values exceeded the threshold for that panel.

FIG. 34A shows the right hand side Skew of the $^{55}$Mn voxels, with the frequency of voxels in a particular bin on the Y axis, and voxel values on the X axis. FIG. 34B illustrates the near symmetrical distribution of $^{66}$Zn voxel values from the same sample.

FIG. 36A and FIG. 36B are photographic images of a standard 5 micron H&E stained tissue section from a formalin-fixed paraffin-embedded block from an invasive ductal carcinoma of the breast from the 48 year old female of FIG. 35A-FIG. 35B, illustrating the heterogeneous tissue and cellular morphology. FIG. 36C to FIG. 36F. 2D relief images of the differential distribution of the four metals $^{55}$Mn (C), $^{66}$Zn (D), $^{56}$Fe (F) and $^{63}$Cu (E) in the areas containing adipocytes and in some parts of the stromal regions.

FIG. 37A. Illustration of the clinical data from patient X with adenocarcinoma of the prostate and a PSA of 8.1 showing the abnormalities in different regions of the prostate with 7 out of 12 regions showing changes of little significance, and five regions with "cancer" as defined by Gleason scores no higher than 7 (FIG. 37A). FIG. 37B. Diagnostic summary (Part A through Part L) of the extent of involvement of the twelve core needle biopsies from patient X.

FIG. 39B. MRI of the same brain region after radiation and immunotherapeutic drug treatment.

FIG. 40: The calibrated signal tracks (arrowed →) of $^{55}$Mn from five separate areas of cancerous cells of the primary melanoma of patient Y. There were six contiguous ablation tracks of standard 35 micron×35 micron×5 micron voxels in each chosen area, with track lengths of 19, 19, 13, 19 and 19 voxels respectively. The raw numerical values of calibrated counts per second for $^{55}$Mn are shown for each of the adjacent voxels in each of six ablation rows.

DETAILED DESCRIPTION OF PREFERRED EMBODIMENTS

Figure 1:
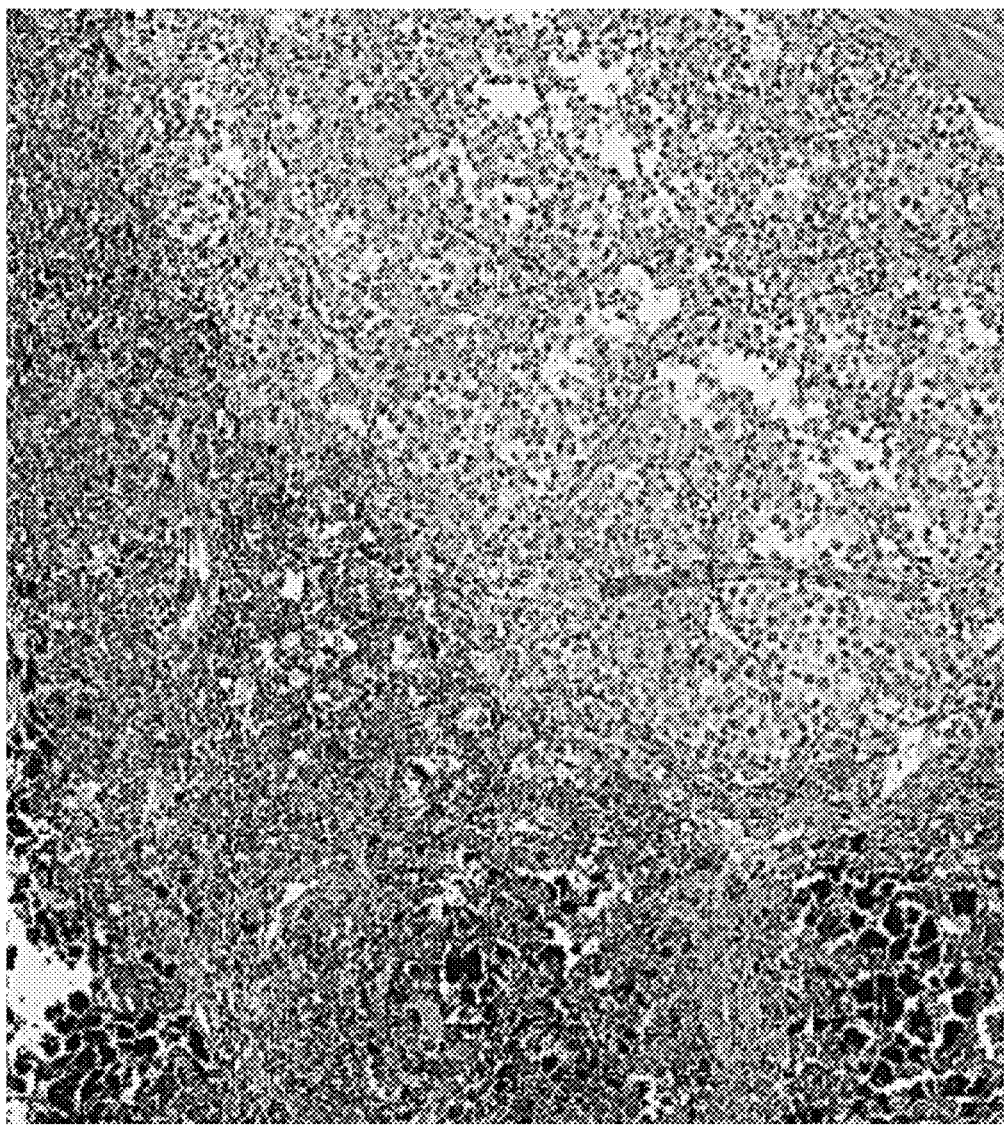
FIG. 1: Photographic image of a standard 5 micron, H&E stained tissue section from a formalin-fixed paraffin-embedded (FFPE) block from a stage Ib malignant melanoma of the neck of a 48 year old male, with the TNM staging criteria of T2aN0M0, where T2 represents invasion of the muscularis propria; N0 represents no lymph node metastasis, and M0 represents no distant metastasis. Note that the top right-hand side of this section consists of pale amelanotic tumour cells, while the darker regions on the left-hand side and bottom of the Figure are composed of cells containing darkly staining melanin, and with even larger patches of melanin, both intra- and extra-cellular, as black spots in the lower part of the image.

In work leading up to the present invention the inventor noted that the 2D spatial characteristics of many tumours, in particular, melanoma, varies greatly, e.g., as shown in FIG. 1 for comparative purposes. FIG. 1 shows a standard 5 micron, H&E stained tissue section from a formalin-fixed paraffin-embedded (FFPE) block from a stage Ib malignant melanoma of the neck of a 48 year old male, with the TNM staging criteria of T2aN0M0, where T2 represents invasion of the muscularis propria; N0 represents no lymph node metastasis, and M0 represents no distant metastasis. Note that the top right-hand side of this section consists of pale amelanotic tumour cells, while the darker regions on the left-hand side and bottom of the Figure are composed of cells containing darkly staining melanin, and with even larger patches of melanin, both intra- and extra-cellular, as black spots in the lower part of the image. As described above herein, the pathological diagnosis of such tumours, which is utilized to determine treatment modalities, and upon which the decision is made as to whether or not radiation will be used, is the subjective analysis of such H&E stained slides. Whilst the pathological diagnosis is also aided by probing such tissue sections with a panel of antibodies that vary from one type of tumour type to the next, such results are also subjective and far from quantitative. Until the present invention, there was no quantitative test available, or a test that predicts sensitivity or resistance to radiation, that aids the oncologist in making a decision on whether or not to utilize radiation as part of a treatment regimen.

In particular, the Lancet Oncology Commission recently presented new evidence on the issues involved in expanding global access to radiotherapy (Atun et al., *Lancet Oncology* 2015, 16, 1153-1186). It highlighted radiotherapy as a fundamental component of effective cancer treatment and control and that it is generally used sub-optimally. The Lancet editors pointed out that radiotherapy is more scalable than other treatment modalities and is uniquely placed to deliver effective curative and palliative care (Coburn & Collingridge, *Lancet Oncology*, 2015, 16, 1143). However, there are two continuing roadblocks to tailoring radiotherapy to the needs of the individual patient.

First, and not until the present invention, there has been no "quantitative test" that measures the extent to which a given tumour, in a given patient, will respond to a given regimen of radiotherapy.

Second, there has been no "quantitative test" that measures the extent to which any tumour is likely to reoccur following radiation therapy.

Until the present invention, clinical decisions were based on medical art, not quantitative measures to determine radiation responsiveness.

Without being bound to any particular theory, the inventor advances the following explanation for the unexpected finding that ATI could be used to predict radiation responsiveness:

ionizing radiation, such as gamma-rays and X-rays lead to the radiolysis of water which leads to the formation of the same type of chemical entities in all cells, be those cells bacterial, algal, fungal, invertebrate, or the hundreds of cell types in a human body, or abnormal cell types which arise as a result of perturbations leading to cancerous cells.

Radiolysis universally generates the same types of reactive molecules, the three key ones being;

the hydroxyl radical OH., the superoxide radical $O_2.^-$ and hydrogen peroxide ($H_2O_2$), (Daly, M; *Nature Reviews Microbiology*, 7, 237-245. 2009).

In normal healthy mammalian cells that have not been irradiated, the same three molecules are also formed as part of the normal mitochondrial respiratory processes occurring via the mitochondrial electron transport chain. If oxygen receives less than its full complement of electrons, the result is the formation of $O_2.^-$ and $H_2O_2$. If the $H_2O_2$ is not dealt with immediately, any stray iron $Fe^{2+}$ atoms will react with it and generate the highly dangerous hydroxyl radical OH.

In mammalian cells, the superoxide radical $O_2.^-$ is handled by mitochondrial, cytosolic and extracellular enzyme systems, namely manganese superoxide dismutase MnSOD located in the mitochondrion, copper-zinc superoxide CuZnSOD in the cytosol and extracellular superoxide dismutase ecSOD predominantly anchored to endothelial cells.

The $H_2O_2$ is cleared by both catalases and glutathione peroxidases to produce water and molecular oxygen.

The highly dangerous hydroxyl radical OH. is not dealt with by enzymological processes. One example of the consequences of the high level of oxidative metabolism is in the mammalian brain, where it makes brain cells very vulnerable to lipid peroxidation from OH.

The inventor reasoned that the chemical elements and levels of elements contributes to radio-responsiveness, for example manganese. The inventor noted that whilst a whole body exposure of 10 Gray (Gy) is lethal to most vertebrates, some bacteria such as *D. radiodurans* survive doses in excess of 17,000 Gy. One contributing mechanism by which it may achieve this is that it accumulates 150 times more manganese and 3 times less iron (Fe) than radiation sensitive bacterial species (Daly, M; *Nature Reviews Microbiology*, 7, 237-245, 2009). Bacterial species with the highest manganese-to-iron ratios are the most radioresistant, whereas those with the lowest Mn/Fe ratios are hypersensitive. The mechanistic underpinnings of radio-responsiveness reveal that manganese accumulation shields proteins with iron-sulphur (Fe—S) complexes from superoxide radicals such as ($O_2.^-$) formed during irradiation. This shielding by manganese prevents the release of ferrous ions ($Fe^{2+}$) from iron-sulphur containing proteins, thus preventing the highly damaging interactions of $Fe^{2+}$ with hydrogen peroxide. If $Fe^{2+}$ manages to react with $H_2O_2$, the result is an hydroxyl radical OH. which is dangerous and will oxidize almost every type of biological molecule.

In contrast to hydrogen peroxide, $O_2.^-$ does not easily cross membranes and hence builds up in cellular compartments. Thus any cellular system that can effectively shield Fe—S containing proteins from exposure to the $O_2.^-$ as well as minimizing the amount of $Fe^{2+}$ available for the Fenton reaction will minimize damage following irradiation and enhance radio-resistance. The inventor reasoned that the bacterial data indicate that the manganese ion is a protective metal and even at high concentrations is largely innocuous to a bacterial cell, and likely well tolerated by many cell types of multi-cellular organisms. Conversely, any bacterial system that is low in manganese and high in free iron is likely less able to protect proteins and lipids from damage and the Fenton reaction will ensure that the damaging OH. will increase its level leading to protein and lipid damage and death of the cell, hence cellular radio-sensitivity. A similar situation will pertain to eukaryotes.

The intracellular availability of free iron is known to play a key role in irreversible protein damage via protein carbonylation. In yeast, carbonylation levels are increased when yeast lack a particular iron storage protein, the homolog of which is the human mitochondrially located frataxin protein. Introduction of the human ferritin into such a defective yeast strain, partially restores the iron storage capacity of such yeast, decreases free iron levels and counteracts the elevated carbonylation levels. Thus, iron storage proteins are likely to be important players in preventing cellular damage following ionizing radiation.

It is noted that although the superoxide radical $O_2.^-$ is highly charged, it does not react with DNA. Rather, it reacts with selected targets, these being any exposed iron-sulphur (Fe—S) groups of certain proteins.

In summary, OH. is extremely damaging to all cellular components, but the collateral damage it causes is restricted to a few Angstroms from its site of formation owing to its short lifetime. $H_2O_2$ by contrast, can diffuse throughout the cell and reacts with $Fe^{2+}$, yielding one of the most powerful oxidizing reactions known. This reaction produces more OH. The bacterial data reveal that responsiveness to ionizing radiation is a continuous biological variable, which has multiple inputs: from cellular manganese concentration and from the associated enzymology that scavenges radicals, sequesters free iron, reduces hydrogen peroxide and minimizes and remanufactures proteins.

In vitro systems have demonstrated that the human manganese superoxide dismutase converts the superoxide radical $O_2.^-$ to $H_2O_2$ and $O_2$. In a number of human in vitro cellular systems, human MnSOD protein levels and activity have been correlated with an increased resistance to ionizing radiation. Similarly, lowering the level of MnSOD protein and activity in cellular systems results in decreased radio-resistance.

Thus, in carefully controlled experimental circumstances, where the genetic background of the experimental and control cells is kept constant, and the only variable is either the introduced gene, its antisense product, or an empty vector, the mitochondrially-located MnSOD protein helps to protect cells from the effects of ionizing radiation.

There are only three superoxide dismutases in human cells that handle the superoxide radical $O_2.^-$ and these superoxide dismutases all have different cellular locations. Manganese superoxide dismutase MnSOD is located in the mitochondrion, copper-zinc superoxide CuZnSOD is found in the cytosol and the nucleus, while extracellular superoxide dismutase ecSOD is predominantly anchored to endothelial cells. The three superoxide dismutases deal with $O_2.^-$ in these three different locations.

Whilst much attention has been focussed on superoxide dismutases, the basic chemistry and biochemistry of chemical elements, such as Mn and Cu, their location and usage within a cell is far more widespread than the specificity of superoxide dismutases e.g., Mn exists in complex formation (Daly et al., PLoS ONE, 5, e12570, 2010; Slade and Radman, Microbiology and Molecular Biology Reviews, 75, 133-191, 2011).

Figure 2:
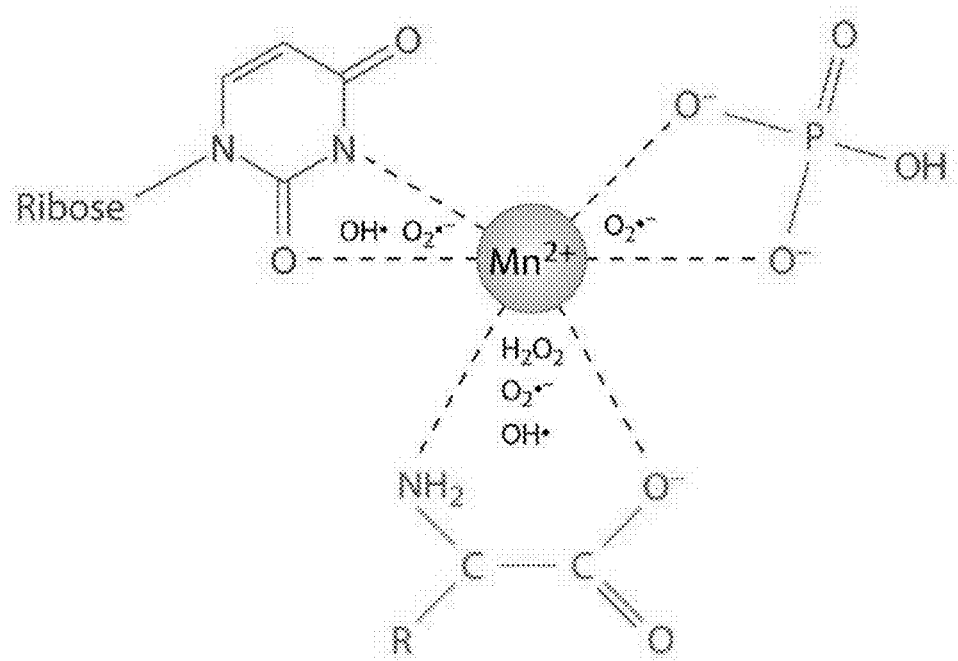
FIG. 2: Illustration of three different manganese-based binding entities. It should be noted that a single $^{55}$Mn$^{2+}$ does not bind all three entities at once (this figure is for illustrative purposes only—taken from Slade and Radman, *Microbiology and Molecular Biology Reviews*, 75, 133-191, 2011.)

FIG. 2 illustrates three different manganese-binding entities. Manganese forms complexes with orthophosphate and scavenges $O_2.^-$. Manganese also forms complexes with free amino acids or peptides to scavenge and decompose hydrogen peroxide, hydroxyl radicals (OH.) and $O_2.^-$. Nucleosides, free amino acids and sundry organic metabolites scavenge hydroxyl radicals (Slade and Radman, Microbiology and Molecular Biology Reviews, 75, 133-191, 2011).

Inorganic metals, such as, iron, copper, zinc and manganese are most commonly thought of as catalytic cofactors for proteins.

Notwithstanding the foregoing suggestion that metals play a role in radio-resistance, until the present invention, manganese has not been quantified in a 2D cancerous context of a tumour compared to normal, whereby the radio-sensitivity/radio-resistance is determined and subsequently utilized to firstly make decisions regarding radiation treatment, and secondly, to predict the probability of tumour reoccurrence after radiation treatment.

All the hardware and software for carrying out the invention are currently available both commercially and clinically. It will be apparent to a person skilled in the art that technological variations may be useful. Preparation of the tissue sections, cells or populations of cells for analysis according to the invention may be performed according to any known method in the art. For example, unstained tissue sections, unstained frozen sections, or cells deposited as a monolayer via a SurePath system are prepared according to the art and for example, as described herein. Any system available in the art may be used, e.g., the SurePath system yields a monolayer of cells on a slide in a compact circular area, and material prepared in this manner would be suitable for LA-ICP-MS methodology. Any method known in the art may be used to prepare the test sample and/or control sample of the invention provided the 2D integrity has not been lost. A number of ablation tracks can be made, e.g. via laser ablation-Inductively coupled plasma-mass spectrometry (LA-ICP-MS), laser ablation-time-of-flight-mass spectrometry (LA-TOF-MS), inductively coupled plasma-optical emission spectroscopy (ICP-OES), microwave plasma-atomic emission spectroscopy (MP-AES), laser induced break down spectroscopy (LIBS), secondary ion mass spectrometry (SIMS), X-ray absorption near edge structure (XANES), atomic absorption spectroscopy (AA) or X-ray fluorescence (XRF).

If the values within a single or multiple ablation tracks all fall either above, or below, a designated threshold, there is no need for an examination by a pathologist. Conversely, for any tracks that are flagged by the computer software, then the companion stained slide is examined by a pathologist.

Alternately, a slide is first examined by a pathologist, who would direct where the preferred ablation tracks should be done.

It should be noted that a single ablation track (of width less than 110 microns) would ablate a 1 cm track of tumour tissue in about 70 seconds. In this respect, multiple tracks across a tumour sample, or multiple dispersed areas within the tumour, located and designated by a pathologist for subsequent ablation analysis, may be run in minutes with current technology.

Laser Ablation-Inductively Coupled Plasma-Mass Spectrometry (LA-ICP-MS), was originally introduced by Gray, *Analyst,* 110, 551-556. 1985, employing a ruby laser. This was subsequently superseded by solid state Nd:YAG and excimer-based lasers. The use of the former is described in Hare, D, et al., *Analyst* 134, 450-453. 2009 (Table 1 of Hare et al. for operational parameters). In regard to excimer lasers, the beam is generated by a gas mixture which is a combination of the noble gases (argon, krypton or xenon) with a reactive gas, such as chlorine or fluorine. Under high pressure and electrical stimulation, a pseudo molecule, (XeCl, KrF or ArF), termed exciplex, is created which gives rise to laser light in the ultraviolet.

A popular excimer-based system in the context of the LA-ICP-MS, is the Agilent 7700 ICP-MS coupled to a New Wave excimer generating a 193 nanometer wavelength, the laser being first used by Gunther et al., *J. Anal. At. Spectrom.* 12, 939-944, 1977. The elemental analysis of free ions is performed on a LA-ICP-MS, e.g., using ICP-MS instrument Agilent Technologies 7700 series which is interfaced with a New Wave Research Excimer 193 laser ablation unit. In addition, the ICP-MS Instrument is fitted with an octopole collision/reaction cell. Other ICP-MS instruments are also available including Thermofisher's iCAP™ Q ICP-MS, Perkin Elmer's Nexion Series, Shimadzu ICP-MS 2030, and Tofwerk's ICP-TOF-MS. Instead of an ICP-MS system, the ATI may also be determined with atomic emission spectroscopy techniques such as inductively coupled plasma-optical emission spectroscopy (ICP-OES), microwave plasma-atomic emission spectroscopy, or laser induced break down spectroscopy (LIBS), or secondary ion mass spectrometry (SIMS), or X-ray absorption near edge structure (XANES), or atomic absorption spectroscopy (AA), or X-ray fluorescence (XRF)

High purity liquid argon (Ar) is used as the carrier gas and plasma source, while ultra-high purity (99.999%) hydrogen (H2) is used as the reaction gas. The LA-ICP-MS system is tuned on a daily basis and for both standard mode and reaction mode using NIST 612 Trace Elements in Glass for maximum sensitivity and to ensure low oxide formation. Low oxide production is assured by measuring a mass-to-charge ratio (m/z) of 248/232 (representing $^{232}Th^{16}O^+/^{232}Th^+$) and is consistently less than 0.3%. The instrument is fine-tuned for tissue analysis using matrix-matched tissue standards.

Typical operational parameters for the LA-ICP-MS system are given below, and for clarity, they are shown separately for the 7700 ICP-MS and for the laser.

ICP-MS Parameters.

The radio frequency power is 1250.0 Watts; the cooling gas flow rate is 15.0 liters/minute; the carrier gas flow rate is 1.2 liters per minute, the sample depth is 4 millimeters; the quadrupole bias is −3.0 Volts; the octopole bias is −6.0 Volts; the dwell time is 62 milliseconds per m/z; extraction lens 1 is 5.0 Volts; extraction lens 2 is −100.0 Volts and the hydrogen collision gas is 3.1 milliliters per minute.

Parameters of the New Wave 193 Excimer Laser.

Wavelength 193 nanometers; repetition frequency 40 Hertz; laser energy density 0.3 to 0.5 Joules per square centimeter; spot diameter 35 micrometers; line spacing 35 micrometers; monitored mass/charge ratio (m/z), 55 (Mn), 56 (Fe), 63 (Cu) and 66 (Zn). The raster speed is 140 micrometers per second (four times 35 micrometers).

In brief, a glass microscope slide with an unstained section from a particular tissue is placed in an ablation chamber and a high energy laser beam (of varying diameter) is focussed onto the section and some of the biological material is vaporized as a result of energy transfer from the laser beam. The resulting particulate matter is moved by a carrier gas, which is usually Argon, Helium, or Argon plus Helium (in the system used for one embodiment of this invention, it is Argon), into the Inductively Coupled Plasma which, at a temperature exceeding 7,000 degrees Celsius, but below 10,000 degrees Celsius, atomizes and ionizes the particulate matter to its constituent elements. The use of collision/reaction cells (Tanner et al., *Spectrochim. Acta.* Part B, 57, 1361-1452, 2002) minimizes spectral interferences, and "removes" polyatomic ions such as oxygen:argon species ($^{16}O^{40}Ar^+$) that would otherwise appear as a 56 signal and be incorrectly attributed to $^{56}Fe$. In the dynamic reaction cell, interfering polyatomic ions are converted to a different species at a higher m/z and no longer interfere with the target ion. Following emergence from the collision cell, the ions are focussed into a quadrupole mass filter where they are separated by their m/z ratios, and detected and quantified.

Instead of a quadrupole system, ICP-MS systems can incorporate a double focussing sector field mass spectrometer, or a Time-of-Flight (TOF) analyser. An ICP-TOF-MS has a very high throughput acquisition capacity of 30,000 full mass spectra per second (Resano et al., *Mass Spectrom. Rev.* 29-55-78, 2010).

To generate a 2D elemental map of the material on a microscope slide, the laser is rastered across a sample from side to side, one track at a time from top to bottom, where the track has a chosen width. The resulting image is visualized as adjacent pixels, but since the ablated material has depth, each pixel represents a volume of tissue, a voxel.

It will be apparent to the skilled artisan that the present invention provides the following advantages:
a) minimal sample preparation to avoid introduced artefacts;
b) the ability to simultaneously and rapidly extract multi-elemental data;
c) the deconvolution of 2D information about the structure of the tumour in terms of its tumour cells, stromal cells, abnormal vasculature, transiting immune cells, and non-cellular material such as collagen bundles, all of which form the interacting milieu that constitutes the tumour and which impinges on its position between the lower boundary of radiation sensitivity and the upper boundary of radiation resistance;
d) it directly translates to the use of, or avoidance of, a therapeutic modality, namely ionising radiation for any tissue or organ type. Where radiation therapy is used, the invention determines the probability of tumour reoccurrence.
e) it is not specific for a particular type of tumour. It is applicable to any tumour, localized or metastatic, benign or malignant. As such, it is pan-diagnostic. For example, a Prostate-Specific Antigen test measures a single circulating entity in the bloodstream which may be indicative of the presence of a benign or malignant tumour, or simply benign prostatic hyperplasia, or strenuous exercise. As such it does not suggest the type of therapeutic intervention that is required. It is also specific to males. In contrast the present invention is not restricted by specificity of gender or tumour type and hence there is no need to develop specific antibodies or drugs to a particular tumour type, such as Tarceva for non-small cell lung cancer.
f) radiation, which can be external beam or implanted "seeds", is delivered to a localized anatomical region, unlike small molecular weight drugs, chemotherapeutics or antibody based biologicals which are delivered via the vascular system, which spread to all tissues, and invariably have off-target effects in normal tissues and cause various levels of toxicity, such as vemurafenib in melanoma, which induces keratoacanthomas.
g) the present invention is direct. It has no intermediate steps as regards multiple preparation steps for a sample. The assay is not confounded by potential biases inherent in methods that rely for signal amplification on processes such as PCR, where the enzymes commonly used in such procedures can introduce systematic bias through differential rates of amplification of different sequences. There is no hybridization of antibodies to tissue sections with its varying specificities of hybridization and measurement of amplification signals. The present invention measures what is in a sample without the distortions that occur as a result of multi-step processing.
h) there is a seven order linear dynamic range over which measurements can be made. Both range and the linearity are crucial since they allow a true measurement of elemental abundance in a cell population without introducing potential errors by the prior art methods that require conversion or amplification of entities.

The present invention is particularly suitable for detection of disease states, differentiation states of stem cells and derivative cell populations, detection or measurement of effects of medication on cell state, and any other situation where an accurate indication of cellular state is useful.

The present invention will now be described in more detail with reference to specific but non-limiting examples describing specific compositions and methods of use. It is to be understood, however, that the detailed description of specific procedures, compositions and methods is included solely for the purpose of exemplifying the present invention. It should not be understood in any way as a restriction on the broad description of the inventive concept as set out above.

Example 1

Preparation of Tissue Standards

Normalisation and calibration experiments were run using 30 μm thick sections of matrix-matched tissue standards. These standards were prepared from chicken breast tissue removed of any fat or connective material, and were partially homogenized using an OmniTech TH tissue homogenizer fitted with a polycarbonate probe (Kelly Scientific, North Sydney, New South Wales, Australia), and subsequently spiked with standard Ca, Mn, Fe, Co, Cu, and Zn solutions. Solutions were prepared using high purity (min 99.995%) soluble chloride, sulfate, or nitrate metal salts (Sigma-Aldrich, Castle Hill, New South Wales, Australia) dissolved in 1% $HNO_3$ (Choice Analytical, Thornleigh, New South Wales, Australia) and diluted to concentrations of ca. 100,000 μg mL-1 and 10,000 μg mL-1. Aliquots of the chicken breast were then spiked with varying concentrations of each of the elements and homogenized at low speed for 5 min. Six ca. 250 mg aliquots of each homogenized tissue standard were digested in 5:1 Seastar Baseline grade $HNO_3$/$H_2O_2$ (Choice Analytical) in a Milestone MLS 1200 closed vessel microwave digester (Kelly Scientific) and analysed using solution ICP-MS to confirm the concentration and homogeneity of each element in the tissue standards. The spiked tissue was frozen and sectioned into 30 μm sections and placed onto glass microscope slides for analysis. This methodology can be simply applied to sections cut at 5 microns, a small part of which is added to each tumour slide.

Calibration and Background Analysis

The prepared matrix-matched tissue standards were used to construct calibration curves for sensitivity normalisation of analytes under conditions described later for running the LA-ICP-MS. Data for a 10 s period prior to ablation of the tissue were collected to obtain a background signal for each m/z from the gas blank. This methodology was used to allow for a comparison between different runs of different tumours. For example, a 2K calibrated counts/second was achieved.

Sensitivity Threshold(s)

An alternate way of setting thresholds to that described earlier as standard deviations relative to means and medians of a radiation sensitive control, or as empirically determined values from any tumour type, is to set a sensitivity threshold by apportioning, for example, the testicular samples in the top histogram of FIG. 11A-FIG. 11F, such that the threshold is defined as a percentage of that histogram. For example, the seminomas of FIG. 11A-FIG. 11F derive from 55 patients and 41/55 of these patients constitute 75% of the histogram who fall below this 75% threshold, and all these patients are radiation sensitive. Next, 47/55 patients constitute 85% of the histogram and will be radiation sensitive. Finally, 52/55 patients constitute nearly 95 of the histogram, but some of these outlier patients are likely to have some degree of radiation resistance. These percentage figures representing a proportion of the histogram are another way of expressing the variable threshold that can be chosen for radio-responsiveness.

Example 2

In one example, a section of normal brain tissue on a microscope slide as described herein, was laser ablated and its metallomic contents were analyzed by the LA-ICP-MS system.

Figure 3A:
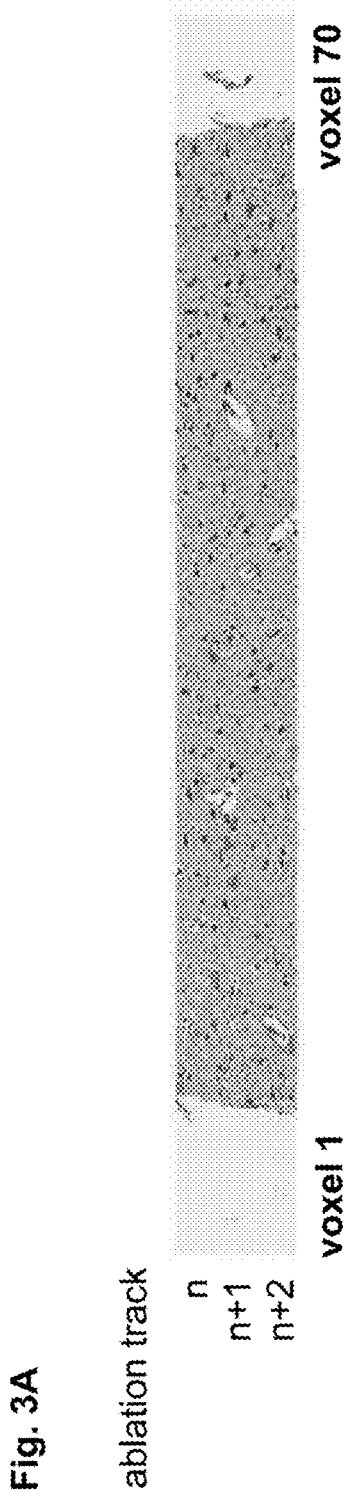
FIG. 3A. Photographic image of an H&E stained 5 micron tissue section from a block of a normal human cortex from a 50 year old human female showing the characteristics of normal cortical tissue. It is illustrative of the position of a three track ablation (taken from the larger multi-track tissue ablation) that was carried out on an adjacent unstained section from the same block, but on a different slide. The H&E stained area shown in the Figure corresponds to the equivalent unstained area analysed by LA-ICP-MS on a different slide.

FIG. 3A shows a representative H&E stained 5 micron tissue section from a block of a normal human cortex from a 50 year old human female showing the characteristics of normal cortical tissue. This Figure illustrates the position of a three-track ablation (taken from the larger multi-track tissue ablation) that was carried out on an adjacent unstained section from the same block, but on a different slide. The H&E stained area shown in FIG. 3A corresponds to the equivalent unstained area analysed by LA-ICP-MS on the different slide. The unstained 5 micron tissue section was cut from the same block, laser ablated and analysed using the Agilent technologies 7700 LA-ICP-MS system, with detailed operational parameters described previously. Unstained tissue sections are generally used in order to avoid the introduction of any chemical elements that occur in the stains, staining solutions or which are leached from the containers during processing. Stained sections can also be used.

To generate an elemental map of the unstained material on the separate microscope slide, the laser was rastered across the slide laterally, one ablation track at a time from top to bottom. Generally, this produces up to hundreds of horizontal tracks depending on the size of the tissue sample, with each track being 35 microns in width. Lateral resolution is a function of the integration time of the quadrupole mass spectrometer and was chosen in these data sets to give a resolution of 35 microns. A complete image was generated, which consists of a basic unit of a 35 micron by 35 micron pixel. Since the tissue section is 5 microns thick, each pixel represents a 35×35×5 volume of tissue, namely a voxel of 6125 cubic microns. An ablation run of 50 horizontal tracks, in which each ablation track consists of, say, 70 voxels, generated a 2D image consisting of 3500 voxels.

The calibrated signal of each of three metals $^{55}$Mn, $^{66}$Zn and $^{56}$Fe was determined. The results are shown for each voxel of three contiguous ablation tracks from a tissue section that ablated 70 voxels per track (FIG. 3B). The background-subtracted median values per voxel for these metals, expressed as calibrated counts per second, are 3,409, 6,651 and 441,317 respectively. Measurements of $^{63}$Cu were unavailable for technical reasons.

Figure 3C:
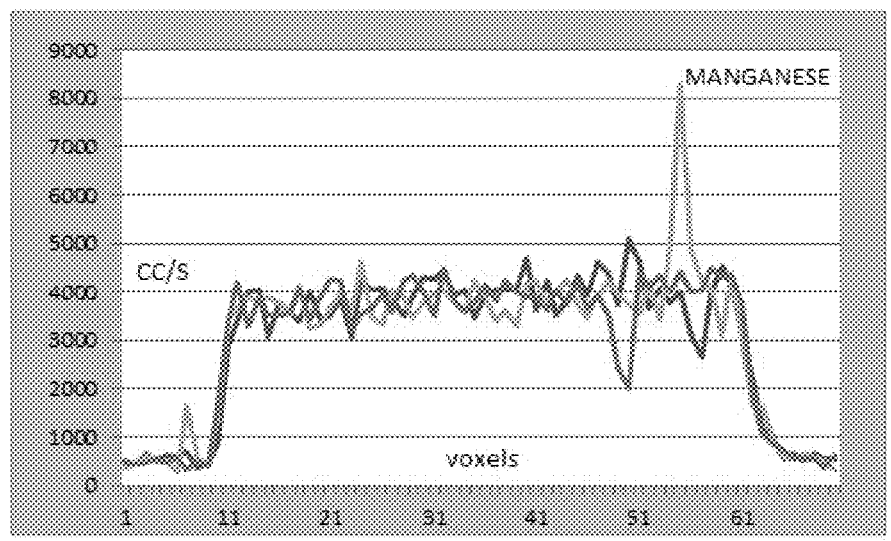
FIG. 3C-FIG. 3E. Graphical representation of the raw numerical values (from FIG. 3B), wherein each track consisted of 70 voxels of calibrated counts per second for the three metals, $^{55}$Mn, $^{66}$Zn and $^{56}$Fe in adjacent voxels in each of three ablation rows.
Figure 3D:
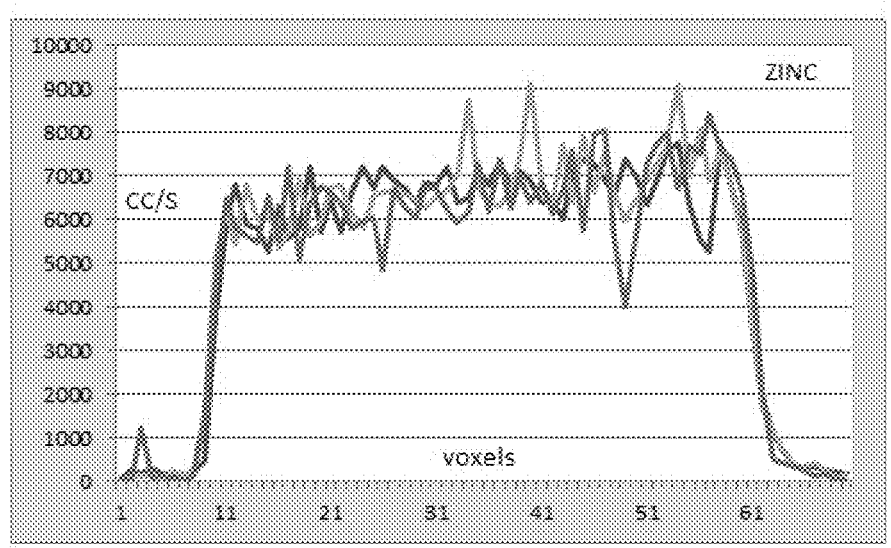
Figure 3E:
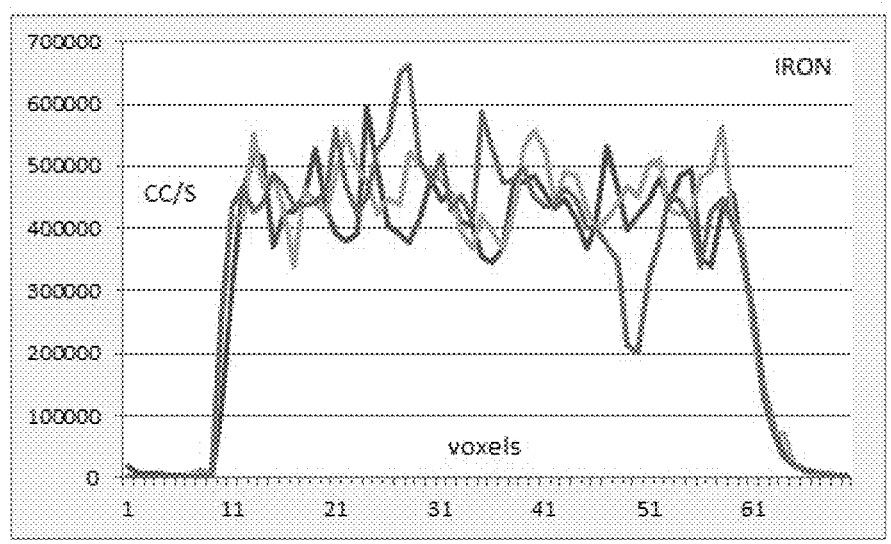

These raw data are presented in graphical form in FIG. 3C-FIG. 3E, where each track consisted of 70 voxels. FIG. 3C-FIG. 3E shows graphs of raw numerical values of calibrated counts per second CC/S for the three metals, $^{55}$Mn, $^{66}$Zn and $^{56}$Fe in adjacent voxels in each of three ablation rows. The unstained 5 micron tissue section was cut from the same block, laser ablated and analysed using the Agilent technologies 7700 LA-ICP-MS system, with detailed operational parameters described below.

As the laser rasters across the unstained tissue section on the slide, the values for each of the metals change from background levels to those characteristic of the tissue sample and then return to background values again. The variation in values generally follows the morphological changes and variations in tumour architectures seen in the stained tissue sections.

In this Example, the raw free ion manganese values in FIG. 3C, reveal that there is a spike in voxel 55 in ablation row two, while none of the eight voxels contiguous to it show this large deviation from the median (as seen from the data of FIG. 3B). These large single spikes for an individual voxel are due to machine "jitter" and such spikes are almost always more than 3 standard deviations from the median value. While shown here for the illustrative purposes of raw data presentation, they will be removed prior to statistical analyses as they represent machine "noise". They are sufficiently infrequent that even if they remained part of the data analysis, they have a miniscule effect on important outcomes such as median values.

Example 3

Neoplastic Samples with Contrasting Radiation Resistances and Sensitivities

As discussed above, the Lancet Oncology Commission highlighted radiotherapy as a fundamental component of effective cancer treatment and control and that it is generally used sub-optimally (Atun et al., *Lancet Oncology* 2015, 16, 1153-1186). Until the present invention, the clinically accepted norm is that some tumour types such as glioblastoma, mesothelioma and melanoma are largely radiation resistant, while most lymphomas, small cell tumours of the lung, and tumours of the testis, such as classic seminomas, are radiation sensitive. Other major tumour types such as cancers of the breast and prostate are generally thought to be of "intermediate" radio-responsiveness, but "intermediate" is context dependent and difficult to determine. The clinical reality relates to what percentage of primary cancers can be eradicated with radiotherapy alone and the dose that is required, as well as the percentage susceptibility of various metastatic lessons to ablative radiotherapy. Thus large seminoma and lymphoma masses are easily eradicated with radiotherapy while sarcomas and pancreatic carcinomas are rarely eradicated, despite the dose. In addition, radiotherapy is considered "curative" for some "low/intermediate" risk prostate cancers and some prostate cancer metastases to the bone, and so such prostate cancers could certainly be classified as very radiosensitive.

Given the above clinical variation, we have chosen six tumour types for evaluating the ATI, as the first three provide the bookends for radiation resistance, and the second three provide the bookends for radiation sensitivity. It is clinically acknowledged, however, that even within each of these six tumour types, there are a minority which do not respond to radiation treatment in the expected manner. This is due to problems with methods used prior to the present invention e.g., low resolving power of H&E stained pathological material and the considerable disagreement among pathologists of the taxonomy within any tumour type. Even with the addition of antibody staining of formalin-fixed paraffin-embedded and Hematoxylin and Eosin (H&E) stained tissue sections, the interpretation of the variation within a tumour type remains subjective and the concordance among pathologists is variable (Elmore et al., JAMA, 313; 1122-1132. 2015).

Melanoma illustrates the challenges of personalizing radiotherapies. Historically it has been considered to be intrinsically radio-resistant, a perception originating from early cell culture studies and analyses of survival curves. This belief has recently been evaluated on the basis of data from 4 decades of the clinical use of radiation therapy in melanoma patients (Mahadevan et al., *Oncology*, 29, (10): 743-751, 2015). The newer interpretation is that the radio-responsiveness of melanoma is diverse. It is accurately summarized by Burmeister; "I've been working with melanoma for over 25 years and it still amazes me how in some patients the disease just melts away and in others it just laughs at you and kills the patient within a few weeks or months . . . there is an incredible variation in the behaviour of this disease in individual patients."

As the atomic data presented herein reveal, there is now, for the first time, (i) a quantitative underpinning of which melanoma patients, (as well as other tumour types) are suitable candidates for radiotherapy, (ii) a quantitative basis for determining in which patients a cancer is likely to re-occur after radiotherapy, and (iii) a measurable basis for tumour variation. It should also be noted that such heterogeneity is not confined to melanoma. Breast and prostate cancer patients and their tumours are also heterogeneous at multiple levels, one being their response to radiation treatment.

1. Radiation Resistant Tumours

In another Example, the metallomic values of neoplasms that are considered to be at the radiation resistant end of the clinical spectrum were analyzed. For example, a deadly brain neoplasm, glioblastoma multiforme, which is considered to be at the radiation resistant end of the clinical spectrum, was analysed as described in Example 2. This example illustrates how the metallomic values of a brain neoplasm differ from those of normal brain tissue, when both the normal and neoplastic samples are present on the same slide and are evaluated on the same LA-ICP-MS system under the same experimental run conditions.

FIG. 4A shows a representative H&E stained 5 micron tissue section from a block of a 19 year old human female with a brain neoplasm classified as glioblastoma multiforme. The H&E stained area shown in the Figure corresponds to the equivalent unstained area analysed by LA-ICP-MS on a different slide.

Figure 4C:
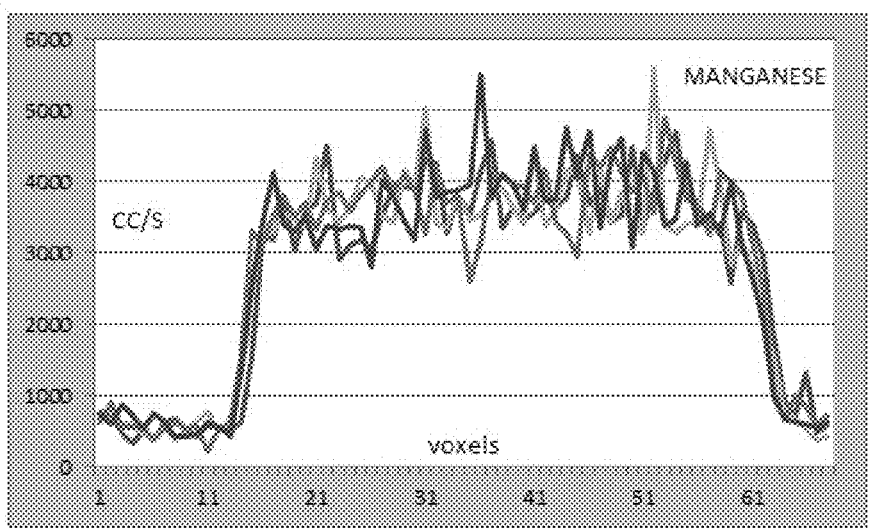
FIG. 4C-FIG. 4E. Graphical representation of the raw numerical values (from FIG. 4B) of calibrated counts per second for the three metals, $^{55}$Mn, $^{66}$Zn and $^{56}$Fe in adjacent voxels in each of three ablation rows from the human female with glioblastoma multiforme. The Y axis shows calibrated counts per second (CC/S) of that metal ion, while the X axis shows the voxel number of the three ablation tracks.
Figure 4D:
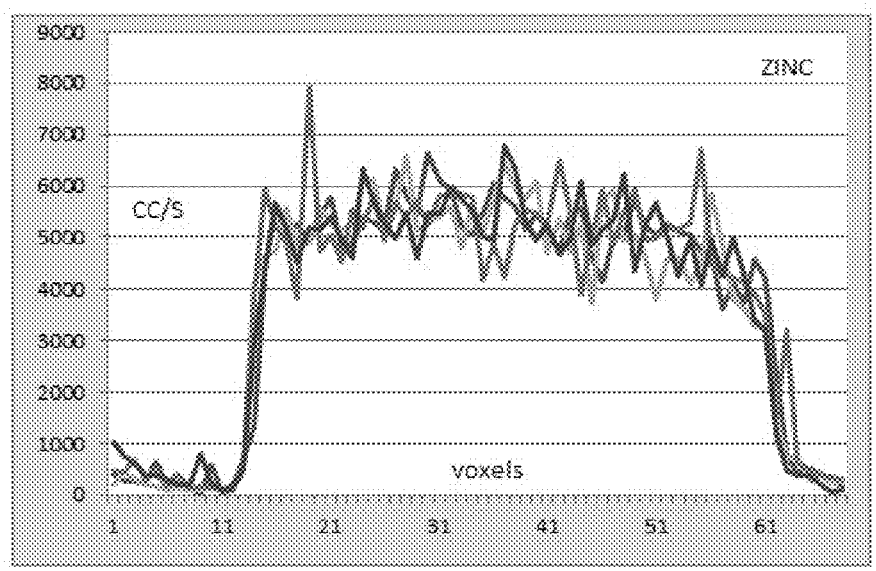
Figure 4E:
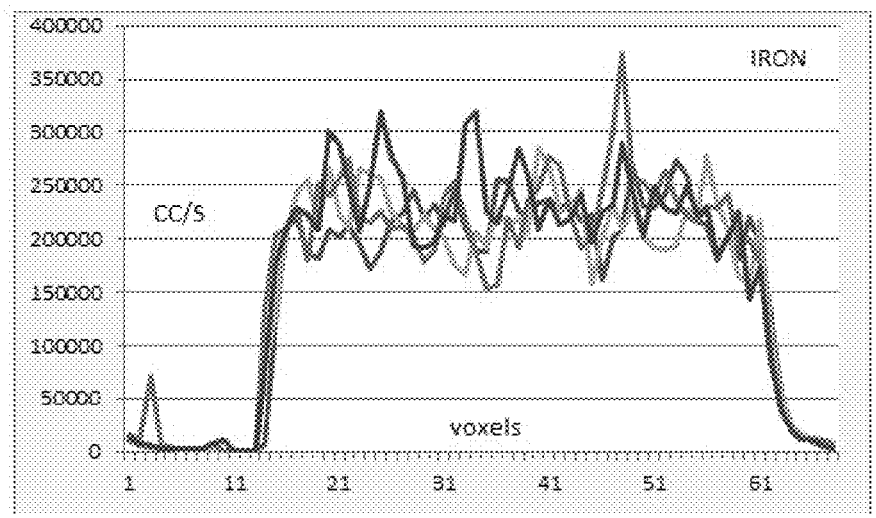

The calibrated signal of each of three metals $^{55}$Mn, $^{66}$Zn and $^{56}$Fe was determined and is shown for each voxel of three contiguous ablation tracks from a tissue section that ablated 68 voxels per track (FIG. 4B). The background-subtracted median values per voxel for these metals, expressed as calibrated counts per second, were found to be 3,198, 5,066 and 219,905 respectively. A graph of raw numerical values of calibrated counts per second for the three metals, $^{55}$Mn, $^{66}$Zn and $^{56}$Fe in adjacent voxels in each of three ablation rows from the human female with glioblastoma multiforme was prepared and is shown in FIG. 4C-FIG. 4E.

To obtain a measure of the variation between different sections taken from the same block of the same human subject with glioblastoma multiforme, two unstained areas on the same slide were analysed by LA-ICP-MS in the same machine run. The results are shown in FIG. 5A-FIG. 5E.

Figure 5A:
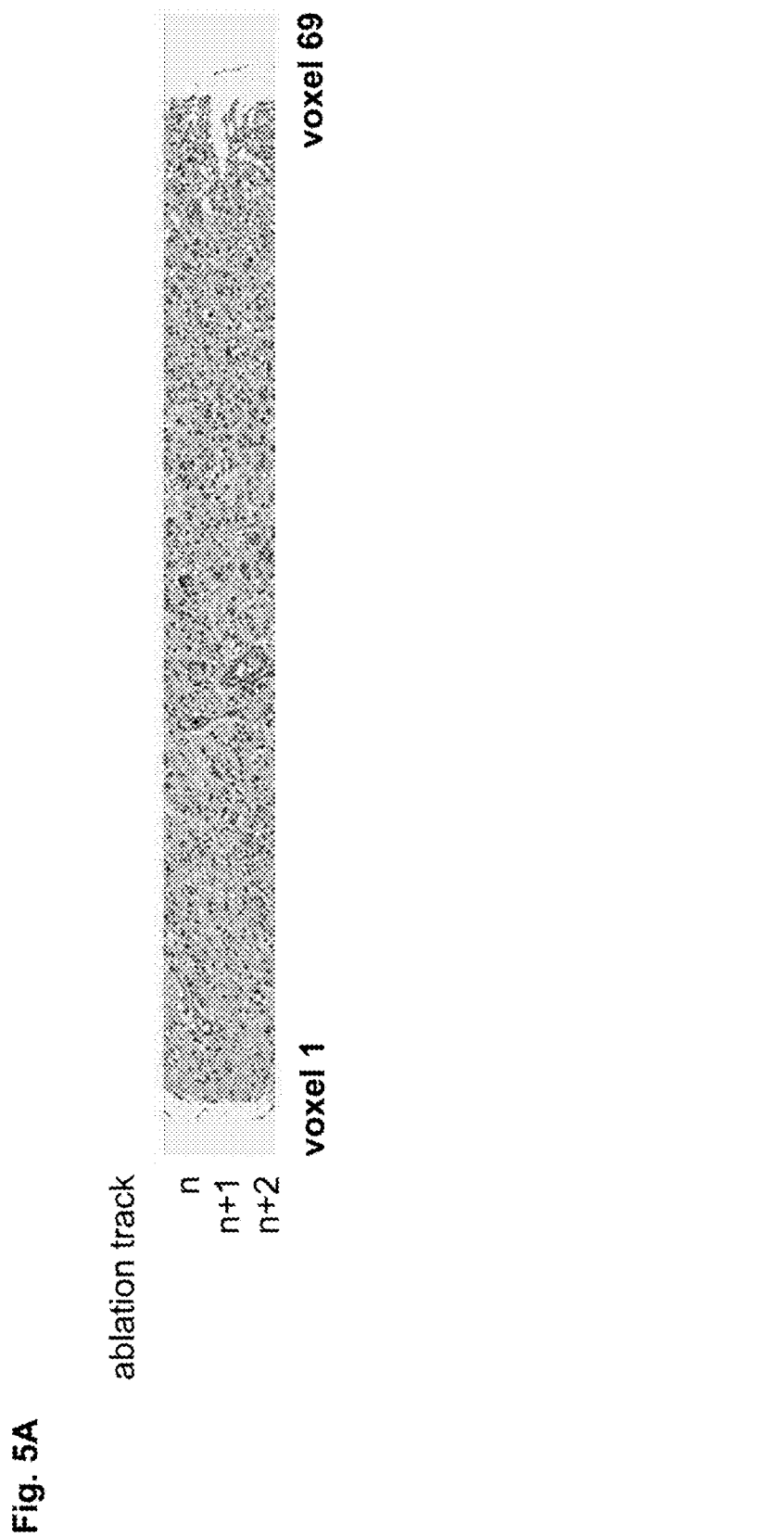
FIG. 5A. Photographic image of an H&E stained 5 micron tissue section from a different region of the same block of the 19 year old human female with glioblastoma multiforme shown in FIG. 4A-FIG. 4E.

FIG. 5A shows a representative H&E stained 5 micron tissue section from a different region of the same block of the 19 year old human female with glioblastoma multiforme shown in FIG. 4A-FIG. 4C.

Figure 5C:
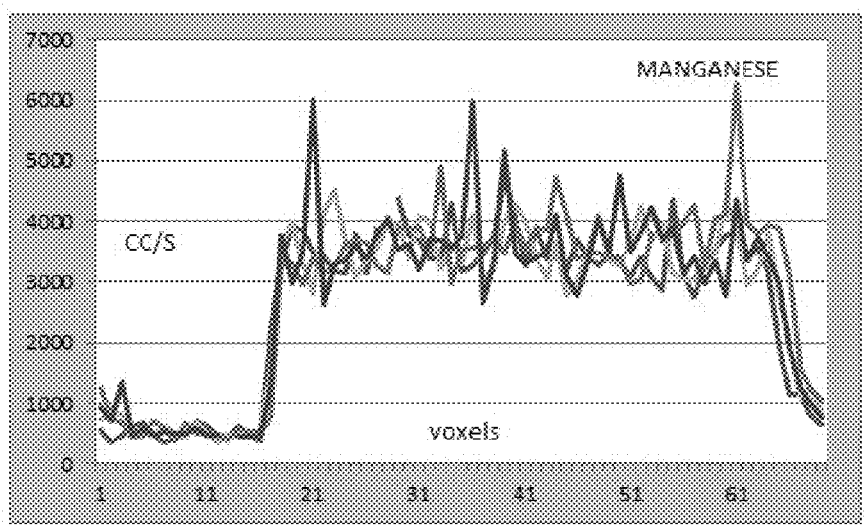
FIG. 5C-FIG. 5E. Graphical representation of raw numerical values (from FIG. 5B) of calibrated counts per second for the three metals, $^{55}$Mn, $^{66}$Zn and $^{56}$Fe in adjacent voxels in each of three ablation rows from the human female with glioblastoma multiforme. The Y axis shows calibrated counts per second (CC/S) of that metal ion, while the X axis shows the voxel number of the three ablation tracks.
Figure 5D:
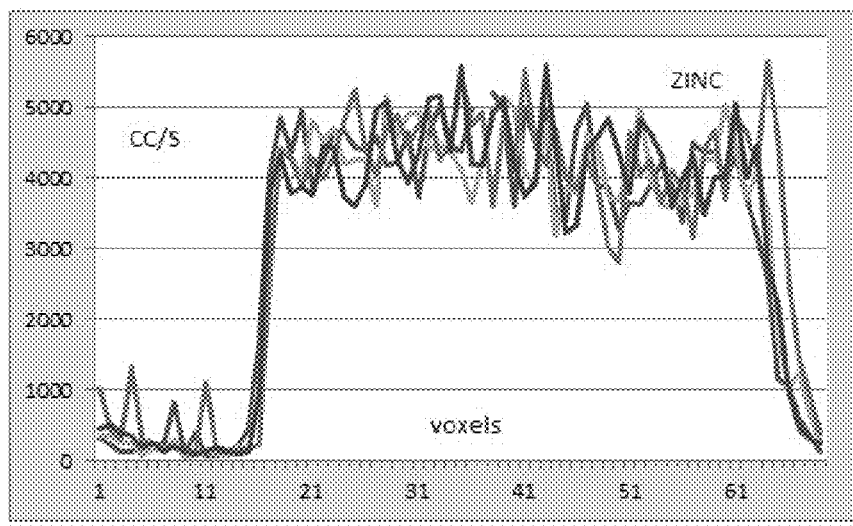
Figure 5E:
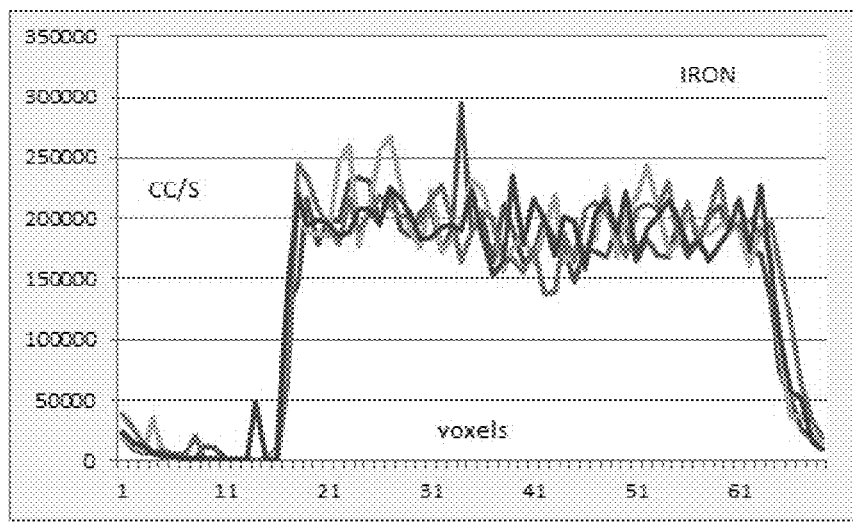

The calibrated signal of each of three metals $^{55}$Mn, $^{66}$Zn and $^{56}$Fe was determined for each voxel of three contiguous ablation tracks from a tissue section that ablated 69 voxels per track (FIG. 5B). The background-subtracted median values per voxel for these metals, expressed as calibrated counts per second, were found to be 2,980, 4,155, and 190,127 respectively. A graph of raw numerical values of calibrated counts per second for the three metals, $^{55}$Mn, $^{66}$Zn and $^{56}$Fe in adjacent voxels in each of three ablation rows from the human female with glioblastoma multiforme was prepared and is shown in FIG. 5C-FIG. 5E.

These results demonstrate that variation in background-subtracted median calibrated counts per second in the same LA-ICP-MS machine run, for different tissue sections taken from the same block of the same individual is excellent. For $^{55}$Mn the CC/S values were 3,198 and 2,980; for $^{66}$Zn the CC/S values were 5,066 and 4,155, and for $^{56}$Fe the CC/S values were 219,905 and 190,127 respectively.

The next example is of a different neoplasm, which is also considered to be at the radiation resistant end of the clinical spectrum. This example is a neoplasm of mesothelial origin and comes from a 60 year old male with malignant mesothelioma of the abdominal cavity, and its characteristics are illustrated in FIG. 6A-FIG. 6F.

FIG. 6A shows a representative H&E stained 5 micron tissue section from a 60 year old human male with malignant mesothelioma.

Figure 6C:
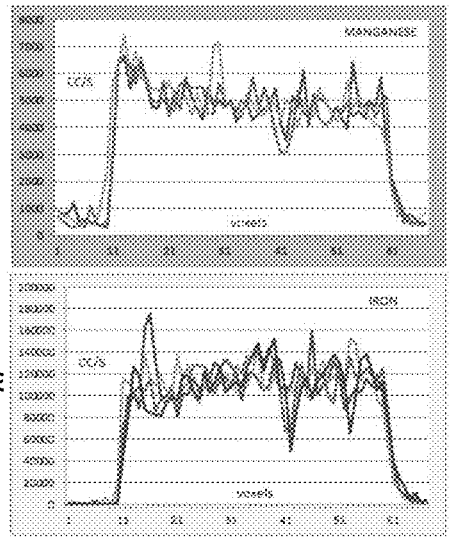
FIG. 6C-FIG. 6F. Graphical representation of the raw numerical values (from FIG. 6B) of calibrated counts per second for the four metals, $^{55}$Mn, $^{66}$Zn, $^{56}$Fe and $^{63}$Cu in adjacent voxels in each of three ablation rows from the 60 year old human male with malignant mesothelioma. The Y axis shows calibrated counts per second (CC/S) of that metal ion, while the X axis shows the voxel number of the three ablation tracks.
Figure 6D:
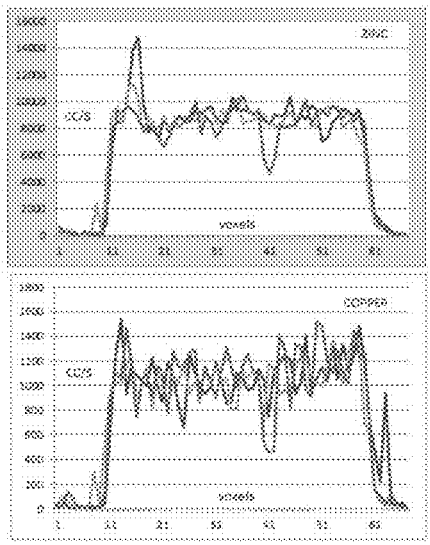
Figure 6E:
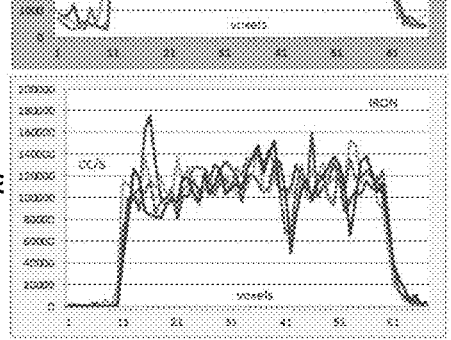
Figure 6F:
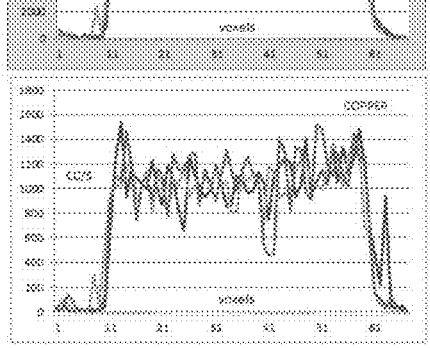

The calibrated signal of each of four metals $^{55}$Mn, $^{66}$Zn, $^{56}$Fe and $^{63}$Cu was determined for each voxel of three contiguous ablation tracks from a tissue section that ablated 67 voxels per track (FIG. 6B). The background-subtracted median values per voxel for these metals, expressed as calibrated counts per second are 4,522, 8,805, 112,772 and 1,097 respectively. A graphical representation of the raw numerical values of calibrated counts per second for the four metals, $^{55}$Mn, $^{66}$Zn, $^{56}$Fe and $^{63}$Cu in adjacent voxels in each of three ablation rows from the 60 year old human male with malignant mesothelioma was determined and is shown in FIG. 6C.

A further example of a different neoplasm, which is also considered to be at the radiation resistant end of the clinical spectrum, comes from a 50 year old male with malignant melanoma of the esophagus (stage IIa, T3N0M0). The metallomic characteristics are illustrated in FIG. 7A-FIG. 7E.

Figure 7A:
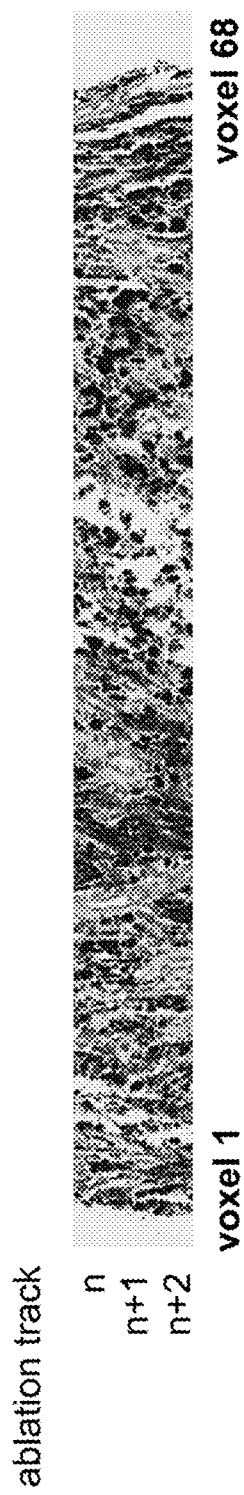
FIG. 7A. Photographic image of an H&E stained 5 micron tissue section from a 50 year old male with malignant melanoma of the esophagus.

FIG. 7A shows a representative H&E stained 5 micron tissue section from a 50 year old male with malignant melanoma of the esophagus.

Figure 7C:
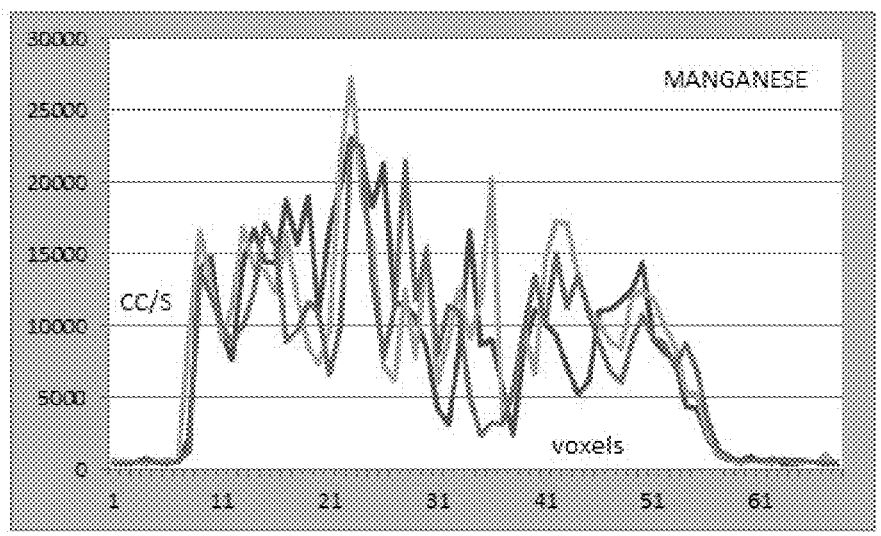
FIG. 7C-FIG. 7E. Graphical representation of the raw numerical values (from FIG. 7B) of calibrated counts per second for the three metals, $^{55}$Mn, $^{66}$Zn and $^{56}$Fe in adjacent voxels in each of three ablation rows from the 50 year old human male with malignant melanoma of the esophagus. The Y axis shows calibrated counts per second (CC/S) of that metal ion, while the X axis shows the voxel number of the three ablation tracks.
Figure 7D:
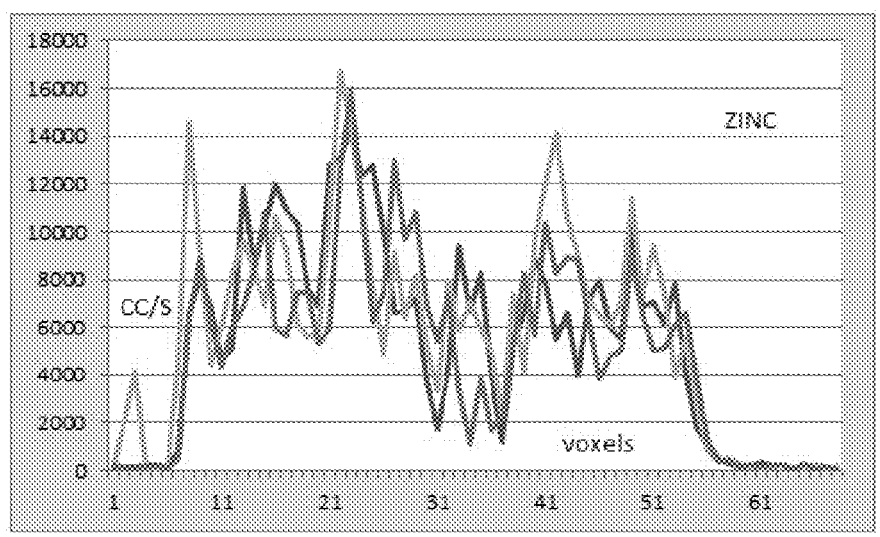
Figure 7E:
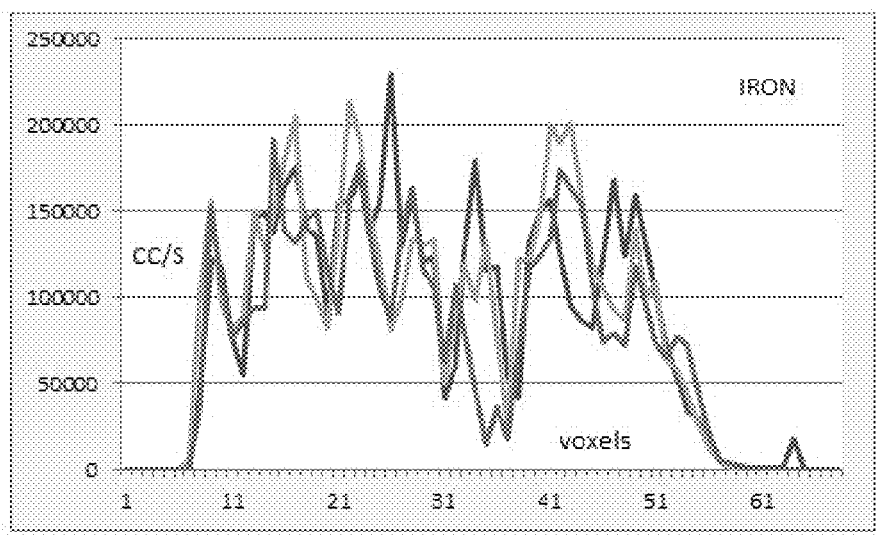

The calibrated signal of each of three metals $^{55}$Mn, $^{66}$Zn and $^{56}$Fe was determined for each voxel of three contiguous ablation tracks from a tissue section that ablated 68 voxels per track (FIG. 7B). The background-subtracted median values per voxel for these metals, expressed as calibrated counts per second are 10,565, 6,961, and 121,495 respectively. A graphical representation of the raw numerical values of calibrated counts per second for the three metals, $^{55}$Mn, $^{66}$Zn and $^{56}$Fe in adjacent voxels in each of three ablation rows from the 50 year old human male with malignant melanoma of the esophagus was determined as shown in FIG. 7C-FIG. 7E.

It should be noted that there is much more variation in metallomic content between voxels in some melanomas than in normal tissues and in other neoplasms. One of the major contributors to this increase in variation is the presence of intracellular and extracellular inhomogeneities in the distribution of melanin, an entity that has storage capacity for different chemical elements, particularly metals. This morphological inhomogeneity is clearly visible in the first figure presented in this application, which is part of an H&E stained section from a stage Ib malignant melanoma of the neck of a 48 year old male (FIG. 1). Within the same tumour, there was an amelanotic lineage and a highly melanised different area. The metallomic characteristics of this tumour are further described herein (see Example 5).

2. Radiation Sensitive Tumours

The characteristics of three different types of neoplasms that are considered to be at the radiation-sensitive end of the clinical spectrum will now be described. They are diffuse B-cell lymphomas, small cell cancers of the lung, and seminomas of the testis.

Lymphomas: the first example of a neoplasm considered to be at the radiation sensitive end of the clinical spectrum, comes from a 57 year old male with diffuse B-cell lymphoma in the testis. Its metallomic characteristics are illustrated in FIG. 8A-FIG. 8E.

FIG. 8A shows a representative H&E stained 5 micron tissue section from a 57 year old male with diffuse B-cell lymphoma.

Figure 8C:
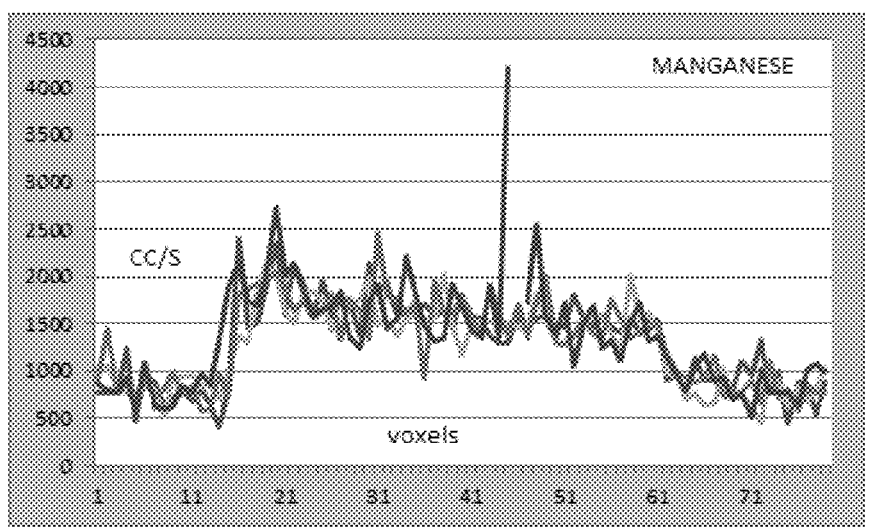
FIG. 8C-FIG. 8E. Graphical representation of the raw numerical values (from FIG. 8B) of calibrated counts per second for the three metals, $^{55}$Mn, $^{66}$Zn and $^{56}$Fe in adjacent voxels in each of three ablation rows from the 57 year old male with diffuse B-cell lymphoma in the testis. The Y axis shows calibrated counts per second (CC/S) of that metal ion, while the X axis shows the voxel number of the three ablation tracks.
Figure 8D:
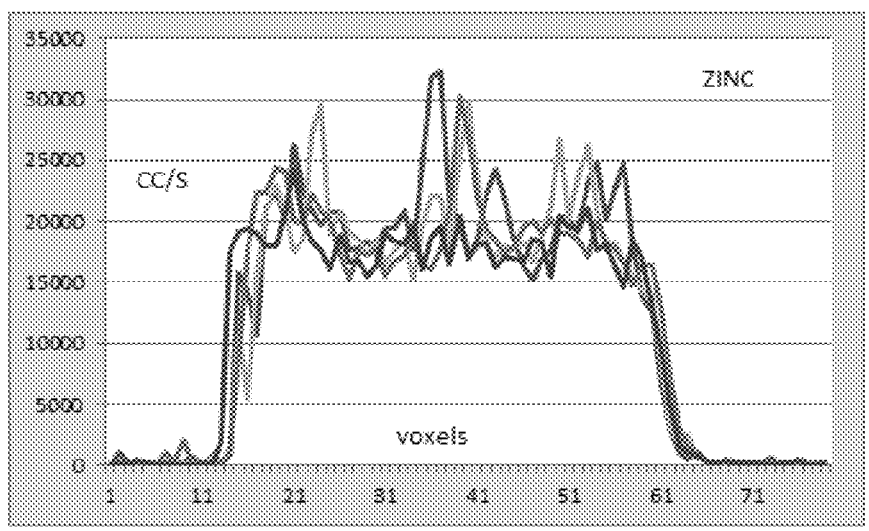
Figure 8E:
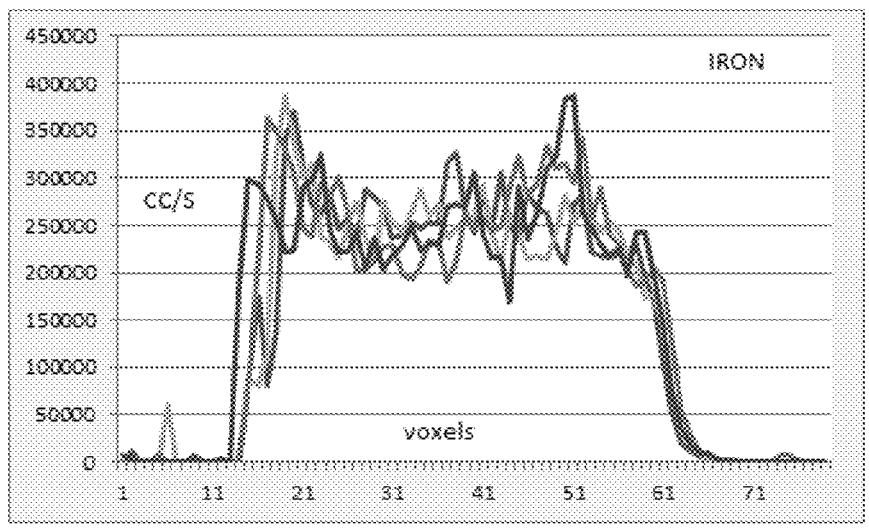

The calibrated signal of each of three metals $^{55}$Mn, $^{66}$Zn and $^{56}$Fe was determined for each voxel of three contiguous ablation tracks from a tissue section that ablated 79 voxels per track (FIG. 8B). The background-subtracted median values per voxel for these metals, expressed as calibrated counts per second are 776, 18,892, and 247,923 respectively. A graphical representation of the raw numerical values of calibrated counts per second for the three metals, $^{55}$Mn, $^{66}$Zn and $^{56}$Fe, in adjacent voxels in each of three ablation rows from the 57 year old male with diffuse B-cell lymphoma in the testis was prepared and is shown in FIG. 8C-FIG. 8E. The Y axis shows calibrated counts per second (CC/S) of that metal ion, while the X axis shows the voxel number of the three ablation tracks.

Malignant carcinoma: The second example of a neoplasm considered to be at the radiation sensitive end of the clinical spectrum, comes from a 38 year old male with a small cell undifferentiated malignant carcinoma of the lung (stage IIIb, T4N1M0). Its metallomic characteristics are illustrated in FIG. 9A-FIG. 9E.

FIG. 9A shows a representative H&E stained 5 micron tissue section from a 38 year old male with a small cell undifferentiated malignant carcinoma of the lung.

Figure 9C:
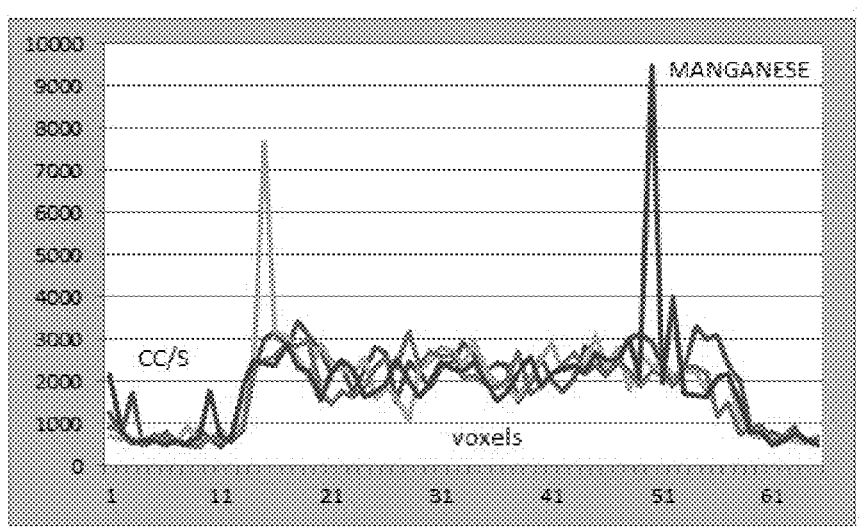
FIG. 9C-FIG. 9E. Graphical representation of the raw numerical values (from FIG. 9B) of calibrated counts per second for the three metals, $^{55}$Mn, $^{66}$Zn and $^{56}$Fe in adjacent voxels in each of three ablation rows from the 38 year old male with a small cell undifferentiated malignant carcinoma of the lung. The Y axis shows calibrated counts per second (CC/S) of that metal ion, while the X axis shows the voxel number of the three ablation tracks.
Figure 9D:
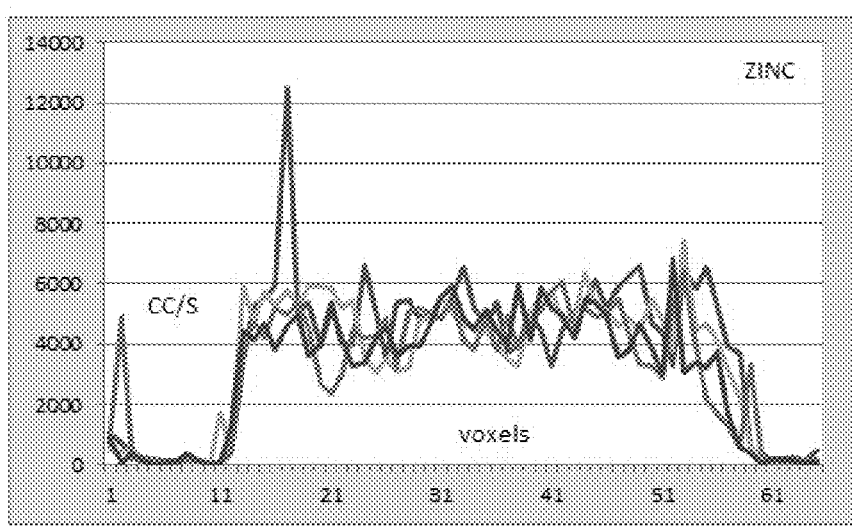
Figure 9E:
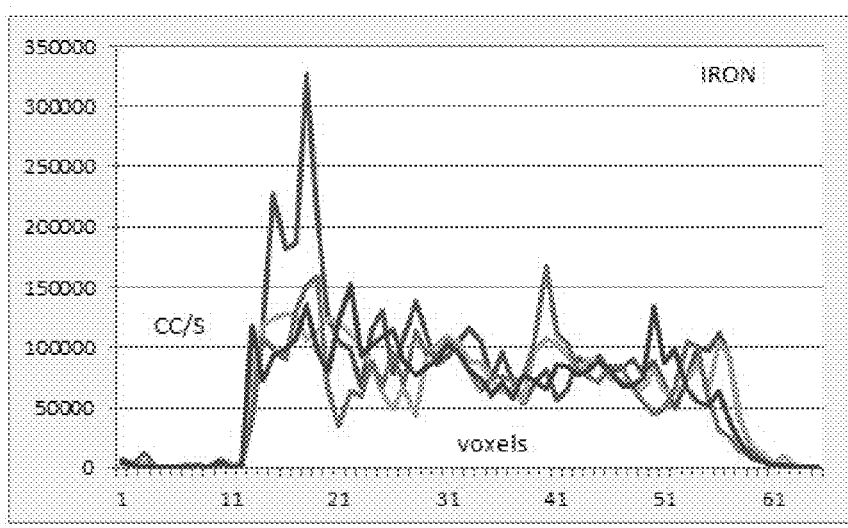

The calibrated signal of each of three metals $^{55}$Mn, $^{66}$Zn and $^{56}$Fe was determined for each voxel of three contiguous ablation tracks from a tissue section that ablated 65 voxels per track (FIG. 9B). The background-subtracted median values per voxel for these metals, expressed as calibrated counts per second are 1,749, 4,836, and 88,317 respectively. A graphical representation of the raw numerical values of calibrated counts per second for the three metals, $^{55}$Mn, $^{66}$Zn and $^{56}$Fe, in adjacent voxels in each of three ablation rows from the 38 year old male with a small cell undifferentiated malignant carcinoma of the lung was prepared and is shown in FIG. 9C-FIG. 9E.

Seminoma: the third example of a neoplasm considered to be at the radiation sensitive end of the clinical spectrum, comes from a 52 year old male with seminoma. Its metallomic characteristics are illustrated in FIG. 10A-FIG. 10E.

FIG. 10A shows a representative H&E stained 5 micron tissue section from a 52 year old male with seminoma.

Figure 10C:
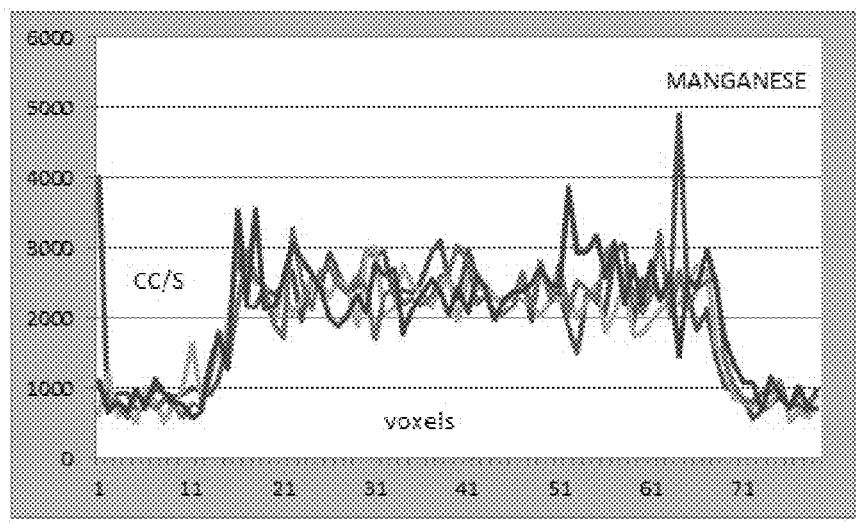
FIG. 10C-FIG. 10E. Graphical representation of the raw numerical values (from FIG. 10B) of calibrated counts per second for the three metals, $^{55}$Mn, $^{66}$Zn and $^{56}$Fe in adjacent voxels in each of three ablation rows from the 52 year old male with seminoma. The Y axis shows calibrated counts per second (CC/S) of that metal ion, while the X axis shows the voxel number of the three ablation tracks.
Figure 10D:
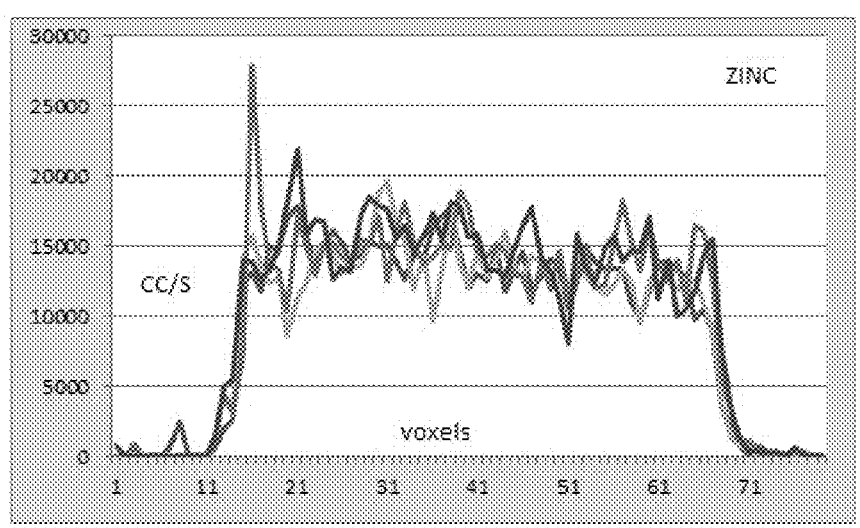
Figure 10E:
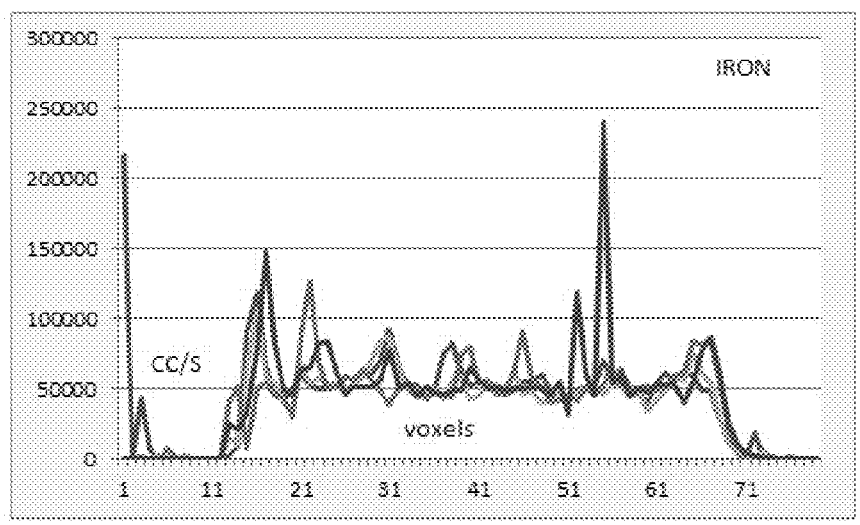
Figure 11A:
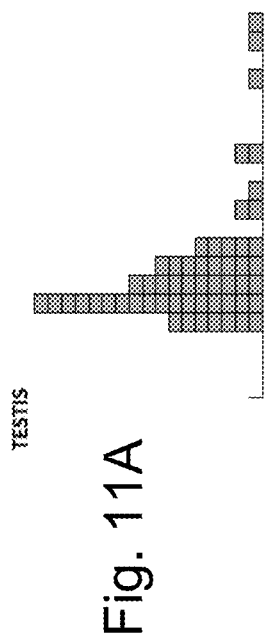
FIG. 11A to FIG. 11F. Graphical representation of total median manganese contents, (expressed as calibrated counts per second, CC/S of $^{55}$Mn), in tumours from patients with seminoma (55) (FIG. 11A), lymphoma (10) (FIG. 11B), small cell carcinoma of the lung (20) (FIG. 11C), melanoma (64) (FIG. 11D), brain (glioblastoma and astrocytoma) (25) (FIG. 11E), and mesothelioma (10) (FIG. 11F). Each square represents a single patient except in the melanomas, where two of the 64 patients each had two major lineages within their tumours, and each lineage was represented separately in the histogram with a square.
Figure 11B:
Figure 11C:
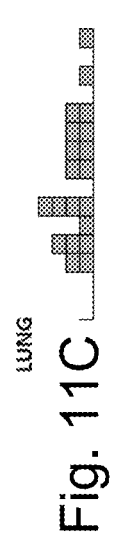
Figure 11D:
Figure 11E:
Figure 11F:
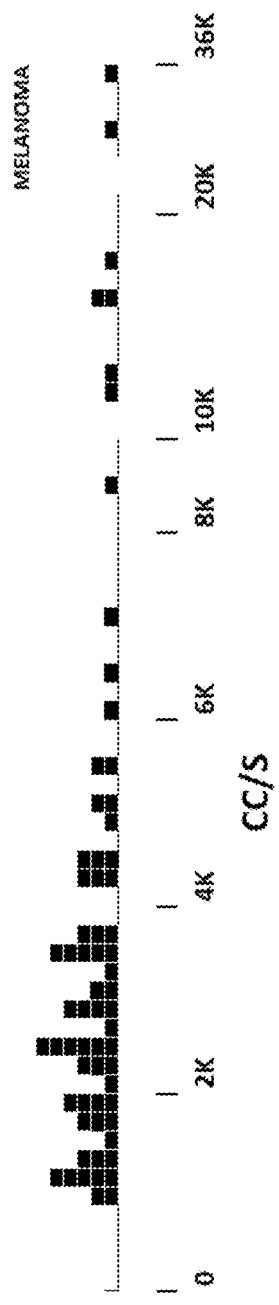
Figure 13A:
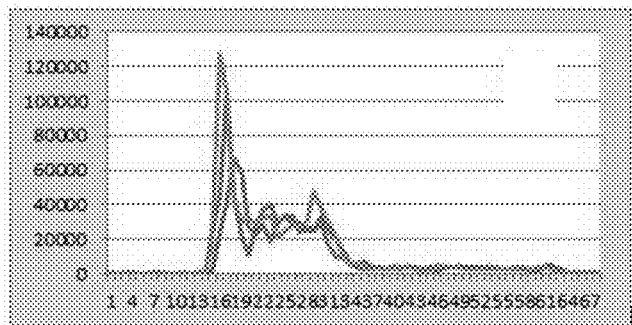
FIG. 13A to FIG. 13D. Graphical representation of an analysis of all four metals, with FIG. 13A, FIG. 13B, FIG. 13C, and FIG. 13D showing $^{55}$Mn, $^{66}$Zn, $^{56}$Fe and $^{63}$Cu respectively of the tumour shown in FIG. 1.
Figure 13B:
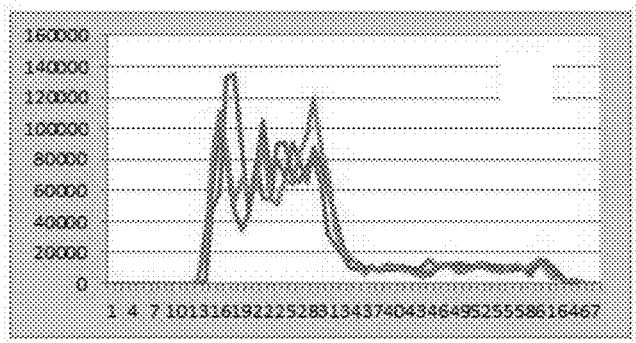
Figure 13C:
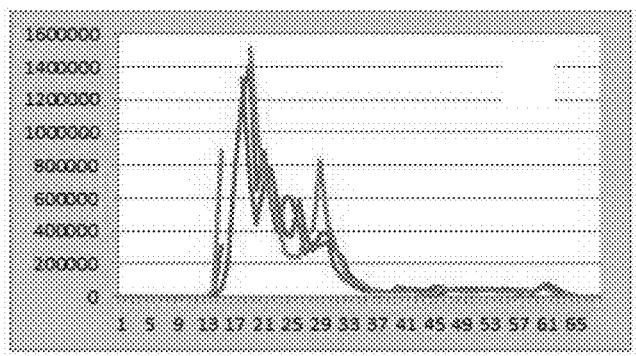
Figure 13D:
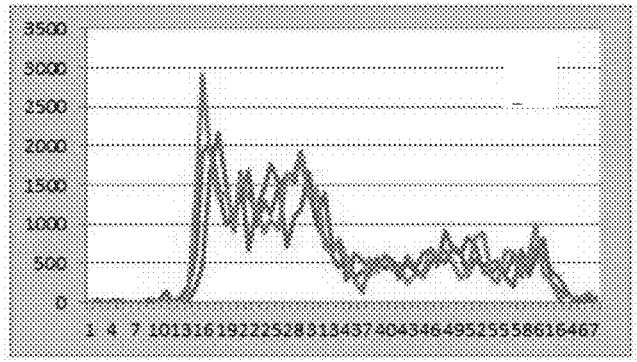

The calibrated signal of each of three metals, $^{55}$Mn, $^{66}$Zn and $^{56}$Fe, was determined for each voxel of three contiguous ablation tracks from a tissue section that ablated 79 voxels per track (FIG. 10B). The background-subtracted median values per voxel for these metals, expressed as calibrated counts per second are 1,565, 13,528, and 52,115 respectively. A graphical representation of the raw numerical values of calibrated counts per second for the three metals, $^{55}$Mn, $^{66}$Zn and $^{56}$Fe, in adjacent voxels in each of three ablation rows from the 52 year old male with seminoma was prepared and is shown in FIG. 10C.

In toto, the above examples demonstrate the metallomic characteristics of three types of neoplasm that are at the radiation resistant end of the clinical spectrum, (glioblastoma, mesothelioma and melanoma), and three types of neoplasms that are at the radiation sensitive end of the clinical spectrum (B-cell lymphomas, small cell cancers of the lung and seminomas of the testis).

Example 4

Application of the LA-ICP-MS Method to Patient Cohorts

While the above examples are illustrative of the metallomic characteristics of single individuals in each category of cancer patients, the in-depth analysis of 55 individuals with seminoma, 10 with lymphoma, 20 with small cell lung cancer, 64 with melanoma, 25 with glioblastoma multiforme or astrocytoma, and 10 with mesothelioma, revealed a dichotomy in regards to their total manganese content and the known clinical outcomes of these cancer types to radiotherapy, was determined and is shown in FIG. 11A-FIG. 11H. The total median manganese free ion contents (expressed as calibrated counts per second, CC/S of $^{55}$Mn), in tumours from patients with cancers of the testis (seminoma), lymphoma, small cell carcinoma of the lung, mesothelioma, brain (glioblastoma multiforme and astrocytoma) and melanoma, were determined and are shown. Each square represents a single patient, except in the case of two melanomas where two of the 64 patients each had two major lineages within their tumours, and each lineage was represented separately in the histogram with a square.

The accepted clinical situation is that approximately 85% of seminomas, lymphomas and small cell carcinomas of the lung are sensitive to radiation, resulting in a great reduction, and sometimes complete elimination, of tumours and increasing life expectancy. Consistent with these values and as determined herein, 89% of the individuals with seminoma, 80% of those with small cell carcinoma of the lung and 90% of those with lymphoma, were found to have total tumour manganese contents that fall below 2,000 CC/S. In this respect, this is the first demonstration of the correlation of such radio-sensitive tumours having values that fall below a threshold of 2,000 CC/S.

In contrast to the above, the three tumour types that are considered to be largely resistant to radiation (mesotheliomas, glioblastoma multiforme, astrocytomas and melanomas), and which have a proportion that are differentially sensitive to it, present a different outcome. Not only is the variance within each of these three tumour types greatly increased, but 90% of the mesotheliomas, 85% of the glioblastoma multiforme, astrocytomas, and 59% of the melanomas, fall above the 2,000 CC/S manganese value.

Given the above dichotomy, the metallomic content e.g., the manganese content of tumours becomes a critical indicator for radiation therapy that has simply not been previously recognized in terms of practical clinical care until the present invention. In these examples using a 35 micron pixel, individuals having tumours with a low total manganese content (e.g., below 2,000 CC/S) are highly likely to benefit from radiation therapy, whereas those with a manganese content (e.g., significantly above 2,000 CC/S) are likely to benefit by avoiding radiation therapy. As pixel size is increased, the CC/S will increase, and hence a higher threshold is contemplated. As the range of values remains well within linearity, there are no statistical issues that are problematic.

Given that the majority of cancer patients receive radiation therapy based on medical art, rather than quantitative data relevant to tumour characteristics, such data support the use of quantitative data using e.g., LA-ICP-MS to clinical practicality. Medical art relates to what percentage of primary cancers can be eradicated with radiotherapy alone and the dose that is required to do so, as well as the percentage susceptibility of various metastatic lesions to ablative radiotherapy. As a population-based approach it does not apply to the tumour(s) of a specific patient and is not "personalized medicine".

Statistical Analysis

The two sample nonparametric Kolmogorov-Smirnov (K-S) test compares the cumulative distributions of two data sets. The null hypothesis is that both data sets were sampled from populations with the same distribution.

From the data above, a comparison of the distribution of values for testicular cancer (seminoma) versus lymphoma yielded a D value of 0.2182, which has an associated non-significant P value of 0.762; seminoma and lymphoma were not significantly different and were sampled from populations with the same distribution.

A comparison of the distribution of values for testicular cancer (seminoma) versus small cell lung yielded a D value of 0.3182, which has an associated non-significant P value of 0.081; seminoma and small cell lung were not significantly different and were sampled from populations with the same distribution.

A comparison of the distribution of values for small cell lung versus lymphoma yielded a D value of 0.3000, which has an associated non-significant P value of 0.507; small cell lung and lymphoma were not significantly different and are sampled from populations with the same distribution.

Conclusion: the data from seminoma, lymphoma and small cell lung represented a statistically valid unitary grouping.

A comparison of the distribution of values for brain cancers (glioblastomas and astrocytomas) versus mesotheliomas yielded a D value of 0.3250, which has an associated non-significant P value of 0.371; brain cancers and mesotheliomas were not significantly different and were sampled from populations with the same distribution.

A comparison of the distribution of values for brain cancers (glioblastomas and astrocytomas) versus melanomas yielded a D value of 0.2226, which has an associated non-significant P value of 0.277; brain cancers and melanomas were not significantly different and were sampled from populations with the same distribution.

A comparison of the distribution of values for melanomas versus mesotheliomas yielded a D value of 0.4303, which has an associated non-significant P value of 0.056; melanomas and mesotheliomas were not significantly different and were sampled from populations with the same distribution.

Conclusion: brain cancers, mesotheliomas and melanomas are a statistically valid unitary grouping.

Comparison Between Groups

A comparison of the distribution of values for testicular cancer (seminoma) versus brain cancers yielded a D value of 0.7712, which has an associated significant P value of 0.000; seminoma and brain cancer were significantly different and were sampled from populations with different distributions.

A comparison of the distribution of values for testicular cancer (seminoma) versus mesothelioma yielded a D value of 0.8455, which has an associated significant P value of 0.000; seminoma and mesothelioma were significantly different and were sampled from populations with different distributions.

A comparison of the distribution of values for testicular cancer (seminoma) versus melanoma yields a D value of 0.6879, which has an associated significant P value of 0.000; seminoma and melanoma are significantly different and are sampled from populations with different distributions.

A comparison of the distribution of values for lymphoma versus brain cancers yields a D value of 0.7750, which has an associated significant P value of 0.000; lymphoma and brain cancer were significantly different and were sampled from populations with different distributions.

A comparison of the distribution of values for lymphoma versus mesothelioma yields a D value of 0.9000, which has an associated significant P value of 0.000; lymphoma and mesothelioma were significantly different and were sampled from populations with different distributions.

A comparison of the distribution of values for lymphoma versus melanoma yielded a D value of 0.6727, which has an associated significant P value of 0.000; lymphoma and melanoma are significantly different and are sampled from populations with different distributions.

A comparison of the distribution of values for small cell lung versus brain cancers yielded a D value of 0.7333 which has an associated significant P value of 0.000; lymphoma and brain cancer were significantly different and were sampled from populations with different distributions.

A comparison of the distribution of values for small cell lung versus mesothelioma yielded a D value of 0.9000, which has an associated significant P value of 0.000; lymphoma and mesothelioma were significantly different and were sampled from populations with different distributions.

A comparison of the distribution of values for small cell lung versus melanoma yielded a D value of 0.6273, which has an associated significant P value of 0.000; lymphoma and melanoma were significantly different and were sampled from populations with different distributions.

Conclusion:

seminomas, lymphomas and small cell lung cancer were found to be a unitary grouping that is statistically distinct from the unitary grouping of brain cancers, mesotheliomas and melanomas.

Whilst the statistical analysis indicates lymphoma, small cell lung, brain, and mesothelioma as being drawn from a normal distribution, such is not the case for the melanomas and the seminomas, neither of which conform to a normal distribution nor to a log normal distribution.

A statistical analysis using the Kolmogorov-Smirnov test indicates that the distribution of melanoma values depicted in FIG. 11A-FIG. 11H neither conforms to a normal distribution, nor a log normal distribution. As shown in later examples, the melanomas exhibit a heterogeneity that is increased by intra- and extra-cellular deposits of melanin, a heterogeneous set of polymers which bind multiple metals, and by the presence of High Metallomic Regions (HMRs), distributed within many melanomas. These HMRs are a source of hidden atomic variation that has been uncovered for the first time owing to the technology described in this application. Such regions are undetectable by conventional pathological examination.

It is likely that the seminomas in FIG. 11A-FIG. 11H consist of two populations, one with a small variance that makes up the bulk of the individuals and one that is more diverse and extends from 2K to 4K CC/S. It is probable that the bulk of the seminomas in FIG. 11A-FIG. 11H correspond to the clinical group that has an excellent response to radiation, whereas the remaining subgroup is relatively more radioresistant. This finding is consistent with clinical data (below). It should also be noted that the seminomas depicted in FIG. 11A-FIG. 11H are a unitary group, namely "classic" seminomas in a pathological context. Despite this outwardly appearing morphological homogeneity, the metallomic analysis has revealed an underlying heterogeneity that is hidden from conventional analyses.

1. Cancers of the Testis

For tumours of the testis, the major division is relatively straightforward with testicular Germ Cell Tumours (GCT) falling into two large categories, seminoma and non-seminoma. For patients presenting with testicular "cancer", approximately 50% are diagnosed with seminoma. Of these, approximately 85% present with stage I disease with the remainder being clinical stage IIA and IIB. (The distinction between stage IIA and stage IIB, is that lymph nodes are ≤2 cms in the former and 2 to 5 cms in the latter).

Postoperative radiation treatment for testicular seminoma has been the mainstay of adjuvant therapy for more than half a century. Seminomas are one of the most sensitive tumour types to radiation, where a clinical trial of stage I testicular seminoma reveals that treatment doses of 20 Gray, given as 10 fractions over 2 weeks, is sufficient to lead to almost 98% cure rates at 5 years (Jones et al., *Journal of clinical Oncology*, 23, 1200-1208, 2005; Medical Research Council Trial TE18/European Organisation for the Research and Treatment of Cancer Trial 30942 (ISRCTN18525328)). This radiation dose compares to 60 Gy (and up to 90 Gy), for high grade gliomas, such as glioblastoma multiforme, where overall survival is increased only by months.

The extreme radio-sensitivity of early stage seminoma is well described, with dose reductions being taken as low as 13 Gy for testicular intraepithelial neoplasia, which is a precursor to a more invasive form of cancer (Sedlmayer et al., *Int J Radiat. Oncol. Biol. Phys.* 50, 909-913, 2001; Classen et al., *Br J Can.* 88, 828-831, 2003). The European Germ Cell Consensus Group summarized its position in 2008, with 20 Gy in single doses of 2 Gy each being the recommended radiotherapy (Krege et al., *Eur. Urol.* 53, 478-496, 2008). The authors point out that for stage II testicular seminoma, a total dose of 30 Gy for stage IIA and a total dose of 36 Gy for stage IIB "seems reasonable". The statement that these two dosages "seem reasonable" highlights the inexactness of the prior art (Krege et al., *Eur. Urol.* 53, 497-513, 2008), It should also be noted that although 36 Gy is the recommended dose, it has been pointed out earlier for stage II by Classen et al., *J Clin Oncol* 21, 1101-1106, 2003), that there is a potential for dose reduction. It should also be noted that relapse-free survival for stage IIA is 95%, and for stage IIB it is 89%. Overall survival is close to 100%.

The American recommendations for stage I and stage II seminomas are in line with the European ones described above. Up to 2015, Mead et al., evaluated the evidence from a number of clinical trials Mead et al., *Journal of the National Cancer Institute*, 103, 241-249, 2011) and the recommendations for stage I seminoma are as above. For stage IIA seminomas, low dose radiotherapy to the paraaortic lymph nodes and superior ipsilateral pelvis is recommended with a total dose of 25 to 35 Gy in areas of gross adenopathy.

The exquisite sensitivity of germ line tumours is put into perspective, by comparing the radio-sensitivity of testicular cancers with those of brain cancers.

2. Cancers of the Brain

There is considerable variation in clinical practice for the management and treatment of adult gliomas, which in Australia and New Zealand occur with the following frequencies; 4% astrocytoma grade I; 10% astrocytoma grade II; 22% astrocytoma grade III; 52% glioblastoma multiforme grade IV; and with oligodendrogliomas and oligoastrocytomas making up the remainder (Cancer Council Australia/Australian Cancer Network/Clinical Oncological Society of Australia, ISBN 978-0-9775060-8-8; 2009). Of interest for this invention is glioblastoma multiforme, the most advanced of these gliomas, as it is considered by radiologists to be radiation resistant. In addition, the comparison of glioblastoma with stage III astrocytomas is revealing in terms of their metallomics, as against the clinical comparisons (see below). The standard radiotherapeutic treatment for high-grade astrocytomas is 60 Gy in 2 Gy fractions (sometimes with a 10 Gy boost), but there are no data in which the optimal dose has been determined for grade IV gliomas such as glioblastoma multiforme. For grade III gliomas many radiologists use 59.4 Gy with a fractionation procedure of 1.8 Gy, on the "expectation" that the 10% reduction per fraction from 2.0 Gy to 1.8 Gy in the case of grade III gliomas may cause less tissue damage.

Two phase III clinical trials bear on these data; the Radiation Therapy Oncology Group (RTOG7401) and the Eastern Cooperative Oncology group (ECOG1374) (Nelson et al., *NCI Monogr.* 6, 279-284, 1988 and Chang et al., *Cancer*, 52, 997-1007, 1983). There were no survival differences between treatment arms (radiation; radiation plus radiation boost; radiation plus BCNU, and radiation plus CCNU) and little difference between anaplastic astrocytoma and glioblastoma. It is salient in the context of minor differences in survival outcome between anaplastic astrocytoma and glioblastoma, that the metallomic data for these categories are heterogeneous, their distributions overlap, and they are not significantly different from each other when tested using the Kolmogorov-Smirnov test (P=0.581).

The central issue with radiation therapy to the whole brain is the occurrence of multiple complications such as neurocognitive problems, leukoencephalopathies and endocrinopathies. While some of these have been ameliorated with Involved Field Radiation Therapy (IFRT), the frequency of relapse has not altered, nor the percentage of patients with multilocal failures.

There is clearly a need to better personalize therapies for patients, e.g., radiotherapy to those patients who are at the radiation sensitive end of the spectrum, while sparing those who are likely to be radiation resistant. The current one-size-fits-all therapy, e.g., radiation therapy, is obsolete, given the new knowledge provided by the date of this application including the metallomic data.

3. Cancers of the Serosal Membranes; Mesotheliomas

Mesotheliomas are considered to be radiation resistant, and treatment protocols are of the order of a dose of 54 Gy delivered in 1.8 Gy fractions.

The clinical situation with mesotheliomas is little different to that confronting physicians with other tumour types. In first examining surgically resectable tumours, there is the classic trimodality: a definitive surgical procedure, radiation therapy and systemic chemotherapy. In the case of mesotheliomas, the role of definitive surgery is controversial and it is unknown whether resection of a tumour yields an improvement in survival for that particular patient and no prospective clinical trials bear on this matter. There are also no adequately powered randomized phase III clinical trials that bear on the integration of radiation therapy and chemotherapy before and or after surgery, the closest being a phase II trial using a hemithoracic radiation therapy of 54 Gy following extrapleural pneumonectomy, (Rusch et al., *J Thorac Cardiovasc Surg* 122, 788-795, 2001).

4. Small Cell Lung Cancer

Radiologists and physicians consider small cell lung cancer to be a radio-sensitive tumour with good response rates to radiotherapy. The European Society of Medical Oncology (ESMO) has documented its modified Tumour Node Metastasis classification and stage grouping, and released its Guidelines for diagnosis, treatment and follow up (Fruh et al., *Annals of Oncology,* 24, (Supplement 6), vi105, 2013; Table 3). The best overall survival outcome with curative intent is from a total dose of 45 Gy, with daily 1.5 Gy fractions, together with chemotherapy (Turrisi et al., *N Engl J Med,* 340, 265-271, 1999).

5. Lymphomas

The Cancer Council Australia and the Australian Cancer Network, have set out clinical practice guidelines for the diagnosis and management of lymphoma, (ISBN: 0-9775060-0-2; 2005). For clinical stage I-Ill low grade follicular lymphoma it recommends involved-field radiation therapy of 30-36 Gy. For adult non-Hodgkin's lymphoma, the US National Cancer Institute recommends doses between 25 Gy and 50 Gy. For the diffuse B-cell lymphomas described herein, the National Comprehensive Cancer Network (NCCN.org; 2015) recommends 30-36 Gy after chemotherapy, 45-55 Gy as primary treatment for refractory to chemotherapy, or non-candidates for chemotherapy, and 30-40 Gy for salvage pre- or post-stem cell transplantation. In the varied spectrum that comprises non-Hodgkin's lymphoma, some patients have tumours that remain indolent for long periods of time, others evolve rapidly and require immediate treatment. As can be seen from the above in terms of radiation therapy, it is largely a one-size-fits-all situation.

6. Melanomas

Melanomas have generally been considered to be a radioresistant tumour, but the data are conflicting, with much of the evidence deriving from cell lines that have demonstrated a wide spectrum of radio-responsiveness. The clinical practice guidelines for the management of melanoma in Australia and New Zealand have been set out in detail by the Cancer Council Australia/Australian Cancer Network/Ministry of Health New Zealand. For Australia see ISBN 978-0-9775060-7-1 and for New Zealand see ISBN (electronic) 978-1-877509-05-6. The clinical data have been reviewed by Wazer et al., UptoDate, 2015 and they too are conflicting. The clinical trials reviewed by Wazer et al., led them to conclude that melanoma is a radio-responsive tumour, "but the optimal dose and fraction remain uncertain". In terms of metastatic disease, there are substantial differences in radio-responsiveness between cutaneous, lymph node, visceral metastases or metastases to bone or brain. (It should be noted that the conflicting clinical trial data make better scientific sense in terms of the metallomic data, where there is a wide range of manganese values between patients, and as revealed in FIG. 1, large differences within a single tumour). Depending on the site of melanoma, doses have varied from 32 Gy up to 100 Gy. Finally, while radiation therapy is useful in palliative care in the settings of bone, brain and visceral metastases, it is quite unclear whether large dose fractions improve palliation.

Example 5

Melanin and Morphological Inhomogeneities and Radiation Sensitivity/Insensitivity As described above, the distribution of melanin, which has storage capacity for different chemical elements, particularly metals, can be a major contributor to variations seen with melanomas. FIG. 1 is an image of an H&E stained melanoma which shows this morphological non-homogeneity, which is clearly visible as two distinct lineages within it; one lineage is light coloured and largely amelanotic and the other is darkly staining and contains both intracellular and extracellular melanin. In addition, the cells of the amelanotic region are more uniform in terms of their nuclear sizes and morphologies, than cells in the heavily melanized regions, a finding that impinges on the ATI. The lower the variance of a population of cells in any of multiple characteristics, the more restricted will be its response to any perturbogen. The metallomic content of the top part of the same tissue section as depicted in FIG. 1 was measured. A two-dimensional representation of the ablation tracks taken through the melanoma is shown in FIG. 12. These data illustrate the variation in manganese level in different parts of the same tumour and emphasize the importance of characterizing a 2D landscape in order to make informed choices on whether a patient should be radiation treated, or not. The background-corrected median values for manganese in these visually-selected areas are 31,939 calibrated counts per second and 3,045 calibrated counts per second.

The 2D landscape provides an estimate, within a tumour, of the proportion of a sampled area that exists above a designated threshold. In the above sample, this can be defined, for example, as to what proportion of the landscape falls below the $10^{th}$ percentile, the $20^{th}$ percentile, the $30^{th}$ percentile, the $40^{th}$ percentile the $50^{th}$ percentile etc. and accordingly, quantitation is achieved. Thus, for example, if 90 percent of the area sampled is very low in manganese, then the tumour as a whole is likely to be susceptible to radiation. On the other hand, there is little point in irradiating a tumour in which 90% of the area is high in manganese, as radiation will leave most of the tumour intact. Note that these percentiles cannot be derived from a sample of a tumour that has been "ground up" for molecular work.

The same tumour of FIG. 1 was analyzed further and the content of all 4 metals, $^{55}$Mn, $^{66}$Zn, $^{56}$Fe and $^{63}$Cu, was determined and shown in FIG. 13A-FIG. 13D. The dichotomy, as seen morphologically, is visible from these results. As the ablation travels from the left hand side with very high values, to the right hand side with far lower values, the inflexion point occurs around voxel 34.

Figure 14A:
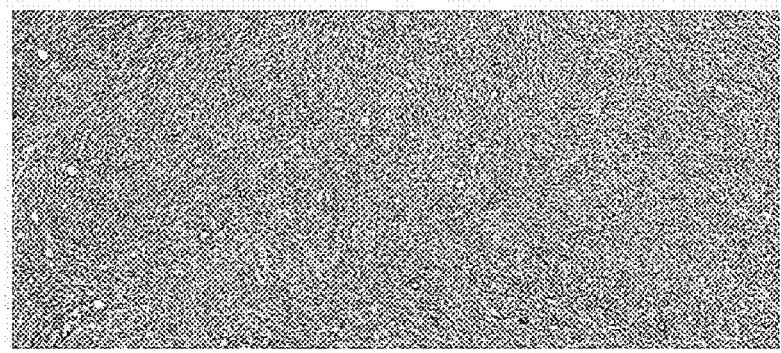
FIG. 14A. Photographic image of an H&E stained tissue section of a melanoma from the left forefinger of a 54 year old male: stage IV, T4N0M1.
Figure 14B:
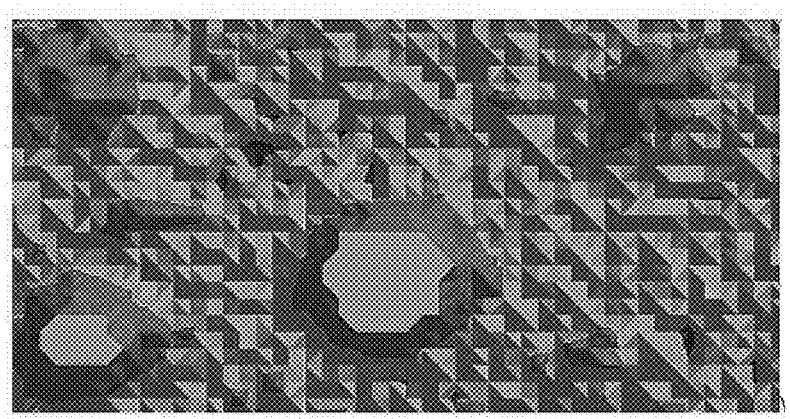
FIG. 14B. Two-dimensional representation of ablation tracks across the tumour. Scale; pale grey (main bulk $^{55}$Mn value of the tumour) 0-2,000 CC/S; whitish flat areas, generically termed herein as High Metallomic Regions (HMRs), which in this particular example correspond to >6,500 calibrated counts per second.

On the other hand, melanomas with uniform morphology, may still display very different metallomic content. For example, FIG. 14A-FIG. 14B shows an H&E stained tissue section of a melanoma from the left forefinger of a 54 year old male: stage IV, T4N0M1. This particular melanoma has a uniform morphology and the pathology would appear unremarkable to an experienced pathologist (FIG. 14A). The metallomic content was measured in this melanoma, and is shown in FIG. 14B. The underlying 2D metallomic content is very different. Indeed, there are 2 large concentrations of cells with very high levels of manganese.

The median $^{55}$Mn value for the bulk of this tumour sample was determined to be 817 background corrected calibrated counts per second, which places this tumor in the very sensitive end of the radio-responsiveness spectrum. On the other hand, the larger of the two whitish flat areas, namely the HMR, was found to have a value exceeding 6,500 calibrated counts per second, placing it at the radio-resistant end of the spectrum.

These two regions are apparent from visual inspection of a voxel matrix. However a rigorous analysis of thresholds is necessary for an in-depth analysis of these two HMR regions and this analysis is illustrated in FIG. 15A-FIG. 15D, and FIG. 16A-FIG. 16C. As used herein, when referring to a specific metal in a High Metallomic Region (HMR), the HMR is designated as e.g., HMR($^{55}$Mn), HMR($^{66}$Zn), HMR ($^{56}$Fe) and HMR($^{63}$Cu) respectively, with HMR($^A$M) referring to the generic case of Any Metal.

Figure 15A:
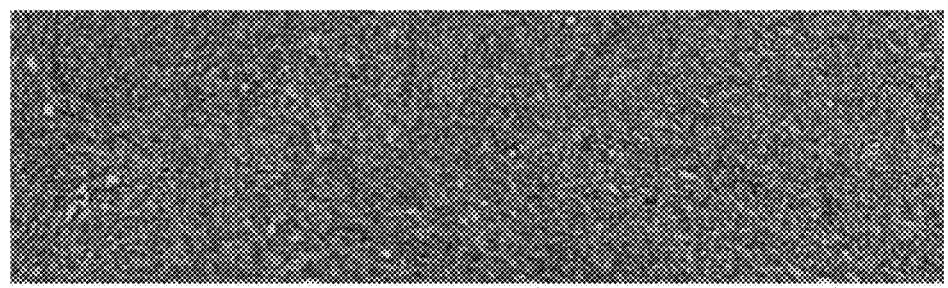
FIG. 15A. Photographic image of a standard 5 micron H&E stained tissue section from a formalin-fixed paraffin-embedded block from a melanoma on the left forefinger of the 54 year old male analyzed in FIG. 14-FIG. 14B illustrating the tissue and cellular morphology.
Figure 15B:
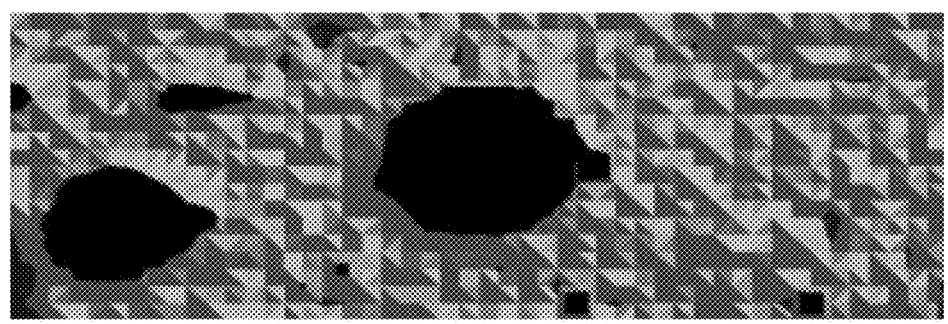
FIG. 15B. The metallomic content of the sample shown in A was measured. Part B is a two-dimensional representation of $^{55}$Mn levels in individual voxels of this section after LA-ICP-MS. Two clusters of contiguous voxels of high $^{55}$Mn content, denoted HMRs ($^{55}$Mn) and shown as black areas, become visible after visual inspection of the data of the voxel matrix. FIG.
Figure 15C:
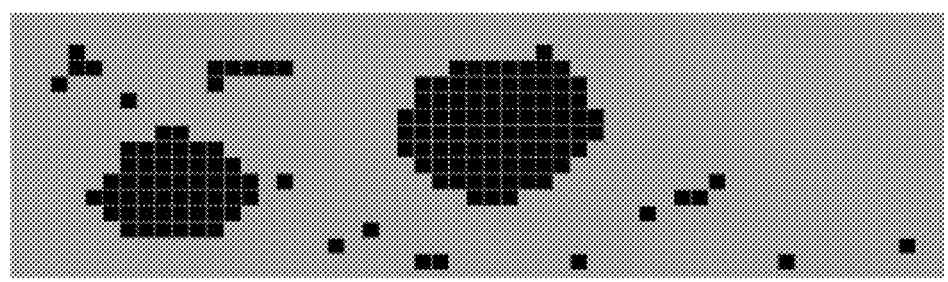
FIG. 15D. Two dimensional representation of $^{55}$Mn levels in each individual voxels of the section of A and B were further analyzed by applying a threshold of the median value per voxel of the whole area, plus the standard deviation (St.Dev.) of the voxel values of the whole area, plus the machine background value. Black squares show those voxels that are above this particular (median+St.Dev) threshold.

FIG. 15A shows the uniform morphological nature of a tumour area of 22×60 voxels (sampled from an approximately 1800 voxel area) as visualized by standard H&E pathology. FIG. 15B shows the two HMR($^{55}$Mn) regions as found by visual inspection of the numbers in each voxel. FIG. 15C shows the HMRs that emerge from this 22×60 voxel 2D landscape when one uses as a threshold the median value per voxel of the whole area plus the standard deviation (St.Dev.) of the voxels of the whole area (median+St.Dev.). A different threshold method also robustly uncovers the same two regions in this 22×60 voxel 2D landscape (FIG. 15D), this second method utilizes two times the median of the voxel values of the whole area (2× median).

Figure 15D:
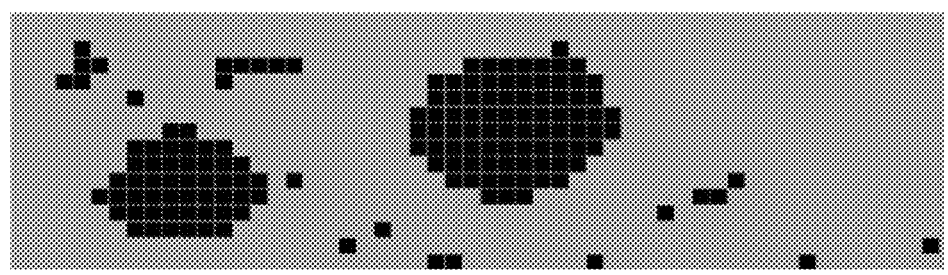

As seen by the distribution of clustered voxels that appear above threshold in FIG. 15C and FIG. 15D (black squares in a background of grey squares), the outcome of using (median plus St.Dev.) versus (2× median), is near identical in terms of finding HMRs($^{55}$Mn). Analysis of the six tumour types reveals that the 2× median method may be more consistent than the median plus St.Dev. method in detecting HMRs($^{55}$Mn), HMRs($^{66}$Zn), HMRs($^{56}$Fe) and HMRs ($^{63}$Cu). Whilst it will be apparent to the skilled artisan that either method may be used according to the invention, by way of non-limiting example, the 2× median methodology has been used in subsequent analyses shown herein.

Figure 16A:
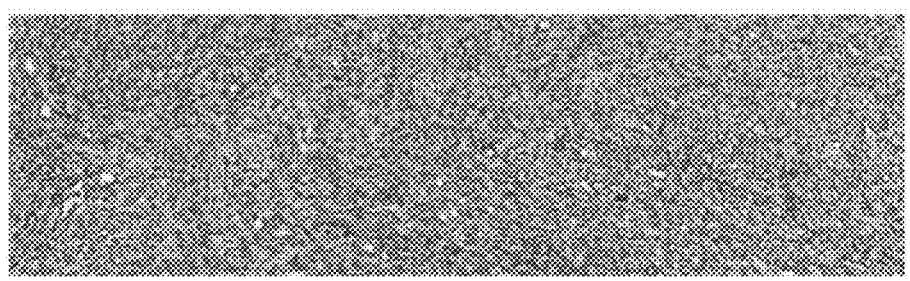
FIG. 16A: Photographic image of the same standard 5 micron H&E stained tissue section from the tumour of the melanoma patient from FIG. 15A.
Figure 16B:
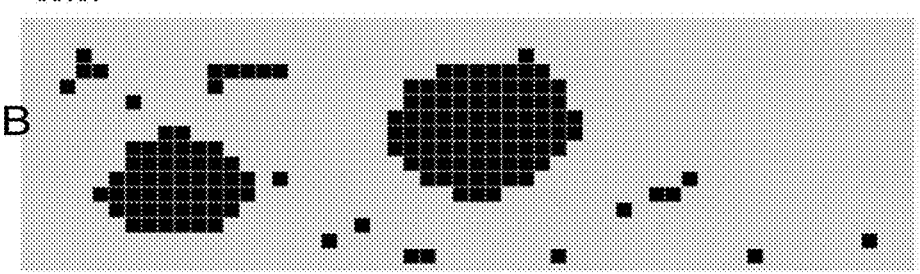
FIG. 16B: Two-dimensional reperesentation of the same voxel matrix of $^{55}$Mn values shown in FIG. 15C showing the two clusters of contiguous voxels that constitute the HMRs ($^{55}$Mn).
Figure 16C:
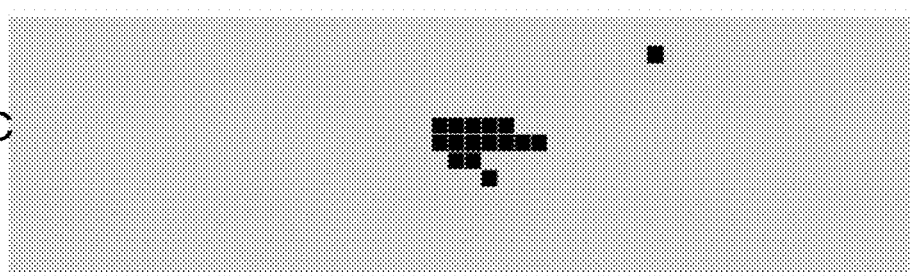
FIG. 16C: $^{66}$Zn voxel values in the identical voxels to those shown in the FIG. 16B and using the same threshold criterion (2× median) for $^{66}$Zn as for $^{55}$Mn.

A further important finding relating to the distribution of HMR($^{55}$Mn) and HMR($^{66}$Zn) in the same atomic landscape, is illustrated in FIG. 16A-FIG. 16C. FIG. 16A shows the identical H&E tumour landscape of FIG. 15A-FIG. 15D, FIG. 16B shows the two detected HMR($^{55}$Mn) areas, and FIG. 16C reveals the distribution of zinc in the identical voxels to those of the voxel matrix in FIG. 16B. In contrast to the two HMRs($^{55}$Mn), only a small region of HMR($^{66}$Zn) emerges above the 2× median of the zinc threshold. Zinc, iron and copper values generally remain at those of the bulk tumour area in regions of HMR($^{55}$Mn). This generalization does not hold in melanin-rich regions of melanoma tumours, where all four metals are found together in high concentrations in concert with melanin granules.

It is acknowledged by the skilled addressee that there are a number of mathematical and statistical methods of arriving at thresholds that are useful in revealing regions of metallomic interest in tumours of most use for clinical decision making for radiotherapy.

FIG. 17A-FIG. 17H provides an example of the extent to which HMRs($^{55}$Mn) occur in different tumour types, such as radiation sensitive versus radiation resistant ones. This comparison is of a 51 year old female patient with a small cell undifferentiated carcinoma of the lung, (Stage 1, T1N0M0) with the 54 year old patient who had a melanoma of the left forefinger (stage IV, T4N0M1). The region used herein for illustrative purposes corresponds to an approximately 1 mm by 1 mm sample of each of the two tumours, (31 by 31 voxels totaling 961 voxels). FIG. 17A-FIG. 17H reveal areas of $^{55}$Mn concentrations using four different thresholds, (i) T1, above a threshold of 0.5× the median value, (ii) T2, above a threshold of 1.0× the median value, (iii) T3, above a threshold of 1.5× the median value, and (iv) T4, above a threshold of 2.0× the median value.

In the case of the small cell carcinoma of the lung, the voxels that remain above the highest threshold of 2× the median value, T4, are generally non-contiguous ones (singletons) that are scattered throughout the sample. There are very few contiguous or adjacent concentrations of HMR ($^{55}$Mn) voxels in this radiation sensitive tumour sample. In contrast, the four right hand side panels (FIG. 17E-FIG. 17H) from the melanoma patient reveal the emergence of contiguous HMR($^{55}$Mn) voxels that are readily discernible at the T3, 1.5× the median value, and these HMRs($^{55}$Mn) remain even at the more stringent T4 level of 2× the median value.

The data of FIG. 18A-FIG. 18H show, by way of non-limiting example, that when the same threshold criteria are applied to the identical voxels of these two tumours, but now simultaneously assayed for HMRs($^{66}$Zn), no HMR($^{66}$Zn) areas are found at thresholds of T1, T2, T3 and T4 in the small cell carcinoma of this particular patient and only a minor concentration of contiguous Zn voxels is apparent in the tumour of the melanoma patient. The distribution of $^{66}$Zn voxel values remains relatively constant in both these two tumours, while HMRs($^{55}$Mn) predominate in the melanoma, as shown in FIG. 17A-FIG. 17H.

This comparison of two tumour types, one radiation sensitive and the other radiation resistant is further highlighted by way of non-limiting example, in the next seven Figures, (FIG. 19A through FIG. 25B). These illustrate the data from the 184 patients whose tumours are exemplary of the two spectral ends of radiation responsiveness: small cell lung, lymphoma and testis at the radio-sensitive end of the spectrum and mesothelioma, tumours of the brain and melanoma at the radio-resistant end of the spectrum.

By way of non-limiting example, an overview of tumour regions with high metallomic concentrations and their clinical implications is provided below.

Figures 19A, 19B:
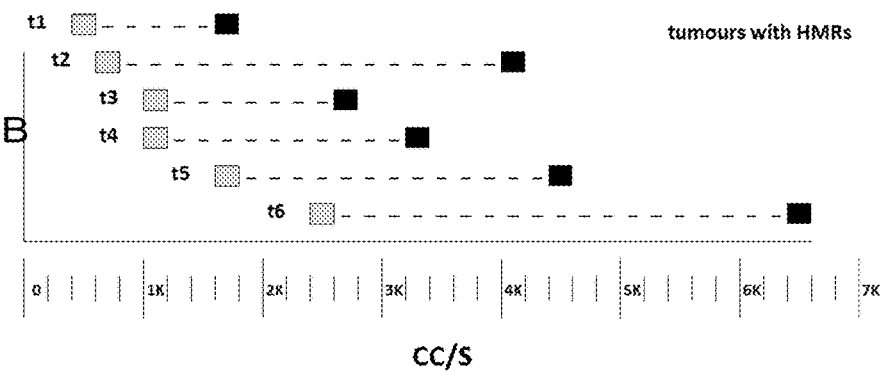
FIG. 19A-FIG. 19B: Histograms showing median $^{55}$Mn contents expressed as Calibrated Counts per Second (CC/S) of $^{55}$Mn in laser ablated samples from tumours of 20 patients with small cell carcinomas of the lung. Each grey square represents the median value calculated from a total area of approximately 1,800 voxels from the tumour of a single patient which was sampled.

FIG. 19A-FIG. 19B shows the $^{55}$Mn voxel data from each of twenty patients with small cell carcinoma of the lung when a tumour area of approximately 1,800 voxels was sampled. The median $^{55}$Mn value of the bulk of the tumour from each patient is represented by a square and is placed in bins of 200 consolidated counts per second over a range from zero CC/S to 7,000 CC/S. All twenty patients have tumours where the bulk $^{55}$Mn values fall below 3,000 CC/S, (grey squares). Fourteen of the twenty patients, shown by the grey squares above the top line, have no HMRs($^{55}$Mn) when a T4 threshold of 2× median is used. By contrast, the tumours of six patients, t1 through t6, contain single HMRs ($^{55}$Mn) (black squares connected to the grey squares by a dotted line). In a specific example, the bulk of the tumour of patient t6 has a median $^{55}$Mn value that falls in the 2,400 to 2,600 bin, (grey square), but this tumour also contains an HMR($^{55}$Mn) whose value falls in the 6,400 to 6,600 bin (black square). The number of above threshold contiguous voxels of the six HMRs($^{55}$Mn) in patient samples t1 through t6 is 4.9%, 3.1%, 2.1%, 12.3%, 12.6% and 5.2% respectively of the sampled tumour areas. In three of these patients, t2, t5 and t6, the $^{55}$Mn levels of their HMRs($^{55}$Mn) exceed 4,000 CC/S. Such regions are likely to contain cells that exhibit a degree of radio-resistance.

By way of non-limiting example a minimum size of 8×8 voxels efficiently revealed regions of high metallomic content. A person skilled in the art will appreciate that below this size, and depending upon the sensitivity of the instrument used, smaller and smaller HMRs are picked up until finally they become indistinguishable from a randomly generated background of singletons, as seen in the small cell lung carcinomas of FIG. 17A-FIG. 17D. An 8×8 HMR-containing landscape is bounded in both the X' and Y' directions. It is contemplated that HMRs above X8×Y8 voxels can individually increase by integers in the X' and Y' directions, yielding HMRs of X[8+1]×Y[8]: X[8]× Y[8+1]: X[8+1]× Y[8+1]: X[8+2]× Y[8]: X[8+2]× Y[8+1]: X[8+2]× Y[8+2]: X[8+1]× Y[8+2]: X[8]×Y[8+2] through X[8+n]× Y[8+n] where n is an integer that can vary from 1 to thousands. Preferably, this integer varies from 1 to 100, more preferably from 1 to 22, when a sample of 30×30 voxels (1 mm$^2$ is sampled). A person skilled in the art will understand that there is no impediment to setting a threshold lower than a minimum of 8 voxels. The value of 8 has been used here because it is empirically-derived and serves as an example of an efficient search tool for HMRs.

Sizes of HMRs

An important descriptor of any HMR is its size, shape and content. Tumours of the six types from a total of 184 patients were analyzed. A person skilled in the art will appreciate that HMRs can be variable in size, shape and content and that defining a minimal area will depend upon machine jitter, and in some instances a single voxel may represent a rare, low frequency electronic "spike" in the data. In addition, machine "stutter" may occasionally produce two or three consecutive high values in the X or Y direction, but is readily recognizable by appropriate image filtering software.

In view of the above, an HMR for any metal [HMR($^4$M), where $^4$M=Any Metal] may contain two adjacent voxels to fulfill the criterion of voxel contiguity. FIG. 20A shows the eight different theoretical ways in which two adjacent voxels (a doublet), can be configured from a reference single voxel (starred). The size of HMR($^4$M) can vary from 2, 3, 4, 5, 6, 7, 8, 9, 10 etc contiguous voxels, to an integer which is the sample size chosen for analysis of that particular tumour. A person skilled in the art will appreciate that size of HMR ($^4$M) according to the invention is in any range measurable using existing technology. For example, HMR($^4$M) size can range from 2 voxels to about 800,000 voxels and any value in between (this being the maximum number of 35×35 micron pixels that can be analysed if a conventional slide is loaded to the edges with tumour material). A person skilled in the art will also appreciate that an HMR can apply to cancer cells in a tumour, or to a region of cellular and non-cellular material, generally referred to as associated stroma, which itself can exist in an "activated" state owing to its interaction with neighbouring cancer cells.

For a clinical application, a single sample size is typically an area of 1 mm$^2$, as such a size has a precedent in routine pathological analysis. Thus when pathologists examine a tumour section for mitotic rate, for example in melanoma, they have typically used the number of mitoses per highpower field, or per ten high-power fields (Burton et al., 2012, *Am. J Surg.* 204, 969-974). By way of non-limiting example, in respect of HMRs($^4$M), a 1 mm$^2$ sample conveniently approximates 1,000 voxels, in this application. Multiple 1 mm$^2$ samples may be laser ablated from a single tissue section on a glass slide. Multiple 1 mm$^2$ samples may be laser ablated from multiple sections from the same tumour block. Multiple 1 mm$^2$ samples may be laser ablated from multiple blocks representing different samples from the same tumour, or its metastatic derivatives. The cumulative HMR($^4$M) size determined from multiple samples can vary from 4 voxels (2 doublets) to many millions for a single tumour. It will be understood that the upper limit is constrained by the practicality of the time required for analysis and health care expense.

Shapes of HMRs

By way of non-limiting example, within a sample size of 1 mm$^2$, or ~1000 voxels of the 35×35×5 micron type, there can exist a large number of HMR($^4$M) shapes that conform to the condition of voxel contiguity. As described herein for the first time, a common shape is that shown by example in the melanoma patient data of FIG. 14A-FIG. 14B and FIG. 15A-FIG. 15D, and represented stylistically in FIG. 20B-FIG. 20C. Patterns such as those depicted in FIG. 20D-FIG. 20H manifest themselves in different tumour types. For example, FIG. 20D is one in which cancerous epithelial cells line a lymphatic vessel or duct, such as in breast and prostate cancer. FIG. 20E and FIG. 20G would be representative of the classic "Indian File" movement of cells which follow a structural motif in a tumour such as a collagen bundle, or a major nerve tract in glioblastomas or astrocytomas, or the single file pattern seen in breast cancer sections. FIG. 20F illustrates the case in which cancerous cells would be contained within a blood or lymphatic vessel, such as in Ductal Carcinoma In Situ (DCIS) in breast cancer. FIG. 20H is representative of the distribution of cells and melanin deposits in some melanotic tumours.

It is understood that any known mathematical and statistical methods may be used to analyze patterns and inhomogeneities in matrices and the associated software. Such methods may reveal concentrations of voxels of many shapes and sizes, which may then be mapped onto the underlying pathological landscape.

Footprints of HMRs($^4$M) and their Value in Radio-Responsiveness

In a sample of 1,000 voxels using a 2× median threshold, the HMRs($^4$M) (black squares in FIG. 20A-FIG. 20H), FIG. 20B, FIG. 20C, FIG. 20D, FIG. 20E, FIG. 20F and FIG. 20G represent 4%, 3.7%, 2.4%, 1.5%, 3.7%, and 0.9% of the sample.

As shown in FIG. 19A-FIG. 19B, it is contemplated that if patients with tumours t2, t5 and t6 are treated with radiotherapy on either an intention-to-treat or palliative basis, the bulk of the cancer cells (with values <800, <1,800 and <2,600) would either be killed or sufficiently damaged as to be unable to undergo further cell division. By contrast, most of the cells of the HMRs($^{55}$Mn) of these tumours (with values >4,000, >4,200 and >6,400) would survive and, in time, generate a new form of the tumour, giving rise to the familiar clinical finding of tumour reoccurrence.

Figure 21:
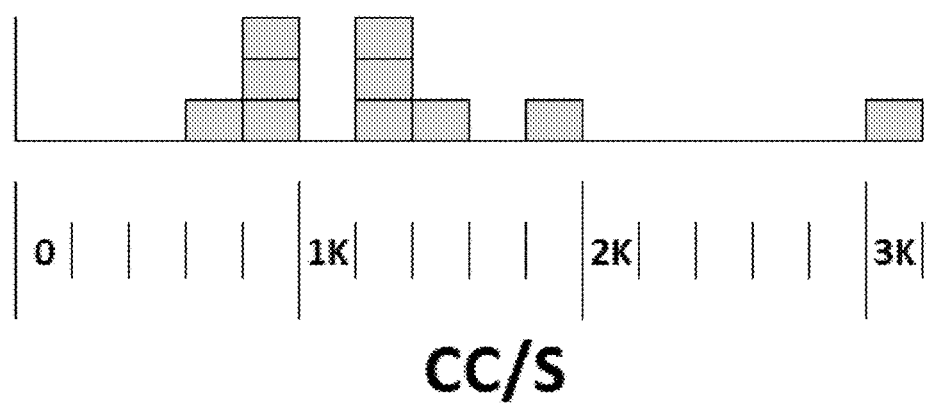
FIG. 21: Histogram showing the median $^{55}$Mn contents expressed as Calibrated Counts per Second (CC/S) of $^{55}$Mn in laser ablated samples from a total area of approximately 1800 voxels of tumours of 10 patients with diffuse B cell lymphoma. Each grey square represents the median value calculated from the tumour of a single patient. The bins in the histogram are 200 CC/S units.
Figure 22:
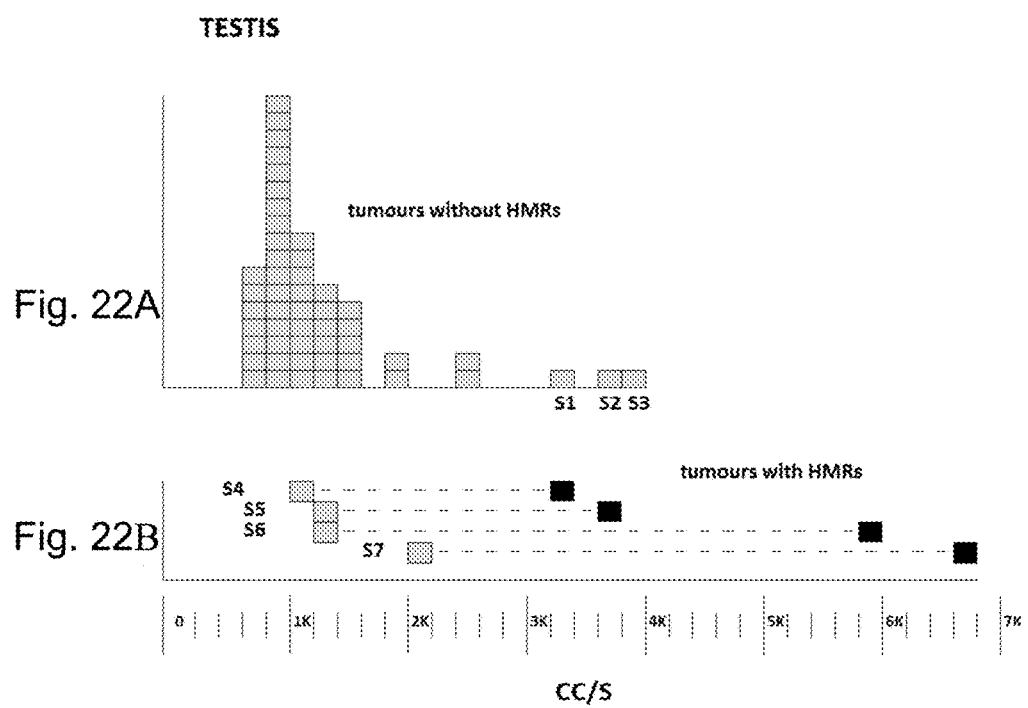
FIG. 22A-FIG. 22B: Histograms of median $^{55}$Mn contents expressed as Calibrated Counts per Second (CC/S) of $^{55}$Mn in laser ablated samples from tumours of 55 patients with classic seminoma. Each grey square represents the median value calculated from a total area of approximately 1,800 voxels of the tumour of a single patient.
Figure 23:
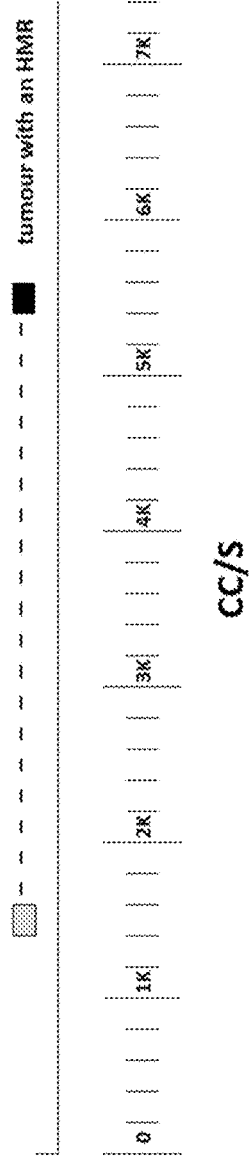
FIG. 23A-FIG. 23B: A histogram of median $^{55}$Mn contents expressed as Calibrated Counts per Second (CC/S) of $^{55}$Mn in laser ablated samples from tumours of 10 patients with mesothelioma. Each grey square represents the median value calculated from a total area of approximately 1,800 voxels of the tumour of a single patient.
Figure 24:
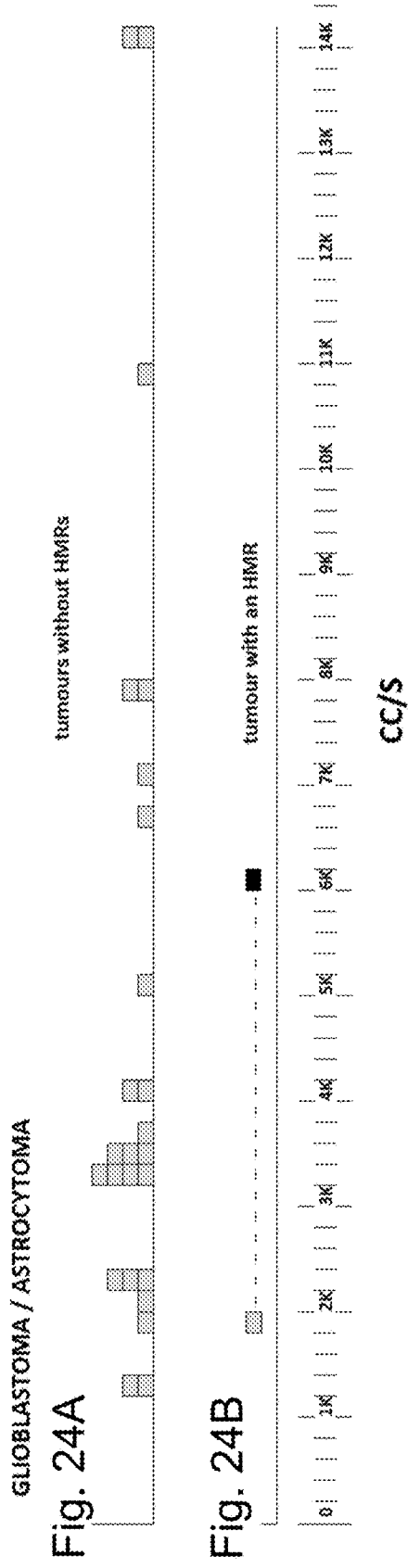
FIG. 24A-FIG. 24B: Histograms showing median $^{55}$Mn contents expressed as Calibrated Counts per Second (CC/S) of $^{55}$Mn in laser ablated samples from tumours of 25 patients with either glioblastoma multiforme or astrocytomas of the brain. Each grey square represents the median value calculated from a total area of approximately 1800 voxels of the tumour of a single patient.
Figure 25:
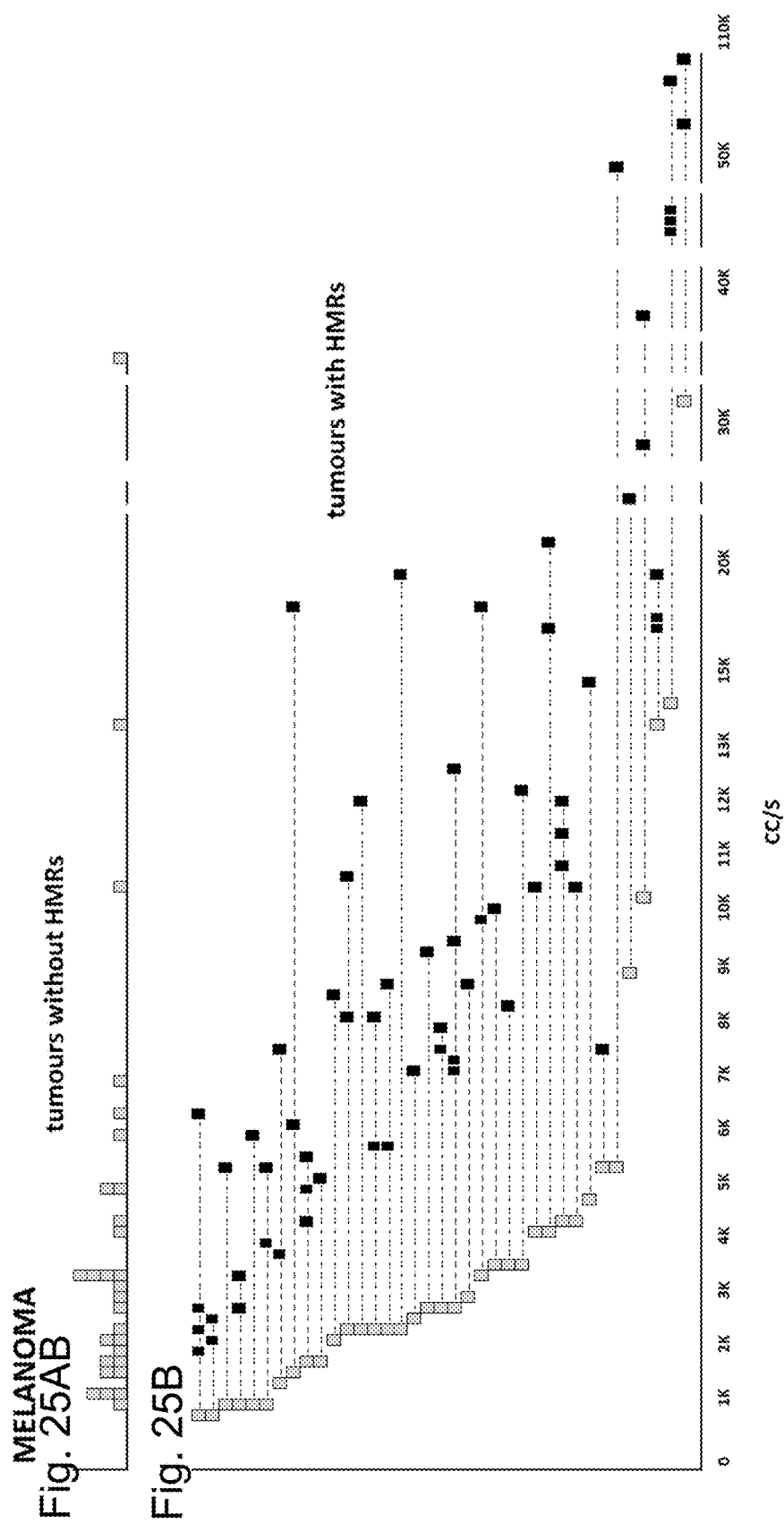
FIG. 25A-FIG. 25B: Histograms showing median $^{55}$Mn contents expressed as Calibrated Counts per Second (CC/S) of $^{55}$Mn in laser ablated samples from tumours of 64 patients with melanoma. Each grey square represents the median value calculated from a total area of approximately 1,800 voxels of the tumour of a single patient, except in the case of the two melanoma patients each with two major lineages within the same tumour, where the sampled area is less than 900 voxels per lineage.

HMR Data from Lymphomas, Tumours of the Testis, Mesotheliomas, the Brain and Melanomas FIG. 21 shows the data from the 10 patients with diffuse B cell lymphomas when a tumour area of approximately 1,800 voxels was sampled for $^{55}$Mn content by the Laser Ablation technology. None of the tumours had HMRs($^{55}$Mn) when a threshold of 2× median was used, as shown by the absence of black squares. In addition, all median $^{55}$Mn values fell below 3,200 CC/S. The expectation is that if the tumours of these 10 patients were treated with radiotherapy on an intention-to-treat or palliative basis, the bulk of the cells would either be killed or sufficiently damaged as to be unable to undergo further cell division. It is accepted from everyday clinical practice in this area that large lymphoma masses are easily eradicated with radiotherapy.

FIG. 22A-FIG. 22B show the data from the 55 patients with tumours of the testis when a tumour area of approximately 1,800 voxels was sampled. These 55 tumours are all classic seminomas and form a unitary group on the basis of pathological criteria. Radiation oncologists and medical oncologists consider them to be very radiation sensitive, since large seminoma masses are easily eradicated with radiotherapy. Fifty one of these seminomas have no HMRs($^{55}$Mn) when a threshold of 2× median is used, as shown by the 51 grey squares above the top line. By contrast, four patients, S4, S5, S6 and S7, have single HMRs($^{55}$Mn) (black squares) relative to their bulk values (grey squares). The sizes of these four HMRs($^{55}$Mn) ranged from 1.8 to 6.3% of the sampled area. In two of these patients, S6 and S7, the CC/S value of the HMRs($^{55}$Mn) exceeds 5,000 CC/S and such regions are likely to contain cells that are radiation resistant. These data support the probability when these 2 patients are treated with radiotherapy on an intention-to-treat basis or palliative basis, the bulk of the cells are killed or sufficiently damaged as to be unable to undergo further cell division, while the cells of the HMRs($^{55}$Mn) survive and in time generate a new form of the tumour.

Finally, as was found from the earlier statistical analysis of these seminomas, they are not a unitary group. It may well be that the tumours of the three seminoma patients, 51, S2 and S3, which populate the extreme right hand tail of the top distribution, and whose bulk median $^{55}$Mn values are between 3,000 and 4,000, have a degree of radio-resistance. The data from these three outliers (and from patients S4, S5, S6 and S7, whose tumours do harbor HMRs($^{55}$Mn)), are consistent with the clinical data which reveal that a small proportion of seminomas exhibit signs of radiation resistance.

FIG. 23A-FIG. 23B show the data from the 10 patients with mesothelioma when a tumour area of approximately 1,800 voxels was sampled (with mesothelioma considered to be a radiation resistant entity). Nine of the patients have no HMRs($^{55}$Mn) when a threshold of 2× median is used, as shown by the grey squares above the top line. The one patient with the lowest median CC/S voxel value has a single HMR($^{55}$Mn) whose CC/S exceeds 5,000 (black square) and the size of which was 3.2% of the sampled area. Importantly, most mesothelioma $^{55}$Mn values exceed those of the three sensitive tumour types.

FIG. 24A-FIG. 24B reveals the findings from the 25 patients with tumours of the brain (glioblastomas and astrocytomas) when a tumour area of approximately 1,800 voxels was sampled (with tumours of the brain considered to be largely radiation resistant). Twenty-four of the patients have no HMRs($^{55}$Mn) when a threshold of 2× median is used, as shown by the grey squares above the top line. One patient with a low median $^{55}$Mn value has a single HMR($^{55}$Mn) whose CC/S exceeds 6,000 and the size of which was 3.6% of the sampled area. While most $^{55}$Mn brain values exceed those of the three sensitive tumour types, these data indicate that some glioblastomas and astrocytomas will respond to radiation treatment, as eight of these patients have median $^{55}$Mn values below 3,000 CC/S.

FIG. 25A-FIG. 25B shows the data from the 64 melanoma patients, when a tumour area of approximately 1,800 voxels was sampled, with melanoma historically considered to be a radiation resistant tumour. The melanomas reveal extensive heterogeneity relative to the other five tumour types, with 29 patients having tumours without HMRs($^{55}$Mn), and 35 patients having tumours with HMRs($^{55}$Mn). Unlike the previous five tumour types where HMRs($^{55}$Mn) have existed as single entities within the tumour sample, half of the melanomas have multiple HMRs within the same tumour. The sizes of the HMRs($^{55}$Mn) vary from 1.6 to 21.8% of the sampled area. Owing to the stringency used herein for the threshold (2× median), the number of HMRs($^{55}$Mn) per sample is actually a minimal estimate. FIG. 25A-FIG. 25B also reveals that for nearly 30% of tumours, the median value of the bulk of a tumour falls below a CC/S threshold of 2K (grey squares) and for two thirds of the tumours, the median value of the majority of voxels falls below a CC/S threshold of 4K (grey squares).

In hindsight, these atomic data indicate that many melanomas have areas of radio-sensitivity. In terms of metastatic disease, there are substantial differences in radio-responsiveness between cutaneous, lymph node, visceral metastases or metastases to bone or brain. The widely held opinion of melanomas being radiation resistant is based on conflicting data, particularly evident by the findings that some melanomas melt away after radiation treatment, while others can rapidly kill the patient in spite of radiation treatment. The metallomic data presented herein, show for the first time, how traditionally conflicting data can be partially resolved by the discovery of the previously unknown HMRs($^{55}$Mn) in melanoma tumours.

FIG. 25A-FIG. 25B also shows that 88% of the melanoma HMRs($^{55}$Mn) exceed a CC/S value of 4,000, (black squares) and nearly half of the HMRs($^{55}$Mn) exceed values of 10,000 and some are near 100,000. These novel data indicate that many melanomas may indeed initially be radiation sensitive, but since most harbour HMRs which contain substantial levels of manganese, such cell populations would likely survive radiation treatment and the tumour would regenerate from radiation resistant remnants. The clinical outcome is that the patient returns post-radiotherapy with a reoccurrence of the cancer, which is now more resistant than the initial tumour. Second, many of the melanomas contain large quantities of extra- and intra-cellular melanin, and as our data show, again for the first time in tissue sections analyzed by laser ablation, melanins can contribute to radiation resistance by the biochemical processes outlined below.

Figure 26:
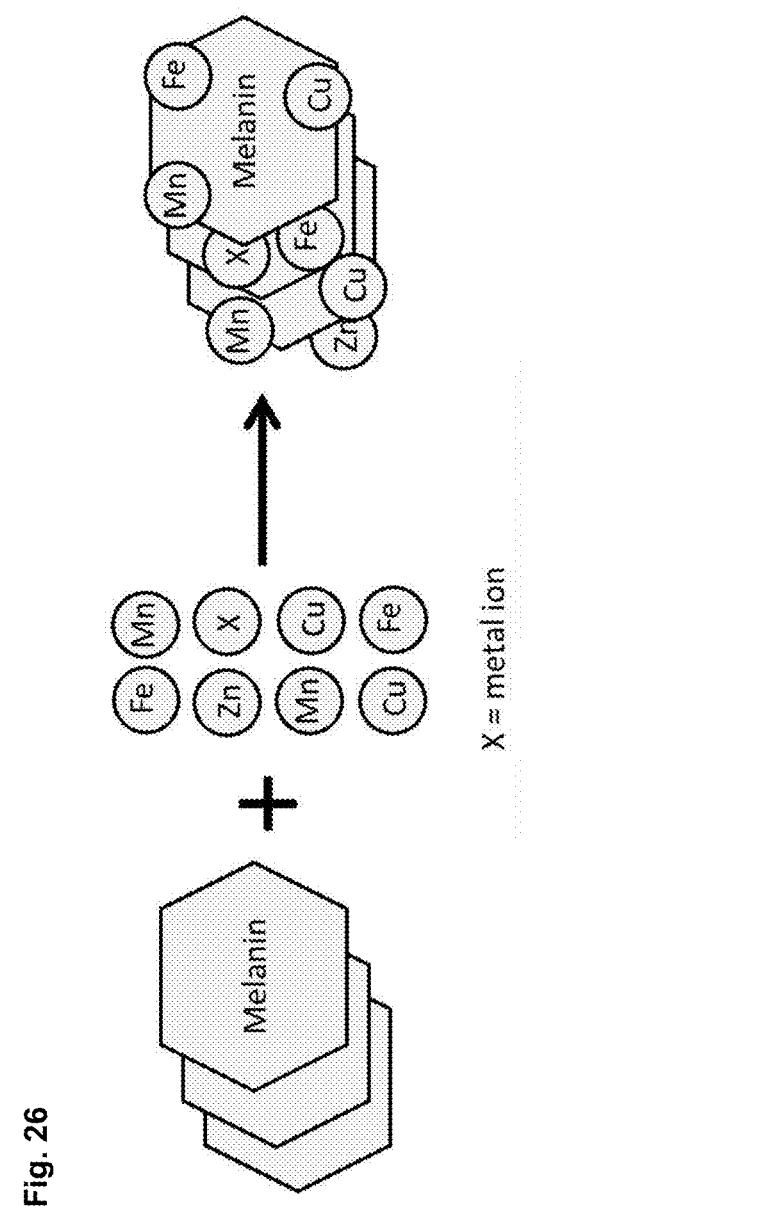
FIG. 26: Schematic diagram of the complex polymeric structure of melanin which binds the metals used for analysis in this application.

Melanins are heterogeneous polymers of uncertain 3D structure that form multilayered complexes consisting of overlapping sheets of dihydroxyindole and benxothiazine rings and sundry unidentified chemical groups (Zecca et al., *Trends in Neurosciences*, 26; 578-580, 2003). In the case of neuromelanin, there is also a large class of polyunsaturated lipids. Neuromelanins act as sinks for many metals including chromium, cobalt, mercury, lead, and cadmium, and significantly for this application, they also contain isotopes of Mn, Zn, Fe and Cu (FIG. 26). Melanins can be released extracellularly and, owing to their chemical characteristics, can survive in the extracellular milieu for long time periods. Melanins have radio-protective properties, attested to by melanized fungi living on the walls of the nuclear reactor at Chernobyl and in the cooling water of currently operational nuclear reactors. Melanins scatter X-rays and act as a shield for radiation. Despite the massive literature on the properties of isolated melanins, the first systematic attempt to explain its radio-protective properties was only made in 2007 (Dadachova et al., *Pigment Cell Melanoma Res.* 21; 192-199, 2007). Until the present invention, the physical explanation of melanin's radio-protective abilities at the level of pathological cancer material and their predictive relevance to patient treatment with radiotherapy has not been realized. Furthermore, most chemical and structural studies to date have been based on isolated melanins, not on their in situ molecular properties, and there has not been a 2D analysis of tissue sections from tumors as described herein. This is highlighted by the examination of melanin concentrations in a melanoma from a 45 year old female with a malignant melanoma of the chest wall (stage II, T4N0M0) (FIG. 27A-FIG. 27F).

Figure 27A:
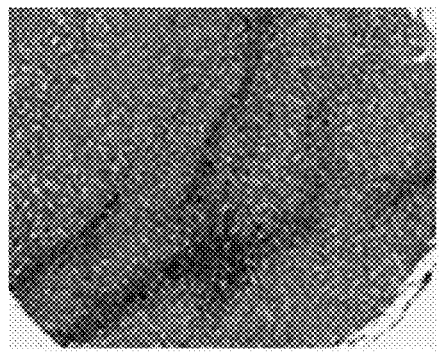
FIG. 27A and FIG. 27B are photographic images of a standard 5 micron H&E stained tissue section from a formalin-fixed paraffin-embedded block from a malignant melanoma of the chest wall of a 45 year old female illustrating the tissue and cellular morphology.
Figure 27B:
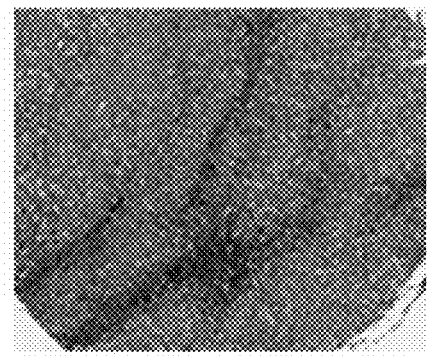

For clarity of presentation and for comparison of the concentrations of different entities, FIG. 27A and FIG. 27B are duplicates of the same H&E stained section. The distribution of melanin within this section is sufficiently high that staining by melanin specific antibodies has not been necessary to reveal it. The distribution of the four metals, $^{66}$Zn, $^{63}$Cu, $^{56}$Fe and $^{55}$Mn, is shown in the FIG. 27C-FIG. 27F, and can be visually compared to the distribution of melanin.

Figure 27C:
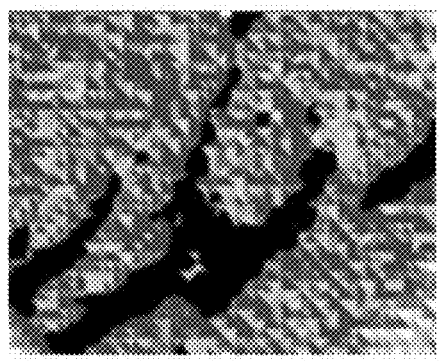
FIG. 27C. $^{66}$Zn levels in individual voxels of this section with contiguous voxels of high $^{66}$Zn content shown as black areas.

FIG. 27C shows the 2D distribution of $^{66}$Zn, the highest concentration of which (in black) co-localizes with the major melanin tracks. The bulk values for $^{66}$Zn in the lightly stained areas are from 3,000 to 18,000 CC/S, while the $^{66}$Zn levels within the melanin tracks are from 18,000 to 45,000.

Figure 27D:
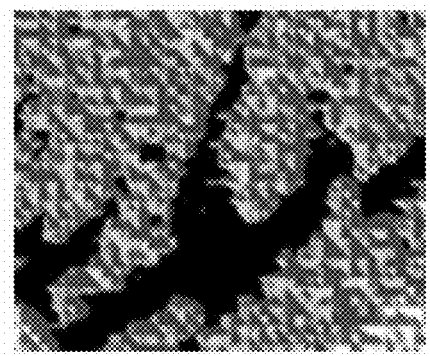
FIG. 27D. $^{63}$Cu levels in individual voxels of this section with contiguous voxels of high $^{63}$Cu content shown as black areas.

FIG. 27D shows the 2D distribution of $^{63}$Cu (in black) which again closely tracks the melanin distribution. The bulk values for $^{63}$Cu in the lightly stained areas are from 200 to 1,000 CC/S, while the $^{63}$Cu levels within the melanin tracks are from 1,000 to 4,000.

Figure 27E:
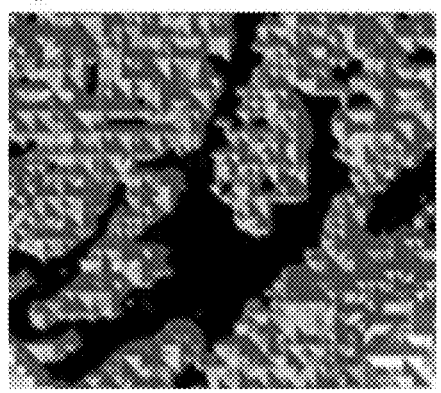
FIG. 27E. $^{56}$Fe levels in individual voxels of this section with contiguous voxels of high $^{56}$Fe content shown as black areas.

FIG. 27E shows the high concentration of $^{56}$Fe (in black) which closely tracks the melanin distribution. The bulk values for $^{56}$Fe in the lightly stained areas are from 20,000 to 80,000 CC/S, while the $^{56}$Fe levels within the melanin tracks are from 80,000 to 100,000.

Figure 27F:
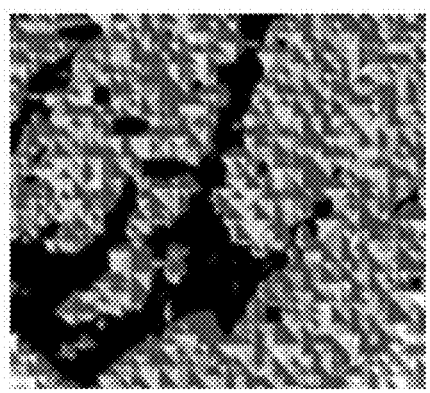
FIG. 27F. $^{55}$Mn levels in individual voxels of this section with contiguous voxels of high $^{55}$Mn content shown as black areas.

FIG. 27F reveals the concentration of $^{55}$Mn which closely follows the melanin tracks. The bulk values for $^{55}$Mn in the lightly stained areas are from 1,000 to 2,500 CC/S, while the $^{55}$Mn levels within the melanin tracks are from 2,500 to 10,000. As the earlier example of FIG. 12 showed, HMRs ($^{55}$Mn) that consist of heavily melanized regions, can reach $^{55}$Mn levels of 100,000. Melanin is thus a repository for high levels of metals that, if released, are likely to be a significant factor in radio-resistance. To our knowledge, this is the first demonstration of in situ $^{55}$Mn concentrations in melanin in a 2D tissue section description of cancerous tissue, and the first quantitative predictions that follow from such co-localization of metals and melanin for patient treatment in radiotherapy. Melanomas have a dual defence to radiation. The first is the accumulation of $^{55}$Mn in cells. The second is the production of large amounts of melanin, which not only act as a storage capacitor for $^{55}$Mn, but also likely provide some structural shielding from ionizing radiation.

The sizes and shapes of the melanin-rich voxel tracks in FIG. 27A-FIG. 27F can be compared with the sizes and shapes of some possible voxel aggregations as outlined in FIG. 20A-FIG. 20H, (particularly in FIG. 20H).

The melanomas are instructive in a further clinical sense, since the data presented in FIG. 25A-FIG. 25B can be subdivided into melanoma samples that are either from primary tumours, or ones that are from metastatic sites. These data are shown in FIG. 28A-FIG. 28C. A comparison of the distribution of median CC/S values for the different patients with primary or metastatic melanomas yielded a D value of 0.1889 which has an associated non-significant P value of 0.557. Thus in terms of the median $^{55}$Mn values derived from a melanoma, the primary and metastatic melanomas are consistent with being sampled from populations with the same distribution.

A statistical comparison of the distribution of $^{55}$Mn values from the primary tumours and specifically from the metastatic ones that have already spread to the lymph nodes, yielded a D value of 0.2222 which has an associated non-significant P value of 0.442. Thus median $^{55}$Mn values from primary tumours and those that have been sampled from lymph nodes, are consistent with being sampled from populations with the same distribution.

An examination of the distribution of tumours with HMRs ($^{55}$Mn) and those without HMRs($^{55}$Mn) to determine if the frequency of HMRs($^{55}$Mn) differs between primary and metastatic tumours reveals that they do not, (yielding a non-significant P value of 0.457). Thus in terms of the distribution of median $^{55}$Mn values, primary and metastatic tumours are indistinguishable. This finding is supported by there being no a priori biochemical set of processes that would favour differential $^{55}$Mn accumulation between the primary tumour and its metastatic derivative(s) in lymph nodes.

While $^{55}$Mn levels and their distribution within a 2D area in tumour tissue are exemplified, another metal, zinc, may also be helpful by way of non-limiting example, as a discriminator in focussing on optimal regions for $^{55}$Mn analysis. Many regions of a tumour contain cancerous cells intermixed with different cell lineages, as well as normal cellular and non-cellular components. The tumour milieu can contain fibroblasts, extracellular matrix components, collagen bundles, capillaries, lymphatics and support cells such as pericytes and smooth muscle cells, macrophages, osteoblasts, osteoclasts and components such as hydroxyapatite in bone niches. If in the first instance it is cancer cell populations that are chosen to be quantified for an ATI, then zinc can be used to differentiate between cells that are cancerous and cells that are not. Hence, zinc can provide a filter for ensuring that only the most relevant cancer cell-containing voxels are used for determining $^{55}$Mn values and their distributions. (Note that zinc does not differentiate between radio-sensitive and radio-resistant cells.) Zinc voxel values allow an initial avoidance of regions that may mislead in identifying HMRs($^{55}$Mn). This is illustrated in FIG. 29A-FIG. 29B and FIG. 30A-FIG. 30B.

Figure 29A:
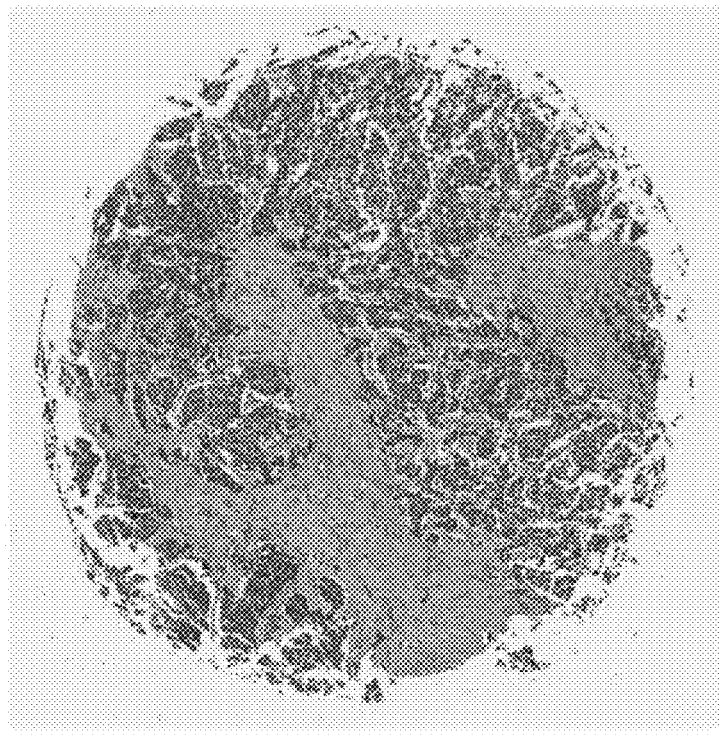
FIG. 29A. Photographic image of a standard 5 micron H&E stained tissue section from a formalin-fixed paraffin-embedded block from a small cell carcinoma of the lung of a 54 year old male illustrating the tissue and cellular morphology of areas of darkly staining cancerous cells and the more lightly staining stromal regions.
Figure 29B:
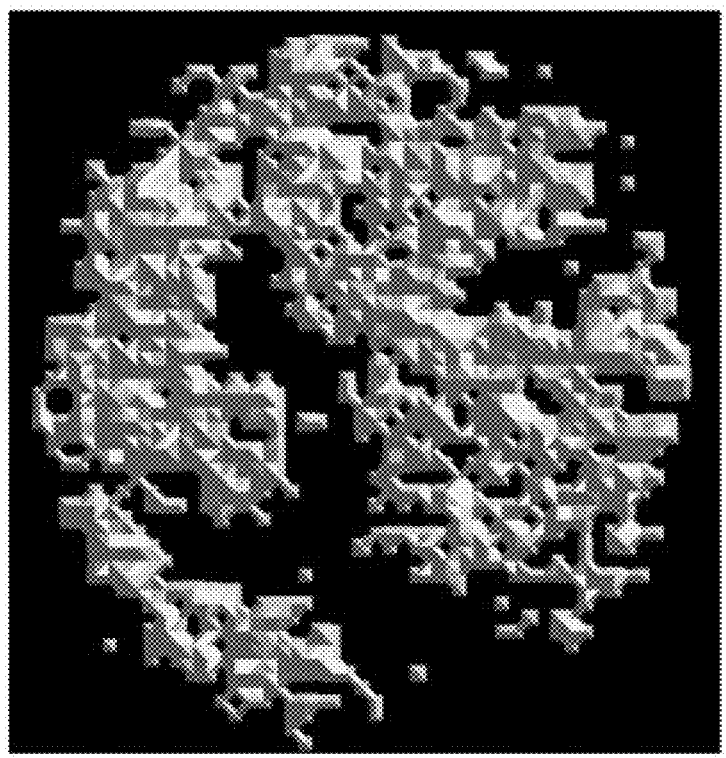
FIG. 29B. 2D relief image of the same section with $^{66}$Zn levels above a selected threshold shown in white/grey and the stromal components below this threshold shown in black.

FIG. 29A illustrates an H&E stained section from a 54 year old male with a small cell undifferentiated carcinoma of the lung (Stage IIIa; T2N2M0). Lightly stained regions of largely non-cancerous and non-cellular material are apparent from the H&E view. This lightly-staining region has low $^{66}$Zn voxel values relative to the cancerous cells that are darkly staining. When an appropriate threshold is applied to the $^{66}$Zn data, the resulting image in FIG. 29B is an excellent approximation to the differing regions seen in the H&E image above it. This means that the analysis of the $^{55}$Mn values in this tumour sample is more appropriately based only on those $^{66}$Zn voxels shown in FIG. 29B, without a contribution from voxels of the non-cancerous regions. This is not meant to downplay the clinical significance of stromal components, it serves simply to compartmentalize data analysis. This pre-screening of a tissue section landscape using $^{66}$Zn, will be particularly useful in tumours such as those of the breast and prostate, where non-cancerous material is much more intimately intermingled with cancer cell-containing voxels. The reciprocal of the above is that zinc can also be useful in determining which parts of a tumour can best yield the ATI of a stromal population.

Figure 30A:
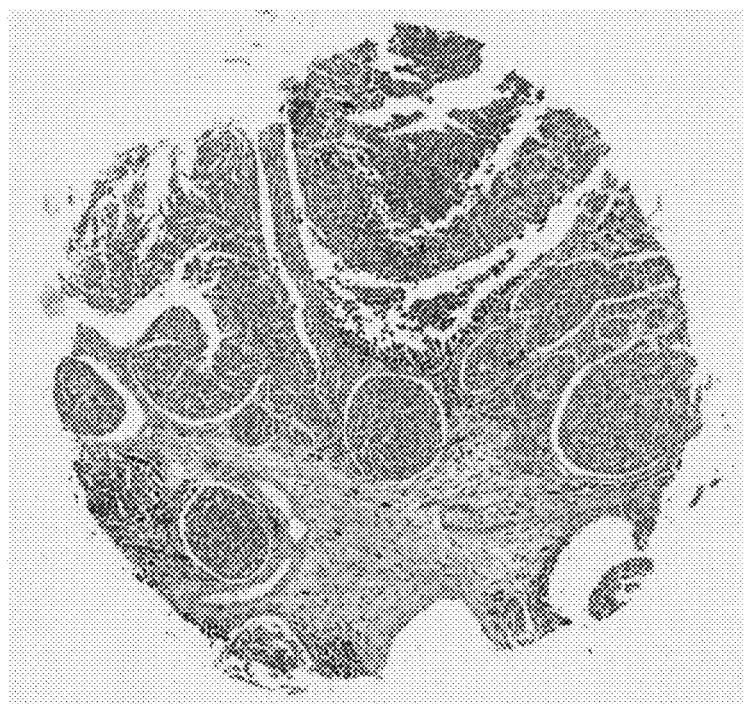
FIG. 30A. Photographic image of a standard 5 micron H&E stained tissue section from a formalin-fixed paraffin-embedded block from a malignant melanoma of the rectum of a 66 year old male illustrating the tissue and cellular morphology of areas of darkly staining cancerous cells, even darker staining melanin concentrations, and the more lightly staining stromal regions.
Figure 30B:
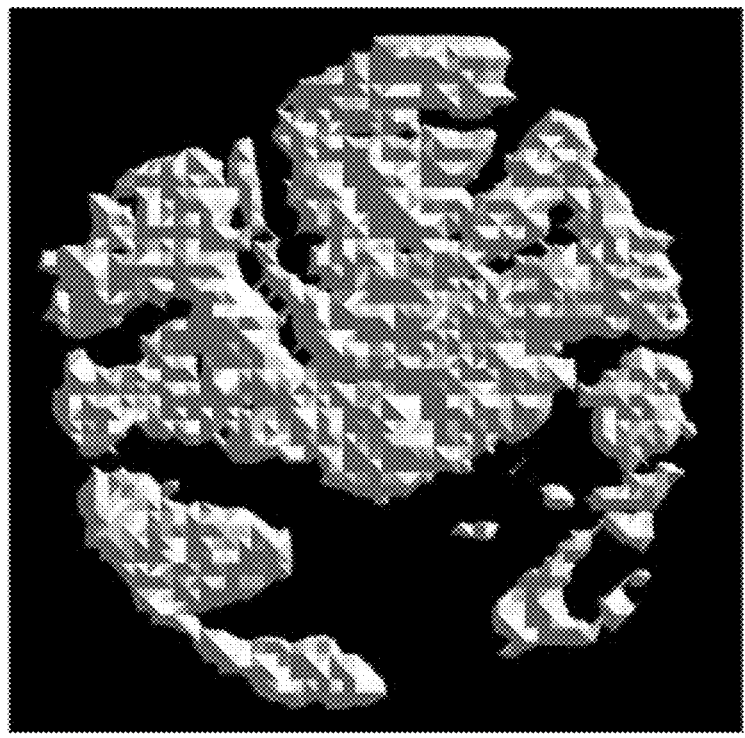
FIG. 30B. 2D relief image of the same section with $^{66}$Zn levels above a selected threshold shown in white/grey and the stromal components below this threshold shown in black.

A similar example is evident in FIG. 30A-FIG. 30B, in which FIG. 30A illustrates an H&E stained section from a 66 year old male with a malignant melanoma of the rectum (Stage IIB; T4N0M0). Non-cancerous cell regions are again evident, particularly in the lower portion of FIG. 30A at 6 o'clock. When an appropriate threshold is applied to the $^{66}$Zn data, the resulting image in FIG. 30B mirrors the differing cellular components seen in the H&E image above it. This pre-screening with $^{66}$Zn again shows that subsequent analysis of the $^{55}$Mn values can be more accurately determined using only those $^{66}$Zn voxels shown in FIG. 30B, without "contamination" from voxels of the non-cancerous/stromal regions.

It will be appreciated by those skilled in the art that other atomic elements and their associated isotopes, besides $^{66}$Zn, may provide the same useful function of differentiating between cancerous, normal, activated and non-cellular components of the stroma, particularly in different tissues.

Example 6

Cancers of the Breast

The data presented herein demonstrate for the first time that there is a correlation between $^{55}$Mn levels and the two spectral ends of tumours that relate to radiation sensitivity and radiation resistance. The data presented herein also provide an insight into the previously unknown existence of HMRs that are hidden from conventional pathological examination and which play a major role in radiation resistance and an indication that a tumour may reoccur after radiation treatment. In addition, the data also provide a basis for metallomic contributions that derive from the interactions between stromal components and cancer cell populations.

By way of non-limiting example, tumours that are loosely classified as being of "intermediate" radiation sensitivity, e.g., breast and prostate, were also analysed according to the invention.

The same quantitative approach of Laser Ablation-Inductively Coupled Plasma-Mass Spectrometry has been applied to 15 tumours of the breast, as was used for the six tumour types described herein. An overview of these data is presented in FIG. 31A-FIG. 31B. Examination of the bulk $^{55}$Mn values of these breast tumours (grey squares), indicates values between 1,000 and 4,400 CC/S. At this level of inspection, they are indeed intermediate between the sensitive values found in the seminomas, small cell lung and lymphomas, and the higher $^{55}$Mn values of the glioblastomas, mesotheliomas and melanomas. However, over 70% of these breast cancers have HMRs($^{55}$Mn) and their values extend from 4,000 to 16,000 CC/S (black squares in FIG. 31B). In addition, some tumours have double and triple HMRs($^{55}$Mn) using the stringent 8×8 detection threshold. Until the present invention, it was not realized that the atomic data are consistent with the clinical observation that "breast cancers are very heterogeneous".

In a personalized medicine context, the current medical art of describing breast cancers as heterogeneous is not helpful in deciding which patients will benefit from radiotherapy and which patients should avoid the harmful effects of radiation treatment. The clinical reality is that in the absence of a useful predictive metric, and in the presence of uniform H&E pathology, most breast cancer patients are irradiated after surgical resection of the tumour, e.g., in the USA, so that all possible treatment modalities have been seen to be applied. The resection margins for tumours of the breast can be large, so that the chance of surgically removing any residual cancer cells that may be at the periphery of a tumour is increased. While radiation treatment further increases the probability of destroying cells that have escaped resection, the harms of radiation could be avoided in those cases where the atomic data indicate very high levels of $^{55}$Mn. In such high $^{55}$Mn cases, radiation treatment in an intent-to-treat situation is largely futile.

Figure 32A:
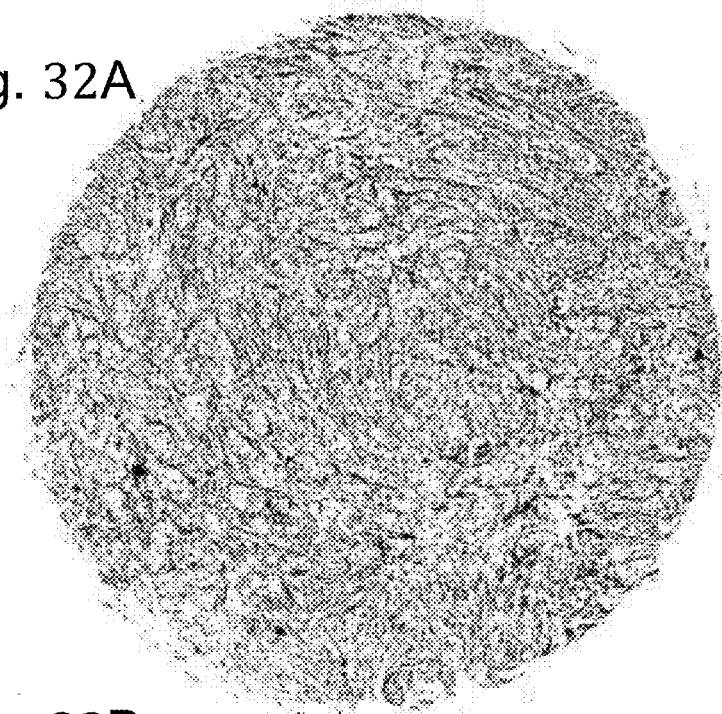
FIG. 32A. Photographic image of a standard 5 micron H&E stained tissue section from a formalin-fixed paraffin-embedded block from well differentiated carcinoma of the breast taken from a 39 old female illustrating the tissue and cellular morphology.
Figure 32B:
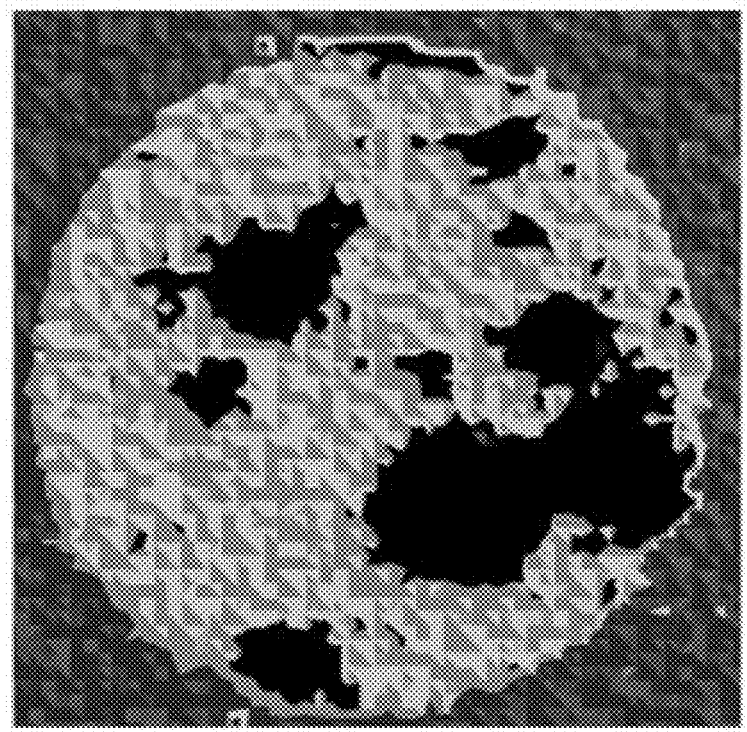
FIG. 32B. 2D relief image of $^{55}$Mn levels in individual voxels of this section after LA-ICP-MS. Multiple clusters of contiguous voxels of high $^{55}$Mn content are shown as black areas.

FIG. 32A illustrates a well differentiated invasive ductal carcinoma of the breast (Stage IIIa, T3N1M0) from a 39 year old female. The H&E section is unremarkable and uniform by pathological inspection. By contrast, the atomic data seen in FIG. 32B reveal the hidden heterogeneity of HMRs ($^{55}$Mn) (large black areas) and their important clinical implications. This breast section has been examined as an approximately 1 mm$^2$ area, to keep it in line with the standard sample size typically used in measuring mitotic rate.

FIG. 33A-FIG. 33H shows the analysis of an approximately 1 mm$^2$ area of 31×31 voxels which was simultaneously analysed for the two atomic elements $^{55}$Mn and $^{66}$Zn using the standard thresholds applied previously (T1, 0.5× median; T2, 1× median; T3, 1.5× median and T4, 2× median). Two HMRs($^{55}$Mn) become evident in the Mn analysis using the T4 threshold, while the identical voxels for $^{66}$Zn remain at their bulk tumour levels. It is $^{55}$Mn levels that are the critical characteristic of these HMRs. A potential HMR($^{55}$Mn) that has a size below the 8×8 threshold, is visible above the other two in panels T3 and T4 (FIG. 33C and FIG. 33D).

Figure 34A:
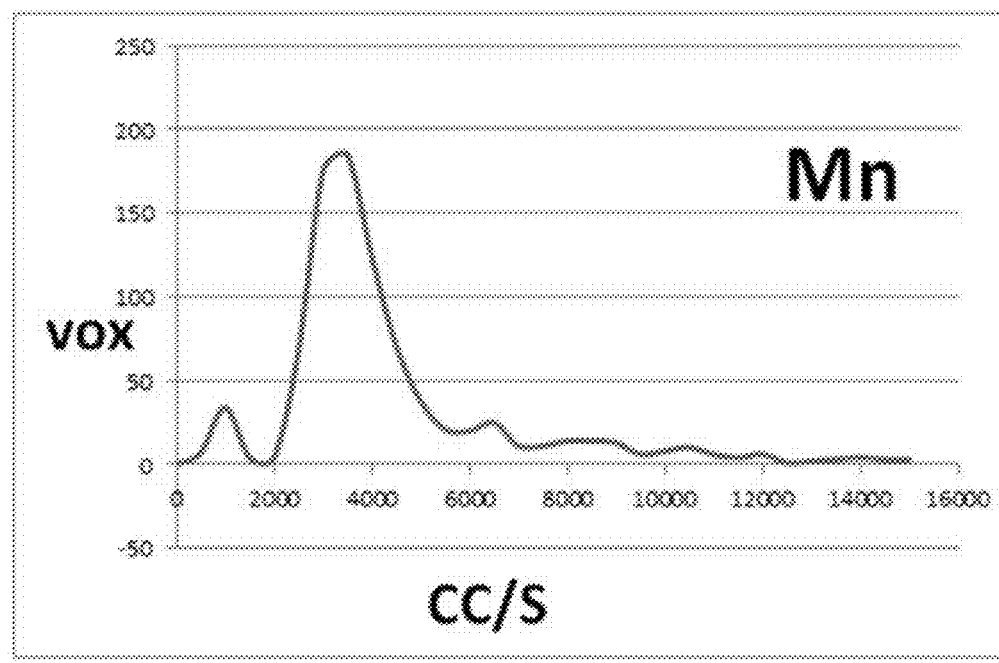
FIG. 34A-FIG. 34B: Analysis of the variation in the distribution of $^{55}$Mn and $^{66}$Zn voxel values in the breast cancer sample from the 39 year old female whose 2D data were presented in FIG. 33A-FIG. 33H.
Figure 34B:
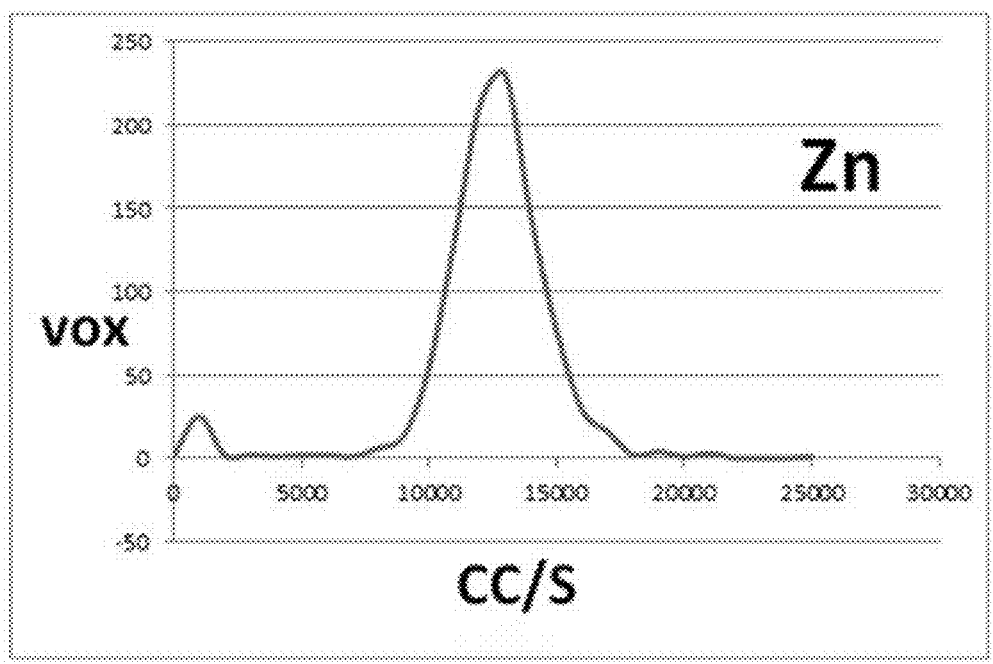

Further analysis of this approximately 1 mm$^2$ area demonstrates the usefulness in analysing HMRs compared with bulk analyses of seemingly homogeneous pathological samples which "pool" data. Analysis of all 961 voxels in this sample in histogram form is shown in FIG. 34A-FIG. 34B for $^{55}$Mn and $^{66}$Zn values. In FIG. 34A, the heterogeneity in high $^{55}$Mn levels in voxels is seen as the peaks and the smear of values that are in excess of 5000 CC/S values and which reach a value around 15,000. This heterogeneity can be examined in a rigorous statistical manner e.g., by an analysis of voxel contents using Bowley's Non Parametric Skew Statistic (NPSS) (Bowley, 1901, *Elements of Statistics*, P S King and Son, publishers, Westminster, London, UK). By way of non-limiting example, this was applied to the $^{55}$Mn data and the NPSS value, [mean minus median]/[St.Dev] and found to be 0.25, whereas for the much more symmetrical $^{66}$Zn data it was found to be 0.02, representing a large difference. It will be clear to a person skilled in the art that there are a multitude of statistical approaches to measuring heterogeneity, which may be used with the Skewness shown herein.

The further area analysis revealed a distribution of the high $^{55}$Mn values that consists of voxels spread uniformly throughout the sample, or their existence as aggregates. Finally, compared to the heterogeneity seen in $^{55}$Mn levels, FIG. 34B shows that the identical Zn voxels were more uniform in their values. This is correlated by the lack of peaks or a smear to the right of the major peak in FIG. 34B.

Cancerous Cells in Lymphatic Vessels/"ducts" in the Process of Metastasis

Figure 35A:
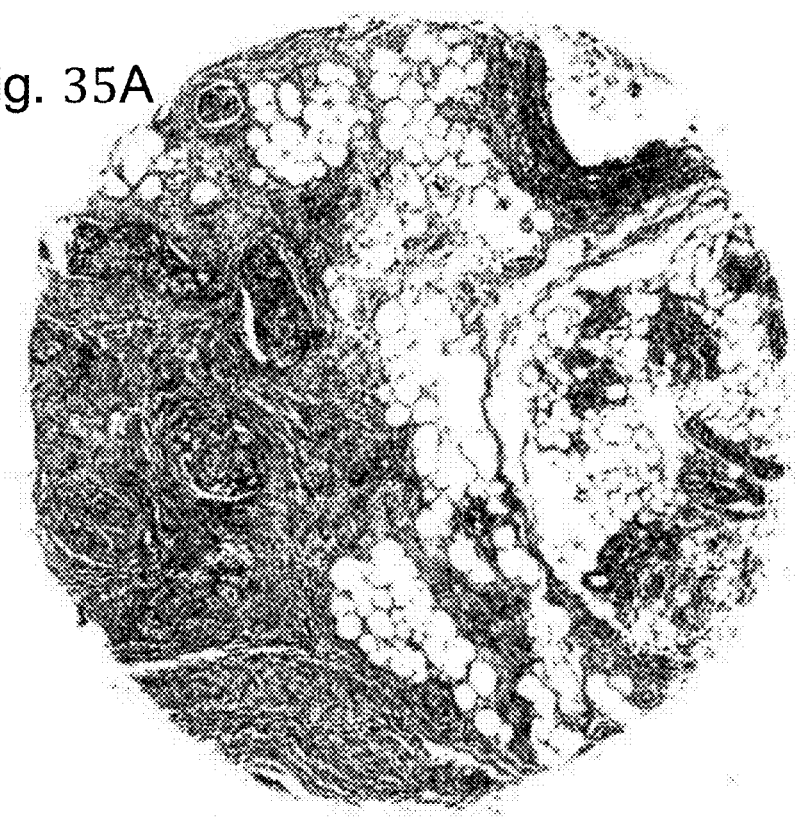
FIG. 35A. Photographic image of a standard 5 micron H&E stained tissue section from a formalin-fixed paraffin-embedded block from an invasive ductal carcinoma of the breast from a 48 year old female illustrating the heterogeneous tissue and cellular morphology.
Figure 35B:
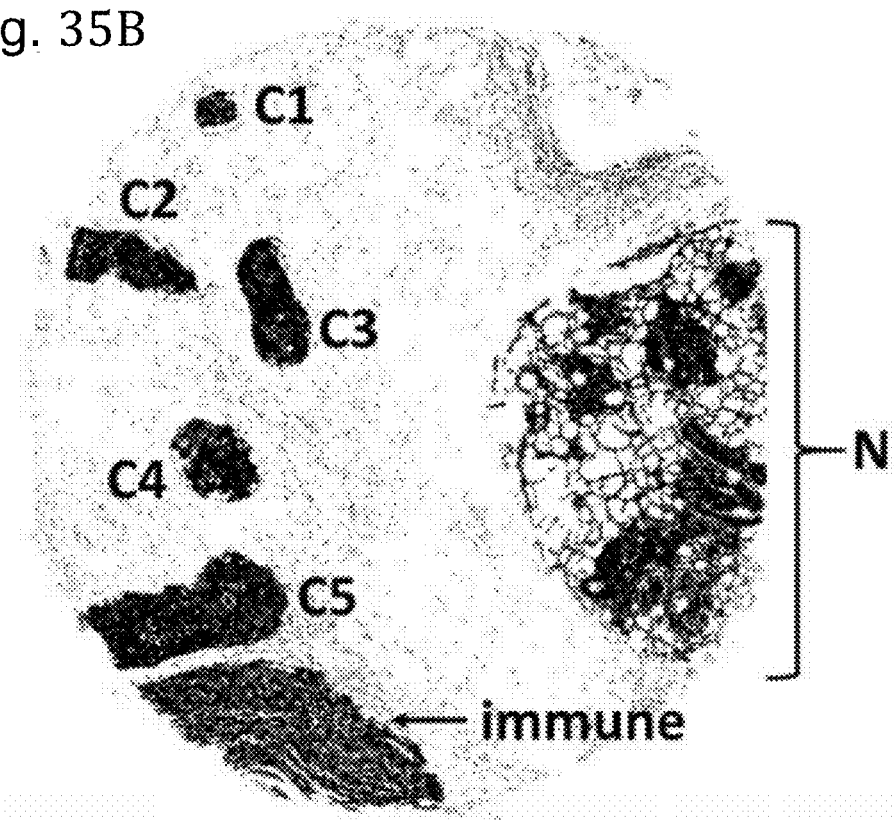
FIG. 35B. Description of the major morphological features of the above image, showing cancerous cells in lymphatic ducts, (C1 through C5), normal ducts (N) surrounded by associated adipocytes, and a concentration of immune cells, (immune), together with other stromal components.

In contrast to the example of the morphological homogeneity of the pathology seen in the invasive carcinoma described above, FIG. 35A illustrates the morphological heterogeneity of an invasive ductal carcinoma of the breast (Stage IIa, T2N0M0) from a 48 year old female as visualized by H&E. It is an informative sample from the perspective of the ATI, as this section contains, (i) an area of normal breast lobules at 3 o'clock (denoted N), with associated adipocytes, (ii) five areas denoted C1 through C5 in which cancer cells (denoted C), are visible inside lymphatic vessels and hence in the process of metastasizing, and (iii) an area of concentrated immune cells (denoted immune), together with a stromal component, including adipocytes spread throughout the middle and right hand side of the sample.

The $^{55}$Mn values of the normal lymphatic vessels, designated N, in the normal portion of the breast, yielded CC/S values of 3,204, 3,104 and 3,155. The lymphatic vessels that contain cancerous cells are informative. Lymphatic vessel C1 yields a value of 2,904, C2 and C3 yield 2,804 and C4 yields 2,771. Thus the $^{55}$Mn contents of these transiting metastatic cells are little different from their progenitor cells constituting a normal duct of the breast. In contrast, the transiting cells in lymphatic vessel 5 have a median CC/S of 8612 and are predicted to be radio-resistant. This example illustrates the atomic microheterogeneity that occurs in a small single sample of the breast. This microheterogeneity cannot be extracted from the pathology of the cancer cells in C1 through C5 which are in the process of metastasis, since at the microscopic level they appear indistinguishable.

The metallomic data reveal that all four metals, $^{55}$Mn, $^{66}$Zn, $^{63}$Cu and $^{56}$Fe readily resolve the areas that consist of adipocytes as against the cellular and acellular regions seen in the H&E stained sections (FIG. 36A-FIG. 36F). The metallomic contents of adipocytes are diluted by the large concentration of lipids in such cells.

The heterogeneity issue, seen so clearly in this breast cancer section at both the morphological and metallomic levels, is also pervasive in other cancer types, even in different large regions within the same organ.

There are a number of important issues that are taken into account by medical professionals regarding the treatment of a patient with cancer, including, but not limited to, the age of the patient; the current health condition of the patient; comorbidities; the locations of the tumour(s) (primary or metastatic); whether surgery, chemotherapy, drug treatment, immunotherapy or radiation is an option and whether the treatment is made as intent-to-cure, or palliative. This list exemplifies the clinical decision network that must be navigated to yield the best options. The central decision-node after blood tests and scans have been completed, is the pathology of the tumours. All other decisions follow from the information obtained at this node, since an inference is made as to whether the tumour is likely to be benign or likely to progress. Except in the case of measuring mitotic rate, until the present invention, the inference is currently not based on quantitative data, but on the general experience with a particular tumour type. For tumours that are relatively uncommon, there are usually few clinical trials that provide guidance on which therapeutic step is the best option. Even for common tumour types, such as those of the breast, prostate, brain, skin and ovary, the shortcomings in the multitude of clinical trials that do exist have lead to continuing controversies. The major problem is that the data gathered at this pivotal pathological-decision node of a particular tumour type are not of requisite quantitative quality, and until this application, are not generalizable to all tumour types.

The clinical "value" of the crucial pathological information (namely a pointer to whether a major therapeutic option such as radiation should be implemented), rests largely on subjective interpretation of staining methodologies, combined with antibody information, or various forms of in situ hybridizations, which are further complemented by newer genomic and proteomic technologies. As reinforced by further examples below, the atomic data provide a new measure of quantitation that has hitherto been lacking at this key pathology/radiation-treatment, decision node. The Atomic Therapeutic Indicator of any tumour type provides for the first time, a quantitative underpinning of which patients are suitable candidates for radiotherapy, and in which patients a tumour is likely to reoccur after radiotherapy.

Example 7

Cancer of the Prostate

FIG. 37A-FIG. 37B shows a clinical example of the heterogeneity in pathological status in different parts of a tissue or organ, in this case the prostate gland. It is illustrated by a Final Prostate Biopsy Report from the USA (with the patients' full permission of disclosure). The patient (hereinafter denoted patient X), has adenocarcinoma of the prostrate with a PSA level of 8.1 ng/ml. The biopsy report documents the abnormalities in different regions of the prostate with 7 out of 12 regions showing changes of little significance, and five regions with "cancer" as defined by Gleason scores no higher than 7 (FIG. 37A). The diagnostic summary of the extent of involvement of each of the twelve core biopsies is also shown (FIG. 37B; Part A through Part L). Before the present invention, this patient would be assessed for radiation treatment without any quantitative measure that demonstrates such treatment would be warranted. This patient underwent radiation treatment on the basis of personal preference after discussions with his primary care physician, the other option offered to him being radical prostatectomy. In accordance with the present invention, the chemical distribution of elements within each of these regions is measured, e.g., the $^{55}$Mn levels, 2D distributions and HMRs($^4$M), is determined by laser ablation. The results are analysed using available statistical methods and statistical theory, including calculating a measure of central tendency, where the common measures of central tendency are the median, arithmetic mean and mode. Any other measures of central tendency known in the art may also be used, including but not limited to geometric mean, medimean, winsorized k-times mean, K-times trimmed mean, and weighted mean, and the data may also be transformed prior to calculating a central tendency. For example, the data are also tested using non-parametric statistics, including the Kolmogorov-Smirnov test, which involves making no assumptions about the distribution of data. Other statistical methods include a combination of Bayesian and more standard statistics, clearly set out by Lee and co-authors in *Demystify Statistical Significance-Time to Move on from the P value to Bayesian Analysis*, (Lee, *J Journal of the National Cancer Institute*, 103, 2-3 2010) and Berry, Carlin, Lee & Muller. Bayesian Adaptive Methods for Clinical Trials. *Chapman and Hall/CRC Biostatistics series*. ISBN 9781439825488. 2010; Nuzzo, *Nature*, 506, 150-152. 2014).

Other statistical methodologies include those set out in: Talfryn et al., *British Medical Journal*, 316, 989-991, 1998; Sterne & Smith, *British Medical Journal*, 322, 226-231, 2001; Bland & Altman, *British Medical Journal*, 328, 1073, 2004. In a clinical setting, other methods include: Rubinstein et al., *Journal of the National Cancer Institute*, 99, 1422-1423, 2007; Krzywinski & Altman, *Nature Methods*, 10, 1041-1042, 2013)

Upon completion of the statistical analysis, a decision is made on the radio-sensitivity or radio-resistance of the different regions of the tumour and the most appropriate treatment. For example, a tumour that is deemed to be radio-sensitive at the bulk level and in its cancer cell-laden HMRs($^{55}$Mn) (if any), is irradiated. For one that is radio-resistant, or has large HMRs($^{55}$Mn), radiation treatment is not recommended. Selective radiation treatment is also recommended for specific areas of a tumour that is radio-sensitive. For example, any radiation treatment that selectively targets a specific area of a tumour is recommended. Such selective radiation treatments that are available and known in the art are contemplated. A person skilled in the art is able to readily determine which selective treatment is warranted.

Figure 38:
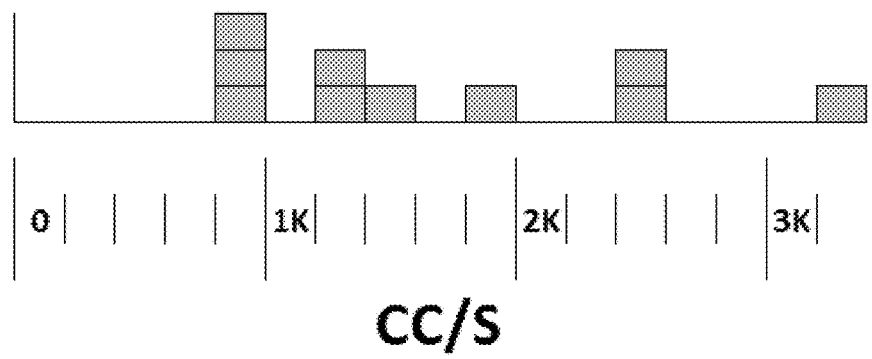
FIG. 38: Histograms of median $^{55}$Mn contents expressed as Calibrated Counts per Second (CC/S) of $^{55}$Mn in laser ablated samples from tumours of 10 patients with cancer of the prostate. Each grey square represents the median value calculated from a total area of approximately 1800 voxels of the tumour of a single patient. No HMRs($^{55}$Mn) were present under the standard threshold conditions of 2× median applied herein.

The same quantitative approach of LA-ICP-MS has been applied to 10 tumours of the prostate as used for the previous seven tumour types described so far. An overview of these data is presented in FIG. 38.

Conclusion: No tumours had high HMRs($^{55}$Mn) and their voxel values are generally at the low end of the ATI spectrum (i.e. low range CC/S) and hence, from this sample, the tumours are expected to be mostly radiation sensitive.

Example 8

Primary Melanoma of the Skin Metastatic to the Brain

FIG. 39A-FIG. 39E and FIG. 40 reveal the detailed clinical data and their comparison to quantitative atomic data from a 70 year old patient (hereinafter denoted patient Y), who first presented with a primary melanoma and was subsequently diagnosed with a brain tumour. The patient was treated with whole brain radiation, sundry drugs, immunotherapy (prembrolizumab) and finally underwent a stereotactic craniotomy. This example illustrates the level of clinical detail that is required to match the atomic data, as well as the clinical baseline involved in placing an ATI into routine medical practice. The patient has provided full permission of disclosure.

Figure 39A:
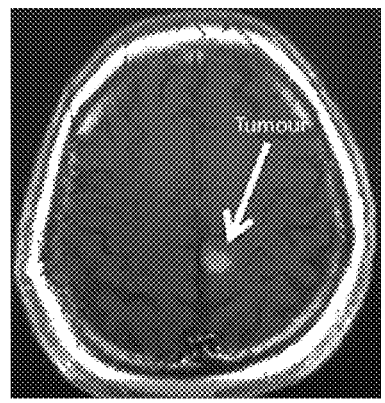
FIG. 39A. Presence of a contrast enhancing lesion in the paramedial left parietal lobe of the brain (arrowed) prior to drug treatment and radiation.
Figure 39:
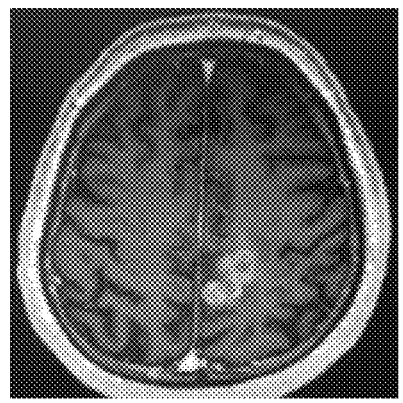
FIG. 39 A-FIG. 39E Magnetic Resonance Images from the brain of patient Y, a 70 year old male.

Patient Y was initially diagnosed with a primary melanoma of the upper back, with clear sentinel lymph nodes, as well as a number of basal cell carcinomas and squamous cell carcinomas. A number of years later, following a fit, MRI scans revealed a cerebral neoplasm of the left parietal lobe (FIG. 39A, arrowed). Following radiation treatment, MRI scans revealed the presence of residual material at the tumour site, with its associated ambiguities of interpretation (FIG. 39B).

Figure 39C:
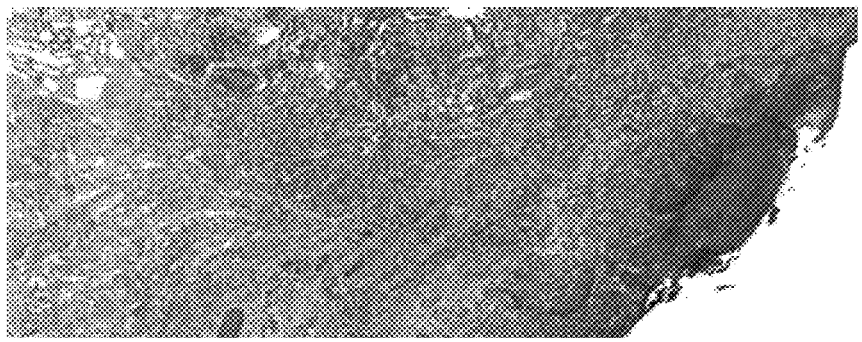
FIG. 39C. Photographic image of a standard 5 micron H&E stained tissue section from a formalin-fixed paraffin-embedded block from a primary melanoma of the same patient resected years prior to the brain scans.

The detailed pathology report stated that the sections from the skin of the primary melanoma showed an ulcerated nodular melanoma with the tumour cells being positive for MelanA and negative for 34Be12, which is consistent with melanoma (FIG. 39C). The Breslow thickness was 3.8 millimeters; Clark level 4; ulceration, 3 millimeters; percent of dermal invasive tumour width, approximately 50%; dermal mitoses 9 per mm$^2$ (which is considered to be a high mitotic rate; dominant cell types, naevoid and epithelioid; intravascular and lymphatic invasion was not seen and actinic/solar elastosis was mild.

The melanotic area was widely excised from the upper right back and excisions of four sentinel nodes were carried out. Sections were treated with S100, HMB45 and MelanA to confirm the lesion as being a primary melanoma.

While the primary ellipse revealed melanoma, no further tumour was evident in the wider excision. The adjacent epidermis did reveal reactive changes. Sentinel lymph nodes 1, 2, 3 and 4 revealed no evidence of further malignancy based on staining with H&E and immunoperoxidases, while the status of node 3 was not reported. Following the excision, the patient was declared "clear of cancer" and after 6 months showed no signs of recurrent melanoma.

Three years later the patient collapsed but recovered, yet exhibited signs of incoordination of the left leg when walking. Similar episodes of involuntary movement of the leg recurred up to 20 times per day and initially they were accompanied by a strange sensation on the left side of the head. A cerebral MRI revealed a 14 mm contrast enhancing lesion in the paramedian left parietal lobe around the pre-central gyrus (FIG. 39A-FIG. 39E). The radiologist gave a differential diagnosis of a low grade glioma, but it was possible that since the patient had a melanoma 3 years previously, that the cranial lesion could instead be a recurrent melanoma. This ambiguity is reflected by the limitations of MRI. The radiologist concluded that "the nature of this lesion is uncertain. It is likely to represent a neoplasm of the brain which is low grade particularly as there is no mass effect or oedema associated with the lesion. The findings on the diffusion weighted scan of the low signal on the ADC (Apparent Diffusion Coefficient) map make it likely to be a low grade lesion such as a ganglioglioma, but also consider a DNET (Dysembryoplastic Neuroepithelial Tumor) or pleomorphic xanthoastrocytoma without any cystic component. A small oligodendroglioma remains a possibility".

It was recommended that neurosurgery not be undertaken at the time, with stereotactic radiosurgery being the appropriate option. Given that the patient had been diagnosed with a primary melanoma, it was possible that the brain lesion was a metastatic melanoma to the brain. The patient underwent radiotherapy for assumed metastatic melanoma with the total delivered radiation dose being 25 Gy and also began an immunotherapeutic regimen course of pembrolizumab 2 months after radiation therapy. A further month later an MRI revealed that the midline frontal metastasis had diminished in diameter from 16 mm to 11 mm. At face value, the tumour had sensitive and resistant components. The tumour became better defined with a thinner enhancing margin and with a more discretely hypointense centre. Most of this reduction in tumour size is due to radiation and not the immunotherapeutic drug pembrolizumab, as tumour regression after one month of this drug treatment averages only 6%, (Hamid et al., 2013, *New England Journal of Medicine*, 369, 134-144). This patient's tumour reduced from diameters of 16 mm:16 mm:16 mm to 11 mm:11 mm:11 mm. This is a reduction of (5+5+5)/(16+16+16), 31%, of which 6% can be attributed to the drug, and 25% to radiation. This means that 80% (25/31) of the tumour's initial regression was due to radiation. A further MRI scan 3 months later revealed a blush of peripheral contrast enhancement in the white matter adjacent to the tumour nidus, suggesting tumour progress since the last examination. The tumour was still at 11 mm longest diameter 2 months later. An even later MRI revealed marked progression around the tumour which now measured 23 mm in the longest diameter (FIG. 39B), however it was not possible to tell if this was radio-necrosis or progressive tumour. The patient also began treatment with Avastin, and it was decided to proceed to craniotomy. Prior to craniotomy, a hyperintense centrally necrotic tumour was noted, approximately 18×33 mm transaxial and 33 mm superior oblique, features in keeping with a high grade tumour. The patient underwent a stereotactic craniotomy to remove this left frontal lesion.

The histopathology of the resected brain tumour revealed 2 pieces of tan and brown ragged friable soft tissue measuring 15 mm×10 mm×5 mm and 9 mm×6 mm×5 mm. There were very few and scattered devitalized "melanoma" cells with smudgy nuclei and no unequivocal evidence of residual viable malignancy in this material. The material was negative for the melanoma markers melanA and HMB45 and no definite pigment was seen. In the absence of marker confirmation, there is insufficient evidence to unequivocally state that this was a metastatic melanoma or an independent brain lesion, although the pathologist leaned towards a melanoma.

Atomic Analysis of the Primary Tumour Biopsy

Figure 39D:
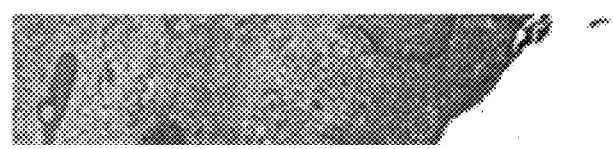
FIG. 39D and FIG. 39E. Higher power illustrations of the regions of interest analyzed by LA-ICP-MS.
Figure 39E:

As there were no biopsies of the brain lesion prior to radiation, the only available evidence for tumour identity and radio-responsiveness stems from the primary tumour (FIG. 39C-FIG. 39E). A standard unstained 5 micron tissue section was obtained (with all ethical, legal and patient consent issues fulfilled), and the entire area of FIG. 39C was laser ablated and then examined for the presence of nests of cancerous cells amongst the normal stromal heterogeneity that is visible in most of FIG. 39C.

The numerical data obtained from the laser ablation are shown in FIG. 40 where five different regions of the primary tumour were analysed. The median $^{55}$Mn value from all five tracks after background subtraction was 3,747 CC/S (ATI) placing the primary tumour in an intermediate range of radio-responsiveness. The clinical data are compatible with this value since the tumour was ablated with radiation.

As noted above, the patient was also treated with an immunotherapeutic regimen of pembrolizumab which targets PD-1, so it is a combination of all these factors that has contributed to the final outcome. However, as pointed out above, 80% of the reduction in initial tumour size can be attributed to the radiation treatment.

Example 9

Tumour Status after Irradiation of a Visible Tumour

Figure 41A:
FIG. 41A: Patient Z with a squamous carcinoma of the oral region prior to radiation treatment.
Figure 41B:
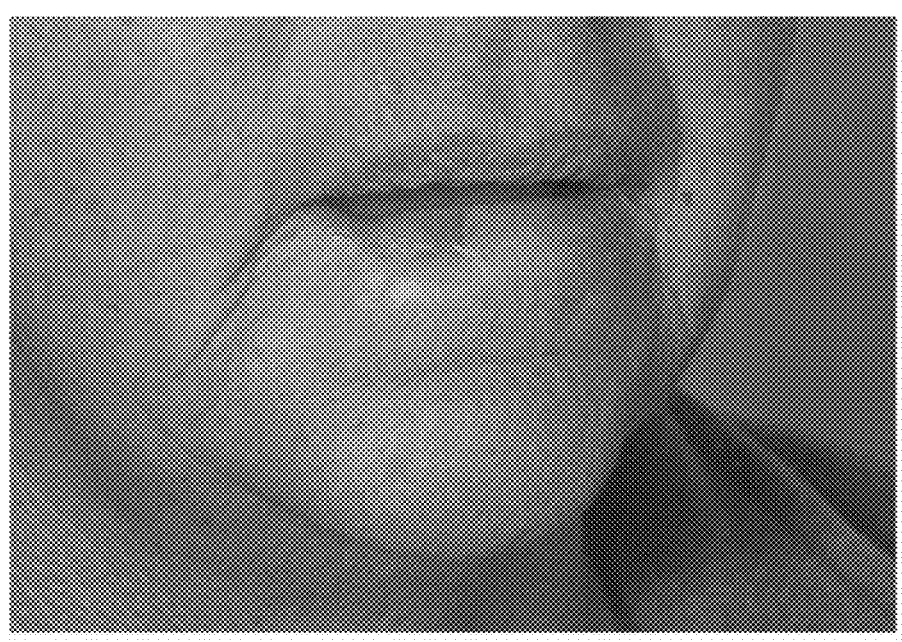
FIG. 41B: Patient Z six months after radiation treatment.

There is one source of tumours that are favourable for a more quantitative approach in terms of ATI and these are "externally visible" tumours whose status, progress, and condition after radiation treatment can be more readily measured than "internal" tumours. Patient Z is an example of such a case (FIG. 41A-FIG. 41B). For privacy reasons, this case serves only as an illustration of the directly measurable and unambiguous outcome of radiation of an externally visible tumour, and highlights the difference between the ambiguities experienced with the internal tumour issues experienced with the brain lesion of patient Y.

Patient Z was radiation treated for a squamous cell carcinoma, (FIG. 41A), which after radiation treatment resolved almost completely within six months (FIG. 41B). Had a biopsy been available for atomic analysis, a comparison of the clinical response and the ATI would have been useful.

Unlike other diagnostics which provide information on whether a patient has a particular tumour type, but do not provide the next therapeutic step tailored specifically for that patient, the ATI is applicable to all tumour types. ATI is pan-diagnostic. It is not restricted in the manner of a PSA test for example, where having obtained a value above 4 ng/ml, the next question is; what is the therapeutic intervention? Is it radical prostatectomy, radiation (external beam, brachytherapy, or proton beam), watchful waiting, cryotherapy, or androgen deprivation therapy? Unlike the ATI, the PSA test itself does not provide the therapeutic pointer.

In the case of cancers of the breast, even if complete resection of a tumour with wide margins is carried out, followed by chemotherapy, radiation treatment, hormone therapy and drug treatment with Herceptin and/or Avastin and/or immune checkpoint inhibitors and/or immune agonists and/or vaccines, what is the probability that the tumour will reoccur if there is no information of the primary source as regards its potential radio-responsiveness? If the breast tumour biopsy had a sub-threshold ATI for example, then the probability of its reoccurrence after radiation would be lower than if the ATI of the biopsy was above threshold and if the tumour had one or multiple HMRs($^{55}$Mn), from which cells may have already migrated. If tumour cells have already spread to the nearby lymph nodes from the breast, then measurements of the ATI (high or low) in these nodes will provide a clinician with an indication of whether a more vigilant monitoring of the patient is required.

Similarly in the BRAF$^{V600E}$ mutation in melanoma, and in many genomic tests, the presence of a targetable "driver" mutation is inferred from a cell sample or from circulating nucleic acids in the vasculature. This does not have the high value of a 2D visualization of the tumour landscape, since the former are a pooled group of entities. This is a critical differentiator between the use of an ATI and a pooled sample, where in the latter, it is impossible to tell whether a high reading derives from the output of a small group of cancer cells or activated stromal cells, or whether most cells in the sample contribute to the reading. The clinical implications for treatment are very different. A melanoma patient treated with vemurafenib, for example, who has a small number of cells in the tumour producing the altered protein, will hardly benefit from treatment, whereas the drug will be far more efficacious in a melanoma patient where a large number of cells in the tumour are producing a defective protein product. This distinction is difficult to make unless a 2D landscape is available.

Example 10

Measurements Using Radiation Sensitizers/Synergizers $^{10}$Boron

The radio-responsiveness of a tumour is determined by measuring $^{55}$Mn and its calibrated signals according to the invention, and the radio-responsiveness may also be influenced by the addition of a sensitizer. In such a case, the success of Boron Neutron Capture Therapy will depend both upon the total $^{55}$Mn calibrated signal and that of the sensitizer. Adding a sensitizer such as p-boronophenylalanine to a tumour cell population that is high in manganese, may not be as useful as adding it to a cell population that is low in manganese. In this example, the ATI for a tumour is determined using LA-ICP-MS, before using Boron Neutron Capture Therapy.

A tumour sample is taken from a patient who has been previously infused intravenously with an FDA approved sensitizer, e.g., a $^{10}$Boron derivative, such as p-boronophenylalanine, or the intravenous infusion of liposomes containing boron derivatives as previously described (Heber et al., Proc. Natl. Acad, Sci. USA, 111, 16077-16081. 2014), or boron nanoparticles as previously described (Petersen et al., Anticancer Research, 28, 571-576, 2008). The tumour sample is then examined for the 2D distribution of $^{10}$Boron to determine whether its levels and distribution will be beneficial in terms of radiation. Simultaneously, or separately, the distribution and level of Mn is determined. The relative amounts of $^{55}$Mn and $^{10}$B determines the suitable tumours of patients for radiation.

Boron Neutron Capture Therapy (BNCT) is briefly described. A number of external entities are known to make tumours more sensitive to radiation e.g., Boron, $^{10}$B. A thermal neutron is captured by the nucleus of $^{10}$B and the ensuing fission reaction yields $^7$Lithium as a recoil, an alpha particle, a weak gamma-ray (0.5 MeV gamma photon), and 2.4 MeV of kinetic energy. The $^7$Li ion and the alpha particle are classified as high linear energy transfer radiation and are highly destructive.

In studies in mice, subcutaneous injection of cells pre-incubated with boron nanoparticles into mice, which were then irradiated with neutron radiation, lead to longer survival, since the growth of tumours was delayed (presumably because the tumours with boron were made more sensitive to neutron irradiation) (Petersen et al., Anticancer Research, 28, 571-576, 2008). A clinical trial for the treatment of head and neck tumours has been initiated by the Boneca Corporation (ClinicalTrials.gov identifier; NCT00114790). In addition, a phase I/II clinical trial on Argentinian patients (with multiple subcutaneous metastases of melanoma), who have been treated with p-boronophenylalanine and neutron radiation yield an almost 70% response rate (Menendez P Appl. Rad. Isot. 67, (7-8 Suppl.)S50-S53). 2009). Boron Neutron Capture Therapy has also been used for non-small cell lung cancer (Farias et al., *Phys. Med.* 30,888-897. 2014).

2 Deoxy-D-Glucose, 2-DG

Other useful radiosensitizers include, for example, those as summarized in Shenoy & Singh, *Cancer Investigation* 10, 533-551, 1992. These include 2 deoxy-D-glucose, 2-DG, which is a close analog of glucose but without the hydroxyl group in position 2.

2-DG is taken up avidly by those tumour cells that preferentially use glucose as available fuel, but upon phosphorylation by hexokinase, 2-DG is not further metabolized. Thus by competing with glucose uptake and subsequent steps, 2-DG causes metabolic stress and renders cells more sensitive to radiation. In cell lines exposed to ionizing radiation and simultaneously treated with 2-DG, radiation damage was increased in some, and the usual heterogeneity between cell lines was observed (Dawrkanath et al., *Int. J Radiat. Oncol. Biol. Phys.* 50, 1051-1061, 2001). It is thought that the radiosensitization of some tumour cell populations occurs via disturbances in thiol metabolism (Lin et al., *Cancer Research*, 63, 3413-3417, 2003).

In early phase I/II clinical trials on patients with advanced brain tumours, the toxicity and feasibility of using 2-DG in combination with large fraction, 5 Gy, radiotherapy, (2-DG plus RT) was found to be well tolerated (Mohanti, B, *Int. J. Radiat. Oncol, Biol. Phys*, 35, 103-11, 1996).

Treatment of glioblastoma multiforme patients with increasing oral doses of 2-DG and radiation revealed that up to 250 milligrams/kilogram of body weight was well tolerated with no significant damage to the normal brain. In addition, some of 60 patients in this cohort revealed median survivals that exceeded those of patients that only received radiotherapy (Singh et al., *Strahentherapie and Onkologie,* 8, 507-514, 2005). A summary of patient treatment and outcomes is found in Dwarakanath, *J. Cancer Research and Therapeutics,* 5, 21-26, 2009).

Finally in nude mice with heterotropic pancreatic tumours, treatment with 2-DG plus radiation resulted in inhibition of tumour growth and increased survival, compared to controls (Coleman et al., *Free Radical Biology and Medicine*, 44, 322-331, 2008).

Testing a tumour for $^{55}$Mn (and any other relevant metallomic data), prior to radiation, is therefore another practical application of the technology of the invention to radiosensitizers, not just 2-DG.

Immunotherapies

Radiation, and the antitumour immune responses that follow, form an interacting system with an increased presentation of antigens on the surfaces of cancer cells and the release of a host of proteins and peptides (and metals bound to proteins and peptides), that influence the responses of antigen-presenting cells. Thus primary tumours that have been irradiated (or distant metastatic growths within the same individual that have not been irradiated), can become sensitized to attack by various immune cells. The mechanistic bases for this increased sensitivity are actively debated but remain unresolved, (Sharabi et al., 2015, *Oncology* [Williston Park] 2015, 29(5), pii:211304; Formenti, *J Natl Cancer Inst.* 105, 256-265, 2013). Melanomas that are highly resistant to radiation have high levels of melanin (which store a host of metals). In the context of the present invention, efficacy of immunotherapies is also addressed. Without being bound by any particular theory, the extensive and very different metabolic properties of radiation resistant cancer cells, versus sensitive ones, will not likely be treated equally by the immune system, either before or after radiation treatment. Thus radiation concomitant with immunotherapy; radiation preceding immunotherapy, or immunotherapy preceding radiation, will yield very different populations of cells within a tumour owing to differential selection. In this example, a tumour is first characterized by its ATI according to the method of any aspect, embodiment or example herein and a useful immunotherapy is then applied. Efficacy of the immunotherapy and/or when to administer radiation treatment, e.g., before, during or after immunotherapy is contemplated by performing the method of the invention according to any aspect, embodiment or example herein. Different types of immunotherapy are thought to interact differently with the same type of radiation. For example, Sipuleucel-T for castration-resistant prostate cancer (a dendritic cell vaccine designed to induce immunity against prostatic acid phosphatase), ipilimumab (anti-CTLA4) for unresectable metastatic melanoma, pembrolizumab and nivolumab (anti-PD-1) for melanoma, nivolumab for melanoma and advanced squamous non-small-cell lung cancer, and tremelimumab and lirilumab, are likely to produce different responses to radiation than immunotherapies involving chimeric antigen receptor T cells (CAR-T based immunotherapies). Checkpoint Blockade Immunotherapy in combination with stereotactic radiation delivery is underway for the treatment of glioblastoma, but glioblastoma is being treated as a unitary entity. Accordingly, any glioblastoma is characterized according to the method of any aspect, embodiment or example herein and an evaluation is provided for patients that best respond to immunotherapies.

Rose Bengal and Melanoma

Rose Bengal (4,5,6,7-tetrachloro-2', 4', 5', 7'-tetraiodofluorescein) is an industrial chemical patented in 1882 that turns yarn and food red. When applied intra-lesionally to cutaneous melanomas, there can be significant shrinkage of some tumour(s) (Thompson et al., *Melanoma Research,* 18, 405-411, 2008; Thompson et al., *Ann. Surg. Oncol.* 22, 2135-2142, 2015). While treated skin lesions decreased in volume after Rose Bengal intra-lesional treatment, some of the distant untreated tumours in the same patient also shrank, indicating that an immune response was likely involved. The addition of radiotherapy (RT) to Rose Bengal (RB) treatment can further enhance tumour ablation, as shown for 3 patients who underwent both therapeutic modalities, RB plus RT (Foote et al., *Melanoma Research,* 2010, 20, 48-51, 2010). Note however, that radiation treatment of these patients was not based on any a priori knowledge of the radio-sensitivity or radio-resistance of their multiple tumours, as radioresponsiveness was not measurable prior to this application. In fact, it was noted that "there is still no consensus on the optimal dose and fractionation in melanoma" (Foote et al., *Melanoma Research,* 20, 48-51, 2010).

Rose Bengal may be considered as an agent that has multiple modes of action: a sensitizer of cells to radiation, a sensitizer via augmentation of the immune system, an "additive cell kill" agent, or a synergizer. It is not possible to differentiate between these as the molecular mechanism(s) of these interactants is unknown, and the spatial arrangement of cancerous and stromal cells that have taken up RB remains unknown. The clinician is thus left with the difficult task of the management of melanoma patients, particularly those with regional metastatic regions, such as local, satellite and in-transit recurrence. The current treatment guidelines predominantly include surgical excision, local ablation, intra-lesional chemotherapy and targeted drugs such as vemurafenib. All of these are challenging "due to disease heterogeneity and frequent and persistent proliferation of lesions" (Thompson et al., 2015, Ann. Surg. Oncol. 22, 2135-2142, 2015).

The relevance of the current application to Rose Bengal and therapeutic treatment options, is that the Rose Bengal molecule contains 4 iodine atoms that are easily measured in tissue sections by LA-ICP-MS. Thus a section of any tumour that has been intra-lesionally injected by Rose Bengal can be simultaneously analysed in each voxel for Iodine, $^{55}$Mn or any other atom, prior to, and after radiation treatment, to determine which cell populations are susceptible to radiation. In this manner one can more precisely target susceptible lesions. There are no data as yet to determine the relative clinical efficacy of RB followed by radiation, or radiation followed by RB. What is clear is that any tumour that is accessible to intra-lesional injection of RB, can be analysed by the methods of this application to provide quantitative data on radiotherapeutic options.

By way of non-limiting examples, injection of RB into the prostate via a multiple core needle approach, and simultaneous Laser Ablation analysis of Iodine and $^{55}$Mn from tissue sections, will provide information on which cell types of normal, cancerous and stromal populations preferentially retain RB. These spatial distributions will enhance decision making as regards radiotherapy.

Similarly, intra-lesional deposition of RB into breast tumour regions will allow simultaneous Laser Ablation analysis of Iodine and $^{55}$Mn from tissue sections, and provide information on which cell types of normal, cancerous and stromal populations preferentially retain RB (as depicted for $^{55}$Mn, $^{66}$Zn, $^{56}$Fe and $^{63}$Cu in FIG. 35A-FIG. 35B and FIG. 36A-FIG. 36F in this application). These spatial distributions will enhance decision making as regards radiotherapy.

Example 11

Clinical Implementation of the Atomic Therapeutic Indicator

Analysis of the data from eight different tumour types has revealed a number of findings that place the technological and clinical aspects of ATI into perspective. Not unexpectedly, the melanomas are different to all other epithelial tumours, since no other tumour types synthesize melanin (unless it is a fortuitous activation of all pathways that culminate in melanin production in an unrelated cell type, or the result of cell fusion between immune cells and melanoma cells). In addition, melanomas derive from the initial embryological derivatives of neural crest cells, which are migratory cells that populate and set up different embryonic structures. Except for the initial migratory nature of germ cells, neural crest cells are the only other transitory cell type that migrates over long distances. As described herein for various melanotic tumours, melanins colocalize with the high concentrations of $^{55}$Mn, $^{66}$Zn, $^{56}$Fe and $^{63}$Cu. Of these, $^{55}$Mn is most likely to provide radiation protection by its ability to bind $O_2.-$, $H_2O_2$ and the highly dangerous hydroxyl radical OH. when $^{55}$Mn is bound to various chemical entities (FIG. 2). In addition, high melanin concentrations throughout a tumour may provide a degree of physical shielding from radiation that is not available to any other tumour type. The only melanomas that can reasonably be placed with all other tumour types, are those melanomas that through the inactivation of steps leading to melanin production, are completely amelanotic. It is salient in this regard that the melanomas that have been examined herein, and which have unambiguously low concentrations of melanin pigment granules by visual microscopical examination (which is not quantitative), have low $^{55}$Mn CC/S values (median voxel values of 1,939, 1,239, 817, 1,439, 1,278, 939, 1,617 and 1,678 CC/S). These all fall below the 2K ATI threshold illustrated in FIG. 11A-FIG. 11F. If this finding is subsequently confirmed quantitatively, then the amelanotic condition, in the absence of HMRs, may be indicative of a low $^{55}$Mn ATI, and radiation sensitivity.

Figure 42:
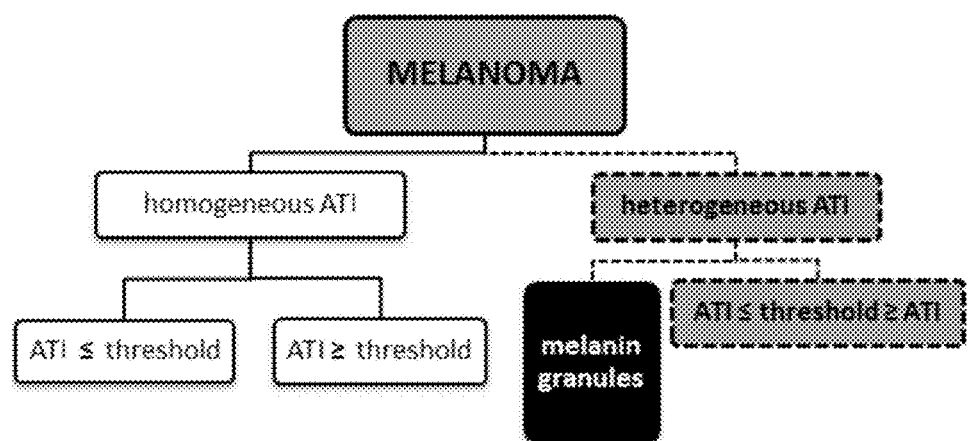
FIG. 42: Flow diagram for melanoma patients whose solid tumour(s) are analyzed by LA-ICP-MS. The optional pathways that provide evidence for a physician as to whether to advise radiation treatment for the patient, or to refrain from the use of such a modality, are based on the homogeneity or heterogeneity of the ATI. The key decision points concern whether the $^{55}$Mn voxel values fall above or below certain designated thresholds, and the degree of melanization of the tumour, in terms of metal binding.
Figure 43:
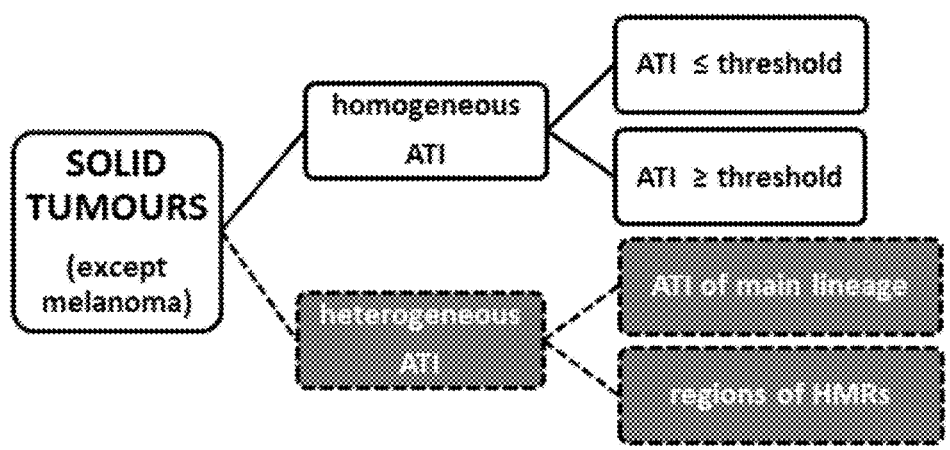
FIG. 43: Flow diagram for the non-melanoma patients whose solid tumour(s) are analyzed by LA-ICP-MS. The optional pathways that provide evidence for a physician as to whether to advise radiation treatment for the patient, or to refrain from the use of such a modality, are based on the homogeneity or heterogeneity of the ATI. The key decision points concern whether the $^{55}$Mn voxel values fall above or below certain designated thresholds.

In a clinical context, one modus operandi for the application of ATI to tumour biopsies are the flow diagrams shown in FIG. 42 and FIG. 43. In the former, easily accessed melanomas would be removed by surgery with wide excision as exemplified by patient Y. Analysis of voxel contents via Bowley's Non Parametric Skew Statistic (NPSS) (Bowley, 1901, Elements of Statistics, P S King and Son, publishers, Westminster, London, UK), would provide the first indication of homogeneity or lack thereof. Second, the conditions for homogeneity would be that, (i) the NPSS values for $^{55}$Mn, $^{66}$Zn, $^{56}$Fe and $^{63}$Cu would all be low, (ii) that the sample had no HMRs($^{55}$Mn) in either the cancer cell or stromal compartments and (iii) no overt melanisation. If the sample was found to be homogeneous, its ATI would be above or below a chosen threshold of clinical importance. As the primary tumour has been resected, such data on homogeneity and above or below thresholds, would provide information on the probable characteristics of any cells that had metastasized earlier, such as the cranial metastasis in patient Y. Analysis of resected lymph nodes from a patient who had undergone removal of the primary melanoma, would be analysed in the same manner as above. An ATI would provide guidance on whether to initiate radiation should a metastatic derivative of the primary tumour arise at a later time. If a biopsy from a metastatic site is available, then the flow diagram of FIG. 42 starts anew.

The right hand panels of FIG. 42 illustrate the situation when a biopsy returns a sample that is heterogeneous in terms of voxel characteristics and when the tumour is resected. The heterogeneity will derive from a number of contributing factors, (i) heterogeneity within the main landscape, (ii) the presence, size and content of HMRs($^{55}$Mn) in both the cancer cell and stromal compartments, and (iii) the presence of melanin granules and the extent of intracellular melanin concentrations. The evaluation of all HMRs($^{55}$Mn), will indicate the probability of reoccurrence of a distant tumour (if any cells had metastasized early prior to the resection of the primary tumour).

The flow diagram of FIG. 42 also applies to any biopsies that are taken from sites that are not amenable to excision by surgery, and where it needs to be ascertained by determining an ATI, if radiation is a useful option as regards intent-to-treat by radiation.

For all other tumour types besides melanomas, the flow diagram of FIG. 43 will lead to a clinical decision point on whether to use radiation, or to spare it. The biopsy will reveal either homogeneity or heterogeneity (the latter being an unavoidable grey area in a clinical sense). The tumour will either be resectable or not, and radiation will be used if the ATI derived from the absence of HMRs($^{55}$Mn) is below threshold. If the tumour is heterogeneous and resectable, the ATI will be an indicator of what to expect if distant metastases arise at a later time in the patient's life. If the tumour is not resectable, then the decision to irradiate or not, is made on the basis of threshold values.

It will be understood by the person skilled in the art that a number of other factors unrelated to the ATI will be considered by both the attending physician and the patient. These will include, but are not limited to, the age of the patient, the current health condition of the patient, comorbidities, the locations of the tumour(s) (primary or metastatic) and any hereditary conditions that make a patient radiation-sensitive. In the case of brain lesions, some tumours will be more radiation resistant than other tumour types, because the cancer cells use a novel mechanism of interconnection via microtubes, which allows damaged cancer cells to be repaired by others within the tumour (Osswald et al., *Nature,* 528, 93-98, 2015).

Example 12

Clinical Implementation of the Atomic Therapeutic Indicator in Combination with Other Entities The key foundation of this application is that focused pulses of high irradiance laser energy applied across a tissue section, and the analysis of the vaporized material via mass spectrometry, provide a 2D spatial atomic map which is of immediate therapeutic importance as regards radiation treatment of cancer patients via an ATI. This ATI/H&E map is the foundation onto which other different maps can be superimposed. A person skilled in the art will recognize that a judicious choice of biological entities providing multilayered/superimposed information, will further increase the clinical impact of an ATI, a situation that was not available prior to this application. We demonstrate below how integrating additional maps employing metal-labelled antibodies using elemental analysis, namely laser ablation-Inductively coupled plasma-mass spectrometry (LA-ICP-MS) or laser ablation-time-of-flight-mass spectrometry (LA-TOF-MS) or inductively coupled plasma-optical emission spectroscopy (ICP-OES), or microwave plasma-atomic emission spectroscopy (MP-AES), or laser induced break down spectroscopy (LIBS), or secondary ion mass spectrometry (SIMS), or X-ray absorption near edge structure (XANES), atomic absorption spectroscopy (AA) or X-ray fluorescence (XRF), can increase the power of the clinical decision making process.

Additional Maps

Gene expression can be measured in tissue sections via "spatial transcriptomics" using arrayed reverse-transcription oligo (dT) primers and fluorescently labelled nucleotides (Stahl et al., *Science,* 353, 78-82, 2016). This provides a spatial map of gene expression relative to the H&E map of the tissue section, but it comes at the cost of being labour intensive, involving library construction, amplification steps, intensity loss of fluorescence with time, staining artefacts and auto-fluorescence as well as deconvolution of large data sets of Entities of Unknown Clinical Significance. To our knowledge, no previous spatial gene expression maps of tissue sections have reported on the clinical question of whether radiation is a preferred treatment option for a patient.

What has not been available, until the present application, is a clinically useful 2D map generated from a simultaneous measurement of an ATI together with specially selected biological parameters at the protein or cellular level. These parameters need to have a presumed involvement in radiotherapeutics and need to be immediately implementable with current pathological and molecular technologies. A number of instantiations of such maps are provided below.

Many tumours are claimed to contain "cancer stem cells" (CSCs) (Clevers, *Nature Medicine,* 17, 313-319, 2011), that are virtually resistant to radiation (Ogawa et al., 2013, *Anticancer Research,* 33, 747-754). This radio-resistance of CSCs is thought to be due to a number of factors including their superior DNA repair capabilities and their heightened defence to Reactive Oxygen Species. Such CSCs are thought to self-renew, divide slowly and are capable of reconstituting a tumour. If such is indeed the case, then it would be clinically advantageous to construct and to superimpose a "properties of cancer stem cells" map, onto the ATI/H&E map. This can be done using metal-labelled antibodies.

Current technology on formalin-fixed paraffin-embedded tissue sections generally employs antibodies to the antigens of interest, but to multiplex several protein tumour markers, say 4 or 5, which may co-localize on the same tissue section, is near impossible using current immunohistochemistry. Use of a primary antibody which is antigen specific, is followed by an amplification step which involves an enzyme labelled secondary antibody. The time factor of staining 5 sequential tissue sections, processed at different times and different staining conditions, is neither conducive to rapid and accurate throughput, nor to interpretation. However, application of antibody labelling using metals (especially lanthanides and their easily distinguished isotopes), means that different antibodies, each tagged with a different isotope, can be applied to the same tissue section which is then directly examined via LA-ICP-MS, (Giesen et al., 2011, *Anal. Chem.* 83, 8177-8183). Here there is no ambiguity with co-localized staining procedures, fluorescence issues or quantification. This methodology has been applied in a diagnostic context to the labelling of primary antibodies, anti-Her2, anti-CK-7 and anti-MUC 1 using the lanthanides holmium, thulium and terbium and their subsequent location in breast cancer tissue sections examined via LA-ICP-MS, (Giesen et al., 2011, *Anal. Chem.* 83, 8177-8183). It has also been applied to directly label anti-tyrosine hydroxylase (TH) with Ytterbium-173, Paul et al., 2015, *Chemical Science*, DOI: 10.1039/c5sc02231b, 2015).

The above data demonstrate that multiple lanthanide-labelled antibodies analysed via elemental analysis can report on the spatial distribution of antigens in the same tissue section and provide clinical information of use for drug-based patient treatment. In the context of radiotherapeutic information, however, the requirement is different. It is to measure an ATI and entities of radiotherapeutic significance in the same tissue section, or in sequential serial sections (for example in the breast cancer section exemplified in FIG. 35A-FIG. 35B, where there are cancerous cells in lymphatic vessels, and where those metastasizing cells have different $^{55}$Mn levels). This can be implemented as follows.

It is known that the 15 lanthanides; Lanthanum, Cerium, Praseodymium, Neodymium, Promethium, Samarium, Europium, Gadolinium, Terbium, Dysprosium, Holmium, Erbium, Thulium, Ytterbium and Lutetium, together with Scandium and Yttrium, have multiple isotopes that are readily distinguished by LA-ICP-MS. Hence instead of 17 elements, one has a minimal palette of around 32 labels from which to choose to label antibodies of choice. In the context of this application, the next step is to select those antigens that are markers for "stemness", DNA repair, ROS, cell division and methylases and demethylases involved in silencing of tumour suppressors in cancer cells, and all of which impinge on radiotherapeutic relevance.

In a non-limiting context, the first steps involve:
(i) selecting proteins involved in "stemness" networks that are relevant to tumour aggressiveness/metastatic potential, such as CD44, (breast, liver and pancreas), CD133 (brain, colorectal, lung, liver), EpCAM, (colorectal and pancreatic) as set out by Clevers (*Nature Medicine,* 17, 313-319, 2011), as well as proteins that are targeted by drugs aimed at cancer stem cells such as NOTCH, DLL4, FAK, STAT3, and NANOG (Kaiser, *Science,* 347, 226-229, 2015).

(ii) selecting proteins involved in DNA repair, such as BRCA1, BRCA2 and ATM, as reviewed by Wood et al. (2001, *Science* 291, 1284-1289, and subsequent updates).

(iii) selecting proteins involved in metabolic networks of Reactive Oxygen Species which have a major role in the tumour niche, such as Hypoxia Inducible Factors, HIF (Simon and Keith, *Nature Reviews Molecular Cell Biology,* 9, 285-296, 2008), carbonic anhydrase IX and catalase.

(iv) selecting proteins involved in cell division networks, such as Ki-67 (Inwald et al., *Breast Cancer Res Treat.* 139, 539-552, 2013).

(v) selecting proteins such as the DNA demethylase TET1 and TET 3 (Forloni et al., *Cell Reports,* 16, 1-15, 2016), and DNA methylases such as the DNMT1, DNMT3a and DNMT3b that silence or activate genomic regions and influence the oncogenic potential of cells within tumours.

The second step involves using primary antibodies to these protein products and then labelling either primary or secondary antibodies with a suitable lanthanide and hybridizing these antibodies to tissue sections.

The third step involves the application of elemental analysis to such an antibody-rich section. This provides a simultaneous readout of the endogenous metals that have been used in this Application, Mn, Zn, Fe and Cu, to generate an ATI and to locate HMRs, plus a spatial readout of the various lanthanides that highlight the positions in the ATI/H&E map of the relevant proteins to which the lanthanides are attached. This is multiplexed rapid cartography of clinical importance. When applied to a tissue section such as that of FIG. 35A-FIG. 35B, it will allow for a more complete understanding of the characteristics of the cell populations in lymphatic vessels and capillaries of the breast (and any other tumour), the heterogeneity within primary and secondary tumours, and in the case of core needle biopsies of the prostate, an expansive view that far exceeds that of current pathological insights.

This logical extension of superimposed multilayered information onto an ATI/H&E map, provides a new pathological taxonomy, not previously seen, that produces rapid, quantitative, clinically relevant information from the same or serial tissue sections which can be evaluated in a radiotherapeutic context.

Advantages of the Present Invention

The 2D cartographic nature of the present invention has a number of significant attributes that are relevant to the clinical radiotherapeutic treatment that can be undertaken compared to the non-cartographic alternative of homogenizing a tumour and measuring the amount of manganese per unit mass of tissue.

First, all tumours are heterogeneous in terms of the amount and type of stromal material, so the relative amount of tumour cells to stromal material, which is only visible and measurable with reference to a 2D map, will influence the median ATI.

Second, even when a 2D region consists of nearly all cancer cells, they can be very different in terms of their Mn levels. FIG. 1 illustrates this perfectly, where a third or so of the section consists of amelanotic tumour cells with median CC/S values around 3,000, and the rest of the section consists of areas where the Mn levels vary between 15,000-45,000 CC/S and then HMRs($^{55}$Mn) that vary between 45,000-150,000 CC/S. If one had homogenized this section, the median ATI would far exceed 10,000 CC/S. What would have been lost in a clinical sense, is that radiation treatment of this patient would have killed the third of the tumour that has a low ATI, and thus the tumour burden would have been reduced, with clinical benefit to the patient.

Even more importantly, homogenizing a section, or a tumour sample, loses one of the important aspects of the invention: HMRs($^{55}$Mn) that are predictive of tumour reoccurrence. Most HMRs represent less than 10% of a section, so homogenization loses that information of the presence of an HMR($^{55}$Mn), as the median ATI is barely moved.

In the example of breast cancer, FIG. 35, with its mixture of normal breast ducts, an area of immune cells, adipocytes and stromal cells, the clinically relevant cells that are most dangerous are the ones that are already in only one lymphatic vessel C5. They are in the process of metastasis and they have a median of 8,612 CC/S. If the entire section were homogenized, this clinically relevant information is completely lost, as the median of the homogenized section is now approximately 1,669 CC/S, a low value that is influenced by the proportion of the adipocyte population, the stroma and the relatively low values in the normal ducts.

The invention claimed is:

1. A method of treating a patient determined to have a cancer resistant to radiation treatment with a cancer treatment not including radiation treatment comprising:
   (A) identifying a cancer patient who is resistant to radiation treatment by:
      (i) obtaining a tumour sample from the patient, wherein the tumour sample corresponds to a total sample volume of at least about 1000×1000×5 cubic microns;
      (ii) quantifying the level of manganese in the tumour sample by generating an Atomic Therapeutic Index (ATI), wherein the ATI corresponds to the median level of manganese as related to a pre-defined volume of the tumour sample expressed in calibrated counts per second (CC/S) as measured by laser ablation-inductively coupled plasma-mass spectrometry (LA-ICP-MS); wherein the pre-defined volume corresponds to about 35×35×5 cubic microns; and
      (iii) comparing the generated ATI to a predetermined ATI threshold, wherein the predetermined ATI threshold corresponds to about 2000 CC/S for a volume of about 35×35×5 cubic microns; wherein the cancer is determined to be resistant to radiation treatment when the ATI of the tumour sample is higher than the predetermined ATI threshold; and
   (B) administering a cancer treatment to the patient with cancer determined to be resistant to radiation treatment, wherein the cancer treatment is not radiation therapy, and wherein the cancer is prostate cancer, breast cancer, seminoma, lymphoma, small cell lung cancer, brain cancer, mesothelioma, or melanoma.

2. The method of claim 1, wherein said cancer treatment is chemotherapy, immunotherapy, hormone therapy, or surgery.

* * * * *